(12) United States Patent
Li et al.

(10) Patent No.: US 10,323,053 B2
(45) Date of Patent: Jun. 18, 2019

(54) POLYDENTATE BINUCLEAR RING METAL COMPLEXES AND DEVICES CONTAINING SAME

(71) Applicants: AAC Microtech (Changzhou) Co., Ltd., Changzhou (CN); Zhejiang University of Technology, Hangzhou (CN)

(72) Inventors: Guijie Li, Shenzhen (CN); Jianxin Dai, Shenzhen (CN); Yuanbin She, Shenzhen (CN); Shaohai Chen, Saratoga, CA (US)

(73) Assignees: AAC MICROTECH(CHANGZHOU)CO., LTD., Changzhou, Jiangsu Province (CN); ZHEJIANG UNIVERSITY OF TECHNOLOGY, Hangzhou, Zhejiang Province (CN)

( * ) Notice: Subject to any disclaimer, the term of this patent is extended or adjusted under 35 U.S.C. 154(b) by 0 days.

(21) Appl. No.: 15/975,590

(22) Filed: May 9, 2018

(65) Prior Publication Data

US 2019/0153007 A1    May 23, 2019

(30) Foreign Application Priority Data

Nov. 17, 2017 (CN) .......................... 2017 1 1143696

(51) Int. Cl.
| | | |
|---|---|---|
| *C07D 239/02* | (2006.01) | |
| *C07D 403/14* | (2006.01) | |
| *C07F 15/00* | (2006.01) | |
| *C09K 11/06* | (2006.01) | |
| *H05B 33/14* | (2006.01) | |
| *H01L 51/50* | (2006.01) | |

(52) U.S. Cl.
CPC .......... *C07F 15/006* (2013.01); *C07D 239/02* (2013.01); *C07D 403/14* (2013.01); *C07F 15/0086* (2013.01); *C09K 11/06* (2013.01); *H01L 51/5016* (2013.01); *H01L 51/5084* (2013.01)

(58) Field of Classification Search
CPC .... C07D 239/02; C07D 403/14; C09K 11/06; H05B 33/14; H01L 51/5032; H01L 51/5063; H01B 33/14
USPC ................. 544/225; 428/690, 917; 313/504; 257/40, E51.044
See application file for complete search history.

(56) References Cited

U.S. PATENT DOCUMENTS 10,020,455 B2 * 7/2018 Li ....................... H01L 51/0087

* cited by examiner

*Primary Examiner* — Venkataraman Balasubramanian
(74) *Attorney, Agent, or Firm* — Na Xu; IPro, PLLC

(57) ABSTRACT

The invention relates to the technical field of organic electroluminescent devices and discloses a polydentate binuclear ring metal complex and a device including the polydentate binuclear ring metal complex or its composition. The polydentate binuclear ring metal complex provided by the invention can not only provide the emission of most visible spectra, but also can be adjusted by changing the structure of ligand or fluorescent luminescence. In addition, the polydentate binuclear ring metal complexes provided by the invention have better stability and efficiency than the traditional emission complexes. The device provided by the invention comprises the polydentate binuclear ring metal complex or its composition, which include optical and electro-optic devices, optical absorption devices, organic light-emitting diode devices, photoemission devices, or devices that are compatible with optical absorption and emission. The polydentate binuclear ring metal complex or its composition has 100% internal quantum efficiency in these devices.

5 Claims, 2 Drawing Sheets

POLYDENTATE BINUCLEAR RING METAL COMPLEXES AND DEVICES CONTAINING SAME

FIELD OF THE PRESENT DISCLOSURE

The invention relates to the technical field of organic electroluminescent devices, in particular to a polydentate binuclear ring metal complex and a device comprising the polydentate binuclear ring metal complex.

DESCRIPTION OF RELATED ART

Compounds capable of absorbing and/or emitting light are ideally suited for use in a variety of optical and electroluminescent devices, including optical absorption devices, such as solar sensitive devices and photosensitive devices; Organic light-emitting diode (OLED); Light emitting device; or can carry on the light absorption as well as the optical emission device and the biomarker device for the biological application. Many studies have been devoted to the discovery and optimization of organic and organometallic materials for use in optical and electroluminescent devices. This includes improvements in absorption and emission efficiency, as well as in processing capacity.

Despite significant advances in research on chemical and electro-optic materials, for example, red-green phosphorescent organometallic materials have been commercialized and used in OLEDs, lighting devices, and phosphorescent materials in advanced displays. However, the available materials still have many shortcomings, including poor mechanical properties, inefficient emission or absorption, and less desirable stability.

Up to now, blue electroluminescent devices are still the most challenging field in this technology, and the stability of blue devices is the most serious problem. It has been proved that the selection of host materials is very important for the stability of blue devices. However, the lowest energy of the triple excited state T1) of the blue luminescent material is very high, which means that the lowest energy of the triple excited state T1) of the host material of the blue device should be higher. This leads to greater difficulties in the development of the host materials of the blue equipment. Therefore, new materials with improved performance in optical emission and absorption applications have become the research and development direction in this field.

In general, the changes in chemical structures will affect the electronic structure of compounds, which in turn will affect the optical properties of compounds (for example, emission and absorption of spectra), regulate or adjust the compound to specific emission or to absorption energy. The internal quantum efficiency of 100% can be obtained by using both singlet and three-wire excitons excited by Phosphorescent polydentate platinum complexes at the same time. Therefore, these complexes can be used as OLEDs alternative luminescent materials. In general, the ligand of multi-toothed platinum complex includes luminescent group and auxiliary group. If the conjugated groups, such as aromatic ring substituents or heteroatomic substituents etc, are introduced into the luminescent part, the energy levels of the Highest Occupied Molecular Orbital (HOMO) and Lowest Unoccupied Molecular Orbital (LOMO) of the luminescent will be changed. At the same time, by adjusting the energy level gap between the HOMO orbital and the LOMO orbital, the phosphorescent multi-toothed platinum can be adjusted, for example, the emission spectrum of the complex is wider or narrower, or makes red shift or blue shift.

BRIEF DESCRIPTION OF THE DRAWINGS

Many aspects of the exemplary embodiments can be better understood with reference to the following drawings. The components in the drawing are not necessarily drawn to scale, the emphasis instead being placed upon clearly illustrating the principles of the present disclosure.

DETAILED DESCRIPTION OF THE EXEMPLARY EMBODIMENTS

Figure 1:
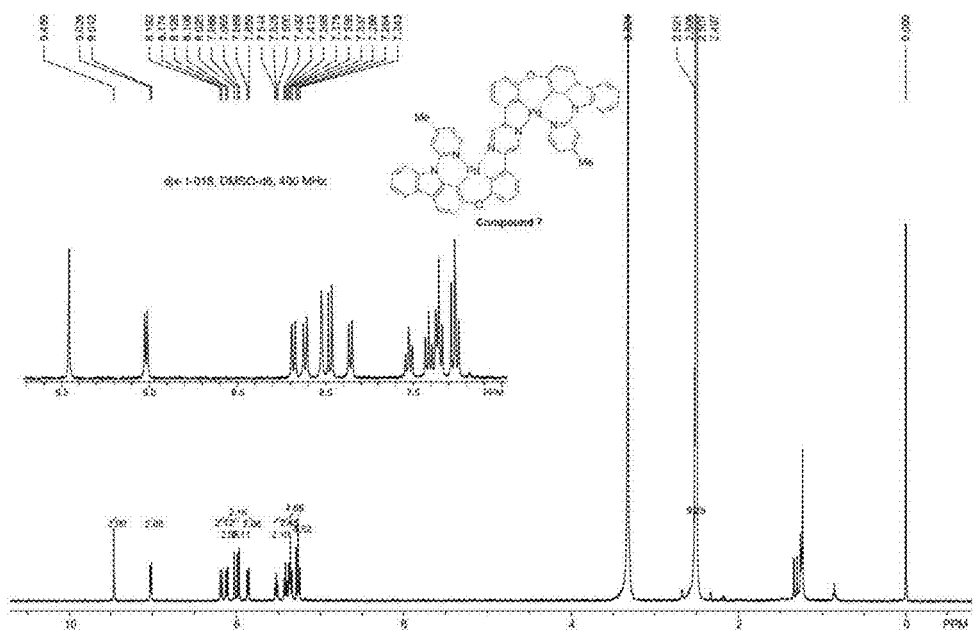
FIG. 1 is the NMR hydrogen spectrum of the Compound Pd7 in deuterated dimethyl sulfoxide (DMSO).
Figure 2:
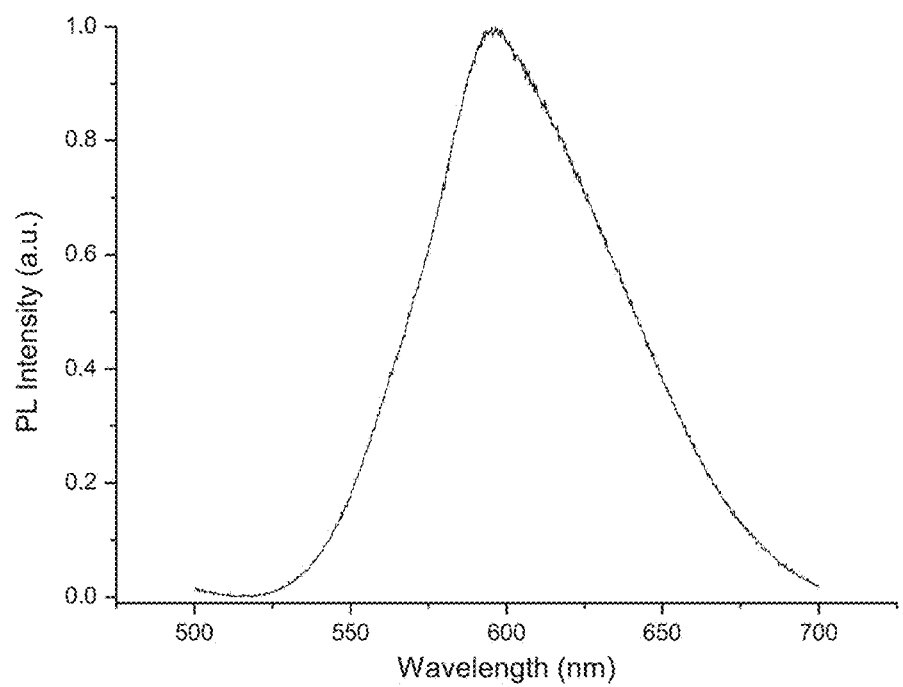
FIG. 2 shows the emission spectra of the Compound Pd7 in dichloromethane solution.

The present disclosure will hereinafter be described in detail with reference to several exemplary embodiments. To make the technical problems to be solved, technical solutions and beneficial effects of the present disclosure more apparent, the present disclosure is described in further detail together with the figure and the embodiments. It should be understood the specific embodiments described hereby is only to explain the disclosure, not intended to limit the disclosure.

In order to make the purpose, technical scheme and advantages of the invention more clear, the embodiments of the invention will be described in detail combining with the attached drawings. However, ordinary technicians in the art can understand that in various embodiments of the present invention, many technical details are presented in order to enable the reader to better understand the invention. Nevertheless, even without these technical details and various changes and modifications based on the following embodiments, the technical schemes to be protected by the claims of the present invention can also be achieved.

The contents disclosed in the present invention can be more easily understood by referring to the following specific embodiments and the embodiments contained therein. Before disclosing and describing the compounds, devices and/or methods of the present invention, it should be understood that they are not limited to specific synthetic methods (otherwise, specific reagents may be identified separately (or otherwise specified separately). Because of course it can change. It should also be understood that the terms used in the present invention are used only for the purpose of describing specific aspects and are not intended to be limitations. While any method and material similar or equivalent to those described in the present invention may be used in the practice or experiment exemplary methods and materials are described below.

The terms "one", "one", and "described" used in the specification and the appended claim contain plural indicators, otherwise the context would clearly indicate. Thus, for example, a reference to a "component" contains a mixture of two or more components.

The term "optionally" used in the present invention means that the event or condition described subsequently may or may not occur and the description includes the occurrence of the event or circumstance and the circumstances that it does not occur.

The present invention discloses a component that can be used to prepare the composition of the invention and the composition itself to be used in the method disclosed in the present invention. These and other substances are disclosed in the present invention and should be understood when a combination, subset, interaction, group, etc. of these substances is disclosed. When each of the individual and general combinations and specific reference for the substitution of these compounds cannot be specifically disclosed, each is specifically anticipated and described in the present invention. For example, if a specific compound is disclosed and discussed, and many modifications that can be made to many molecules containing the compound are discussed, the variety and each combination and substitution of the compound is specifically expected. And the modification may be carried out, otherwise it will be separately specified to the contrary. Thus, if an example of a class of molecules A, B, and C, and a class of molecules D, E, and F, and a combination molecule A-D is disclosed, then each is not separately documented. Consideration has also been given to disclosing each combination of individual and total expected meanings, namely A-E, A-F, B-D, B-E, B-F, C-D, C-E and C-F. Similarly, any subset or combination of these is disclosed. Therefore, for example, consideration should be given to disclosing the panels A-E, B—F and C-E. These concepts apply to all aspects of the present invention including but not limited to the steps of a method for preparing and using the composition. Therefore if there are various additional steps that can be carried out it should be understood that each of these additional steps can be carried out in a specific embodiment or combination of embodiments of the method.

The connecting atoms used in the present invention are capable of connecting two groups, such as N and C groups. The connected atom can optionally (if the valence bond permits) have other attached chemical parts. For example, on one hand, oxygen does not have any other chemical groups attached, because once it is bonded to two atoms (such as N or C) valence bonds have been satisfied. On the contrary, when the carbon is connected to the atom, two other chemical parts can be attached to the carbon atom. Appropriate chemical components include, but are not limited to, hydrogen, hydroxyl, alkyl, alkoxy, halogen, nitro, amine, amide, mercaptan, aryl, heteraryl, cycloalkyl, and heterocyclic.

The term "ring structure" or similar term used in the present invention refers to any ring chemical structure which includes, but is not limited to, aryl, hetero-aryl, cycloalkyl, cyclenyl, heterocyclic, carbene, and N-heterocyclic carbene.

The term "substituted" used in the present invention is expected to contain all permitted substituents of organic compounds. In broad terms, the allowable substituents include non-ring and ring, branched and unbranched, carbon-ring and heterocyclic, and aromatic and non-aromatic substituents of organic compounds. Illustrative substituents include, for example, those described below. For suitable organic compounds, the allowed substituents may be one or more, the same or different. For the purposes of the present invention, a hetero atom, such as nitrogen, can have a hydrogen substituent and/or any permitted substituent of an organic compound described in the present invention, which satisfies the valence bond of the hetero atom. This disclosure does not purport to impose any restriction in any way with the substituents permitted by organic compounds. Similarly, the term "substitution" or "substitution has" contains implied conditions that the substitution conforms to the substituted atom and the allowed valence bond of the substituent, and that the substitution leads to a stable compound (for example, a compound that does not spontaneously transform, e.g.: by rearrangement, cyclization, elimination, etc). It is also expected that, in some respects, the individual substituents may be further optionally substituted (i.e., further substituted or unsubstituted) unless clearly indicated to the contrary.

In defining various terms, "$R^1$", "$R^2$", "$R^3$" and "$R^4$" are used as general symbols in the present invention to denote various specific substituents. These symbols may be any substituents, not limited to those disclosed in the present invention, and when they are limited to certain substituents in one case, they may in other cases be limited to some other substituents.

The term "alkyl" used in the present invention is a saturated hydrocarbon group of branched or unbranched 1-24 carbon atoms, such as methyl, ethyl, n-propyl, isopropyl, normal-butyl, isobutyl, intermediate butyl, and tert-butyl group, N-pentyl, isoamyl, secondary pentyl, neopentyl, hexyl, heptyl, hemisyl, nonyl, decyl, 12 alkyl, 14 alkyl, cetyl, 20 alkyl, 24 alkyl, etc. The alkyl may be annular or non-cyclic. The alkyl may be branched or unbranched. The alkyl may also be substituted or unsubstituted. For example, the alkyl may be substituted by one or more groups, including, but not limited to, optional substituted alkyl, cycloalkyl, alkoxy, amino, ether, halogen, hydroxyl, nitro, methylsilyl, as described in the present invention. Sulfo-oxo, or mercaptan. The "lower alkyl" group is an alkyl containing 1 to 6 (e.g., 1 to 4) carbon atoms.

Throughout the specification, "alkyl" is usually used to refer to both unsubstituted alkyl and substituted alkyl; however, substituted alkyl is also specifically referred to in the present invention by identifying specific substituents on alkyl. For example, the term "halogenated alkyl" or "haloalkyl" specifically refers to the substitution of alkyl groups containing one or more halogens (e.g. fluorine, chlorine, bromine, or iodine). The term "alkoxy alkyl" specifically refers to the substitution of alkyl groups with one or more alkoxyl groups, as described below. The term "alkylamino" specifically refers to the substitution of alkyl groups with one or more amino groups, as described below, etc. The use of "alkyl" in one case and a specific term such as "alkyl alcohol" in another does not imply that the term "alkyl" does not refer to a specific term such as "alkyl alcohol" at the same time.

The present embodiment is also used for other groups described in the present invention. That is, when a term such as "cycloalkyl" refers to both an unsubstituted and a substituted naphthenic portion, the substituted portion may be separately specifically determined in the present invention; For example, a specific substituted cycloalkyl may be called, for example, an "alkyl cycloalkyl". Similarly, substituted alkoxy groups may be specifically referred to as "halogenated alkoxyl", and specific substituted alkyl groups may be "enols", for example. Similarly, the practice of using general terms such as "cycloalkyl" and specific terms such as "alkyl cycloalkyl" is not intended to imply that the general term does not contain the specific term at the same time.

The term "cycloalkyl" used in the present invention is a non-aromatic carbon-based ring consisting of at least three carbon atoms. Examples of cycloalkyl include, but are not limited to, cyclopropyl, cyclic Butyl, cyclopentyl, cyclohexyl, cyclononyl, etc. The term "heterocyclic alkyl" is a class of cycloalkyl as defined above and is included in the term "cycloalkyl", in which at least one ring carbon atom is replaced by a heterocyclic atom, for example, but not limited to nitrogen, oxygen, sulfur, or phosphorus. The ring alkyl and heterocyclic alkyl may be substituted or unsubstituted. The cycloalkyl and heterocyclic alkyl may be substituted by one or more groups, including, but not limited to, alkyl, naphthenic, alkoxy, amino, ether, halogen, hydroxyl, nitro, methylsilyl, sulfo-oxo, or thiol group as described in the present invention.

The term "polyolefin group" is used in the present invention to refer to two or more $CH_2$ groups that are connected to other identical parts. The term "polyolefin group" may be expressed as $—(CH_2)_a—$ where "a" is an integer of 2 to 500.

The terms "alkoxy" and "alkoxy groups", used in the present invention to refer to alkyl or naphthenic groups bonded by ether; That is, "alkoxy" can be defined as $—OR^1$, where $R^1$ is alkyl or cycloalkyl as defined above. The "alkoxy" also contains the alkoxyl polymers that have just been described; That is, the alkoxy group may be polyether, such as $—OR^1—OR^2$ or $—OR^1—(OR^2)_a—OR^3$, where "a" is an integer from 1 to 200, while $R^1$, $R^2$. And $R^3$ are independently alkyl, cycloalkyl, or combination thereof.

The term "alkyl" used in the present invention is a hydrocarbon group of 2 to 24 carbon atoms, the structural formula of which contains at least one carbon-carbon double bond. The asymmetric structure, for example, $(R^1R^2)C=C(R^3R^4)$, is intended to contain the E and Z isomers. This may be presumed in the structural formula of the present invention in which asymmetric olefins are present, or it may be explicitly indicated by the key symbol C=C. The alkyl group may be substituted by one or more groups, including, but not limited to, alkyl, naphthyl, alkoxy, alkyl, cyclenyl, alkynyl, cycloacetyl, aryl, heteraryl, aldehyde, amino, carboxylic acid, ester, ether, halogen, hydroxyl, ketone, azide, nitro, methylsilyl, sulfo-oxo, or mercaptan.

The term "cyclienyl" used in the present invention is a non-aromatic carbon-based ring consisting of at least three carbon atoms and containing at least one carbon-carbon double bond, namely, C=C. Examples of cyclienes include, but are not limited to, cyclopentenyl, cyclopentenyl, cyclopentadienyl, cyclohexenyl, cyclohexenyl, norbornenyl, norbornenyll, etc. The term "heterocyclic alkenyl" is a class of cyclists as defined above and is included in the meaning of the term "cyclenyl", in which at least one of the carbon atoms of the ring is substituted by, for example, but not limited to, nitrogen, oxygen, sulfur, or phosphorus. Cyclienes and heterocyclic alkenyl groups may be substituted or unsubstituted. The cycloenyl and heterocyclic groups may be substituted with one or more groups, including, but not limited to, alkyl, naphthyl, alkoxy, alkenyl, cyclienyl, aryl, heteraryl, aldehydes, amino group, alkyl group, alkyl group, alkyl group, cycloalkynyl group, aryl group, heteraryl group, aldehydes and amino group, carboxylic acids, esters, ethers, halogens, hydroxyl groups, ketones, azide, nitro, methylsilyl, sulfo-oxo, or mercaptan as described in the present invention.

The term "acetyl" used in the present invention is a hydrocarbon group having 2 to 24 carbon atoms having a structural formula containing at least one carbon-carbon triple bond. The alkynyl group may be an unsubstituted or substituted group or groups comprising, but not limited to, alkyl, cycloalkyl, alkoxy, alkenyl, cyclenyl, alkynyl, cycloacetyl, aryl, heteraryl, aldehyde, amino, carboxylic acid, ester, ether, halogen, hydroxyl, ketone, azide, nitro, methylsilyl, sulfo-oxo or mercaptan as described in the present invention.

The term "cycloacetyl" used in the present invention is a non-aromatic carbon-based ring containing at least seven carbon atoms and at least one carbon-carbon triple bond. Examples of cyclic alkynes include, but are not limited to, cycloheptynyl, cyclooctynyl, cyclononynene, etc. The term "heterocyclic alkynyl" is a type of cycloalkynyl as defined above and is contained within the meaning of the term "cycloacetl", in which at least one of the carbon atoms of the ring is replaced by a hetero atom. The heteroatoms are, for example, but not limited to nitrogen, oxygen, sulfur, or phosphorus. Cycloacetyl and heterocyclic alkynyl may be substituted or unsubstituted. Cycloalkynyl and heterocyclic alkynyl groups may be substituted with one or more groups including, but not limited to, alkyl, cycloalkyl, alkoxy, alkyl, cyclenyl, alkynyl, cyclienyl, aryl, heteraryl, aldehyde, amino, carboxylic acid, ester, ether, halogen, hydroxyl, ketone, azide, nitro, methylsilyl, sulfo-oxo, or mercaptan as described in the present invention.

The term "aryl" used in the present invention is a group containing any carbon-based aromatic group including, but not limited to, benzene, naphthalene, phenyl, biphenyl, phenoxy benzene, etc. The term "aryl" also includes "hetero aryl", which is defined as a group containing aromatic groups having at least one heteroatomic atom in a ring in which aromatic groups are introduced. Examples of heteroatoms include, but are not limited to, nitrogen, oxygen, sulfur, and phosphorus. Similarly, the term "non-hetero-aryl" (which is to also included in the term "aryl") defines groups containing aromatic groups, which do not contain heteroatoms. Aryl may be substituted or unsubstituted. Aryl may replace having one or more groups. The groups include, but are not limited to, alkyl, naphthyl, alkoxy, enyl, cyclenyl, acetyl, cycloacetyl, aryl, heteraryl, aldehyde group, amino group, carboxylic acid group, ester group, ether group, Halogen, hydroxyl group, ketone group, azide group, nitro group, methylsilyl group, thio-oxygen group or mercapto. The term "biaryl" is a specific type of aryl and is included in the definition of "aryl". A biaryl is two aryl groups bound together by a fused ring structure, as in naphthalene, or two aryl groups joined by one or more carbon-carbon bonds, as in biphenyls.

The term "aldehydes" used in the present invention is represented by a formula —C(O)H. Throughout the manual, "C(0)" is a shorthand form of carbonyl (i.e.: C=O).

The term "amine" or "amino" used in the present invention is indicated by the formula $—NR^1R^2$, wherein $R^1$ and $R^2$ may be independently selected from hydrogen, alkyl, cycloalkyl, alkenyl, cyclenyl, alkynyl, cycloacetyl, aryl or hetero-aryl.

The term "alkylamino" used in the present invention is denoted by the formula —NH (-alkyl), in which alkyl is described in the present invention. The representative examples include, but are not limited to, methyl amino, ethyl amino, propyl amino, butyl amino, isobutyl amino, (intermediate butyl) amino, (tertiary Butyl) amino, amyl amino, isoamyl amino, (tert-amyl) amino, hexyl amino, etc.

The term "dialkylamino" used in the present invention is represented by the formula —N(alkyl group)$_2$, in which alkyl is described in the present invention. Representative examples include, but are not limited to, dimethyl amino, diethyl amino, dipropyl amino, diisopropylamino, di#china_person0# amino, diisobutyl amino, bis (intermediate butyl) amino, di (tert-butyl group) amino, Diamyl amino, diisoamyl amino, bis (tert-amyl) amino, dihexylamino, N-ethyl-N-methyl amino, N-methyl-N-propyl amino, N-ethyl-N-propyl amino, etc.

The term "carboxylic acid" used in the present invention is expressed by the formula —C(O)OH.

The term "ester" used in the present invention is indicated by the formula $—OC(O)R^1$ or $—C(O)OR^1$. The $R^1$ may be alkyl, naphthyl, alkyl, cyclenyl, alkynyl, cyclienyl, aryl, or hetero-aryl, as described in the present invention. The term "polyester" used in the present invention is indicated by the formula $—(R^1O(O)C-R^2—C(O)O)_a—$ or $—(R^1O(O)C—$ $R^2$—OC(O))$_a$—, where $R^1$ and $R^2$ may be independent integers of alkyl, cycloalkyl, alkenyl, cyclenyl, alkynyl, cycloacetyl, aryl, or hetero-aryl and "a" is an integer from 1 to 500 as described in the present invention. The term "polyester" is used to describe groups produced by reactions between compounds having at least two carboxyl groups and compounds having at least two hydroxyl groups.

The term "ether" used in the present invention is expressed by the formula $R^1OR^2$, wherein $R^1$ and $R^2$ may be alkyl, cycloalkyl, alkenyl, cyclenyl, alkynyl, cyclienyl, aryl or hetero aryl respectively, as described in the present invention. The term "polyether" used in the present invention is represented by the formula —($R^1O$—$R^2O$)$_a$—, where $R^1$ and $R^2$ may be independent integers of alkyl, cycloalkyl, alkenyl, cyclenyl, alkynyl, cycloacetyl, aryl, or hetero-aryl and "a" is an integer 1 to 500 as described in the present invention. Examples of polyether groups include polyvinyl oxide, propylene oxide, and polybutene oxide.

The term "halogen" used in the present invention refers to halogen fluoride, chlorine, bromine, and iodine.

The term "heterocyclic group" used in the invention refers to a non-aromatic ring system of a single ring and a polycyclic ring, and the "hetero aryl" used by the invention refers to an aromatic ring system of a single ring and a polycyclic ring; at least one of its ring members is not carbon. The term includes azacyclic butyl alkyl, dioxane, furyl, imidazolyl, isothiazolyl, isooxazolyl, morpholine, oxazolyl, including 1,2,3-oxadiazolyl, 1,2,5-oxadiazolyl and 1,3,4 oxazolyl, piperazine, piperidyl, pyrazinyl, pyridyl, pyridyl, pyrimidine, pyrrolidone, pyrrolidine, tetrahydrofuryl, tetrahydropyranyl, including 1 pyrazolyl, pyridazinyl, pyrazinyl, pyrazinyl, pyrazinyl, pyrazinyl, pyrazinyl, piperazinyl, piperazinyl, pyrazin, a tetrazine group comprising 1,2,4,5-tetrazine group, a tetrazole group comprising 1,2,3,4-tetrazole group and 1,2,4,5-tetrazole group, a thiadiazole group comprising 1,2,3-thiadiazole group, 1,2,5-thiadiazole group and 1,3,4-thiadiazole group, a thiazolyl group, a thienyl group, a triazine group comprising 1,3,5-triazine group and 1,2,4-triazine group, triazolyl comprising 1,2,3-triazolyl and 1,3,4-triazolyl, etc.

The term "hydroxyl" used in the present invention is expressed by —OH.

The term "ketone" used in the present invention is expressed by the formula $R^1C(O)R^2$, wherein $R^1$ and $R^2$ may independently be alkyl, cycloalkyl, alkenyl, alkynyl, cyclienyl, aryl, alkyl, cycloalkyl, aryl, or hetero aryl as described in the present invention.

The term "azide group" used in the present invention is represented by formula —$N_3$.

The term "nitro" used in the present invention is represented by —$NO_2$.

The term "nitrile" used in the present invention is represented by the formula —CN.

The term "methylsilyl" used in the present invention is represented by the formula —Si$R^1R^2R^3$, wherein $R^1$, $R^2$ and $R^3$ may independently be hydrogen or alkyl, naphthyl, alkoxy, alkyl, alkyl, cyclenyl, alkynyl, cycloacetyl, aryl, or hetero-aryl as described in the present invention.

The term "thiooxygenated group" used in the present invention is indicated by the expressions —S(O)$R^1$, —S(O)$_2R'$, —OS(O)$_2R^1$ or —OS(O)$_2OR^1$. The $R^1$ may be hydrogen or alkyl, cycloalkyl, alkenyl, cyclenyl, alkynyl, cyclienyl, aryl, or hetero-aryl, as described in the present invention. Throughout the manual, "S(O)" is the shorthand form of S=O. The term "sulfonyl" used in the present invention refers to the thiooxygenated groups expressed by the formula —S(O)$_2R'$, where $R^1$ may be alkyl, cycloalkyl, alkenyl, cyclenyl, alkynyl, cyclienyl and aryl, or hetero aryl. The term "sarcasm" used in the present invention is not expressed by the formula $R'S(O)_2R^2$, in which $R^1$ and $R^2$ may independently be alkyl, cycloalkyl, alkyl, cyclenyl, alkynyl, cyclienyl, aryl, as described in the present invention. Or hetero aryl. The term "sulfoxide" used in the present invention is expressed by the formula $R^1S(O)R^2$, wherein $R^1$ and $R^2$ may independently be alkyl, naphthyl, alkyl, cyclenyl, alkynyl, cyclienyl, aryl, or hetero aryl as described in the present invention.

The term "mercapto" used in the present invention is expressed by —SH.

The "R1," "$R^2$," "$R^3$," "$R'''$" (where n is an integer) used by the present invention may independently have one or more of the groups listed above. For example, if $R^1$ is a straight chain alkyl, then one hydrogen atom of alkyl can be substituted for hydroxyl, alkoxy, alkyl, halogen and so on. Depending on the selected group, the first group may be combined within the second group, or optionally, the first group may be suspended (that is, connected) to the second group. For example, for the phrase "alkyl containing amino groups," amino groups can be bound to the main chain of alkyl groups. Optionally, the amino group can be connected to the main chain of alkyl. The nature of the selected group will determine whether the first group is embedded or connected to the second group.

The compound of the invention may contain an "optional substitution" portion. In general, the term "substituted" (whether or not the term "optional" exists before) means that one or more hydrogen in the indicated part is replaced by a suitable substituent. Unless otherwise stated, the "optional substitute" group may have a suitable substituent at each substitutable position of the group. And when more than one position may replace more than one substituent with more than one selected group in any given structure, the substituents at each position may be the same or different. The combination of substituents envisaged in the present invention is selected as those that form stable or chemically feasible compounds. In some respects, unless it is clearly indicated to the contrary, it is also covered that the individual substituents may be further substituted (i.e., further substituted or unsubstituted).

The structure of the compound may be expressed by:

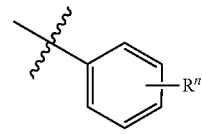

It is understood to be equivalent to the following:

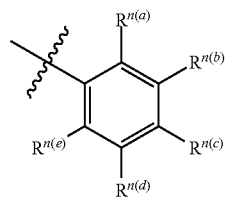

Where n is usually an integer. That is, $R''$ is understood to mean five separate substituents $R^{n(a)}$, $R^{n(b)}$, $R^{n(c)}$, $R^{n(d)}$, $R^{n(e)}$. "Individual substituents" means that each r substituent can be independently defined. For example, if $R^{n(a)}$ is halogen in one case, then $R^{n(b)}$ need not be halogen in this case.

$R^1$, $R^2$, $R^3$, $R^4$, $R^5$, $R^6$, $R^7$, $R^8$ etc are referred to several times in the chemical structures and portions disclosed and described in the present invention. Any description in the specification $R^1$, $R^2$, $R^3$, $R^4$, $R^5$, $R^6$, $R^7$, $R^8$, etc., applies to references $R^1$, $R^2$, $R^3$, $R^4$, $R^5$, respectively. Any structure or part of $R^6$, $R^7$, $R^8$, etc., unless otherwise stated.

Compound

The structure of the polydentate binuclear ring metal complexes disclosed in the present invention is as shown in Formula I:

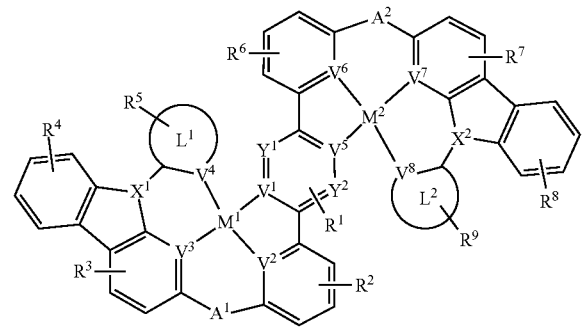

Formula I

In which:

Group M:

$M^1$ and $M^2$ are platinum or palladium independently.

In some embodiments of the invention, $M^1$ is platinum and $M^2$ is palladium; In other embodiments of the invention, $M^1$ is palladium and $M^2$ is platinum; In some embodiments of the present invention, $M^1$ is platinum and $M^2$ is platinum; In some embodiments of the present invention, $M^1$ is palladium and $M^2$ is palladium;

L-Group:

$L^1$ and $L^2$ are carbon, heterocyclic or heterocyclic respectively.

In some embodiments of the invention, $L^1$ is a six-member carbon ring, a heterocyclic ring, a heterocyclic ring $L^2$ is each independent of a six-member carbon ring, a heterocyclic ring, and a heterocyclic ring.

Group V:

$V^1$, $V^2$, $V^3$, $V^4$, $V^5$, $V^6$, $V^7$ and $V^8$ are coordinated with platinum, and are N or C. at least two of $V^1$, $V^2$, $V^3$ and $V^4$ are N, and at least two of $V^5$, $V^6$, $V^7$ and $V^8$ are N;

In some embodiments of the present invention, $V^1$ and $V^4$ are N. $V^2$ and $V^3$ are C $V^5$ and $V^8$ are N, $V^6$ and $V^7$ are C; In other embodiments of the present invention, $V^1$, $V^2$ and $V^3$ are C, $V^4$ is N, $V^5$ and $V^8$ are N and $V^6$ and $V^7$ are C; In further embodiments of the present invention, $V^1$ and $V^3$ are C, $V^2$ and $V^4$ are N, $V^5$ and $V^7$ are C and $V^6$ and $V^8$ are N.

Y Group:

$Y^1$ and $Y^2$ are CH or N respectively;

In some embodiments of the present invention, $Y^1$ and $Y^2$ are N; In other embodiments of the invention, $Y^1$ and $Y^2$ are CHs; In some other embodiments of the invention, the Chloria $Y^2$ is the Cho $Y^2$; In further embodiments of the present invention, $Y^1$ are N, $Y^2$ are CH.

A Group:

$A^1$ and $A^2$ are O, S, $CH_2$, $CD_2$, $CR^aR^b$, C=O, $SiR^aR^b$, $GeH_2$, $GeR^aR^b$, NH, $NR^c$, PH, $PR^c$, $R^cP=O$, $AsR^c$, $R^cAs=O$, S=O, $SO_2$, Se, Se=O, $SeO_2$, BH, $BR^c$, $R^cBi=O$, BiH or $BiR^c$ respectively.

In some embodiments of the invention, $A^1$ is O and $A^2$ is O; In some embodiments of the present invention, an $A^1$ is O and $A^2$ is S; In some embodiments of the present invention, $A^1$ is $CR^aR^b$, $A^2$ is $CR^aR^b$; In some embodiments of the present invention, $A^1$ is $NR^c$ and $A^2$ is $NR^c$; In some embodiments of the invention, $A^1$ is O, $A^2$ is $NR^c$; In some embodiments of the present invention, a $A^1$ is CRaRb and $A^2$ is $NR^c$; In some embodiments of the present invention, $A^1$ is $BR^c$ and $A^2$ is $BR^c$;

X Group:

$X^1$ and $X^2$ are N, B, CH, CD, $CR^a$, SiH, SiD, $SiR^a$, GeH, GeD, $GeR^d$, P, P=O, As, As=O, Bi or Bi=O respectively;

In some embodiments of the invention, $X^1$ is N and $X^2$ is N; In some embodiments of the invention. $X^1$ is B and $X^2$ is B; In some embodiments of the invention, $X^1$ is B and $X^2$ is N; In some embodiments of the invention, $X^1$ is N and $X^2$ is B; In some embodiments of the present invention, the $X^1$ is P=O and $X^2$ is N; In some embodiments of the invention, $X^1$ is N and $X^2$ is P=O; In some embodiments of the invention, $X^1$ is $SiR^a$, $X^2$ is $CR^a$. In some embodiments of the invention, $X^1$ is $SiR^a$ $X^2$ is N; In some embodiments of the invention, $X^1$ is $CR^a$, $X^2$ is $CR^a$. In some embodiments of the invention, $X^1$ is $CR^a$, $X^2$ is $CR^a$. In some embodiments of the invention, $X^1$ is $CR^a$, $X^2$ is N; In some embodiments of the invention, $X^1$ is $SiR^a$ $X^2$ is N; In some embodiments of the invention, $X^1$ is N, $X^2$ is $SiR^a$, in some embodiments of the invention, $X^1$ is $SiR^a$, $X^2$ is $SiR^a$. In some embodiments of the present invention, $X^1$ is $SiR^a$ $X^2$ is N.

Group R:

$R^1$, $R^2$, $R^3$, $R^4$, $R^5$, $R^6$, $R^7$, $R^8$ and $R^9$ are either single, double, triple, or quadruple substitution or non-substitution respectively; at the same time, $R^1$, $R^2$, $R^3$, $R^4$, $R^5$, $R^6$, $R^7$, $R^8$ and $R^9$ are hydrogen, deuterium, aryl, cycloalkyl, heterocyclic, heterocyclic, heteraryl, alkyl, alkyl, alkyl, alkyl, alkyl, alkyl, alkyl, Halogens, hydroxyl, mercapto, nitro, cyanide, amino, monoor dialkylamino, monoor diaryl amino, alkoxy, aryl, haloalkyl, ester, nitrile, isonitrile, hetero-aryl, alkoxy carbonyl, acyl amino, alkoxy carbonyl amino, aryloxycarbonyl amino, sulfonyl amino, ammonia sulfonyl, carbamate, alkyl thioyl, sulfonyl group, ureyl group, phosphoramide group, imino group, sulfonyl group, carboxyl group, hydrazine group r, substituted methylsilyl, polymerized group, or combination, respectively; at the same time, two or more adjacent $R^1$, $R^2$, $R^3$, $R^4$, $R^5$, $R^6$, $R^7$, $R^8$ and $R^9$ can selectively join to form a dense ring.

$R^a$, $R^b$, $R^c$ and $R^d$ are single, double, triple, or quadruple substitution or non-substitution respectively; at the same time, $R^a$, $R^b$, $R^c$ and $R^d$ are hydrogen, deuterium, aryl, cycloalkyl, heterocyclic, heterocyclic, heteraryl, alkyl, alkyl, alkyl, alkyl, alkyl, alkyl, alkyl, Halogens, hydroxyl, mercapto, nitro, cyanide, amino, monoor dialkylamino, monoor diaryl amino, alkoxy, aryl, haloalkyl, ester, nitrile, isonitrile, hetero-aryl, alkoxy carbonyl, acyl amino, alkoxy carbonyl amino, aryloxycarbonyl amino, sulfonyl amino, ammonia sulfonyl, carbamate, alkyl thioyl, sulfonyl group, ureyl group, phosphoramide group, imino group, sulfonyl group, carboxyl group, hydrazine group r, substituted methylsilyl, polymerized group, or combination, respectively.

In some embodiments of the invention, the polydentate binuclear ring metal complex structure, Said

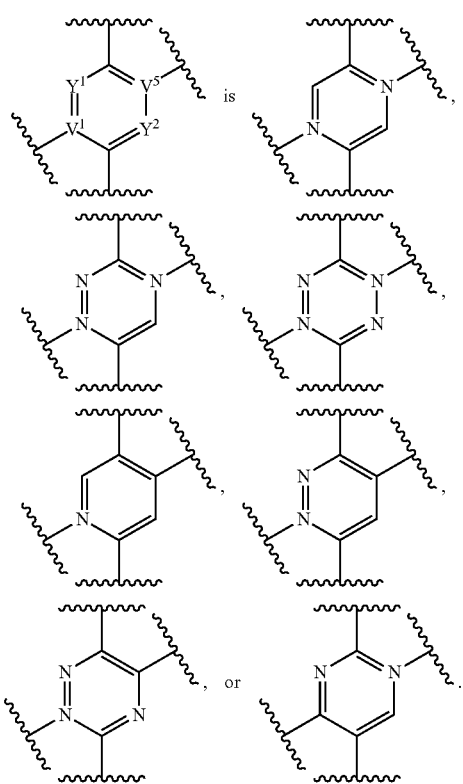

In some embodiments of the present invention, the structure of the complex is as shown in Formula II, Formula III or Formula IV:

Formula II

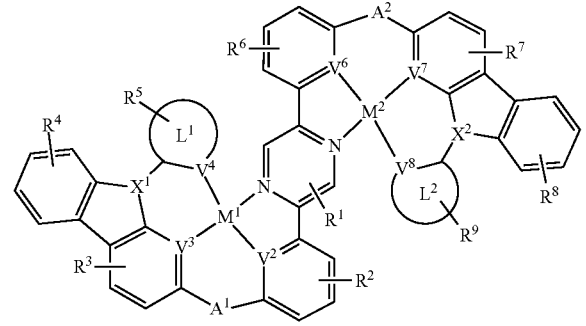

Formula III

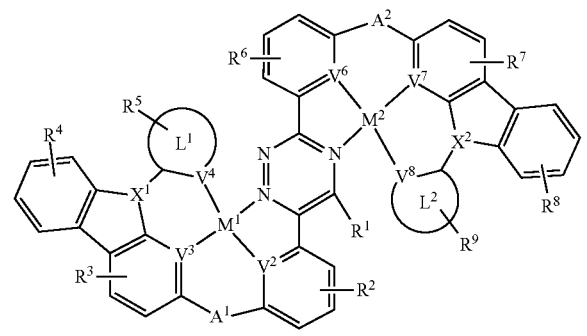

Formula IV

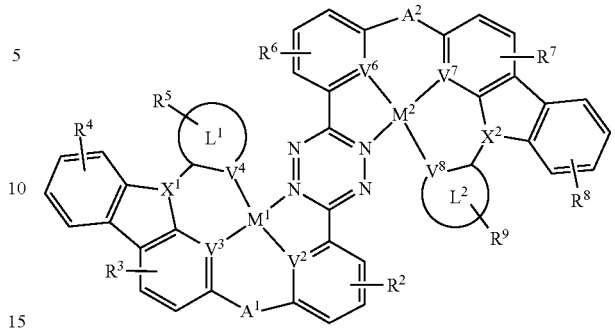

$M^1$ and $M^2$ are platinum or palladium independently.

$L^1$ and $L^2$ are carbon, heterocyclic or heterocyclic respectively.

$V^1$, $V^2$, $V^3$, $V^4$, $V^5$, $V^6$, $V^7$ and $V^8$ are coordinated with platinum, and are N or C, at least two of $V^1$, $V^2$, $V^3$ and $V^4$ are N, and at least two of $V^1$, $V^6$, $V^7$ and $V^8$ are N;

$A^1$ are $A^2$ are O, S, $CH_2$, $CD_2$, $CR^aR^b$, C=O, $SiR^aR^b$, $GeH_2$, $GeR^aR^b$, NH, $NR^c$, PH, $PR^c$, $R^cP$=O, $AsR^c$, $R^cAs$=O, S=O, $SO_2$, Se, Se=O, $SeO_2$, BH, $BR^c$, $R^cBi$=O, BiH, or $BiR^c$ respectively:

$X^1$ and $X^2$ are N, B, CH, CD, $CR^a$, SiH, SiD, $SiR^a$, GeH, GeD, $GeR^d$, P, P=O, As, As=O, Bi or Bi=O respectively;

$R^1$, $R^2$, $R^3$, $R^4$, $R^5$, $R^6$, $R^7$, $R^8$ and $R^9$ are either single, double, triple, or quadruple substitution or non-substitution respectively; at the same time, $R^1$, $R^2$, $R^3$, $R^4$, $R^5$, $R^6$, $R^7$, $R^8$ and $R^9$ are hydrogen, deuterium, aryl, cycloalkyl, heterocyclic, heterocyclic, heteraryl, alkyl, alkyl, alkyl, alkyl, alkyl, alkyl, alkyl, Halogens, hydroxyl, mercapto, nitro, cyanide, amino, monoor dialkylamino, monoor diaryl amino, alkoxy, aryl, haloalkyl, ester, nitrile, isonitrile, hetero-aryl, alkoxy carbonyl, acyl amino, alkoxy carbonyl amino, aryloxycarbonyl amino, sulfonyl amino, ammonia sulfonyl, carbamate, alkyl thioyl, sulfonyl group, ureyl group, phosphoramide group, imino group, sulfonyl group, carboxyl group, hydrazine group r, substituted methylsilyl, polymerized group, or combination, respectively; at the same time, two or more adjacent $R^1$, $R^2$, $R^3$, $R^4$, $R^5$, $R^6$, $R^7$, $R^8$ and $R^9$ can selectively join to form a dense ring.

$R^a$, $R^b$, $R^c$ and $R^d$ are single, double, triple, or quadruple substitution or non-substitution respectively; at the same time, $R^a$, $R^b$, $R^c$ and $R^d$ are hydrogen, deuterium, aryl, cycloalkyl, heterocyclic, heterocyclic, heteraryl, alkyl, alkyl, alkyl, alkyl, alkyl, alkyl, alkyl. Halogens, hydroxyl, mercapto, nitro, cyanide, amino, monoor dialkylamino, monoor diaryl amino, alkoxy, aryl, haloalkyl, ester, nitrile, isonitrile, hetero-aryl, alkoxy carbonyl, acyl amino, alkoxy carbonyl amino, aryloxycarbonyl amino, sulfonyl amino, ammonia sulfonyl, carbamate, alkyl thioyl, sulfonyl group, ureyl group, phosphoramide group, imino group, sulfonyl group, carboxyl group, hydrazine group r, substituted methylsilyl, polymerized group, or combination, respectively.

Any platinum complex disclosed in some embodiments of the present invention may include one or more of the following structures. In addition, platinum complexes may also include other structures or parts, which are not specifically listed herein, and the scope of protection of the current invention is not limited to the structures and parts listed in this patent:

Example Compound
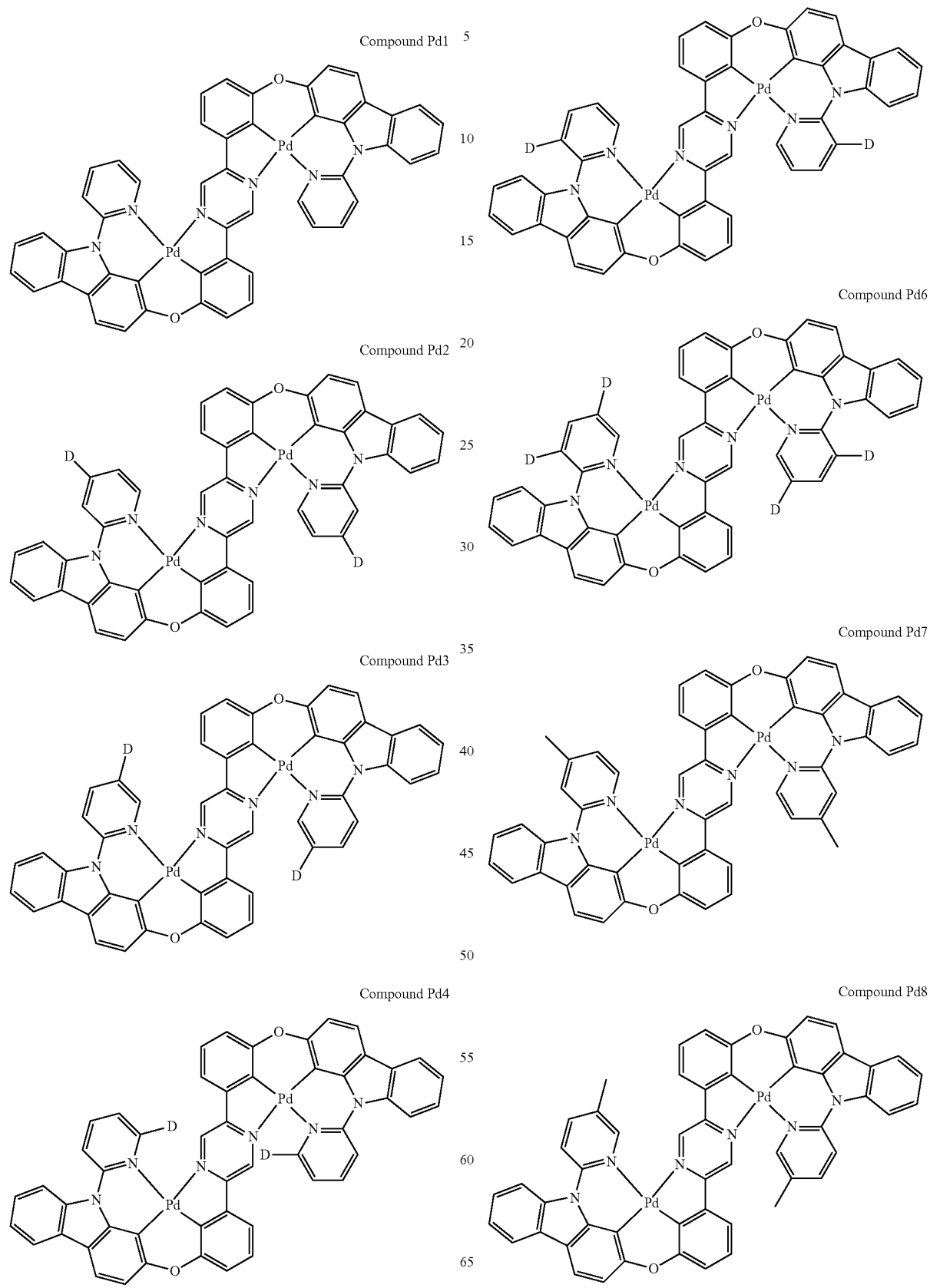

Compound Pd9
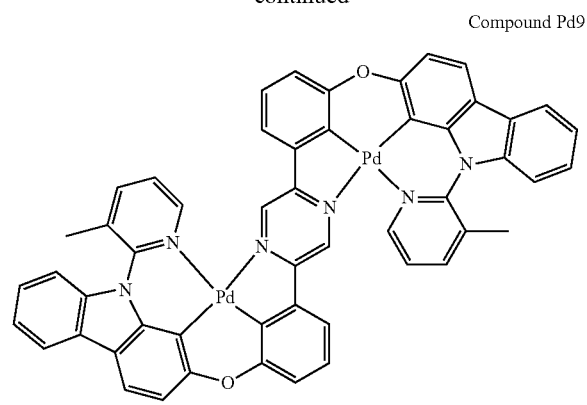
Compound Pd13
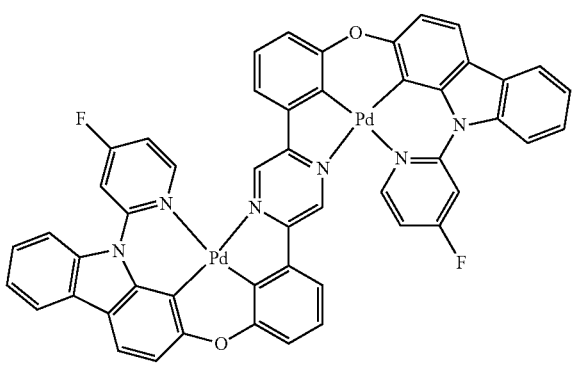
Compound Pd10
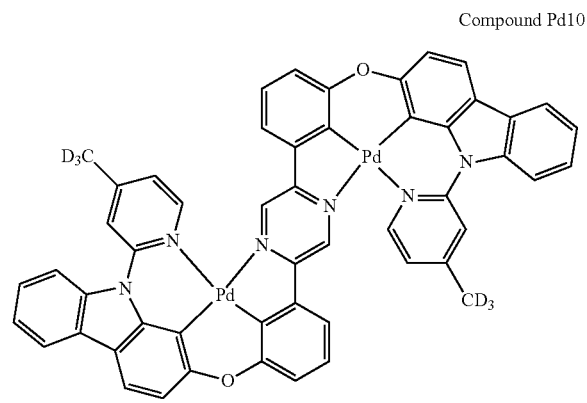
Compound Pd14
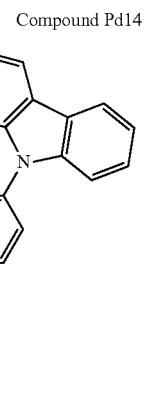
Compound Pd11
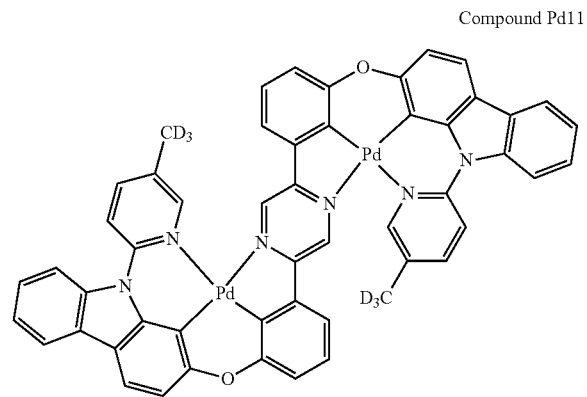
Compound Pd15
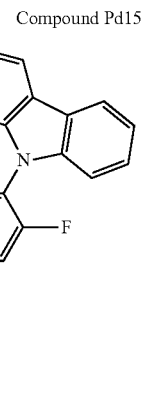
Compound Pd12
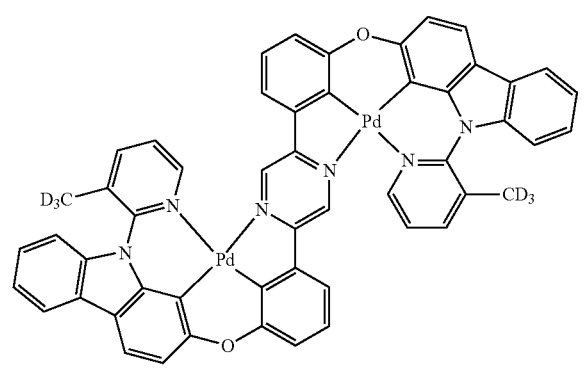
Compound Pd16
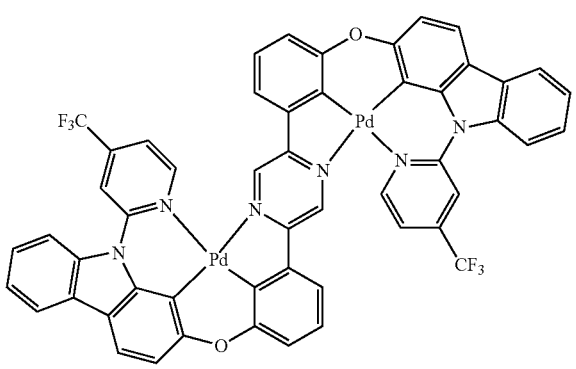

Compound Pd17
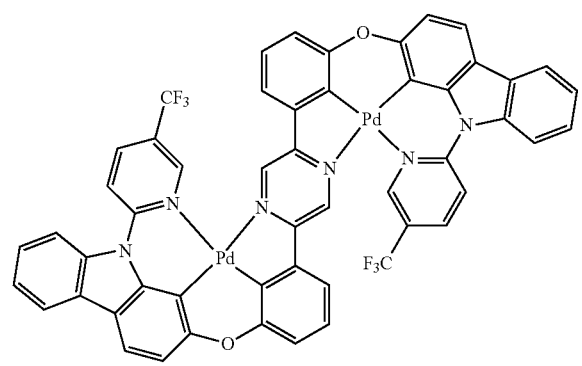
Compound Pd18
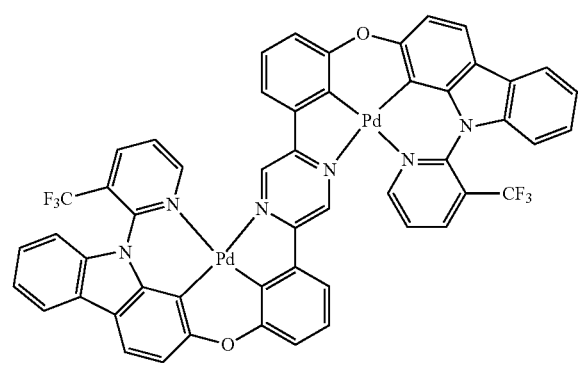
Compound Pd19
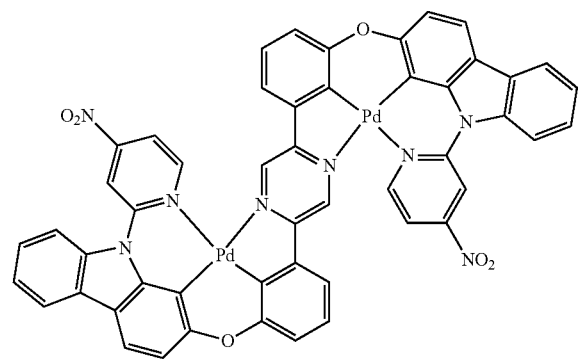
Compound Pd20
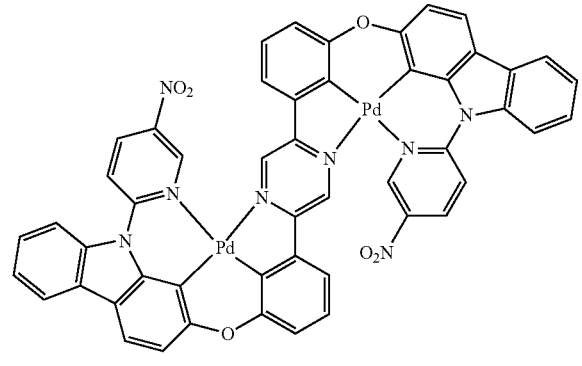
Compound Pd21
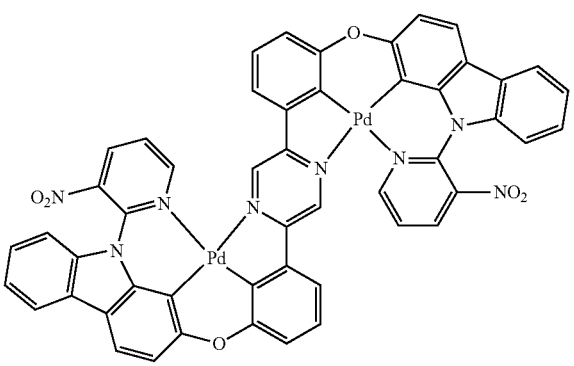
Compound Pd22
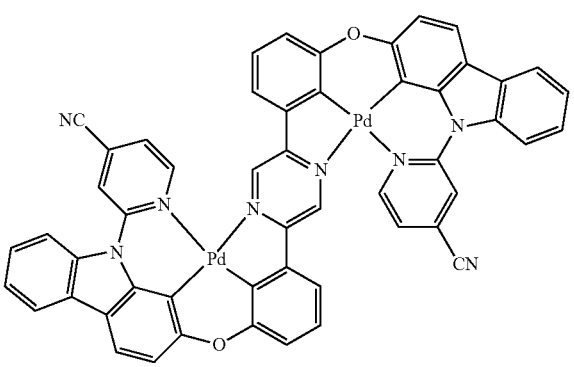
Compound Pd23
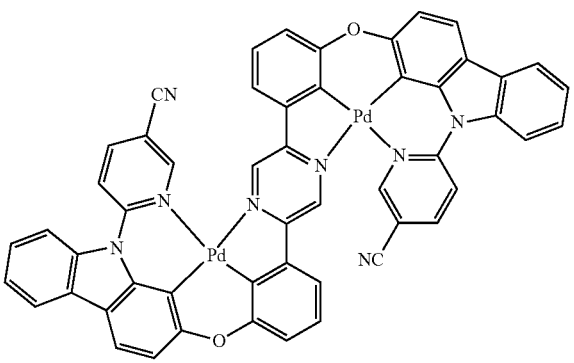
Compound Pd24
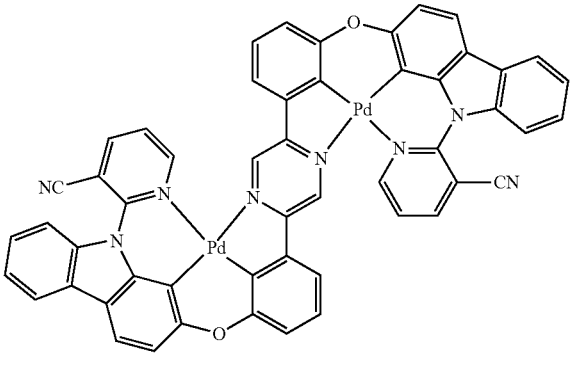

Compound Pd25
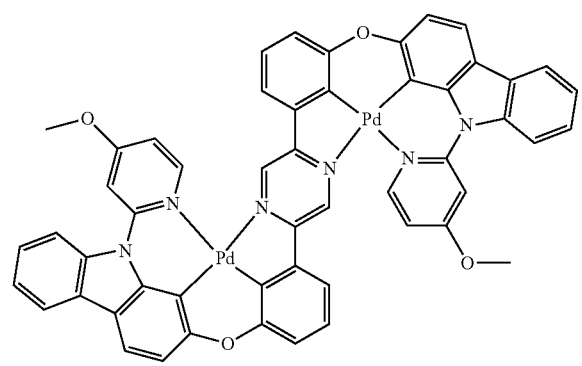
Compound Pd26
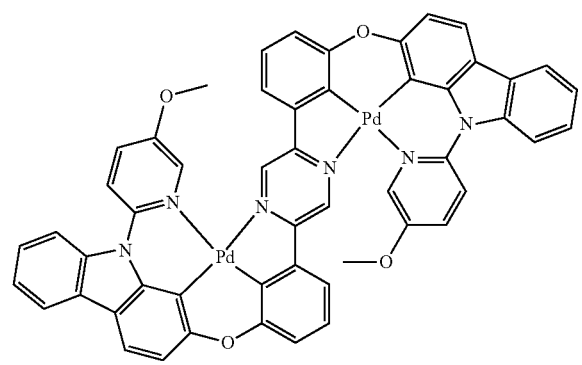
Compound Pd27
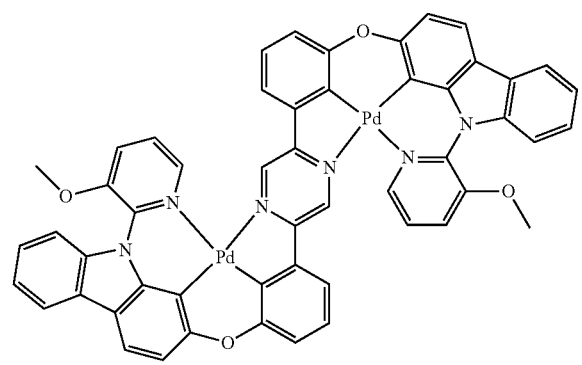
Compound Pd28
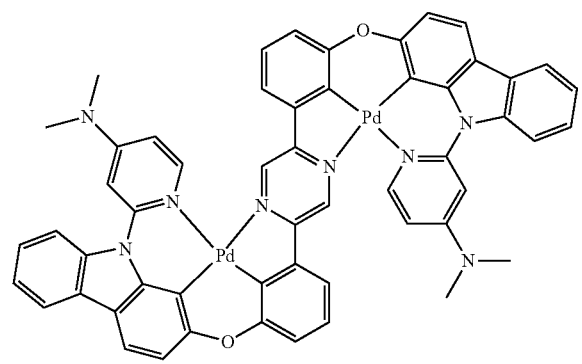
Compound Pd29
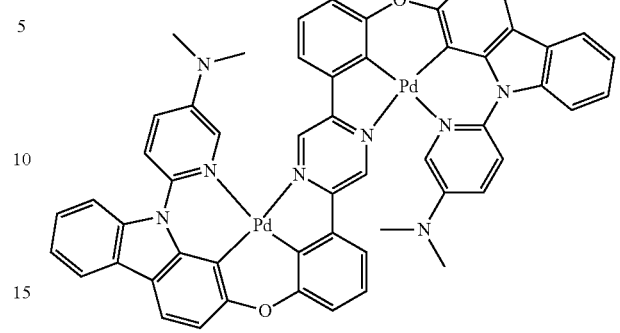
Compound Pd30
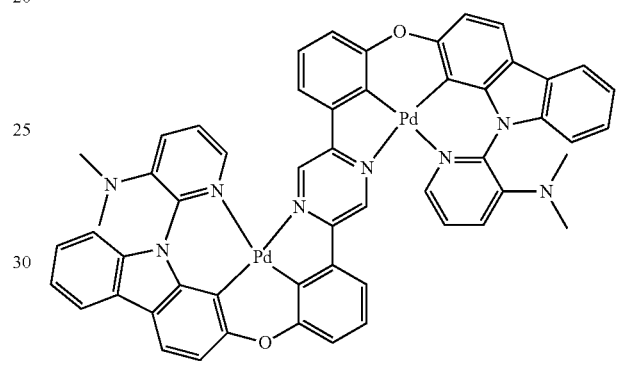
Compound Pd31
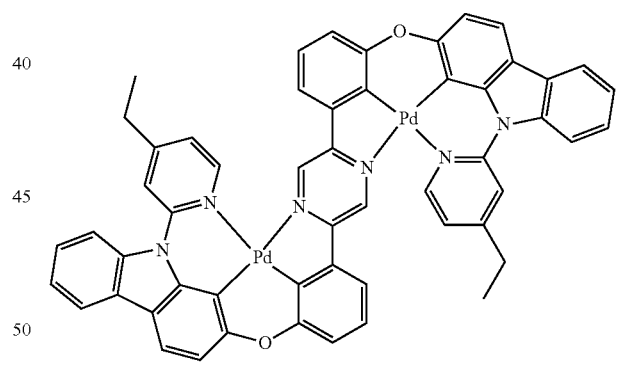
Compound Pd32
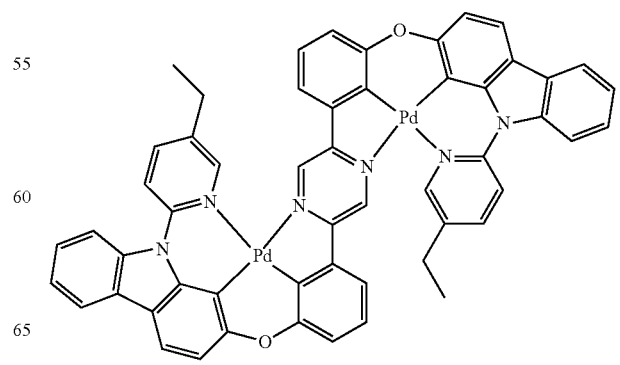

Compound Pd33
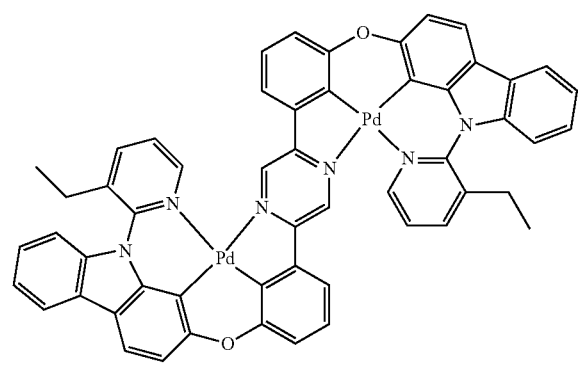
Compound Pd34
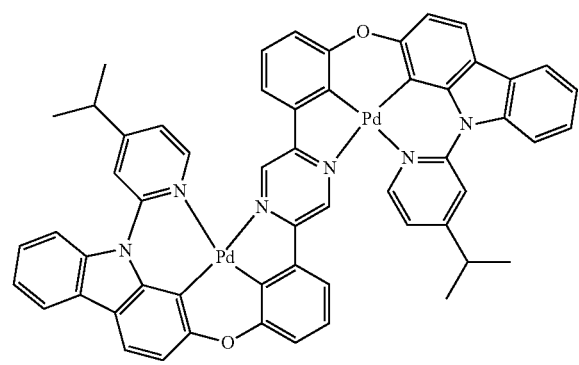
Compound Pd35
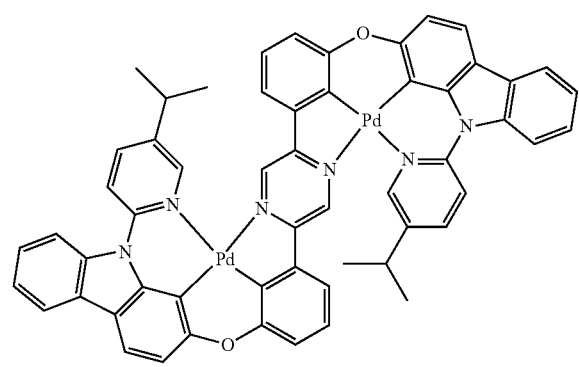
Compound Pd36
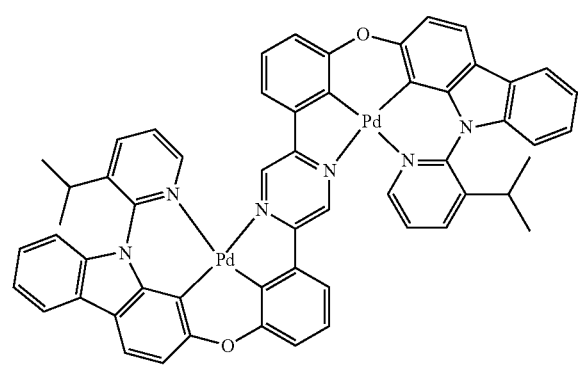
Compound Pd37
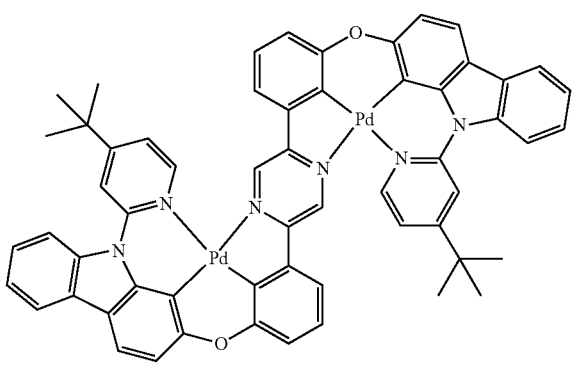
Compound Pd38
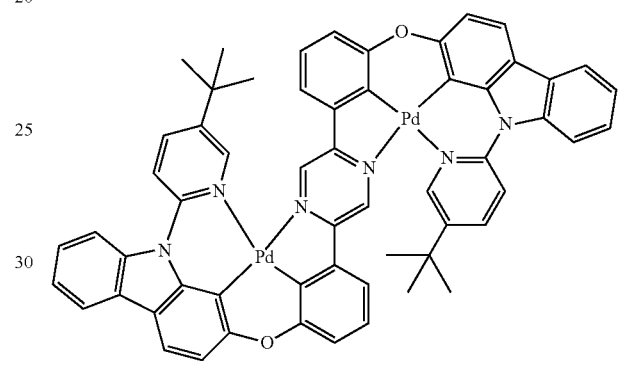
Compound Pd39
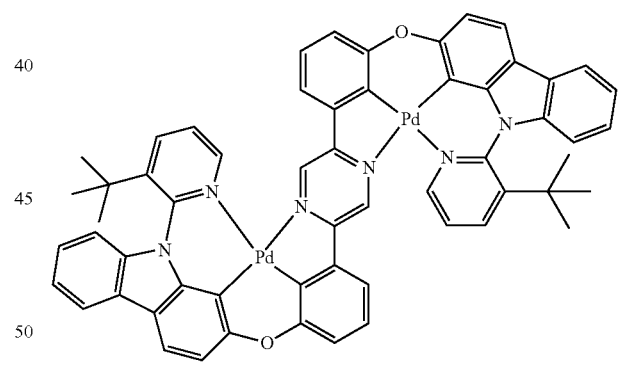
Compound Pd40
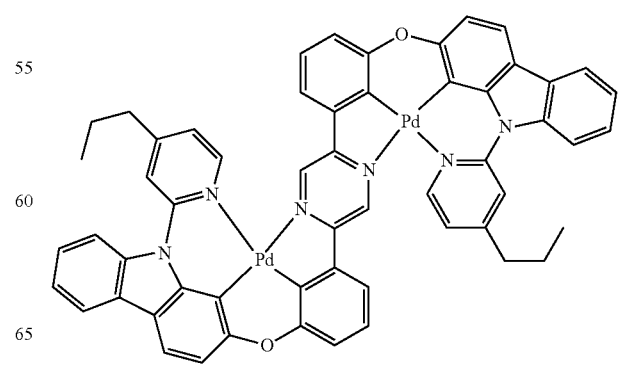

Compound Pd41
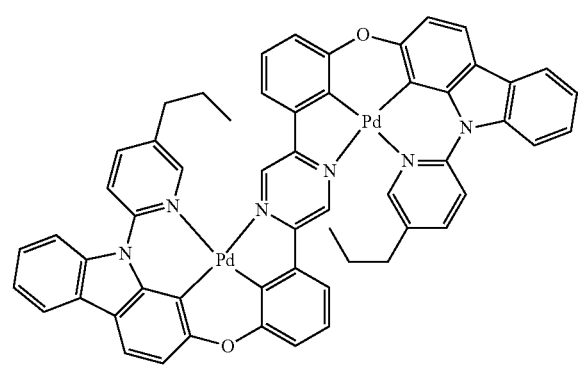
Compound Pd45
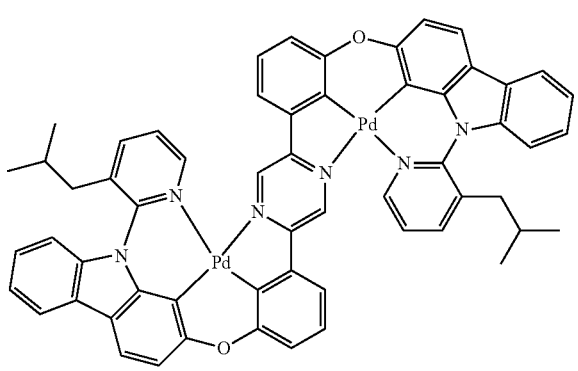
Compound Pd42
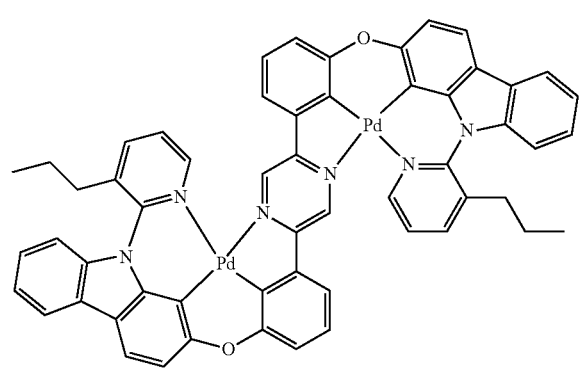
Compound Pd46
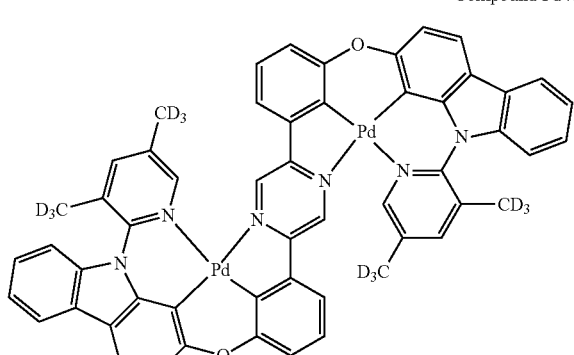
Compound Pd43
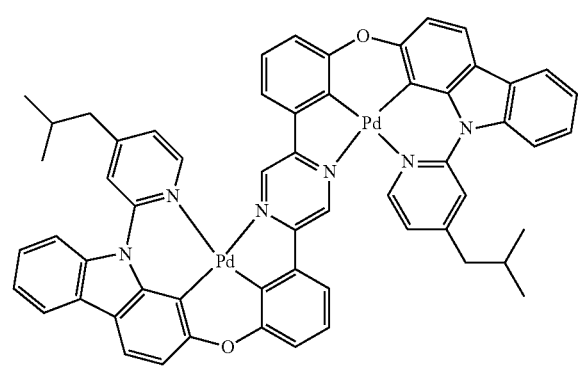
Compound Pd47
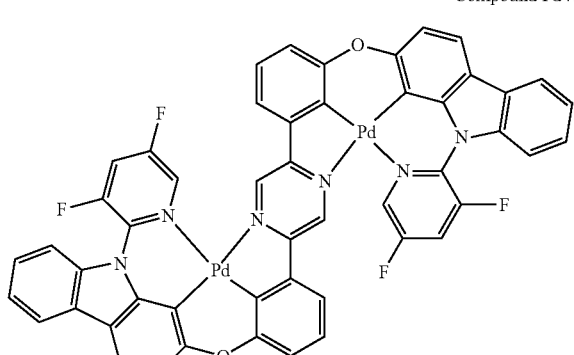
Compound Pd44
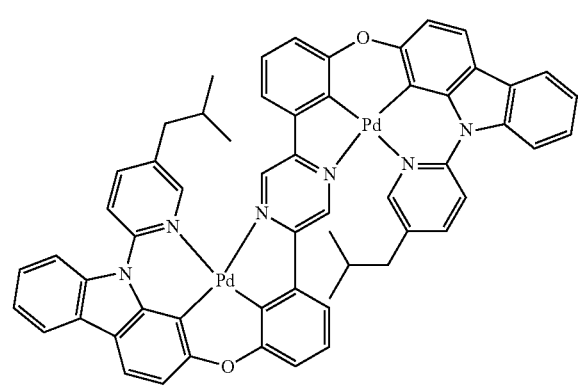
Compound Pd48
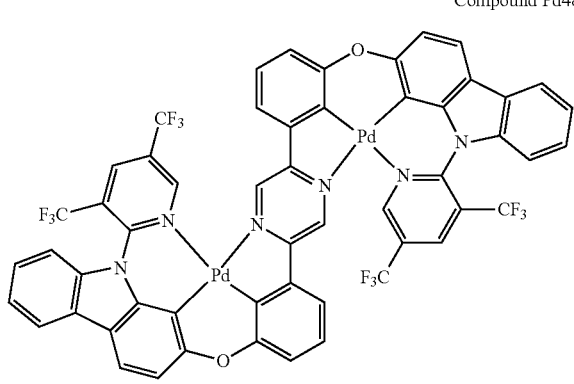

Compound Pd49
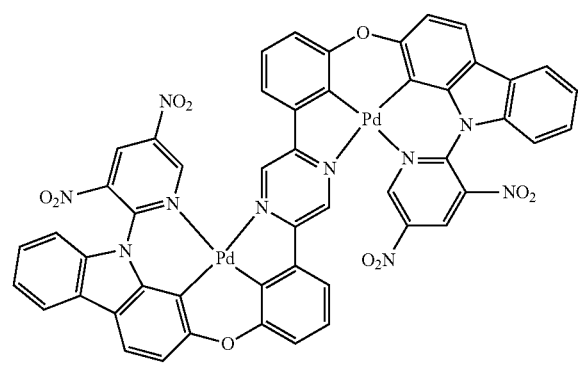
Compound Pd50
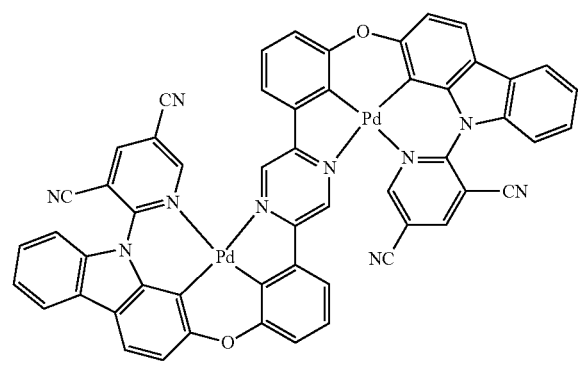
Compound Pd51
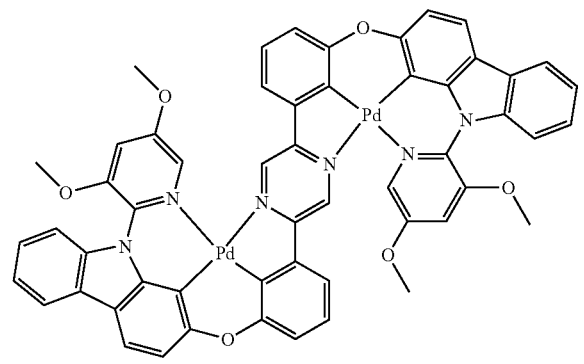
Compound Pd52
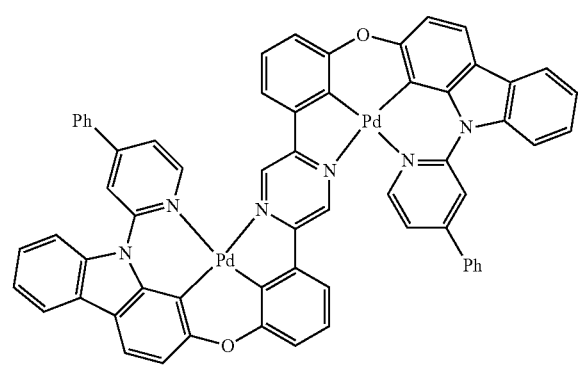
Compound Pd53
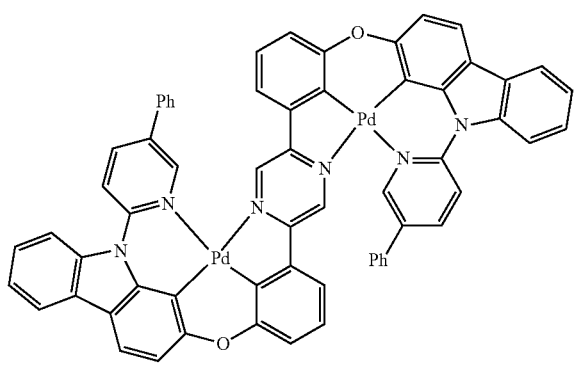
Compound Pd54
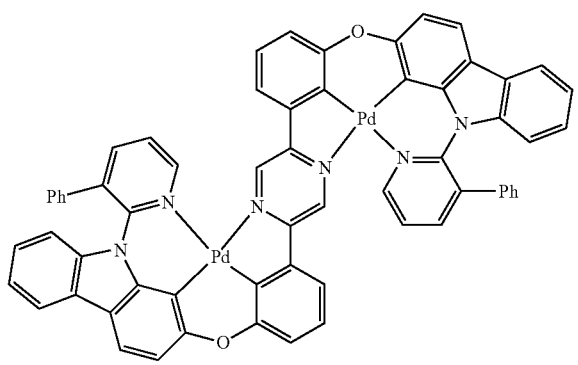
Compound Pd55
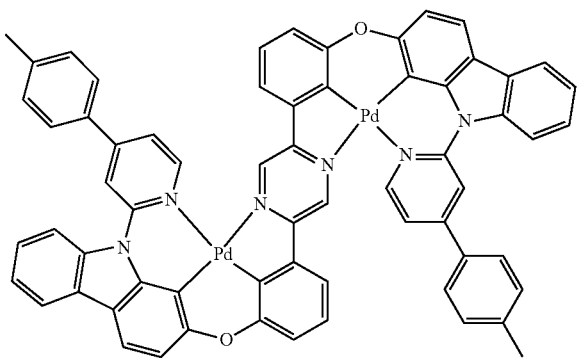
Compound Pd56
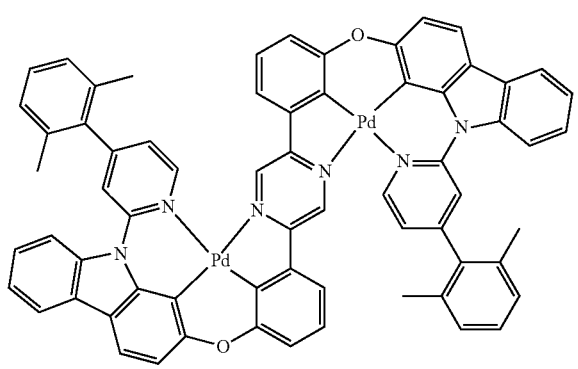

Compound Pd57
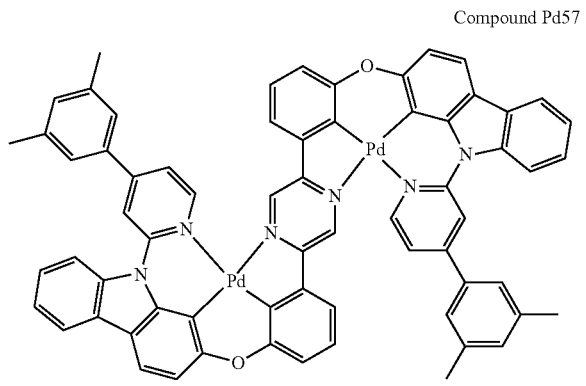
Compound Pd61
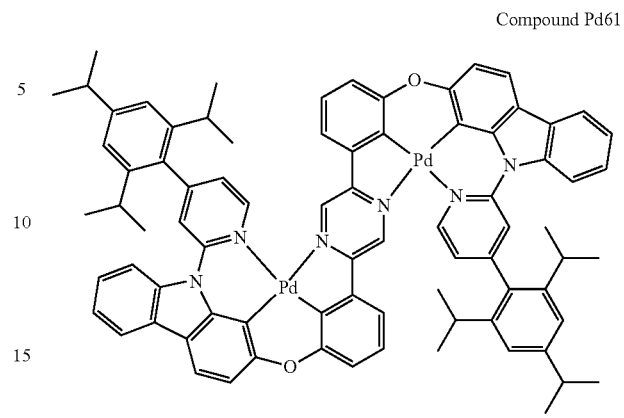
Compound Pd58
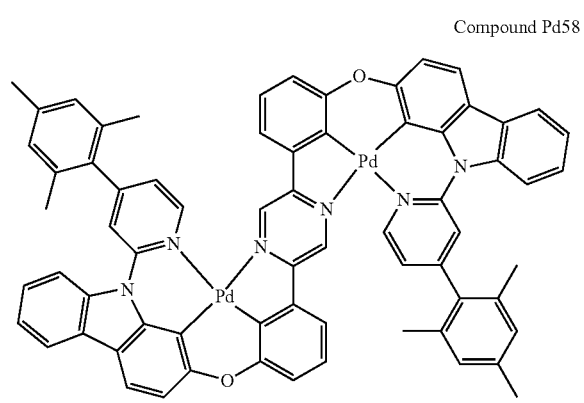
Compound Pd62
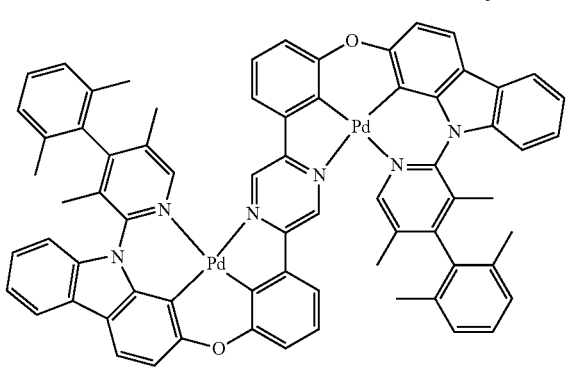
Compound Pd59
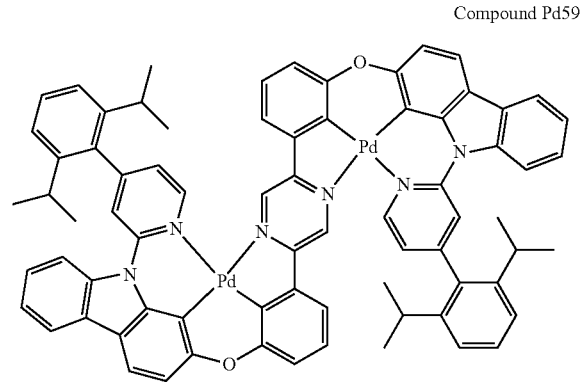
Compound Pd63
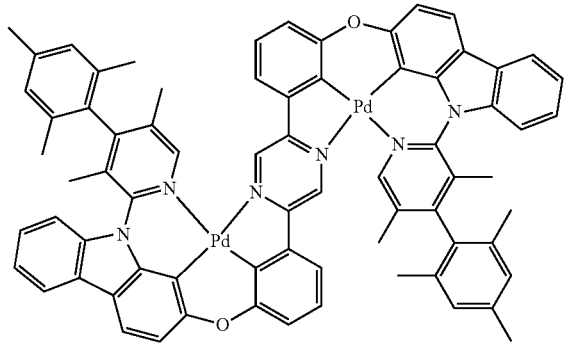
Compound Pd60
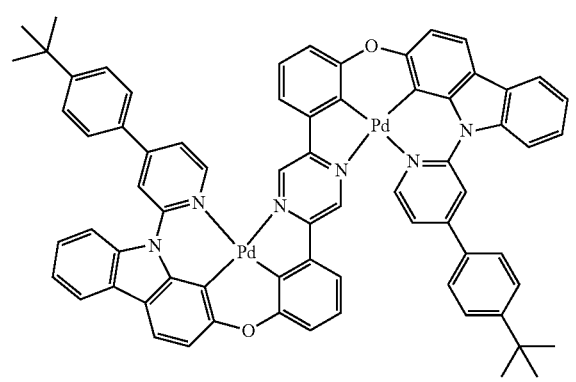
Compound Pd64
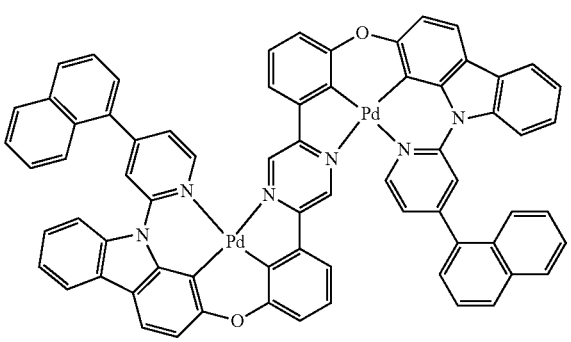

Compound Pd65
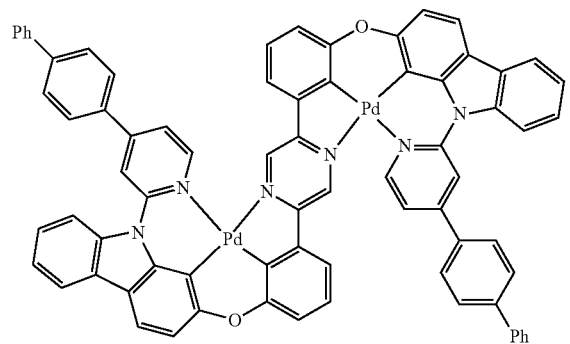
Compound Pd66
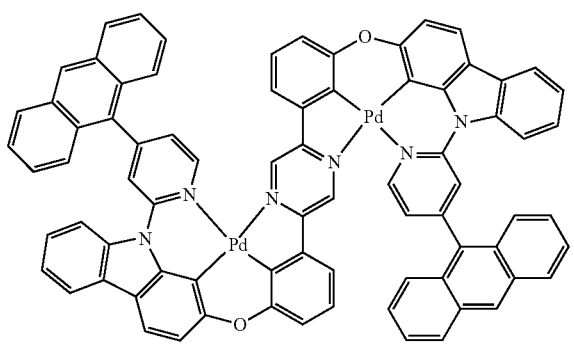
Compound Pd67
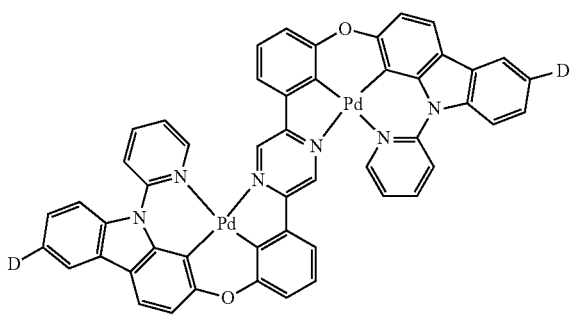
Compound Pd68
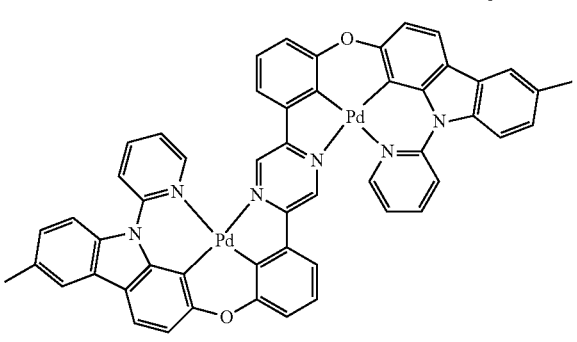
Compound Pd69
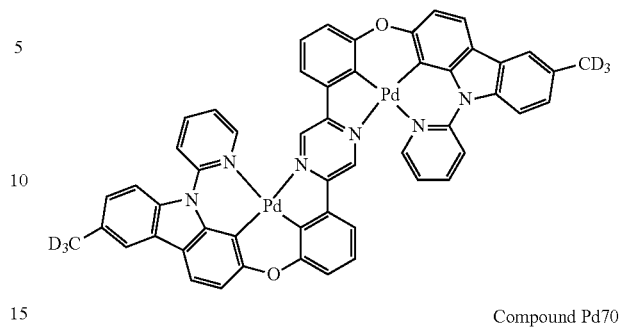
Compound Pd70
Compound Pd71
Compound Pd72
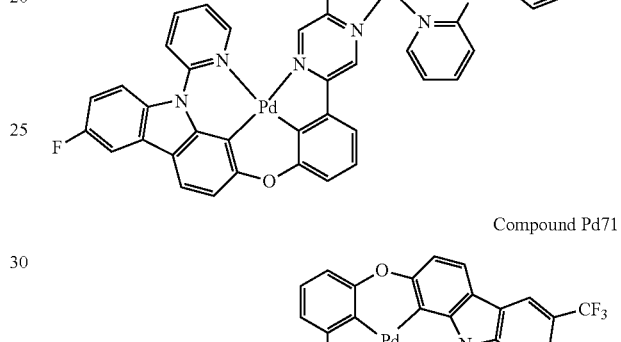
Compound Pd73
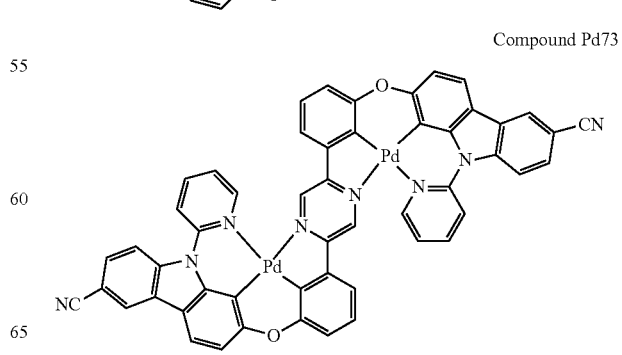

Compound Pd74
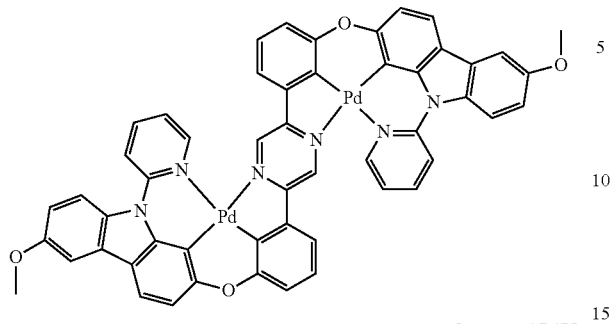
Compound Pd75
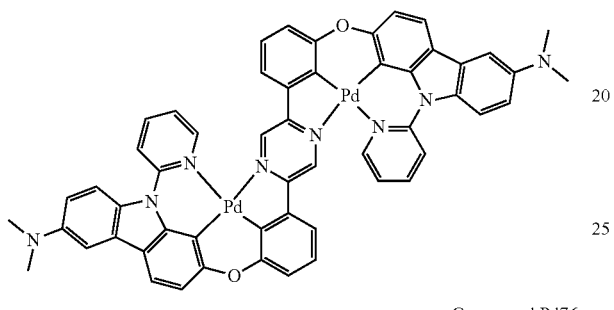
Compound Pd76
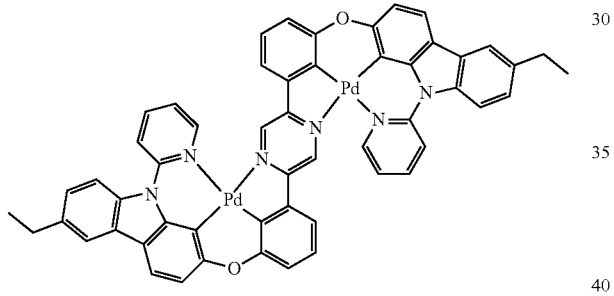
Compound Pd77
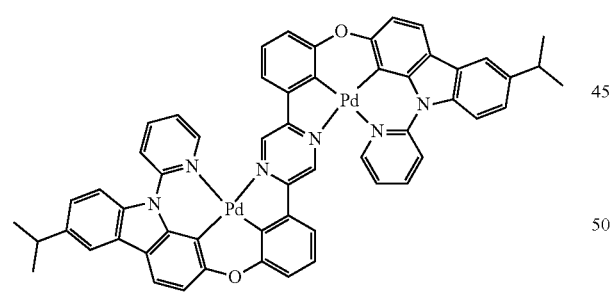
Compound Pd78
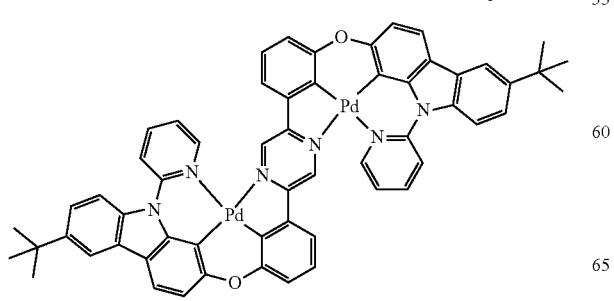
Compound Pd79
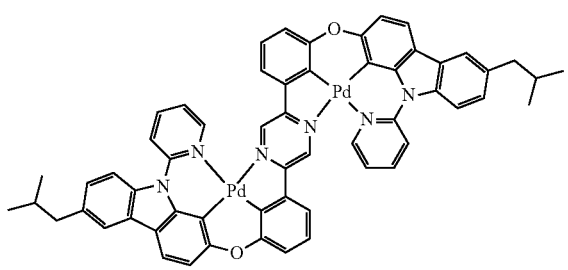
Compound Pd80
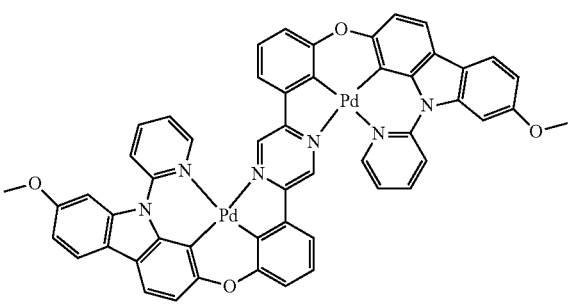
Compound Pd81
Compound Pd82
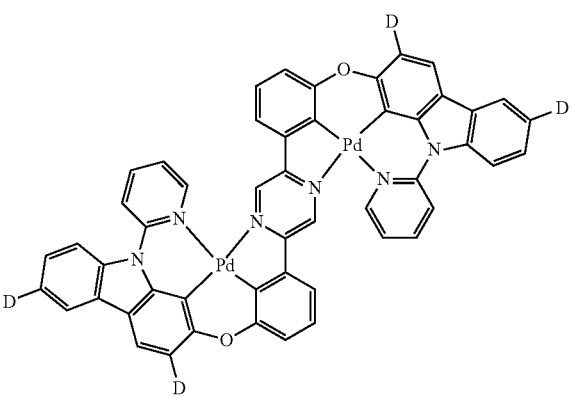

Compound Pd83
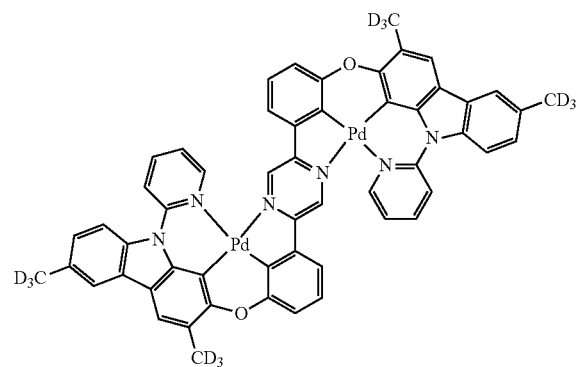
Compound Pd84
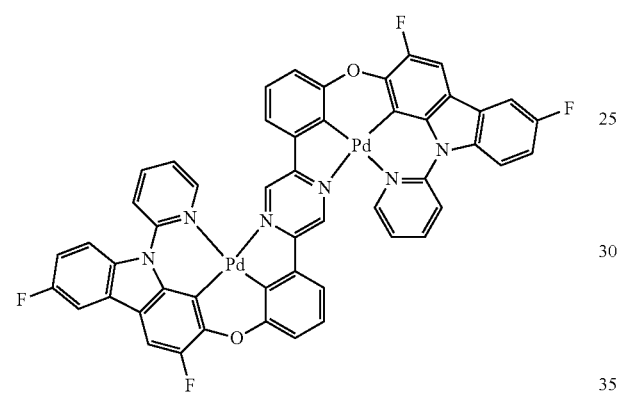
Compound Pd85
Compound Pd86
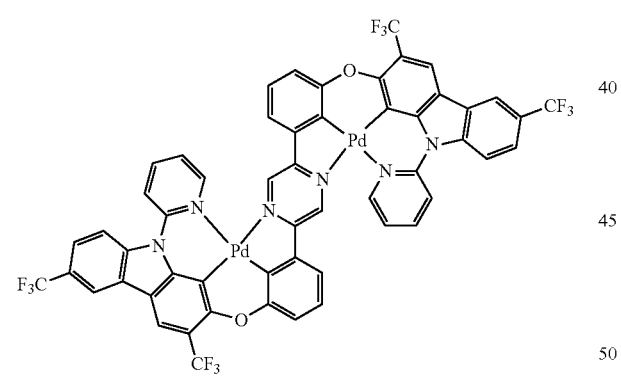
Compound Pd87
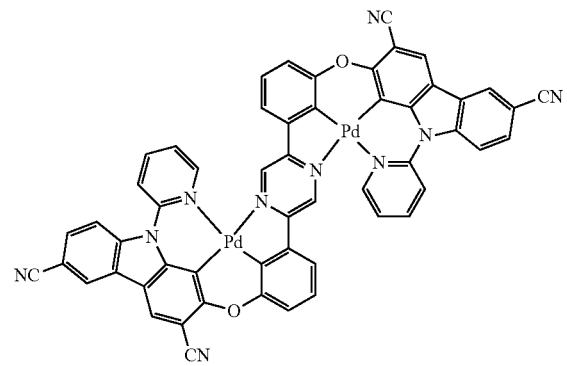
Compound Pd88
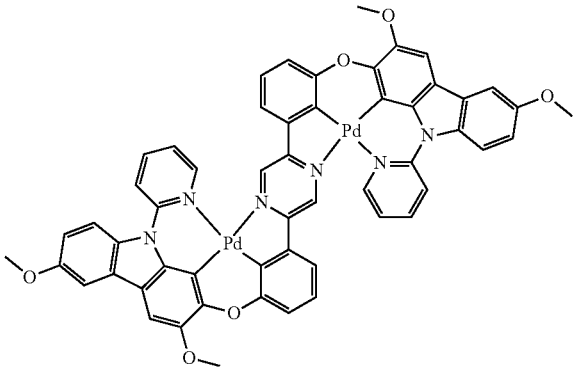
Compound Pd89
Compound Pd90
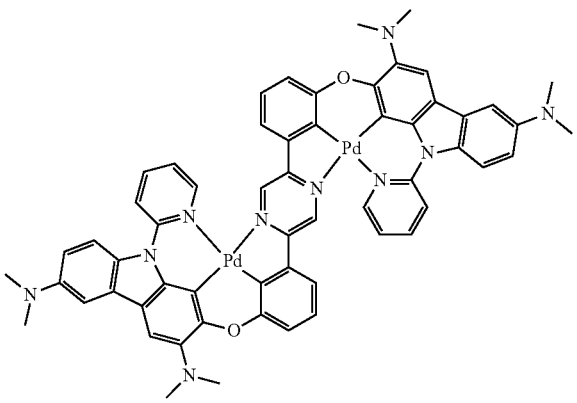
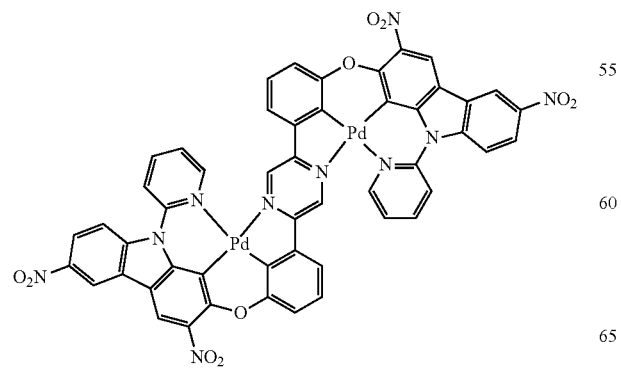
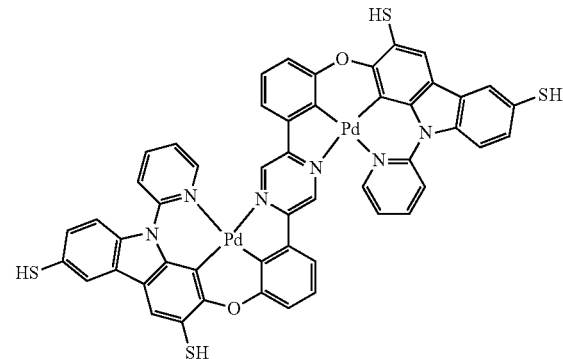

Compound Pd91
Compound Pd95
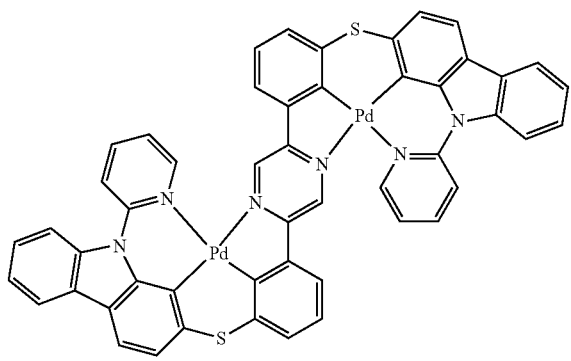
Compound Pd92
Compound Pd96
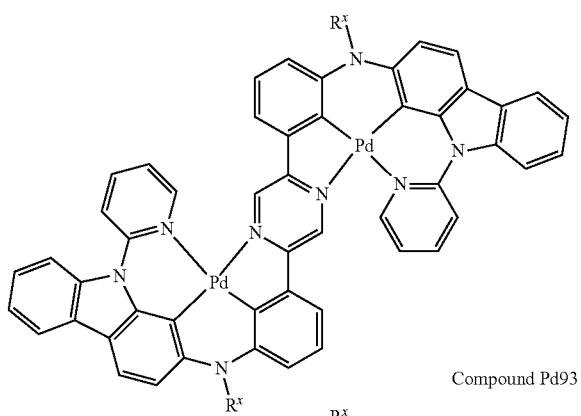
Compound Pd93
Compound Pd97
1p;-2p
Compound Pd94
Compound Pd98
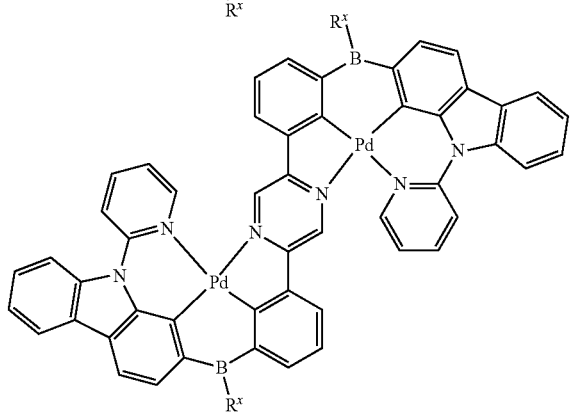

Compound Pd99
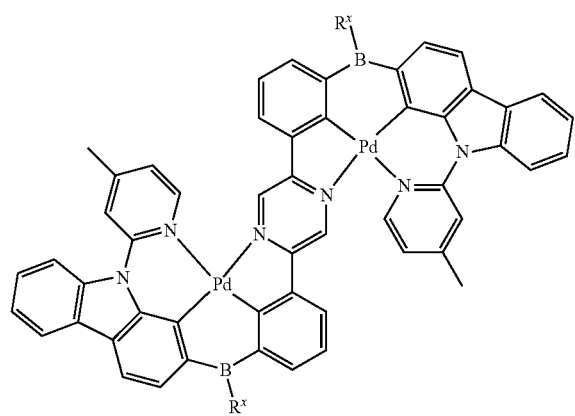
Compound Pd100
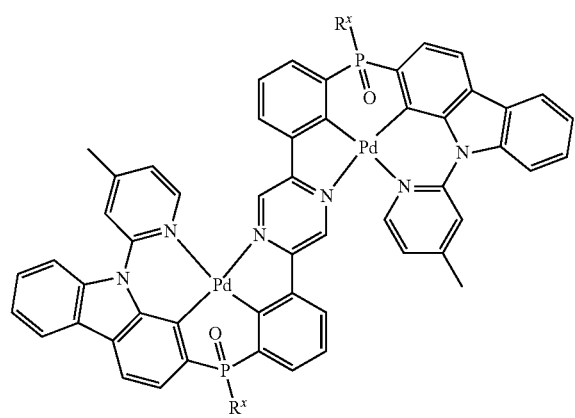
Compound Pd101
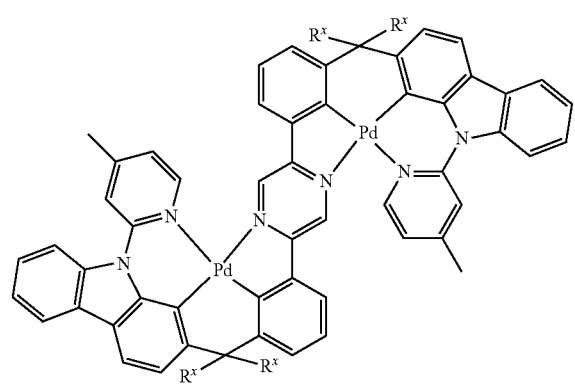
Compound Pd102
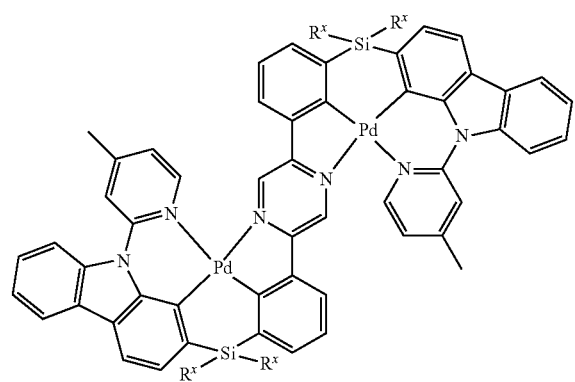
Compound Pd103
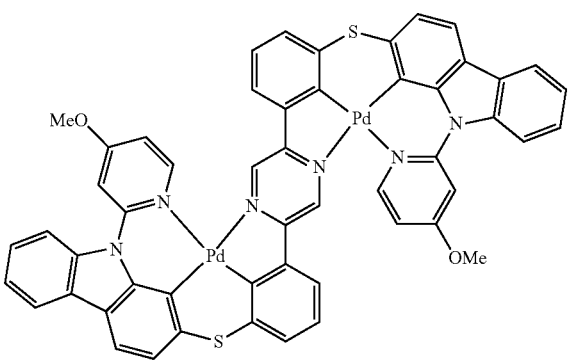
Compound Pd104
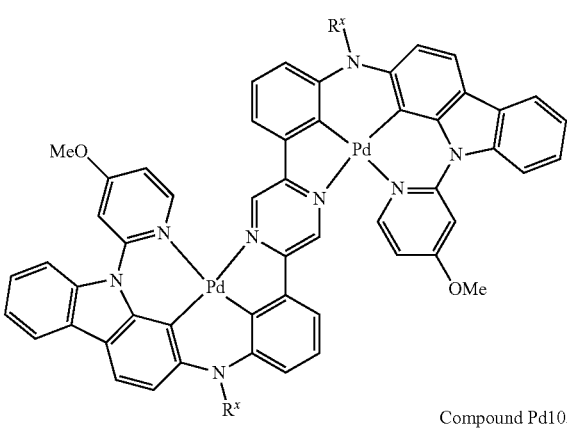
Compound Pd105
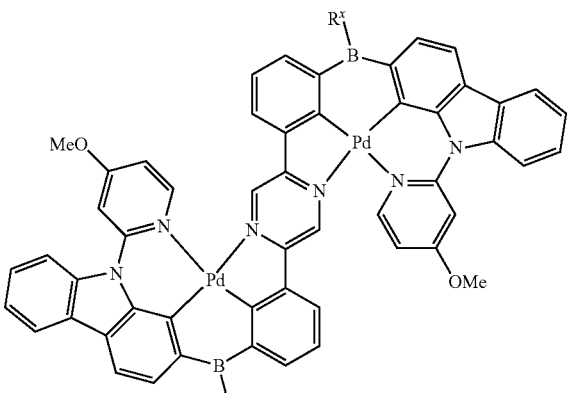
Compound Pd106
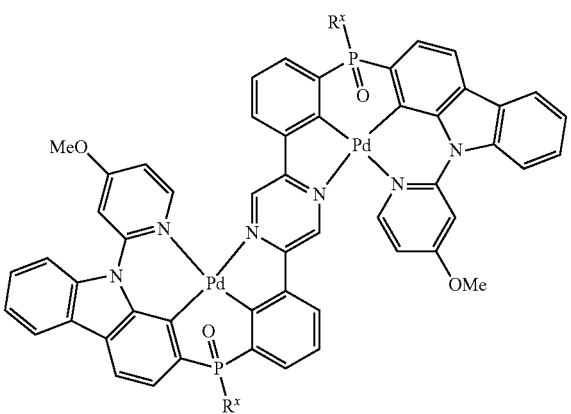

Compound Pd107
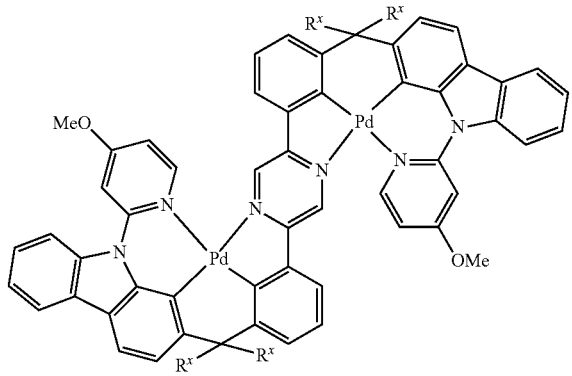
Compound Pd111
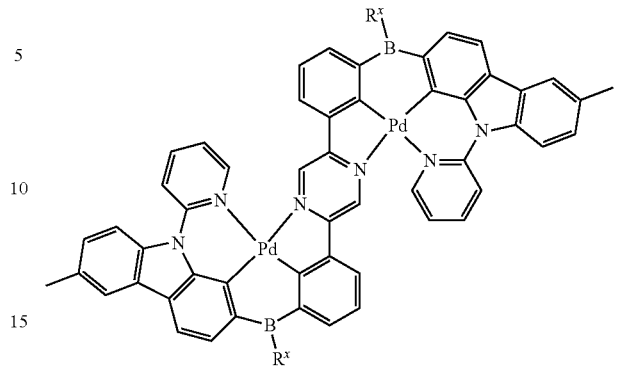
Compound Pd108
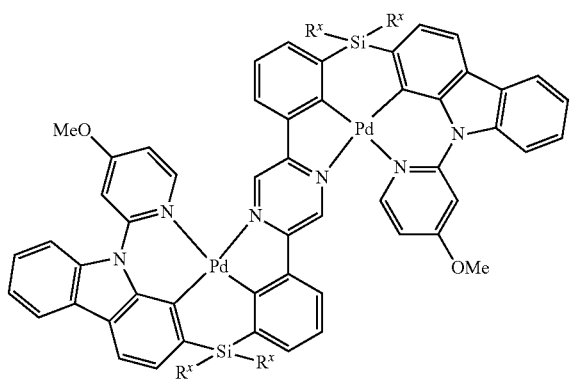
Compound Pd112
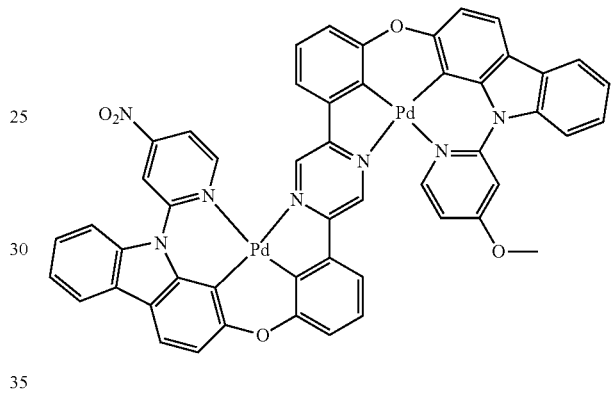
Compound Pd109
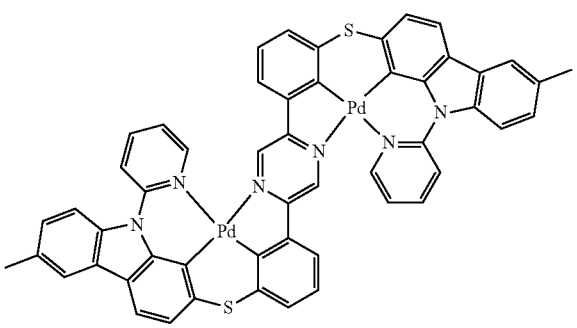
Compound Pd113
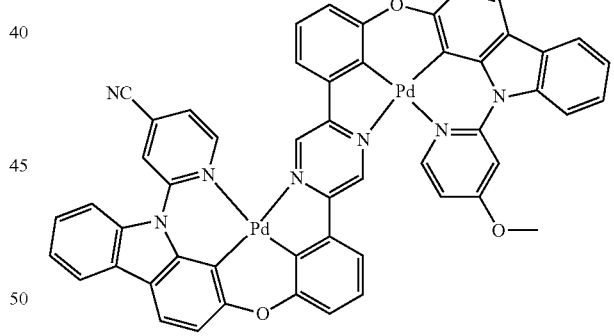
Compound Pd110
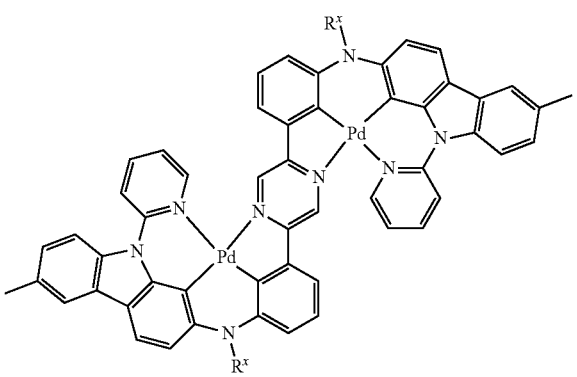
Compound Pd114
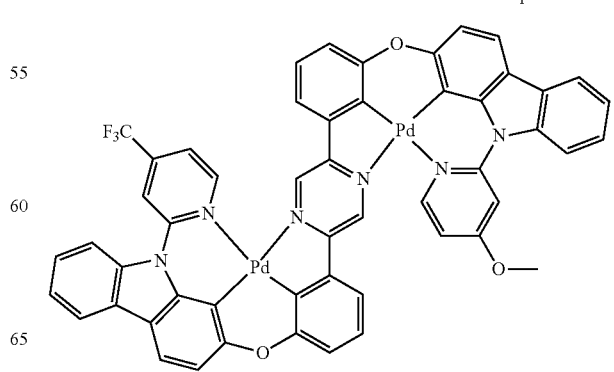

Compound Pd115
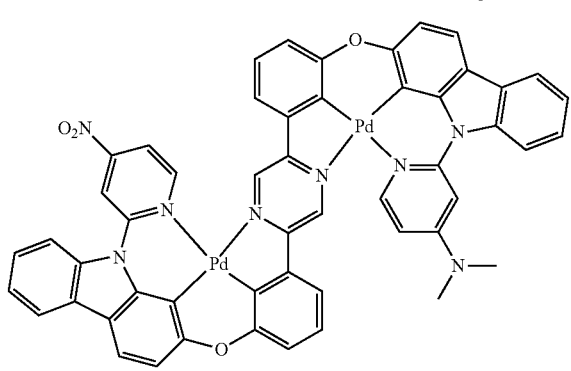
Compound Pd116
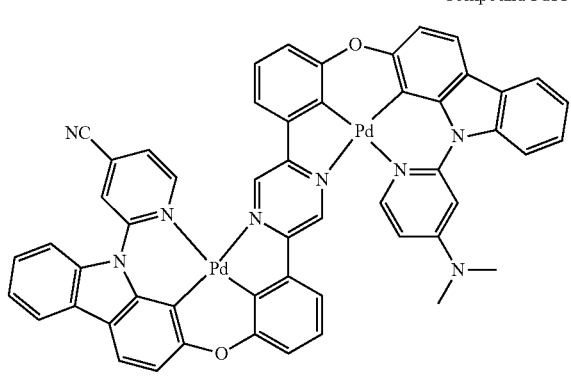
Compound Pd117
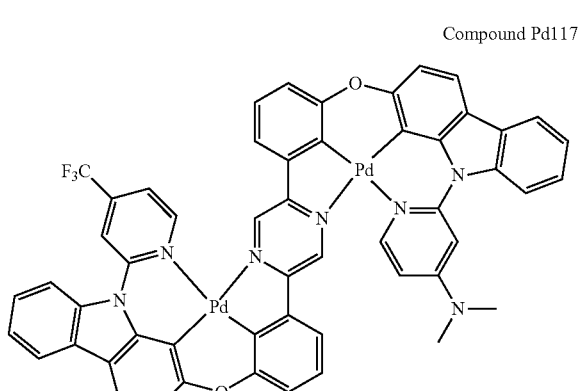
Compound Pd118
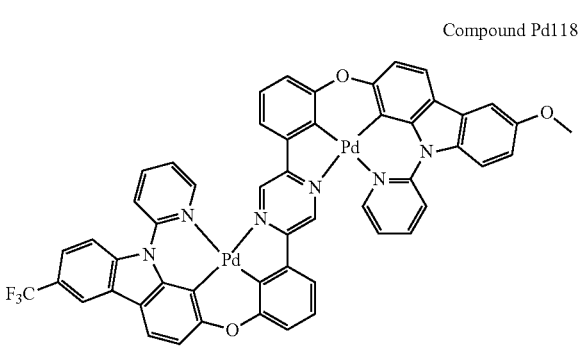
Compound Pd119
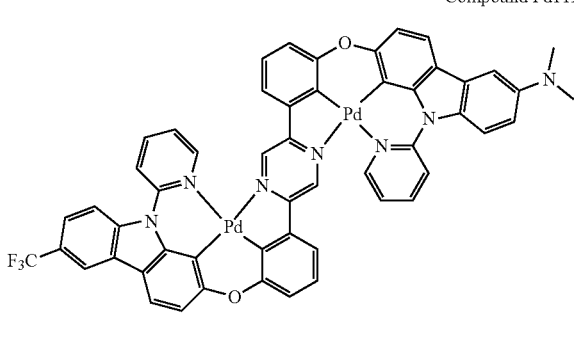
Compound Pd120
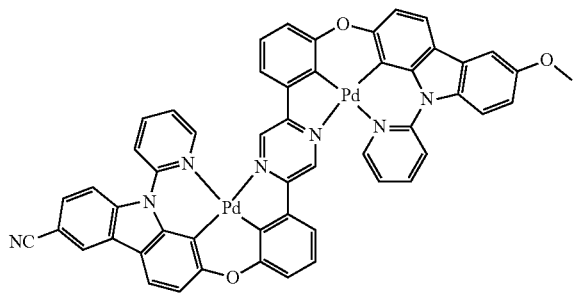
Compound Pd121
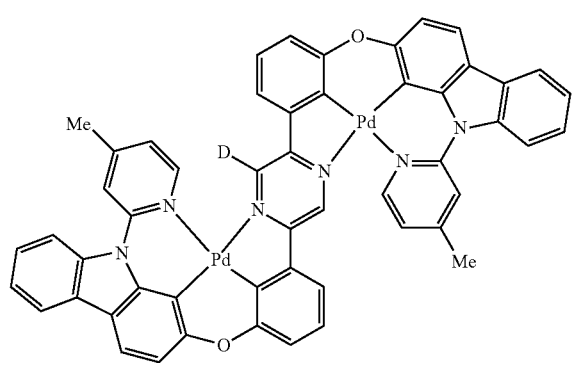
Compound Pd122

-continued
Compound Pd123
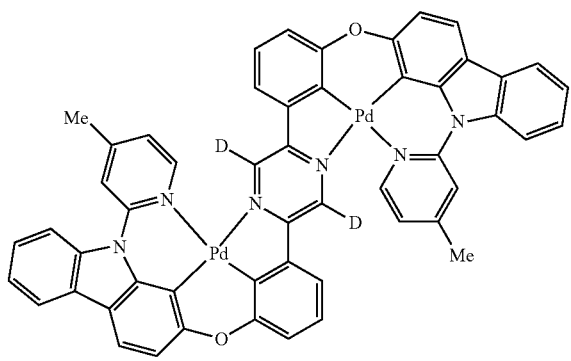
Compound Pd127
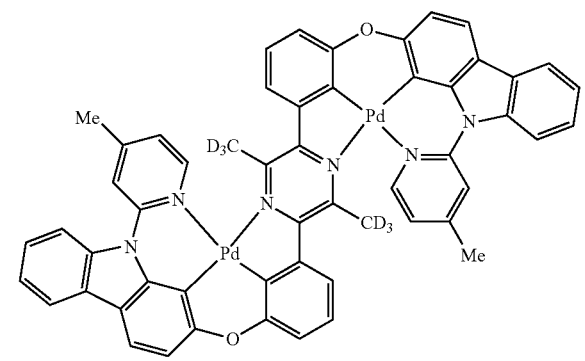
Compound Pd124
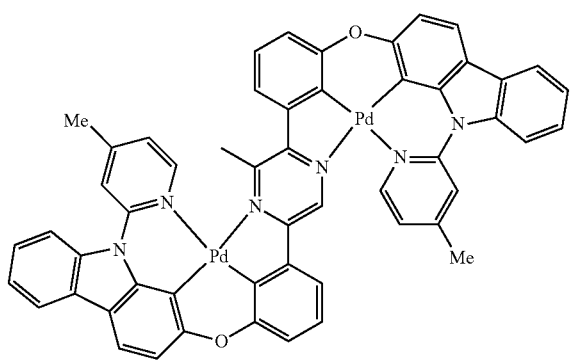
Compound Pd128
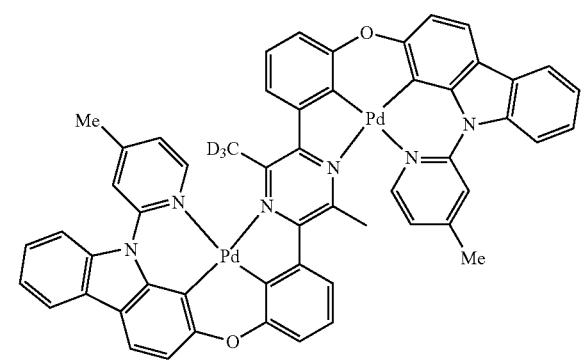
Compound Pd125
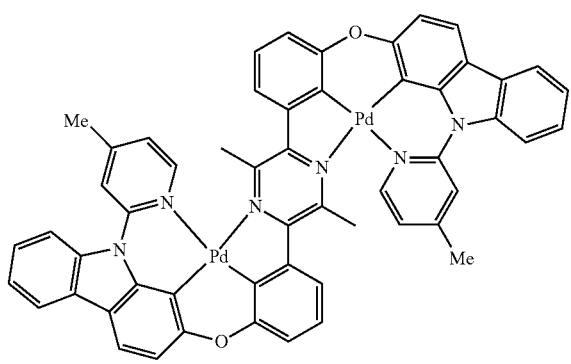
Compound Pd129
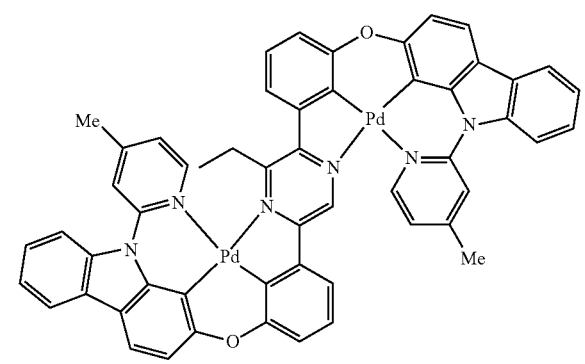
Compound Pd126
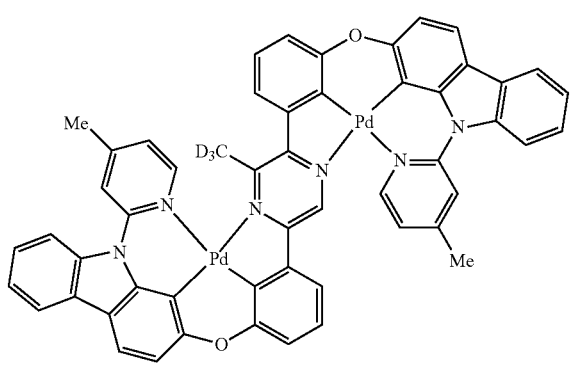
Compound Pd130
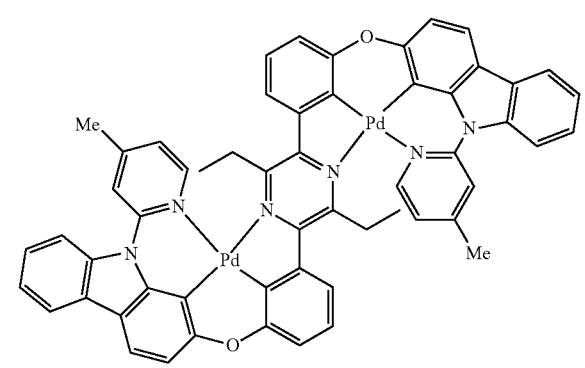

Compound Pd131
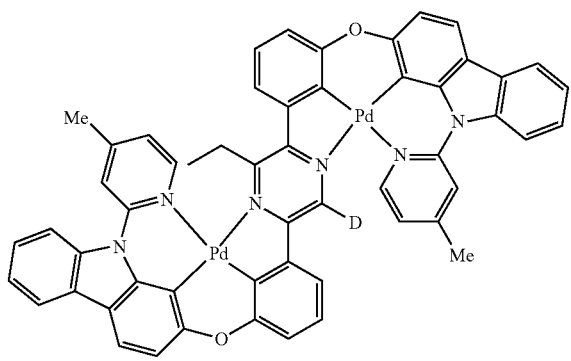
Compound Pd135
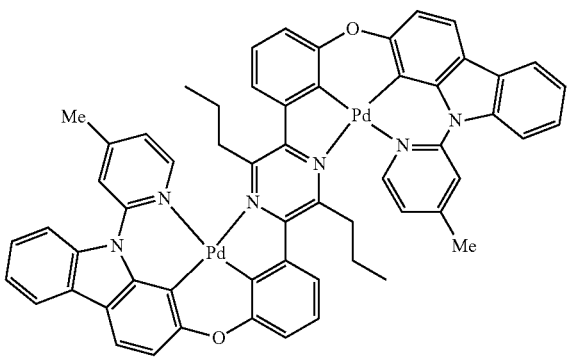
Compound Pd132
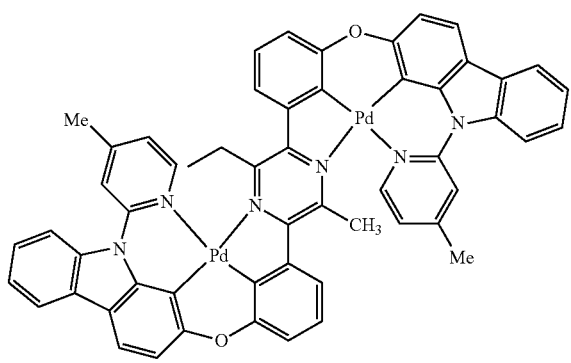
Compound Pd136
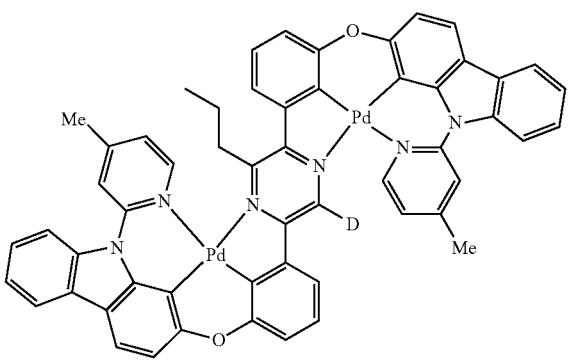
Compound Pd133
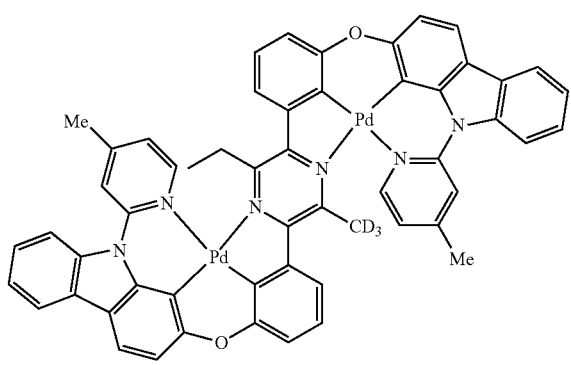
Compound Pd137
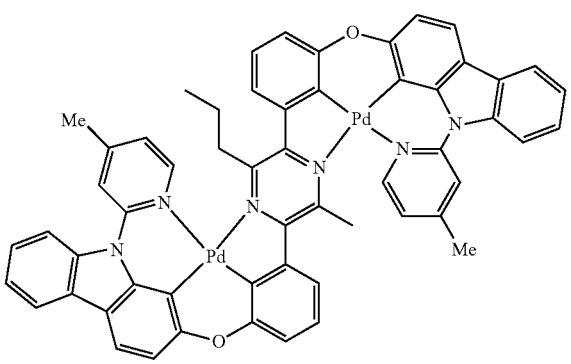
Compound Pd134
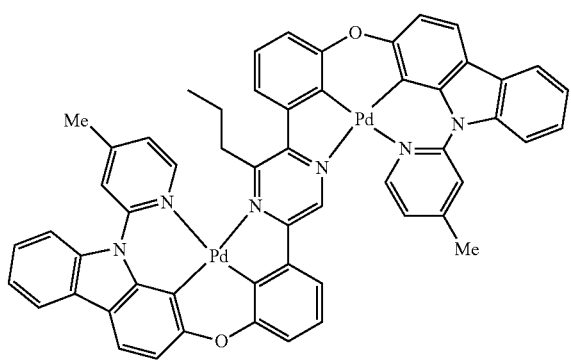
Compound Pd138
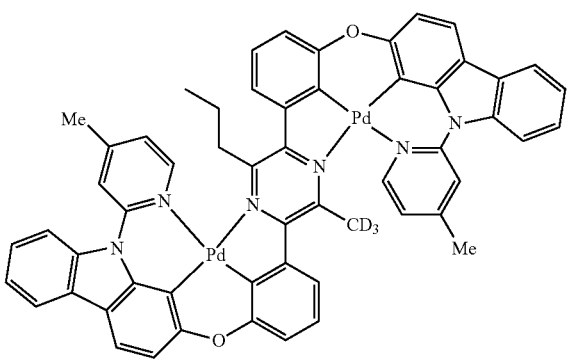

Compound Pd139
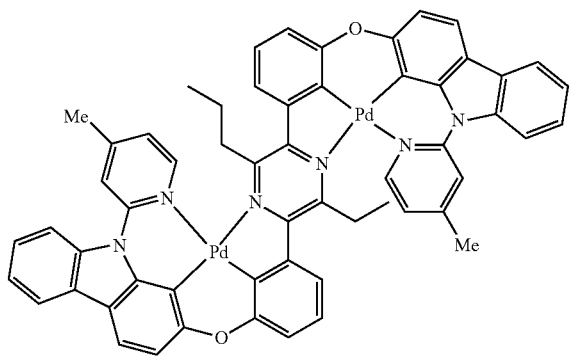
Compound Pd143
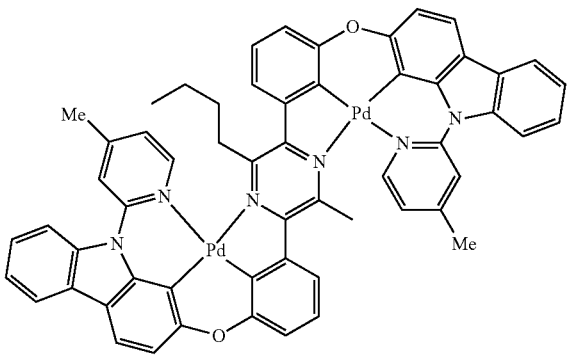
Compound Pd140
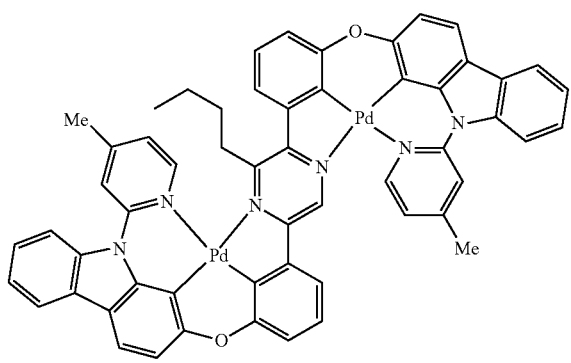
Compound Pd144
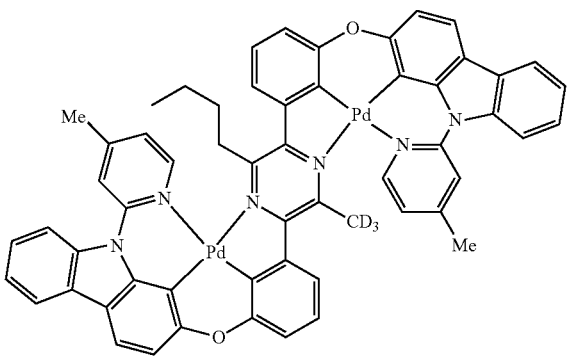
Compound Pd141
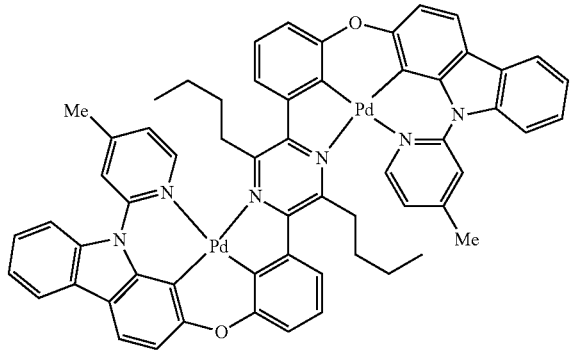
Compound Pd145
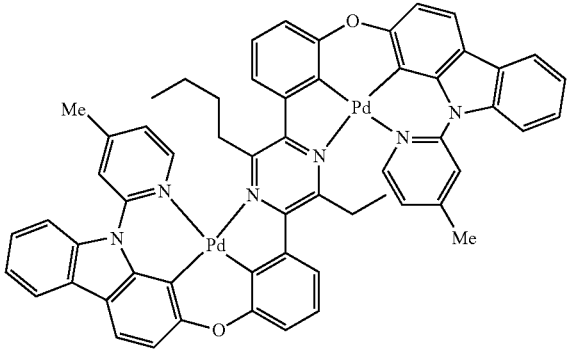
Compound Pd142
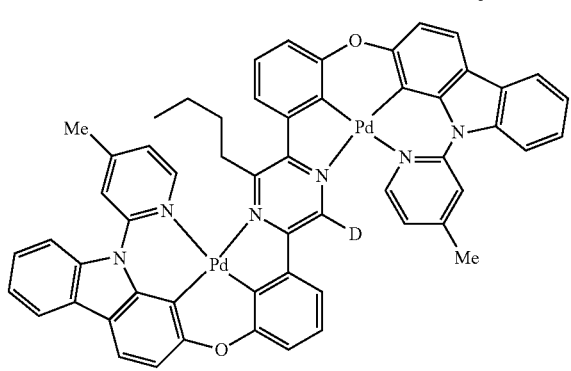
Compound Pd146
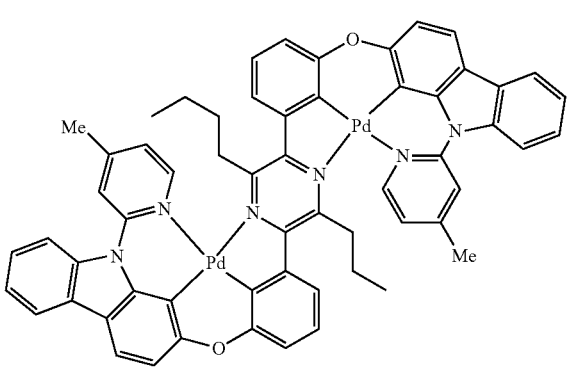

Compound Pd147
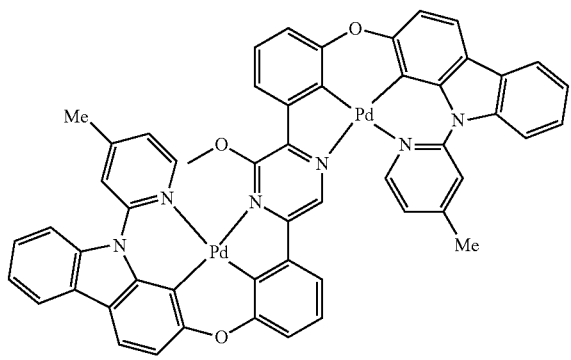
Compound Pd151
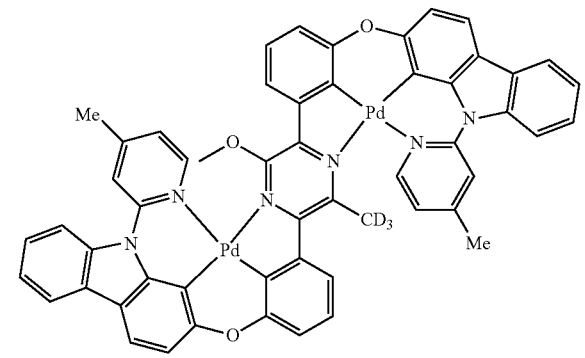
Compound Pd148
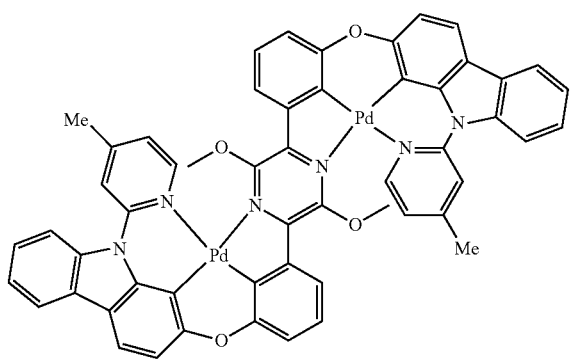
Compound Pd152
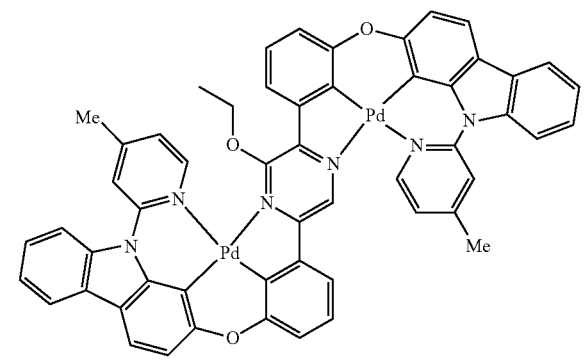
Compound Pd149
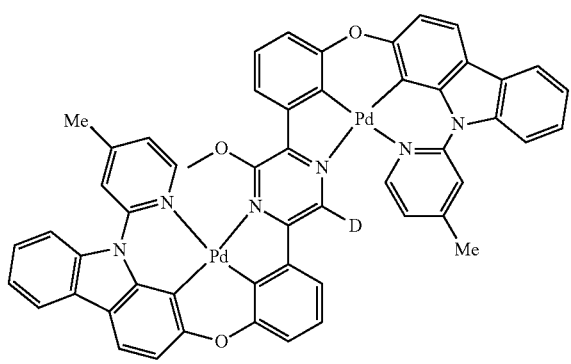
Compound Pd153
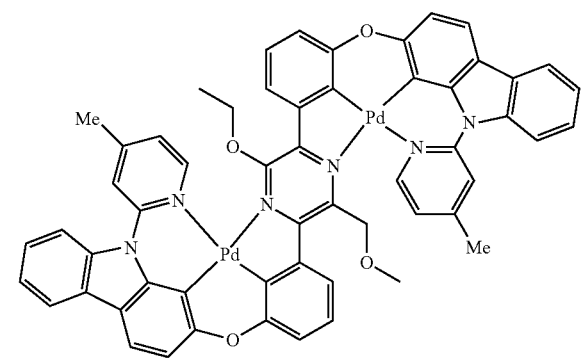
Compound Pd150
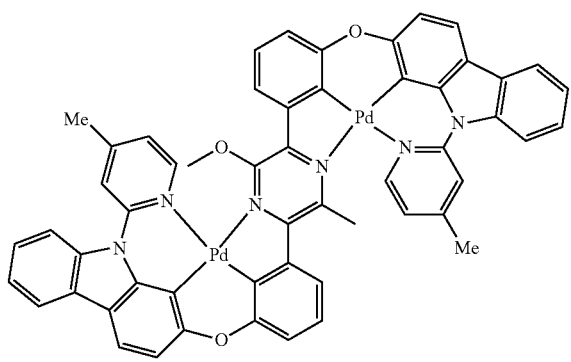
Compound Pd154
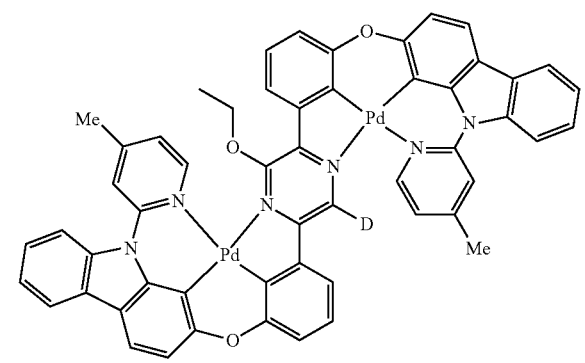

Compound Pd155
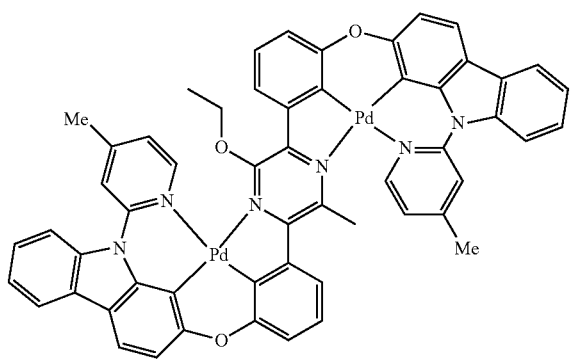
Compound Pd159
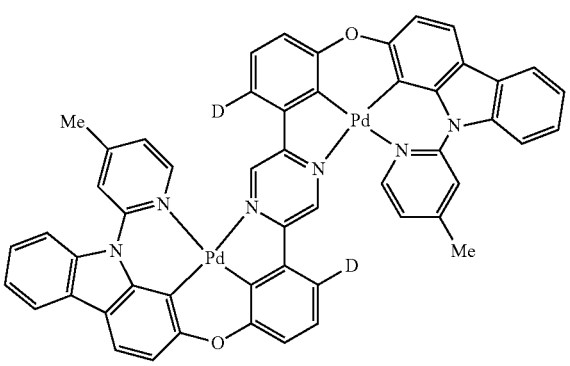
Compound Pd156
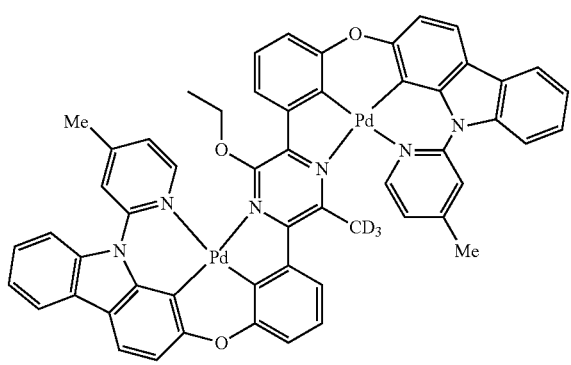
Compound Pd160
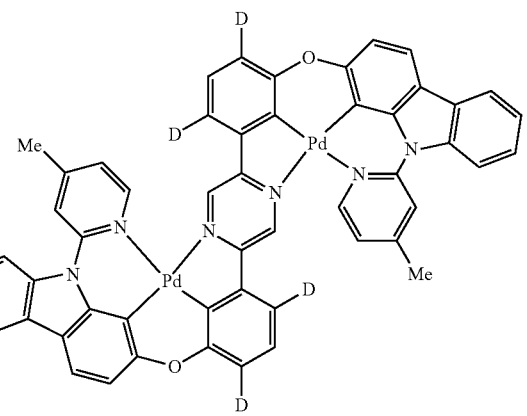
Compound Pd157
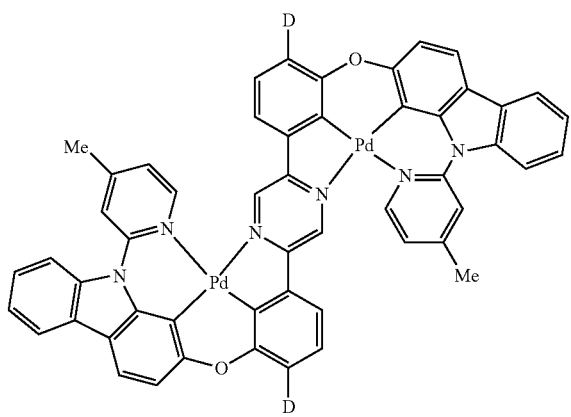
Compound Pd161
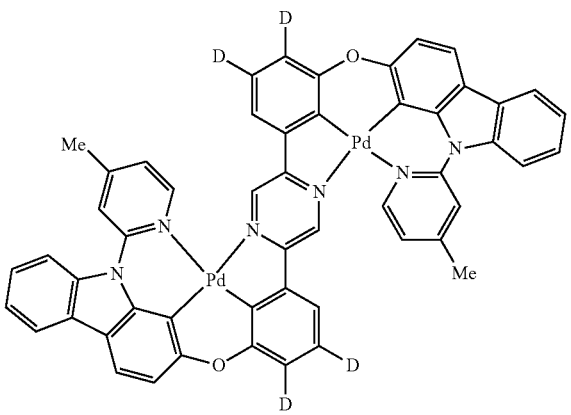
Compound Pd158
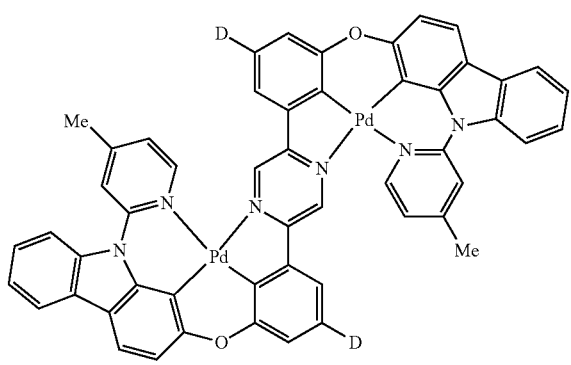
Compound Pd162
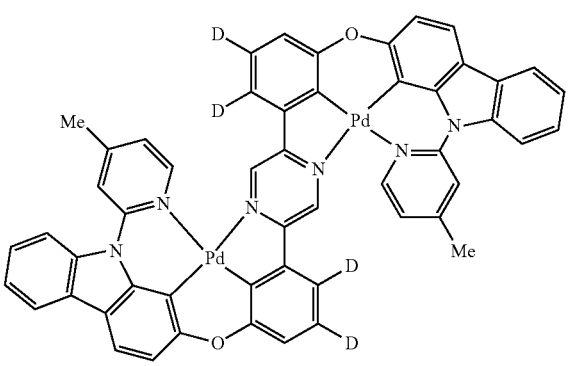

-continued
Compound Pd163
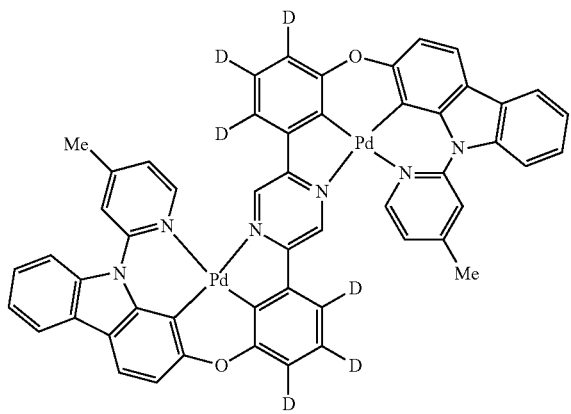
Compound Pd164
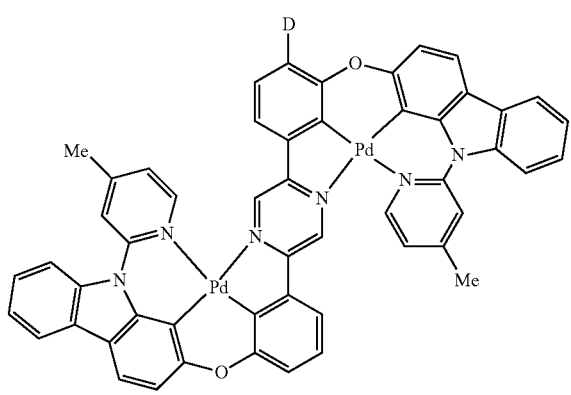
Compound Pd165
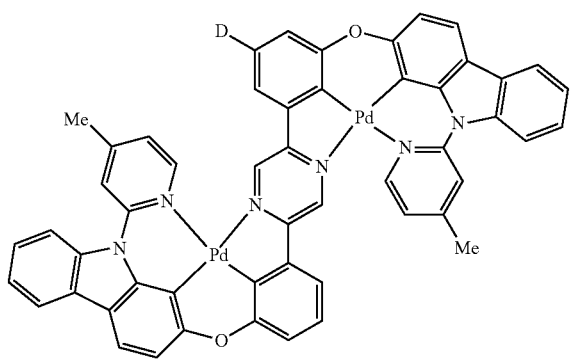
Compound Pd166
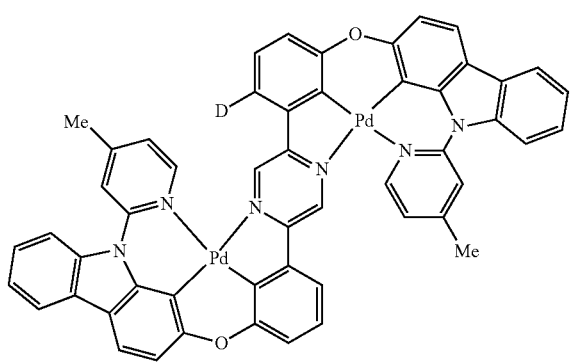
-continued
Compound Pd167
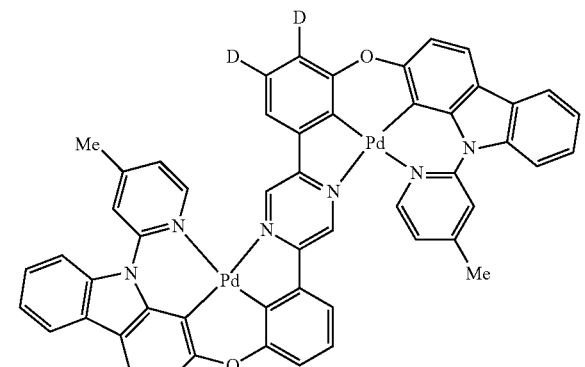
Compound Pd168
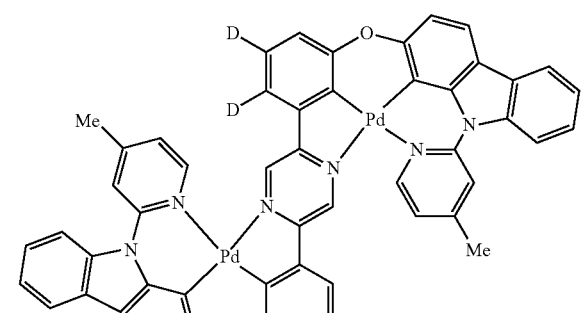
Compound Pd169
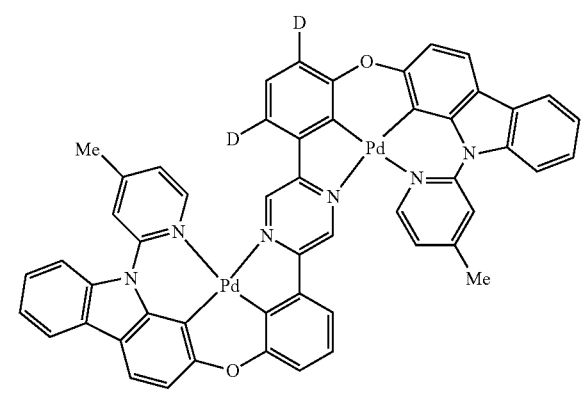
Compound Pd170
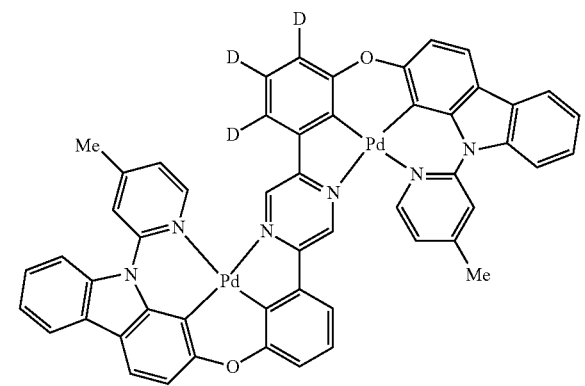

Compound Pd171
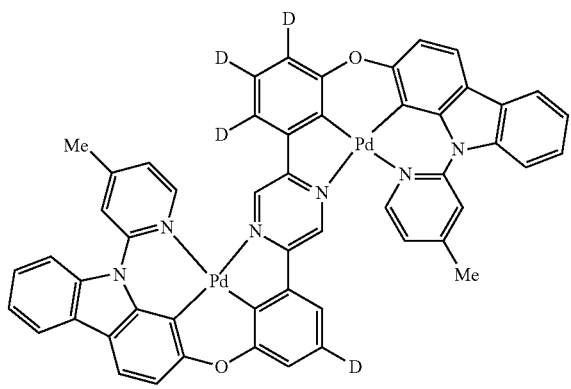
Compound Pd172
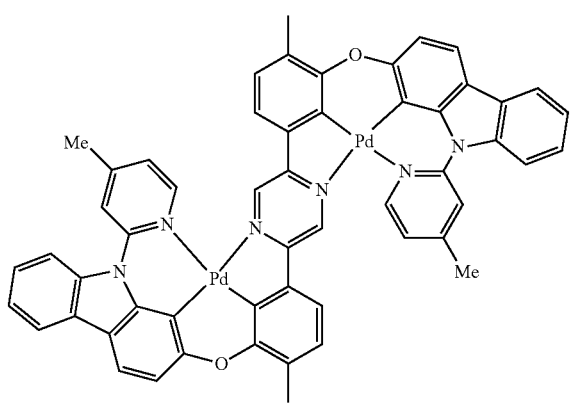
Compound Pd173
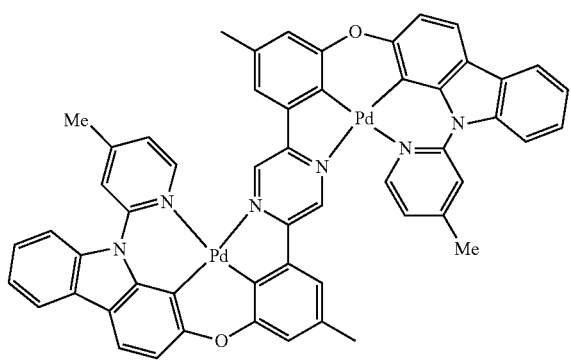
Compound Pd174
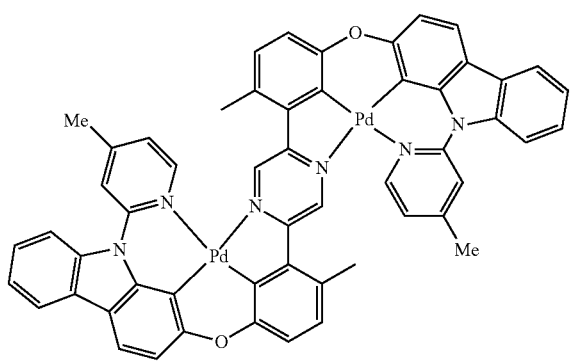
Compound Pd175
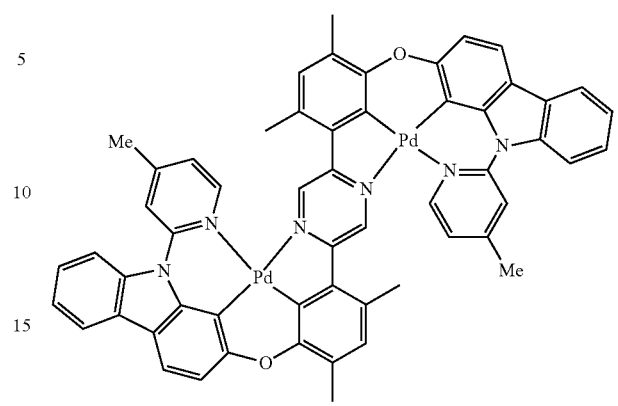
Compound Pd176
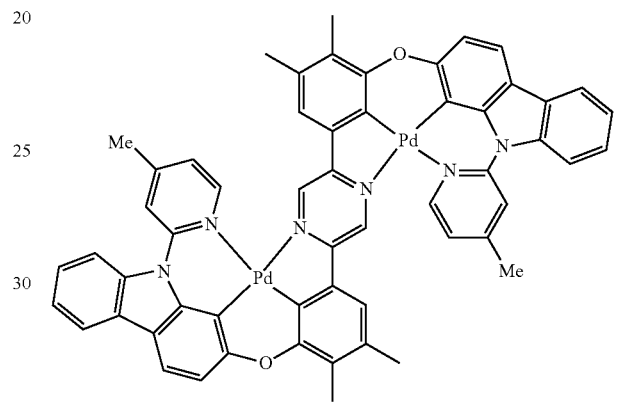
Compound Pd177
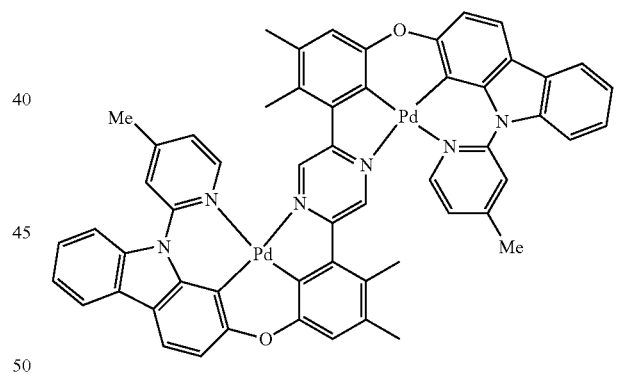
Compound Pd178
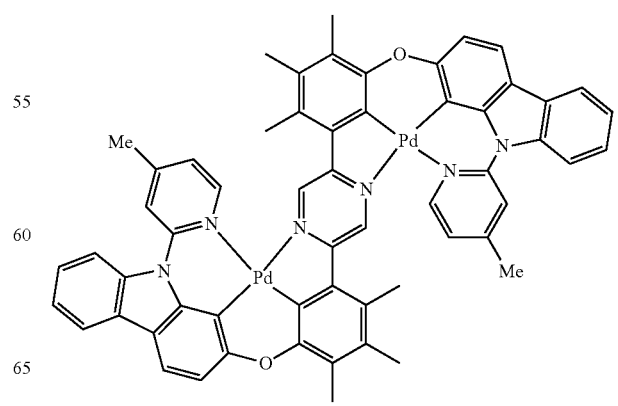

Compound Pd179
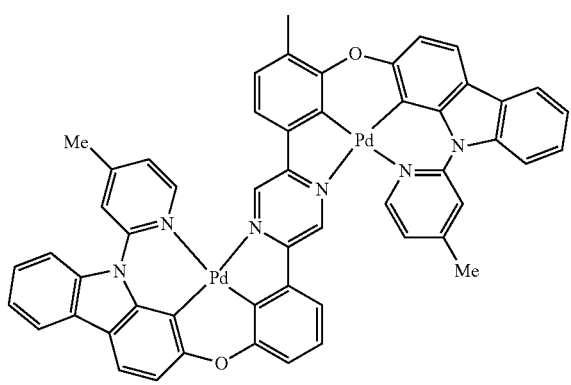
Compound Pd183
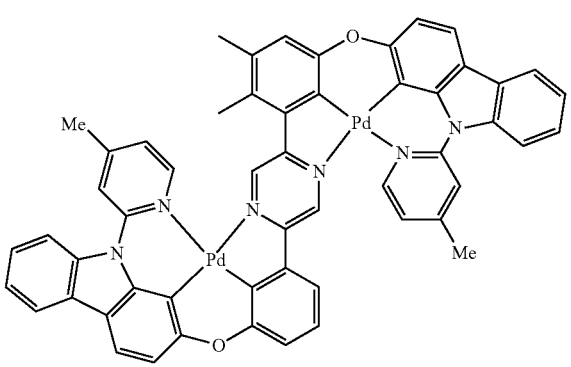
Compound Pd180
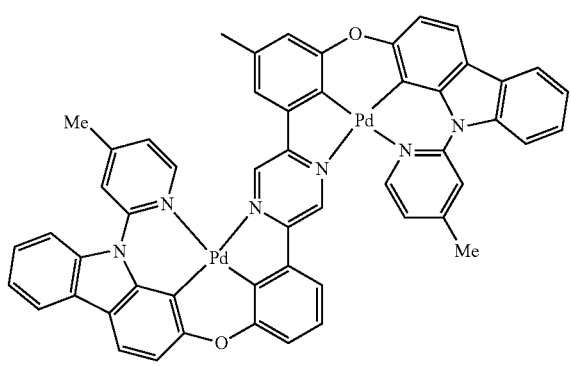
Compound Pd184
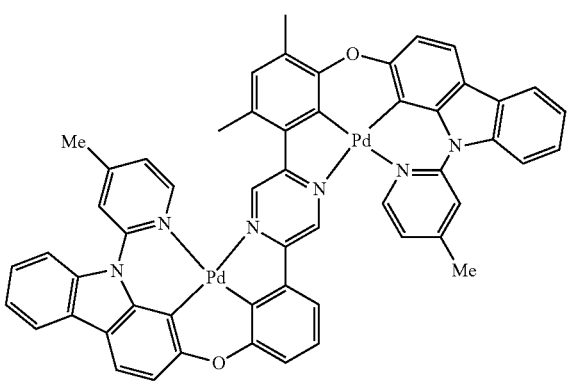
Compound Pd181
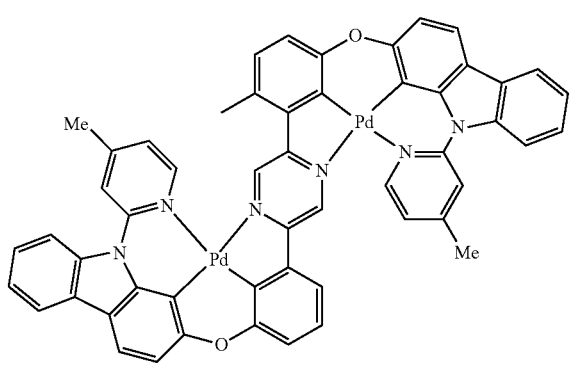
Compound Pd185
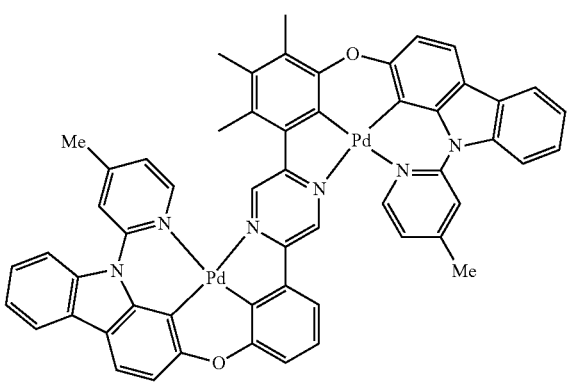
Compound Pd182
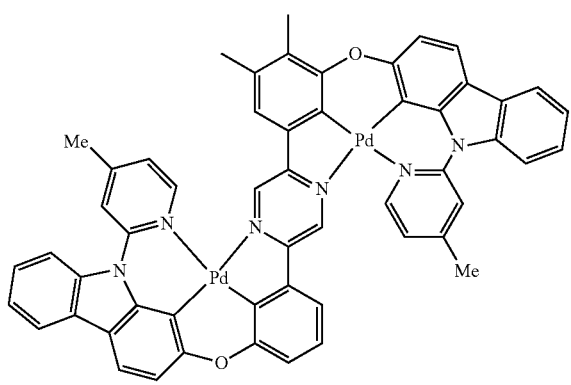
Compound Pd186
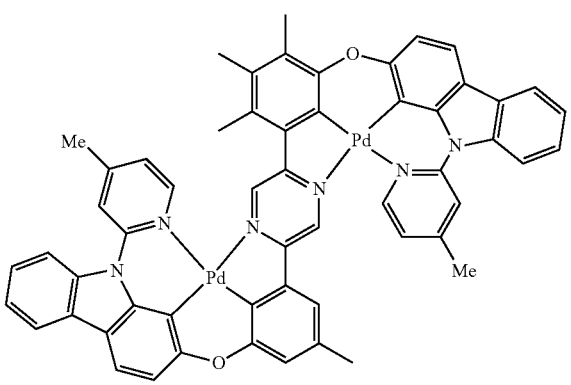

Compound Pd187
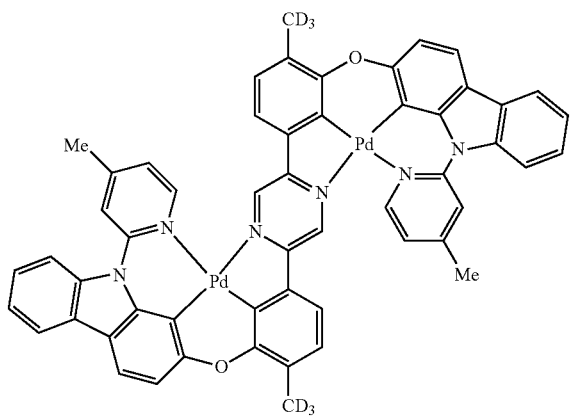
Compound Pd188
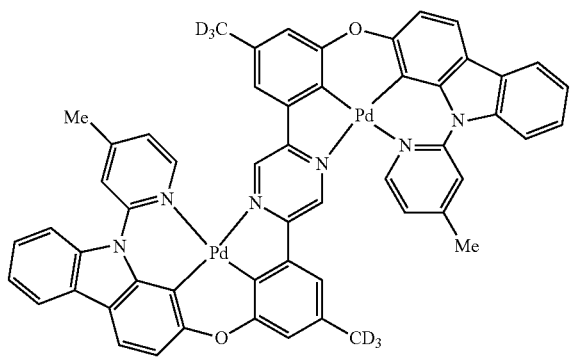
Compound Pd189
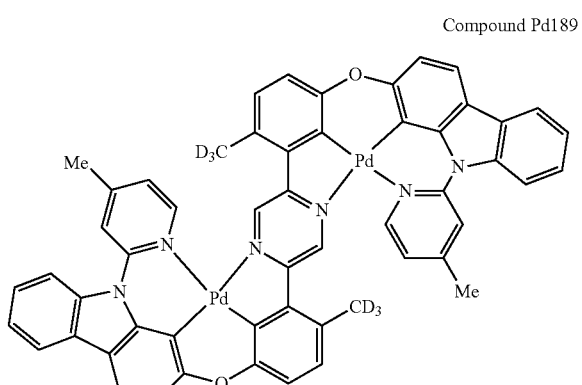
Compound Pd190
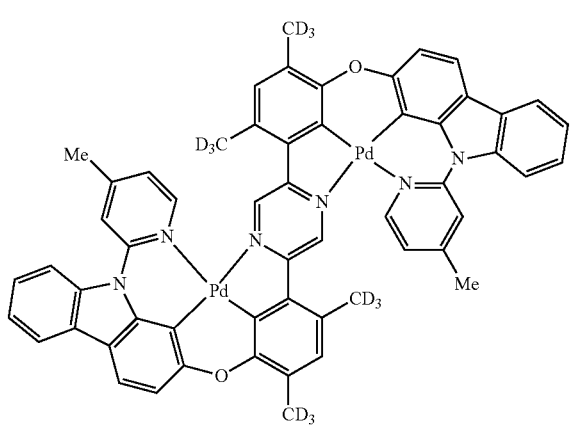
Compound Pd191
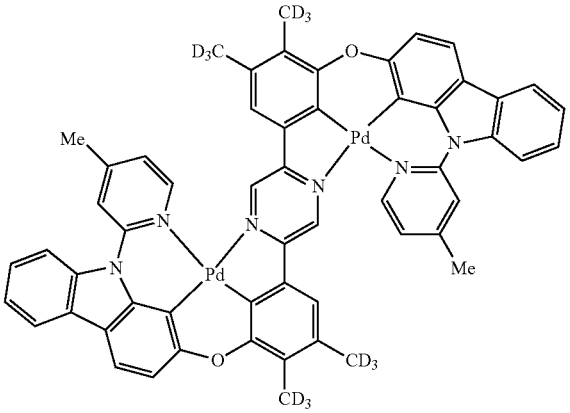
Compound Pd192
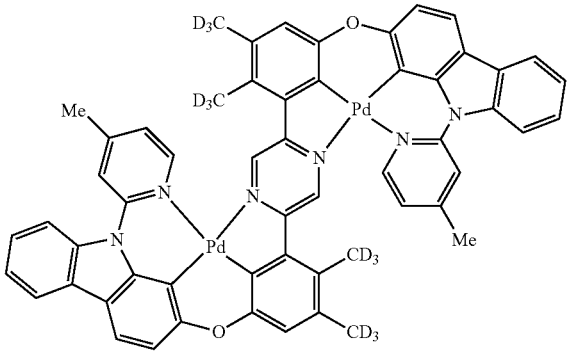
Compound Pd193
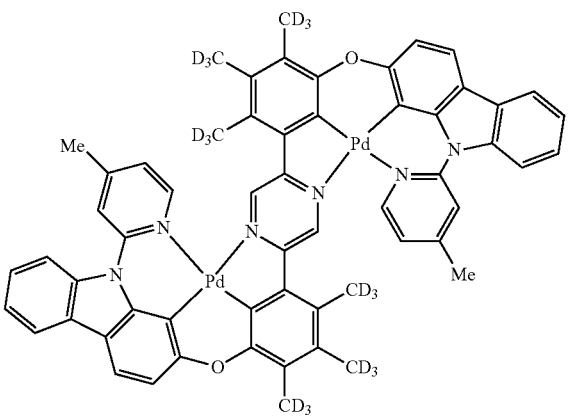
Compound Pd194
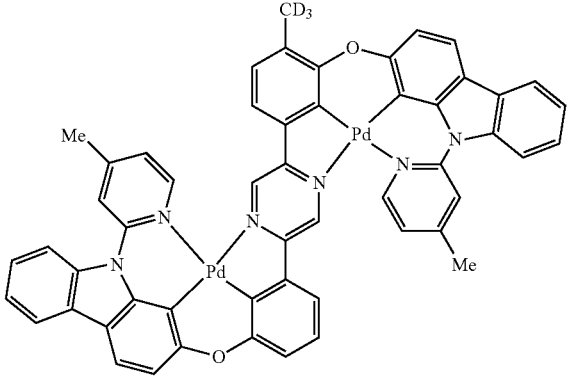

Compound Pd195
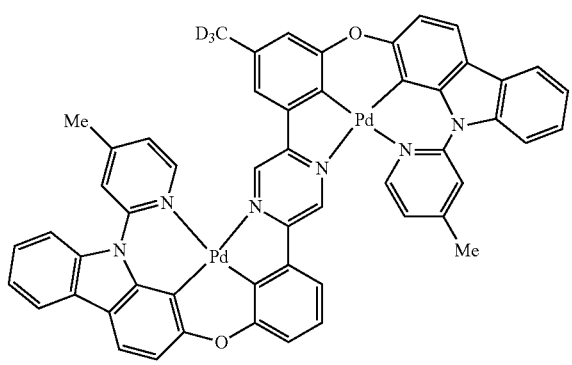
Compound Pd196
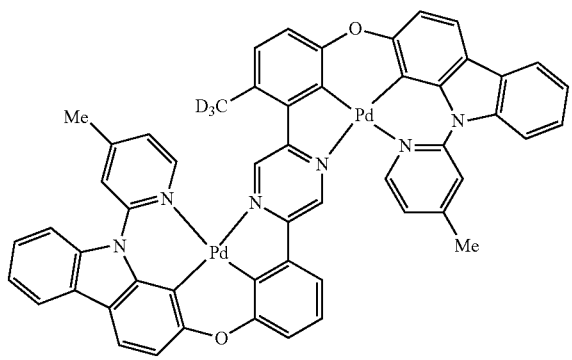
Compound Pd197
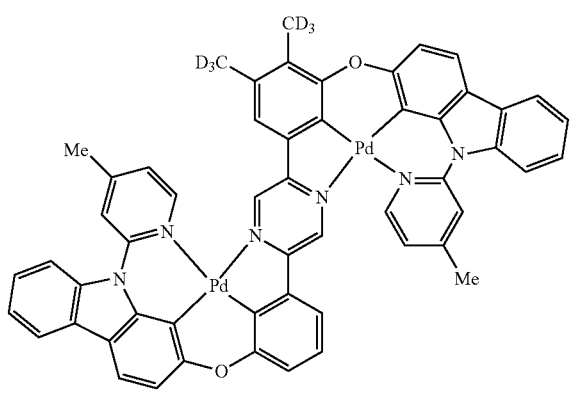
Compound Pd198
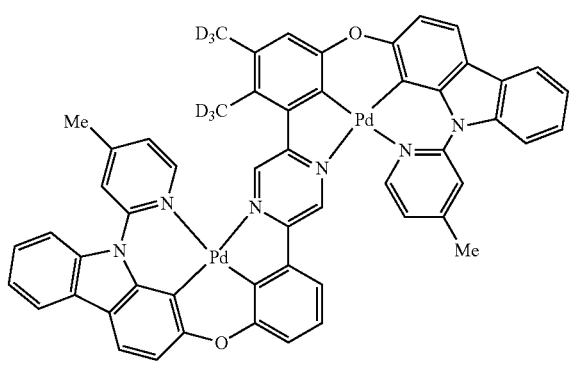
Compound Pd199
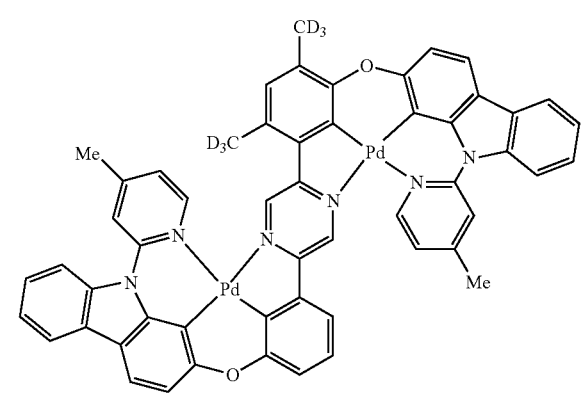
Compound Pd200
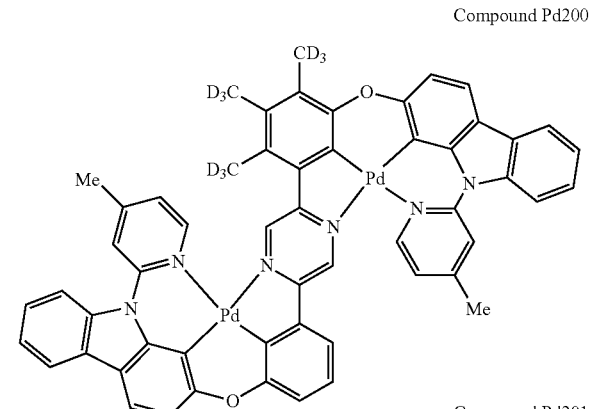
Compound Pd201
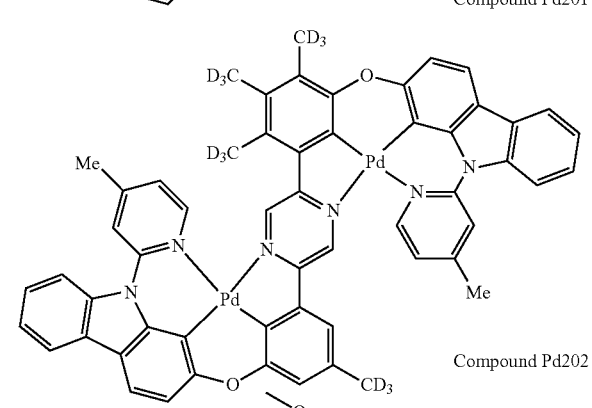
Compound Pd202
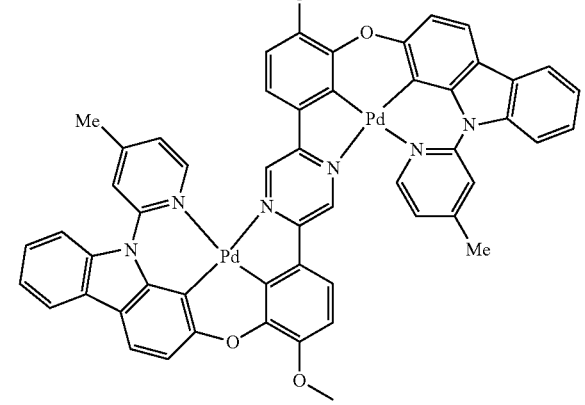

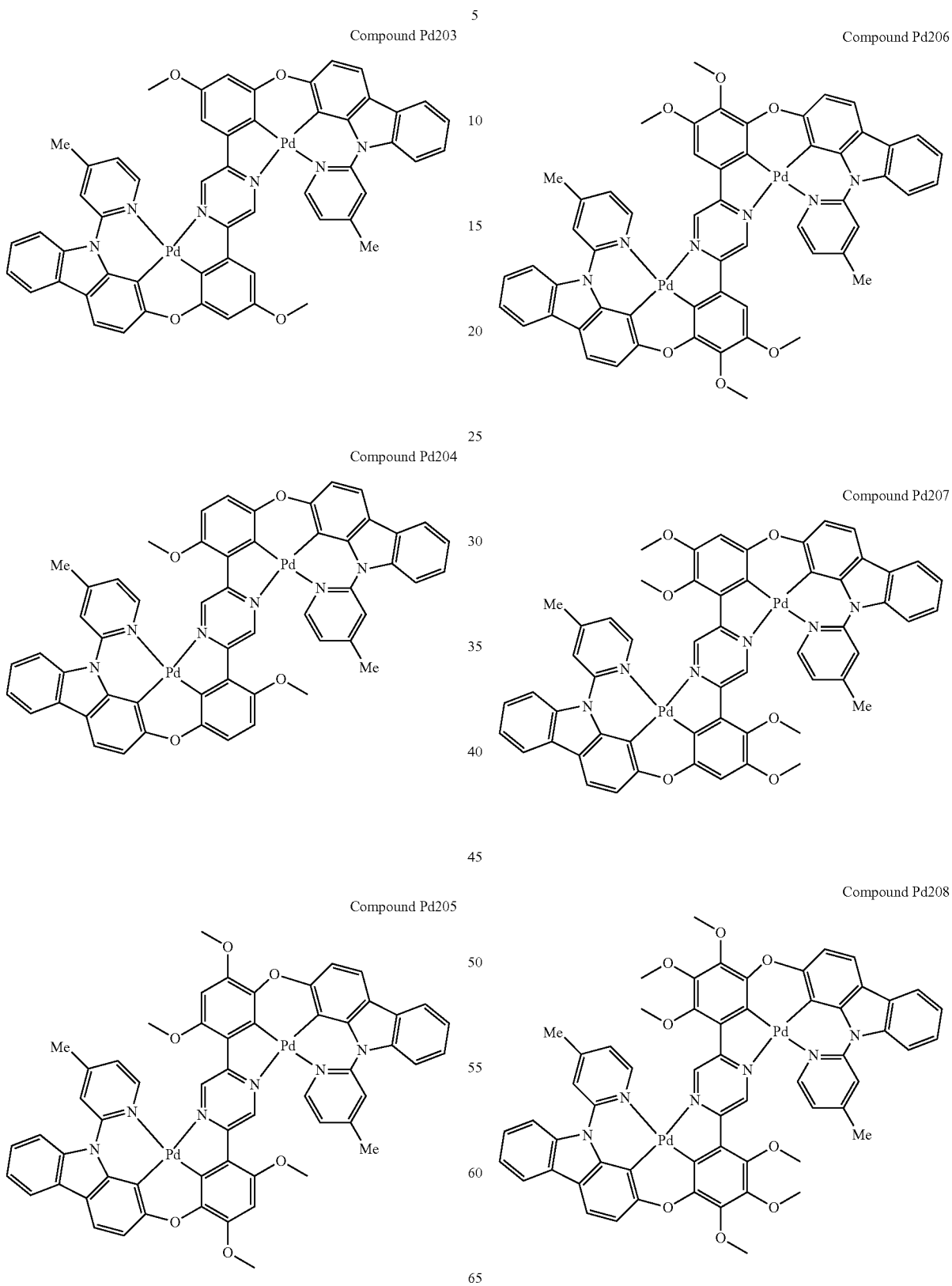

Compound Pd209
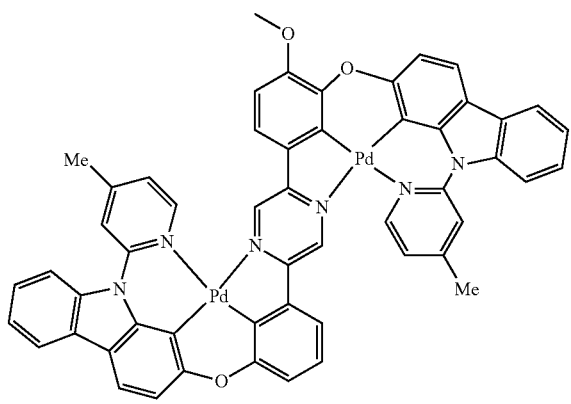
Compound Pd210
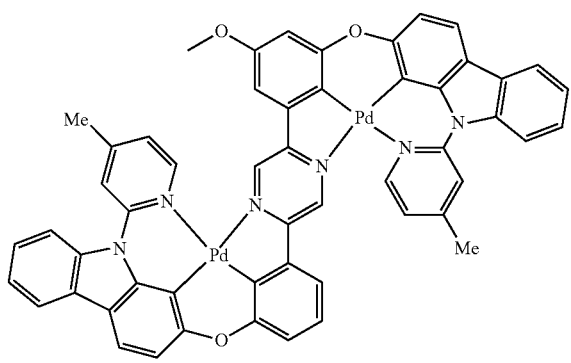
Compound Pd211
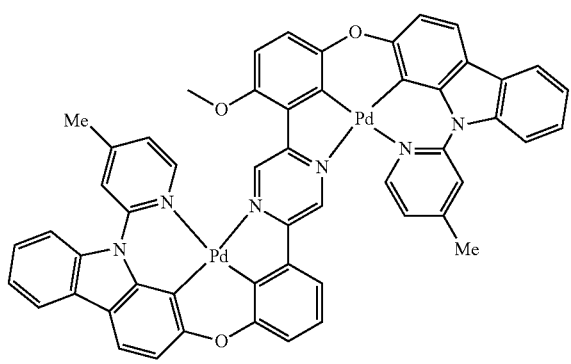
Compound Pd212
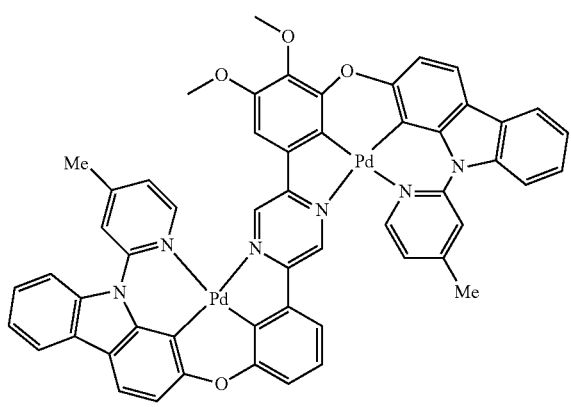
Compound Pd213
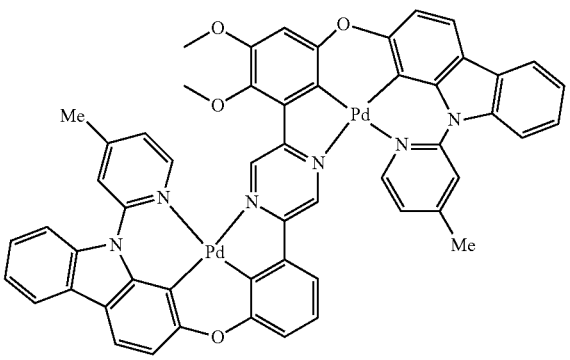
Compound Pd214
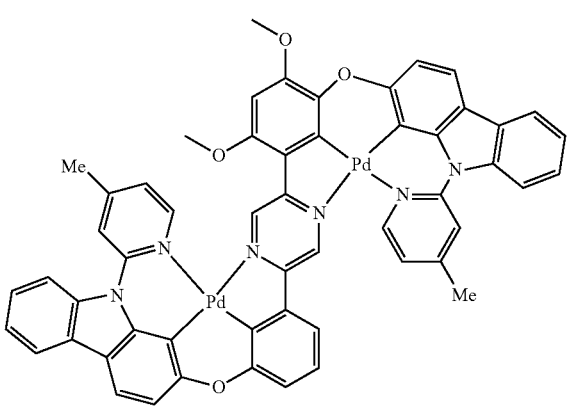
Compound Pd215
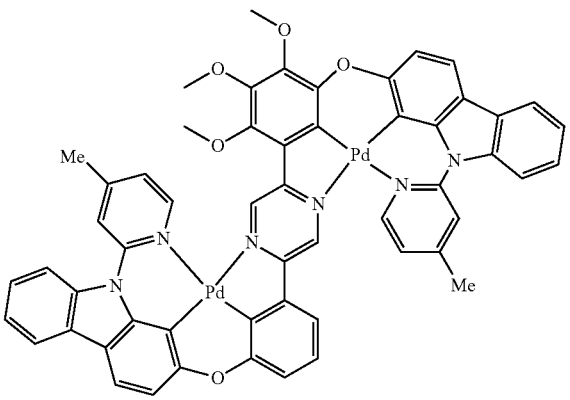
Compound Pd216
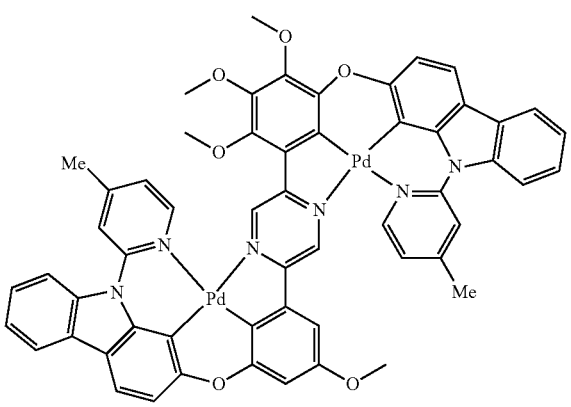

Compound Pd217
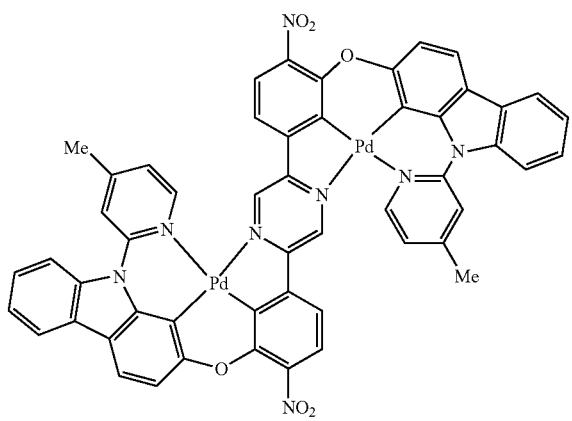
Compound Pd218
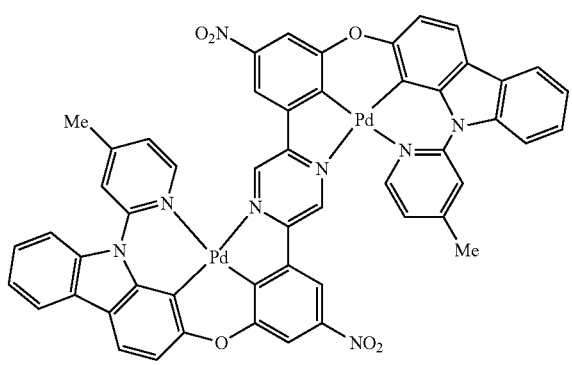
Compound Pd219
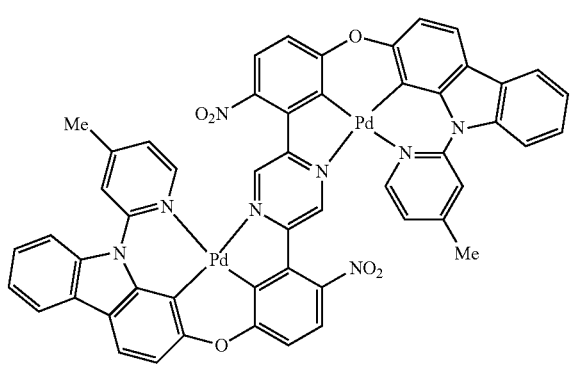
Compound Pd220
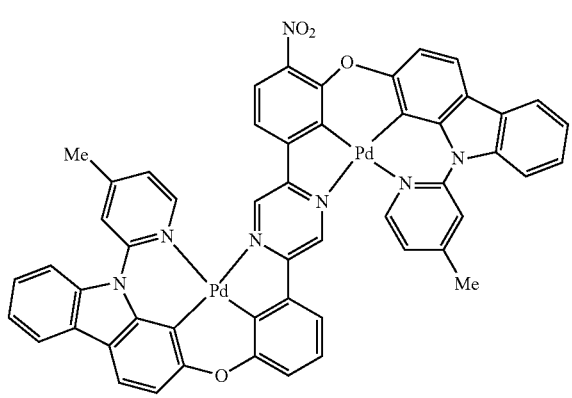
Compound Pd221
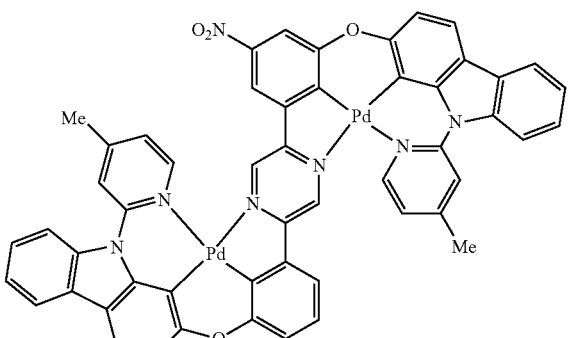
Compound Pd222
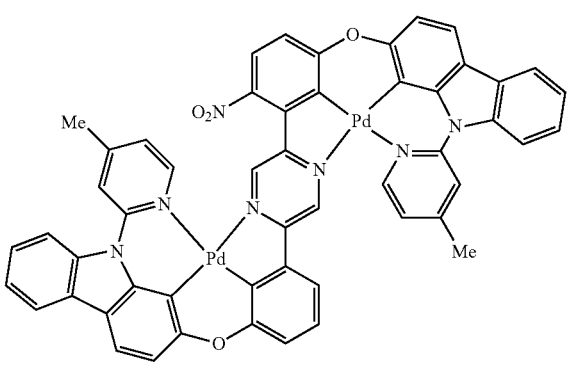
Compound Pd223
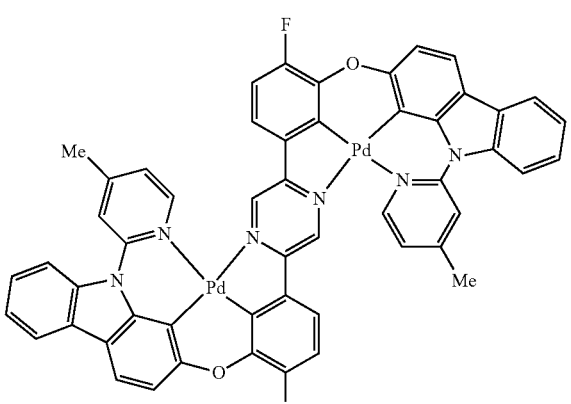
Compound Pd224
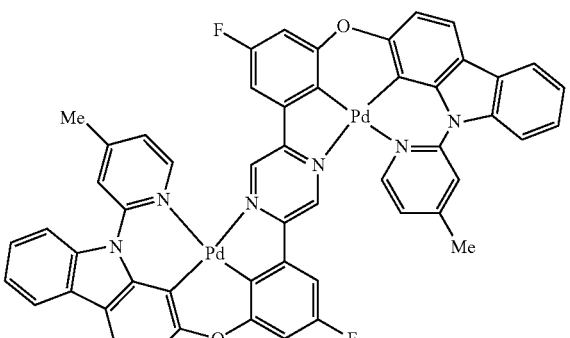

Compound Pd225
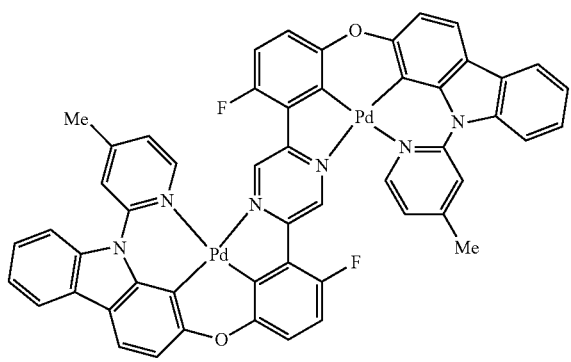
Compound Pd226
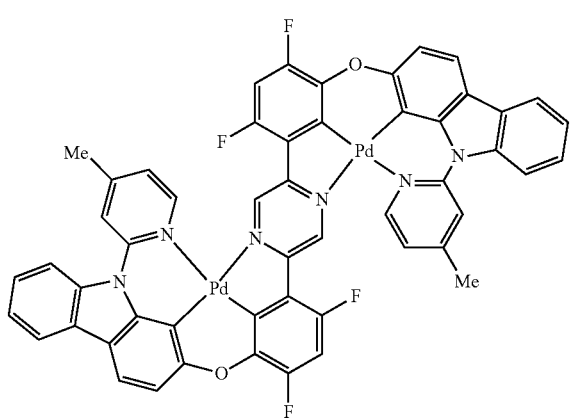
Compound Pd227
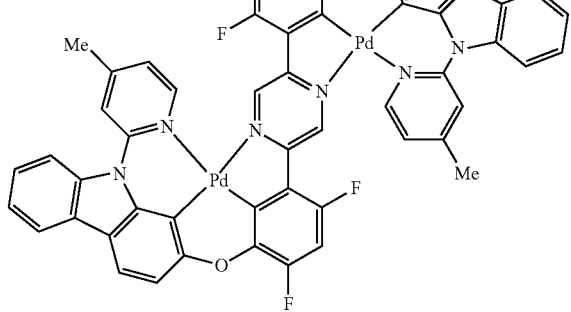
Compound Pd228
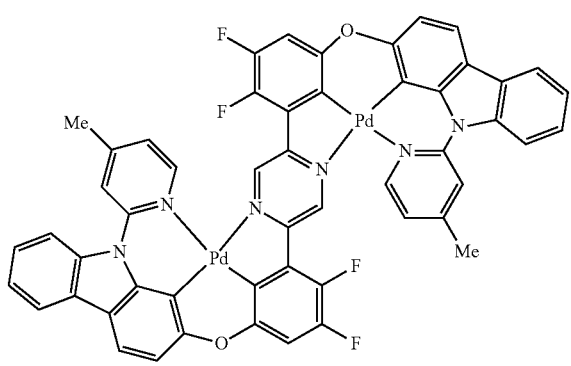
Compound Pd229
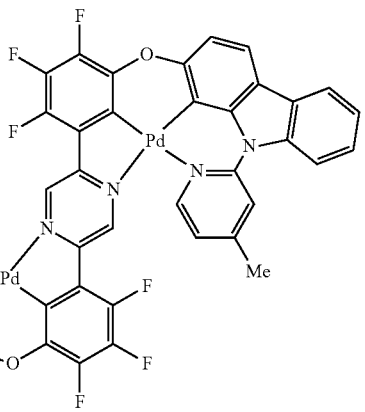
Compound Pd230
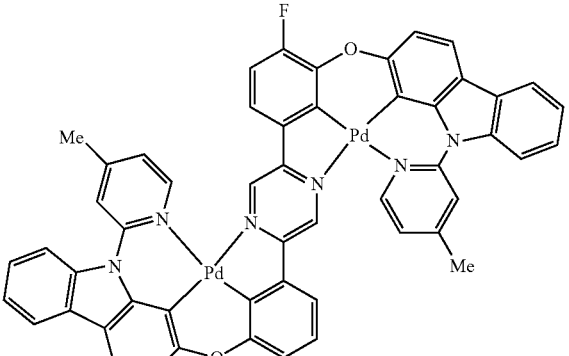
Compound Pd231
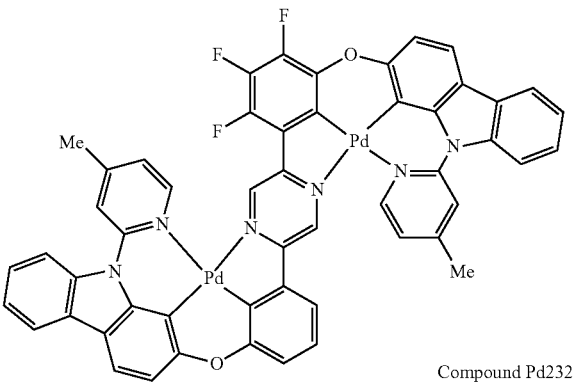
Compound Pd232
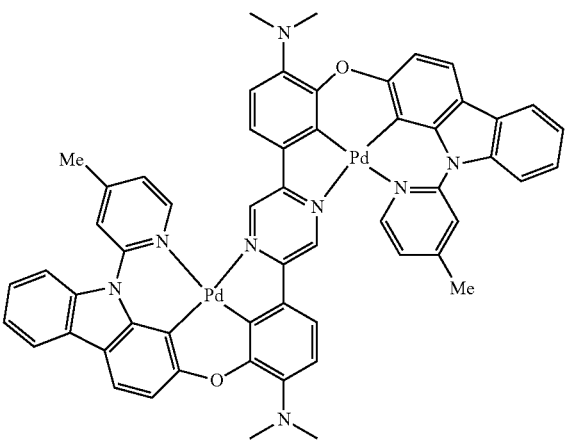

-continued
Compound Pd233
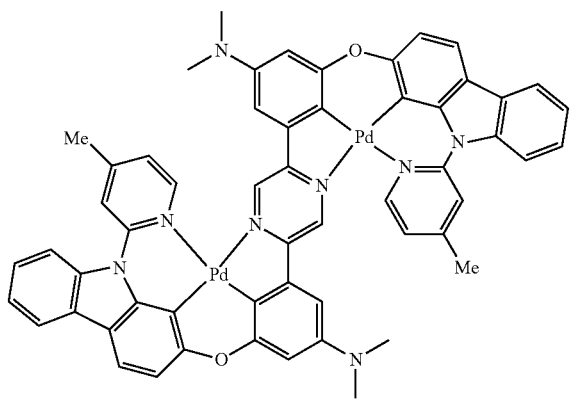
Compound Pd234
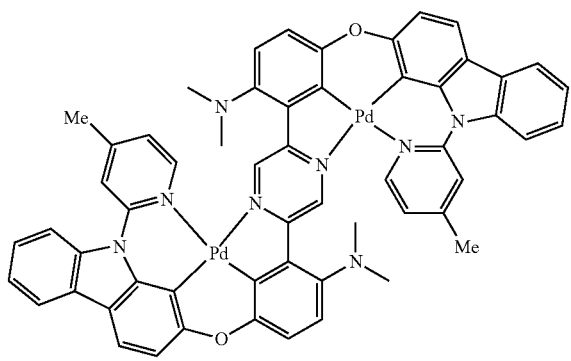
Compound Pd235
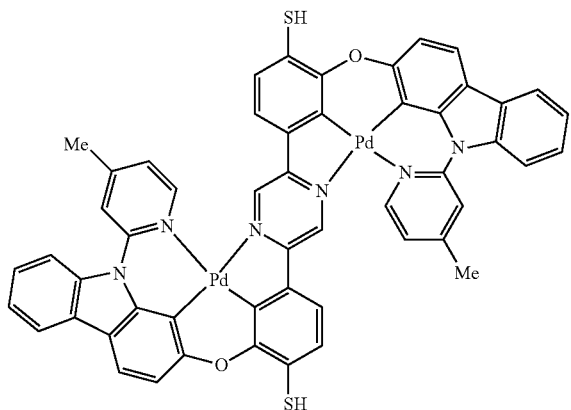
Compound Pd236
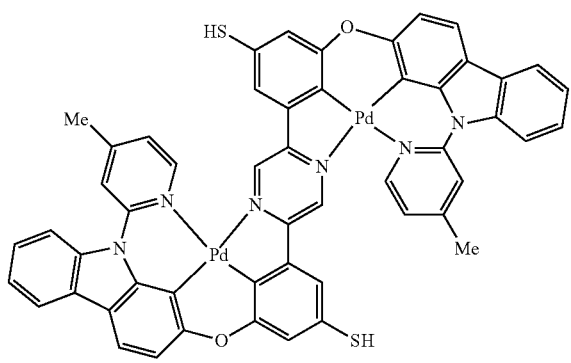
-continued
Compound Pd237
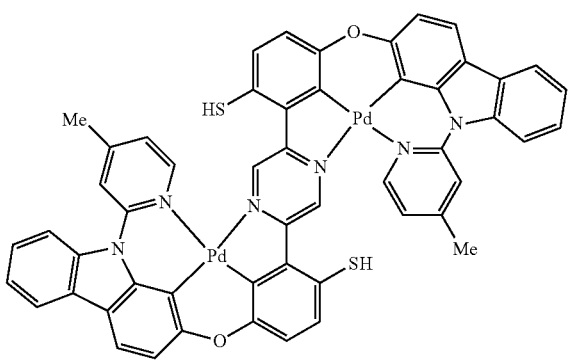
Compound Pd238
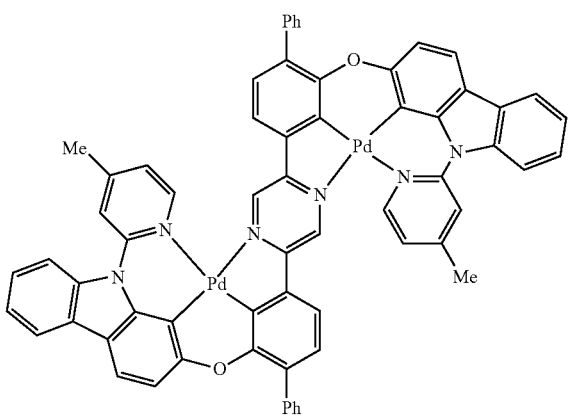
Compound Pd239
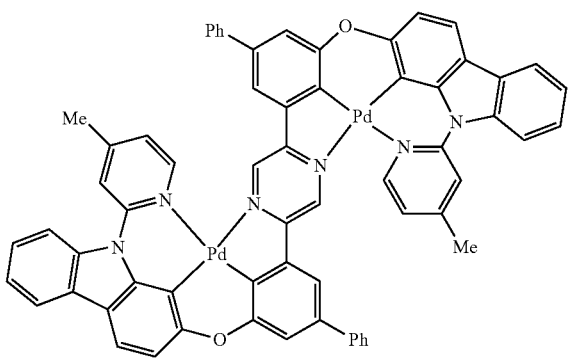
Compound Pd240
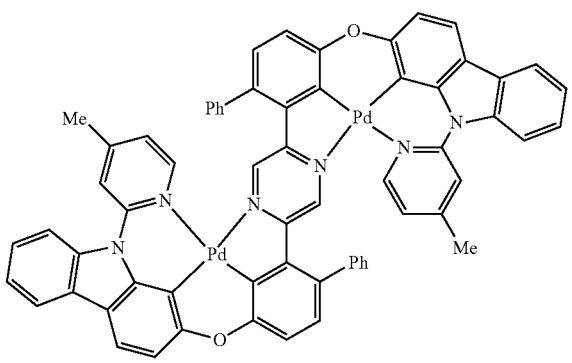

Compound Pd241
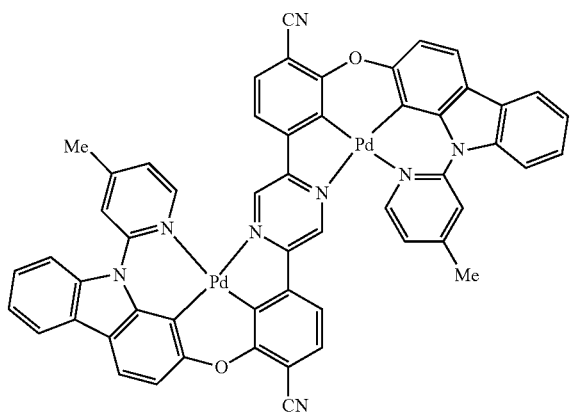
Compound Pd242
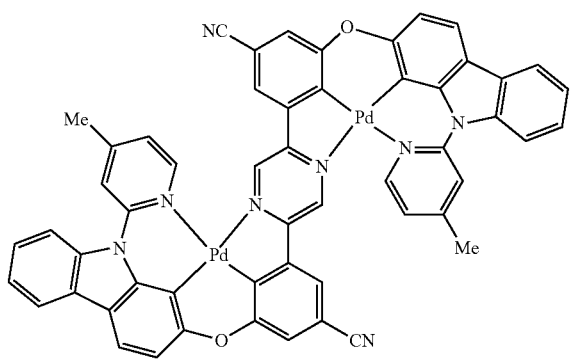
Compound Pd243
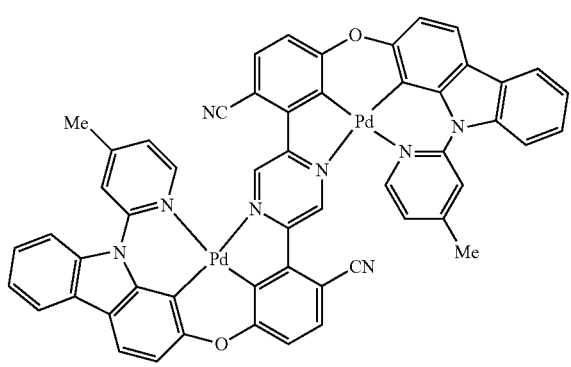
Compound Pd244
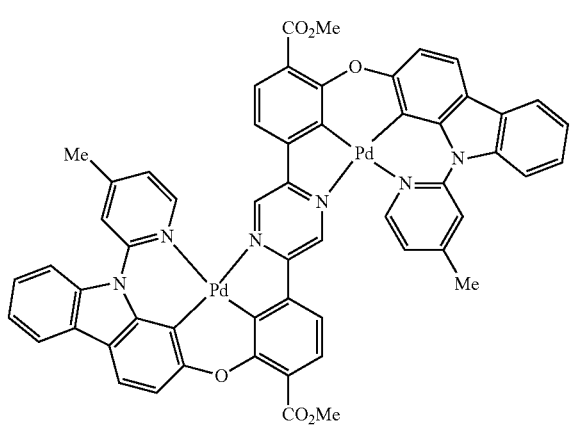
Compound Pd245
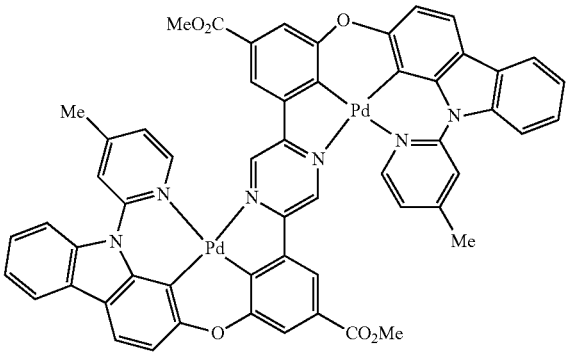
Compound Pd246
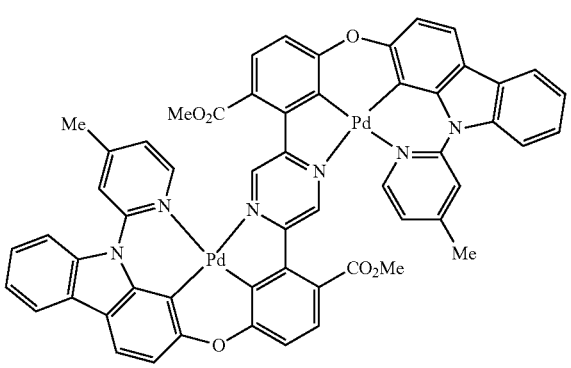
Compound Pd247
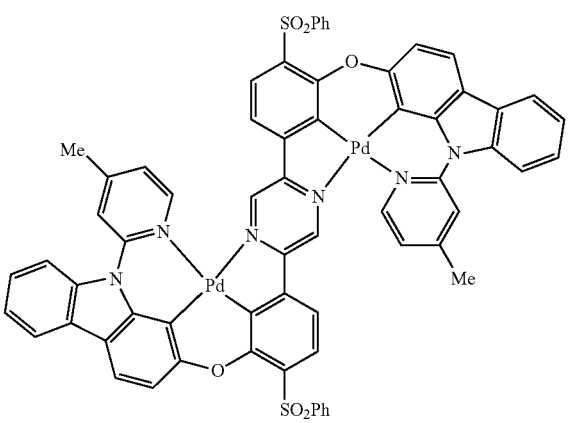
Compound Pd248
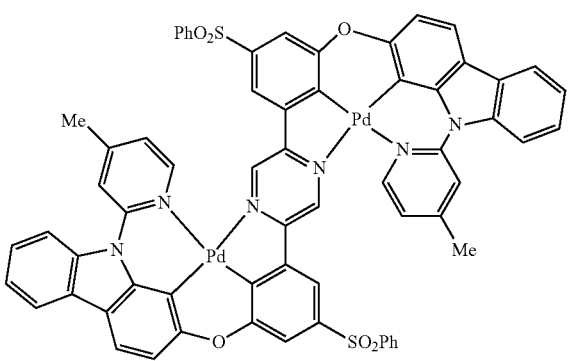

-continued
Compound Pd249
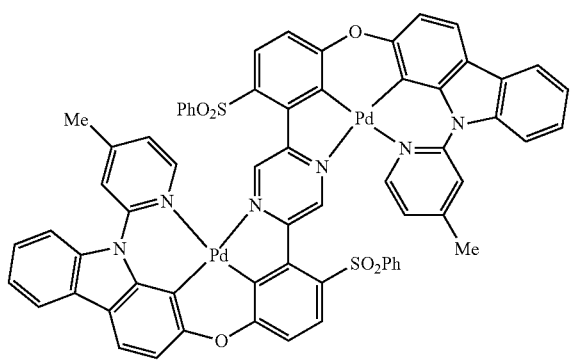
Compound Pd250
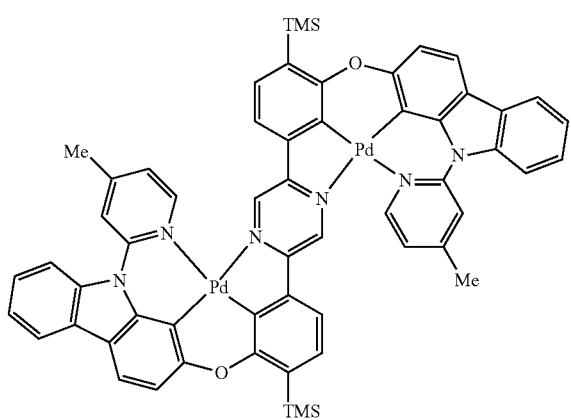
Compound Pd251
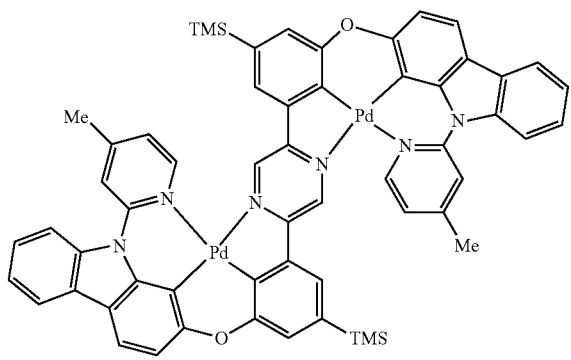
Compound Pd252
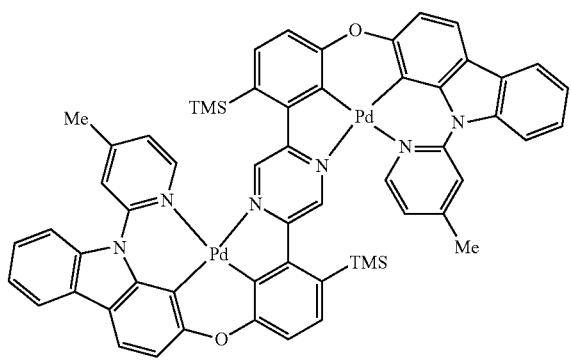
-continued
Compound Pd253
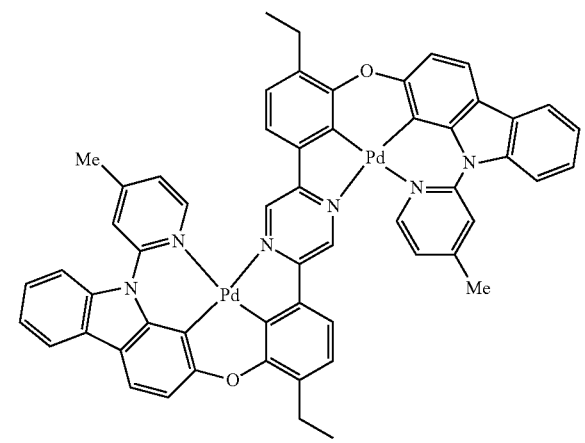
Compound Pd254
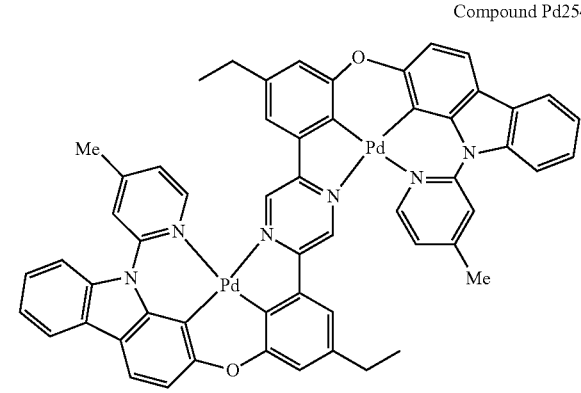
Compound Pd255
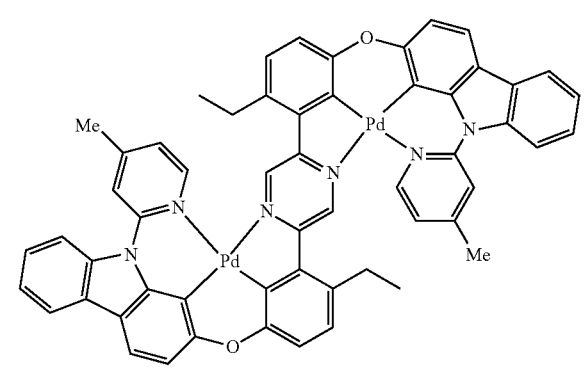
Compound Pd256
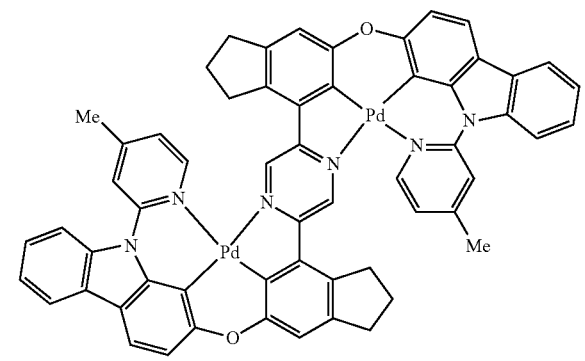

Compound Pd257
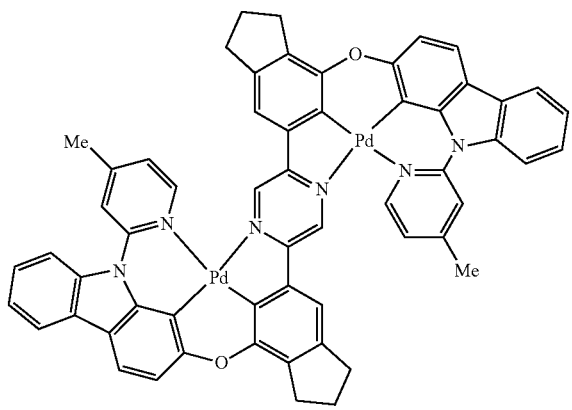
Compound Pd258
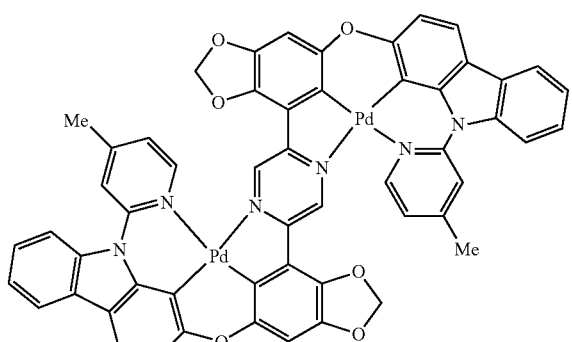
Compound Pd259
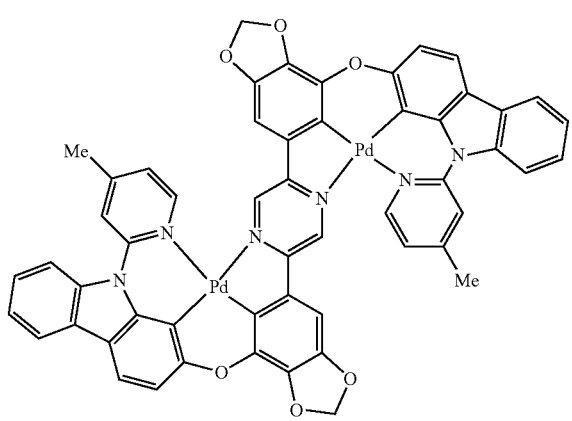
Compound Pd260
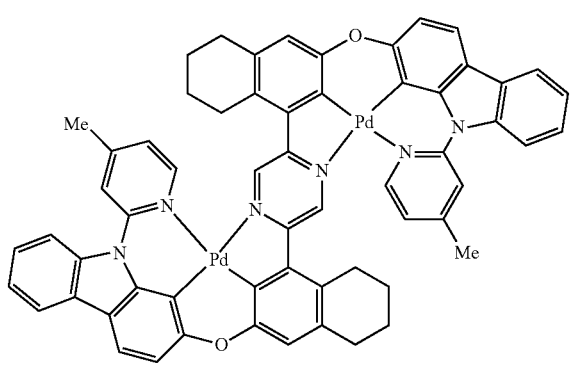
Compound Pd261
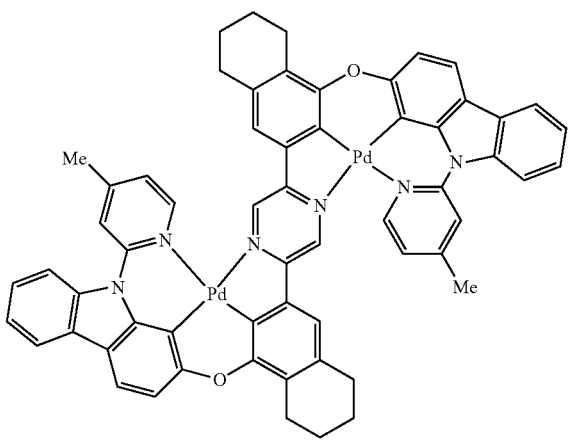
Compound Pd262
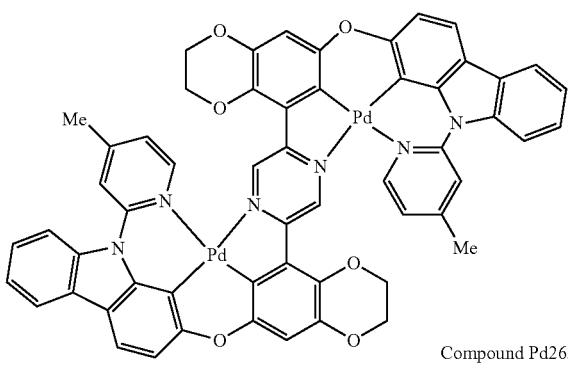
Compound Pd263
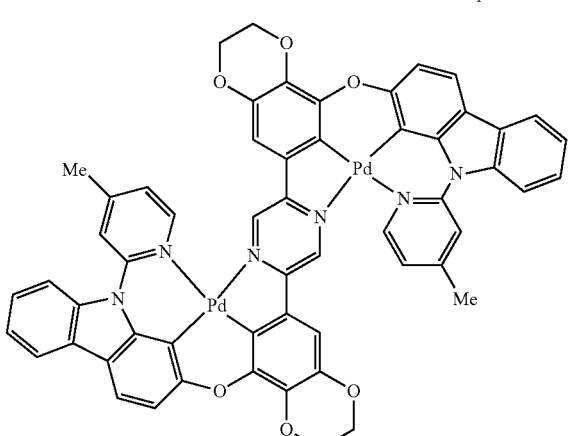
Compound Pd264
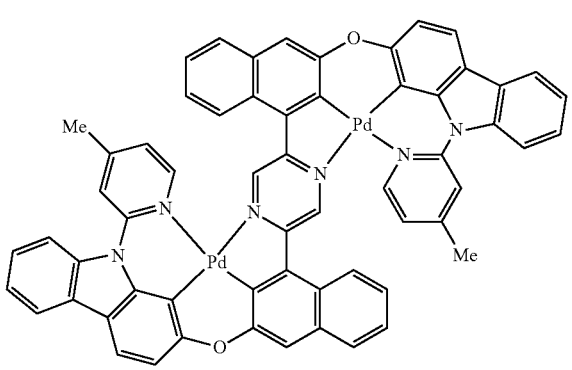

Compound Pd265
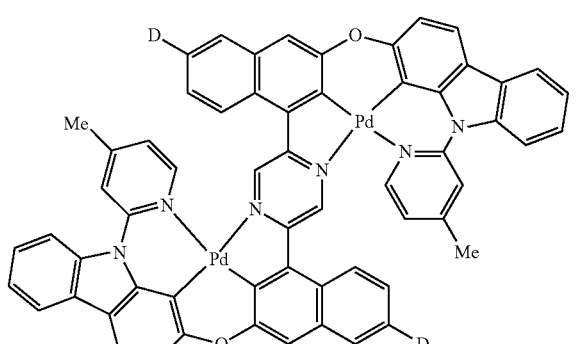
Compound Pd266
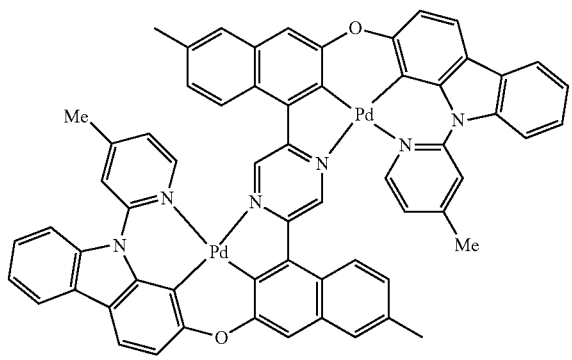
Compound Pd267
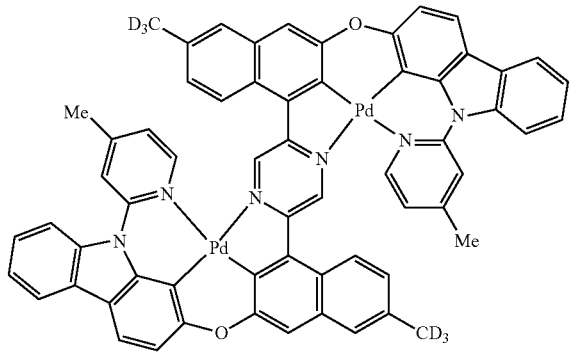
Compound Pd268
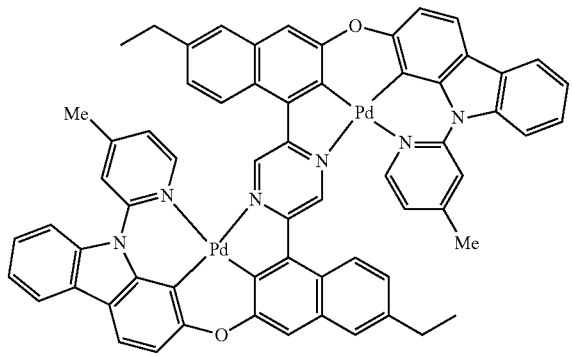
Compound Pd269
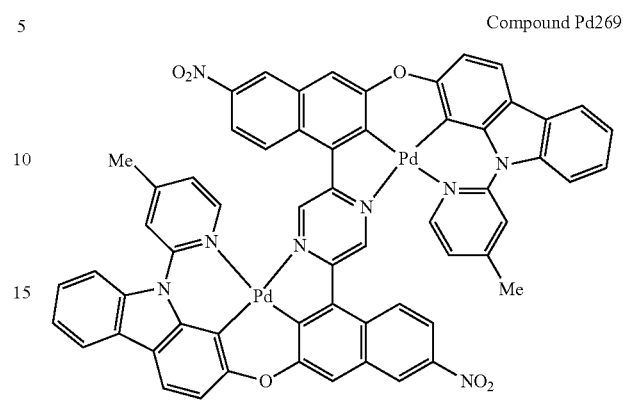
Compound Pd270
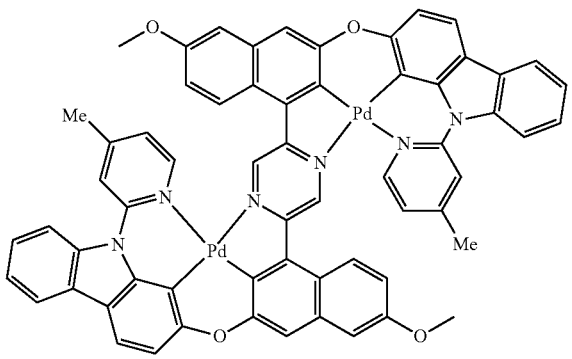
Compound Pd271
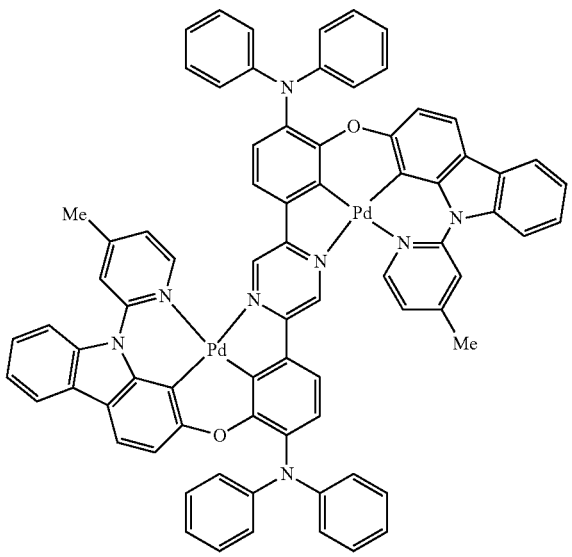

Compound Pd272
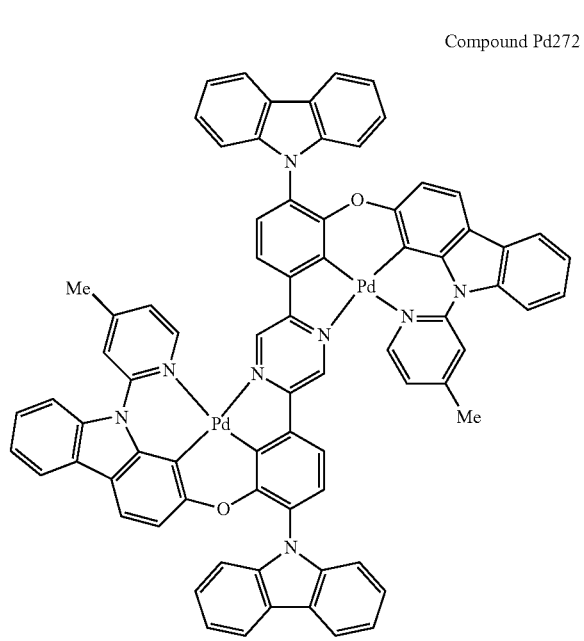
Compound Pd274
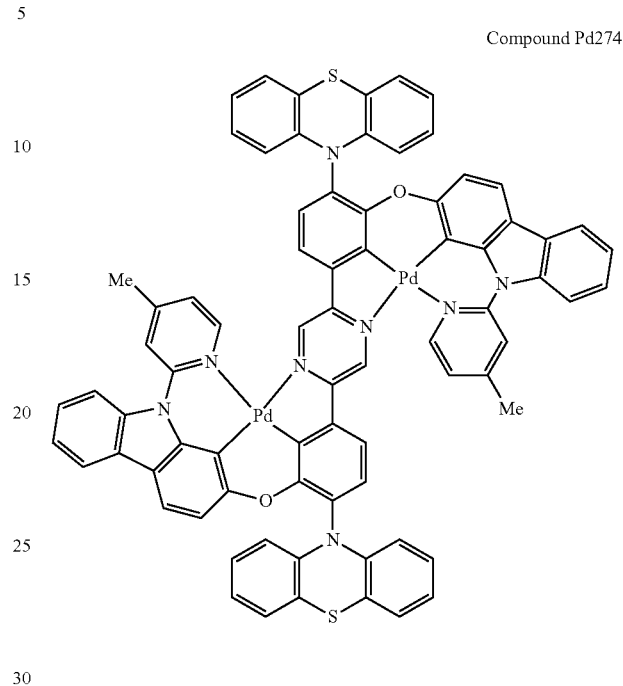
Compound Pd273
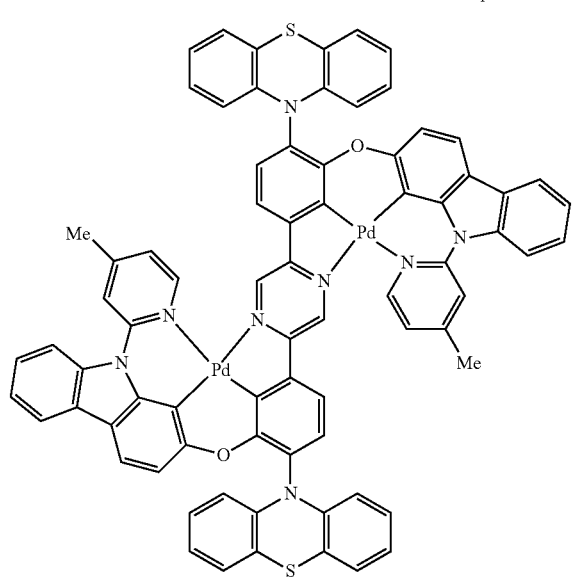
Compound Pd275
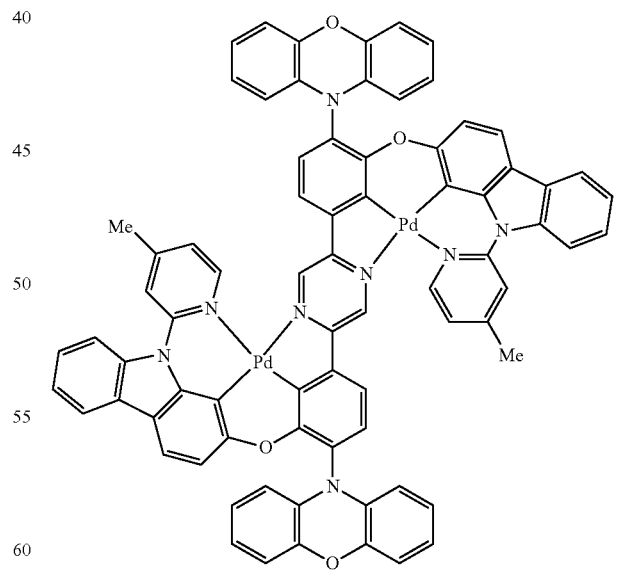

Compound Pd276
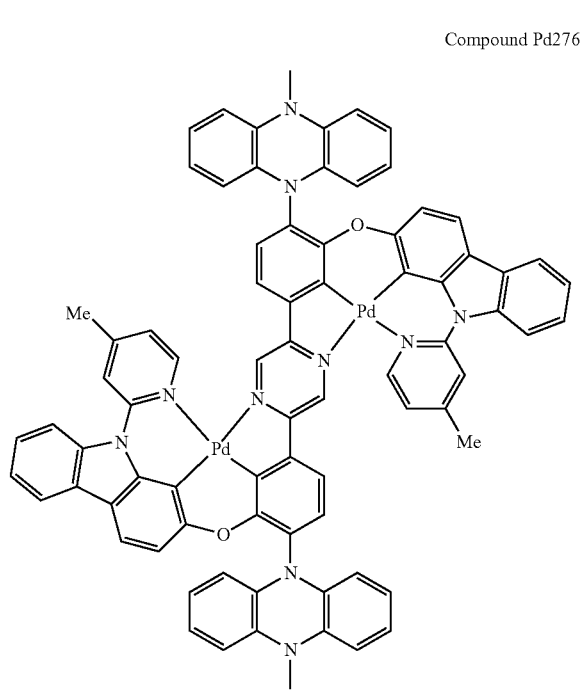
Compound Pd278
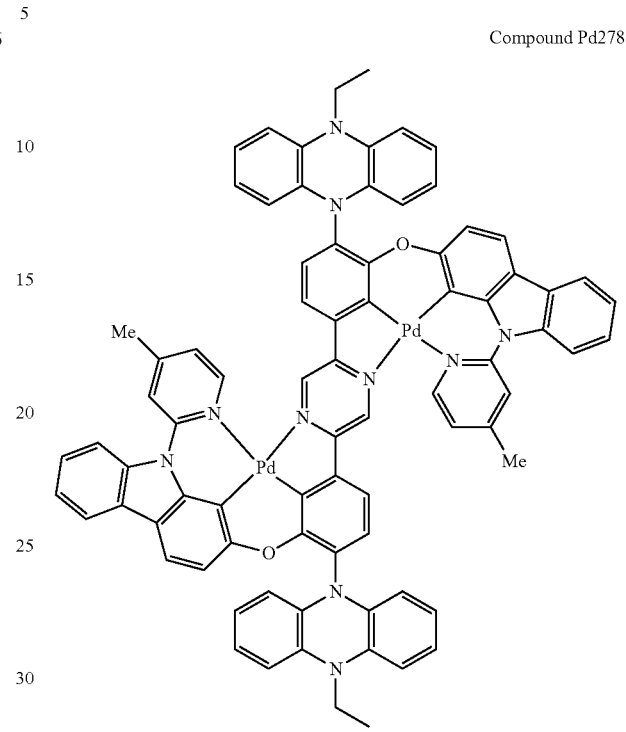
Compound Pd277
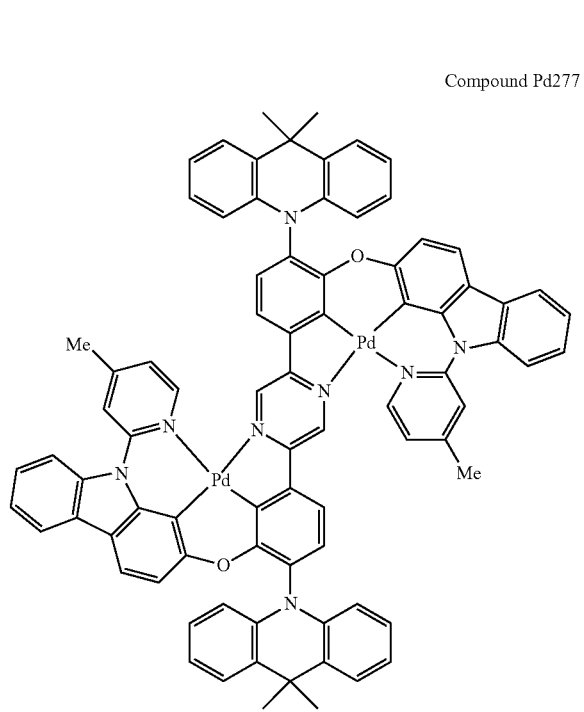
Compound Pd279
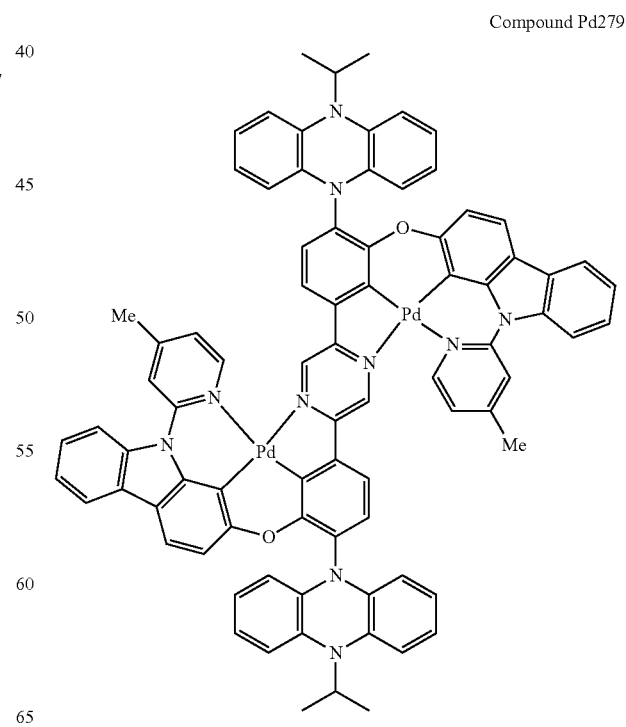

Compound Pd280
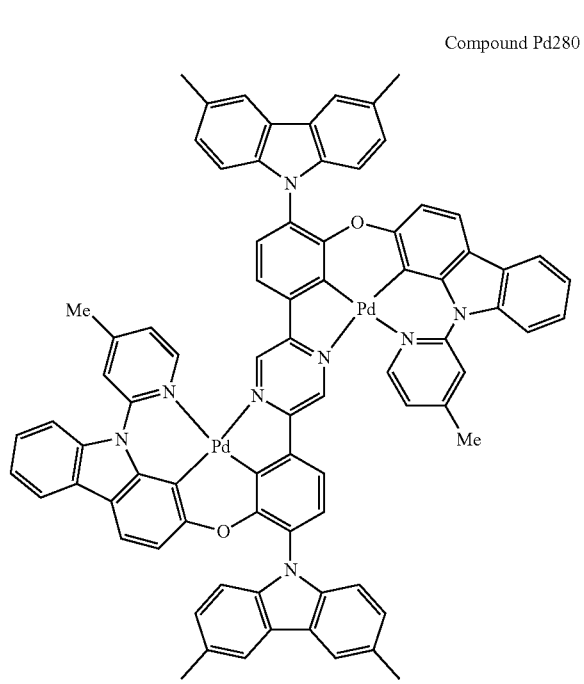
Compound Pd282
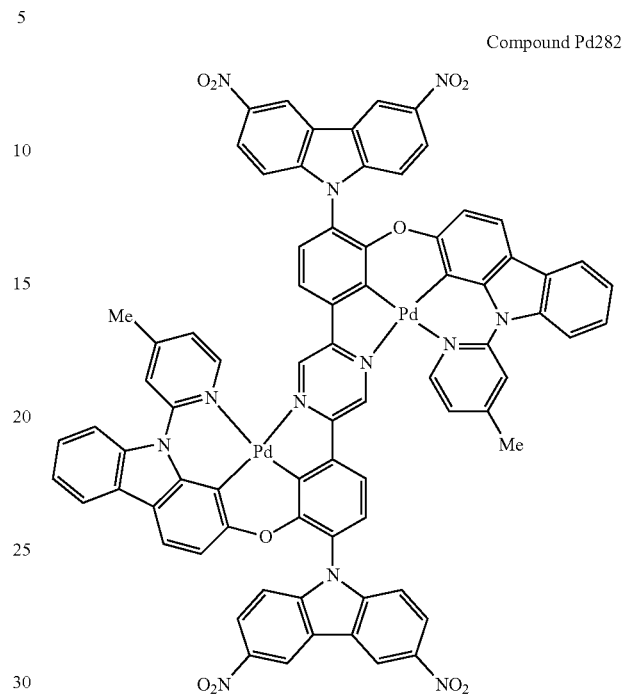
Compound Pd281
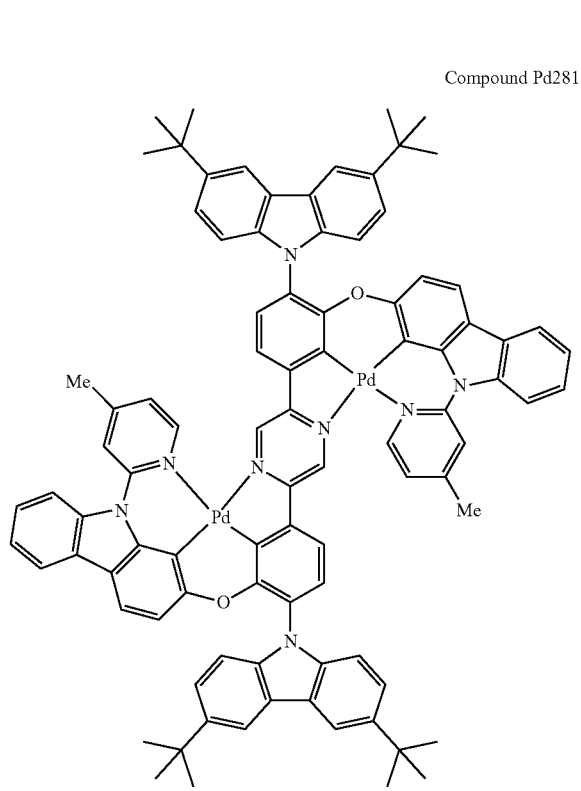
Compound Pd283
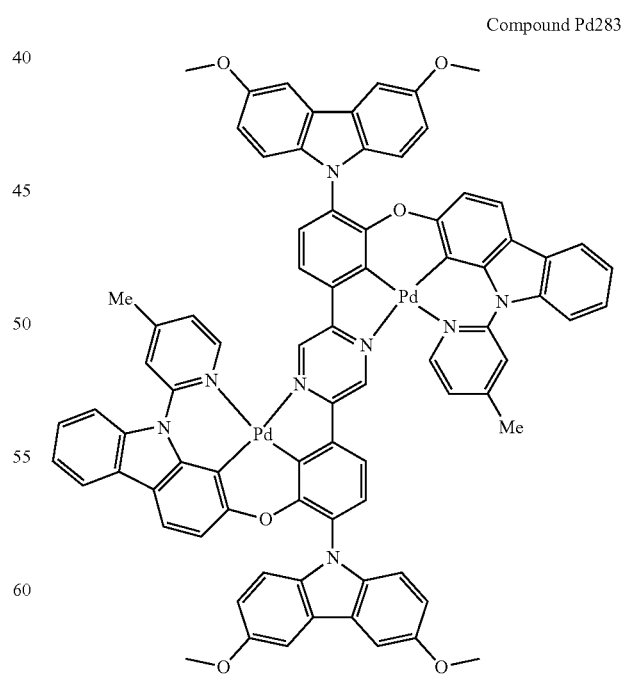

Compound Pd284
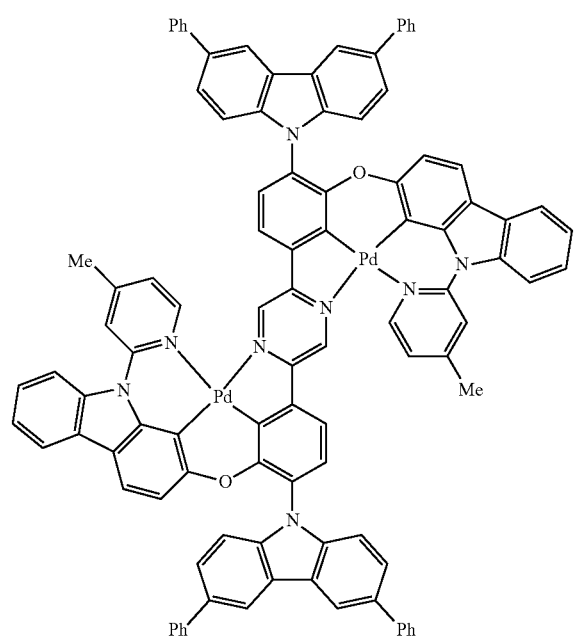
Compound Pd285
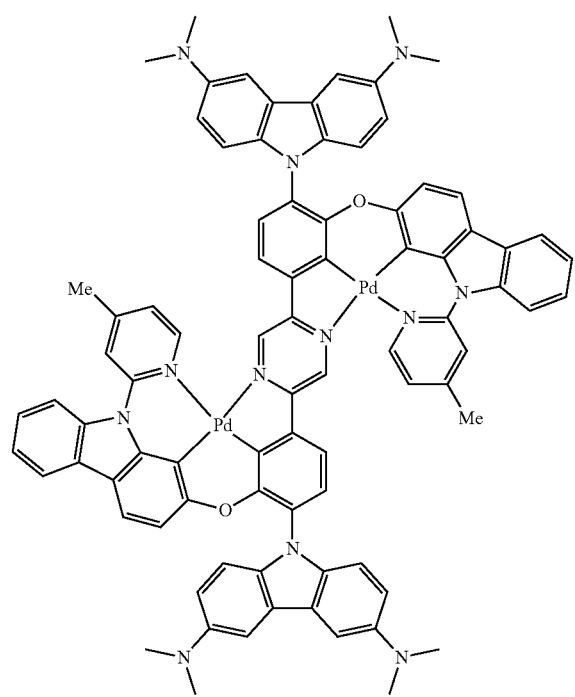
Compound Pd286
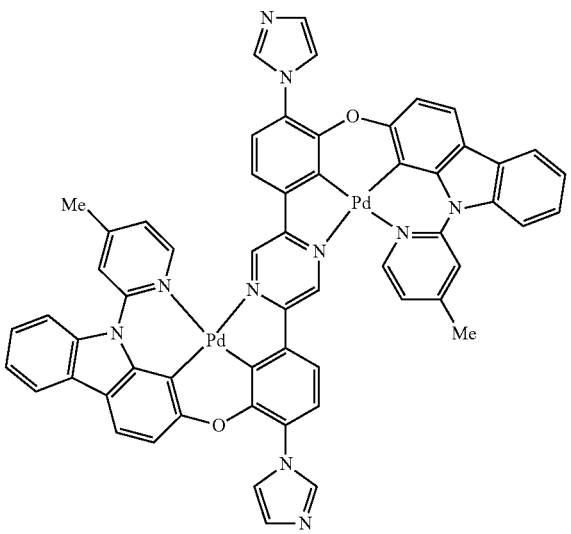
Compound Pd287
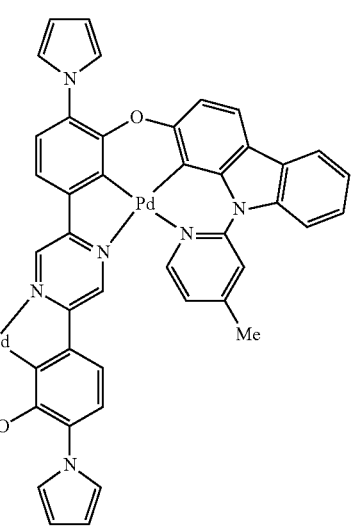
Compound Pd288
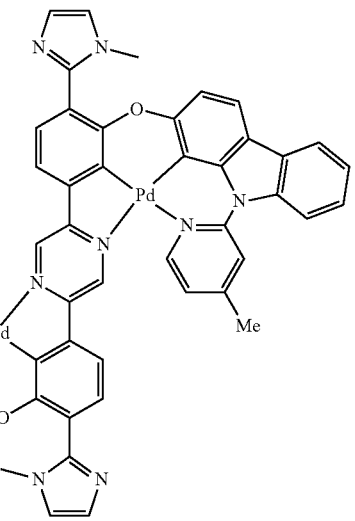

Compound Pd289
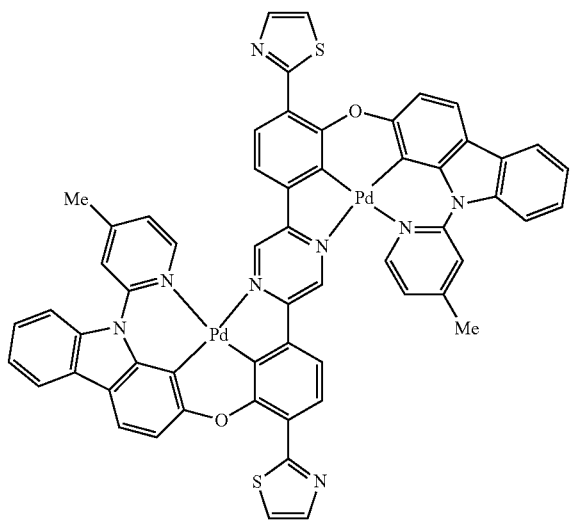
Compound Pd290
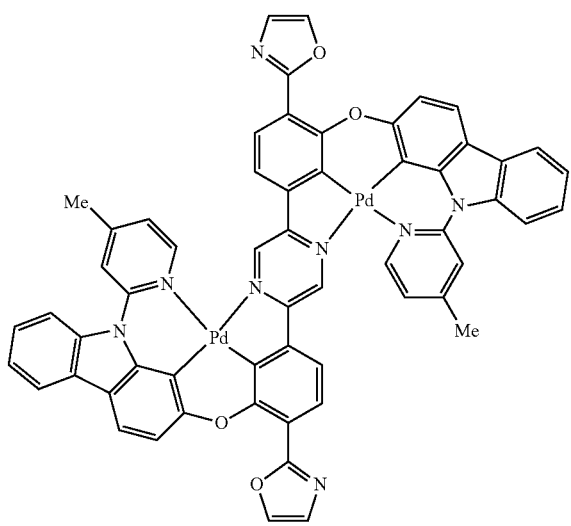
Compound Pd291
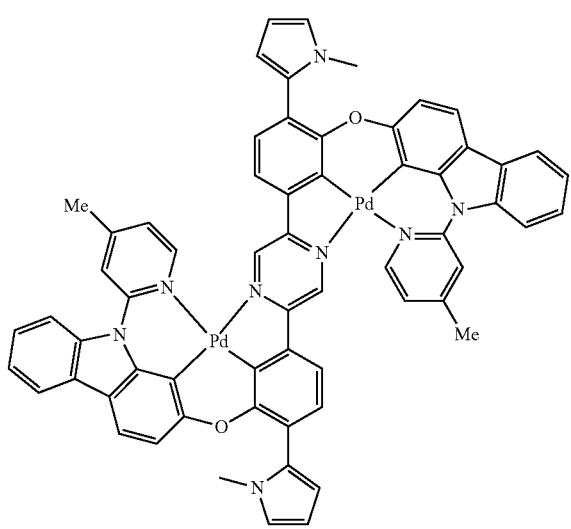
Compound Pd292
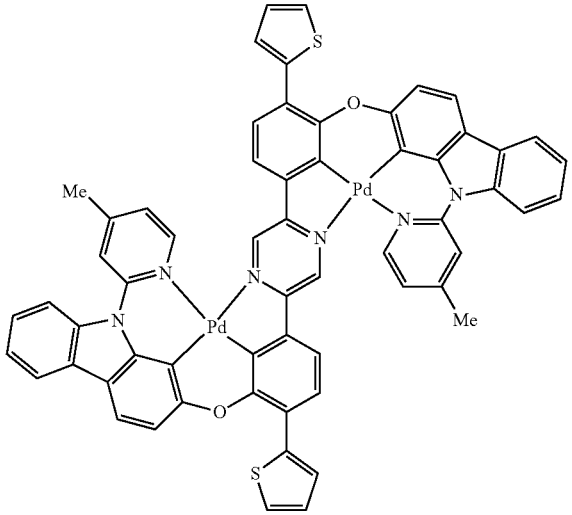
Compound Pd293
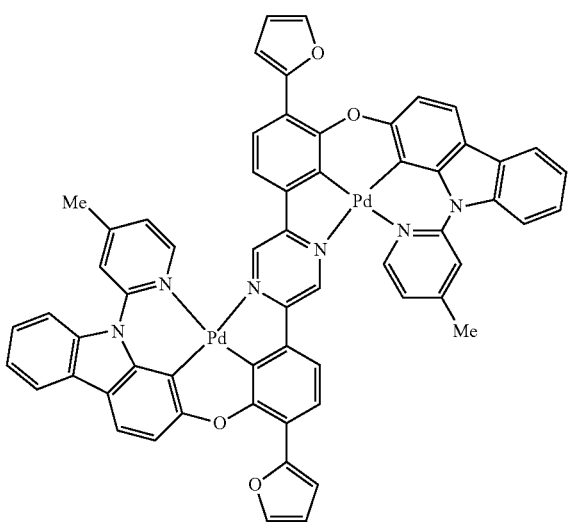
Compound Pd294
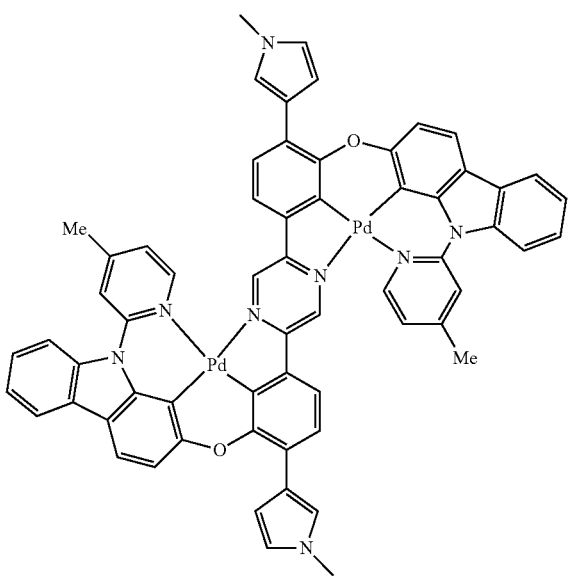

-continued
Compound Pd295
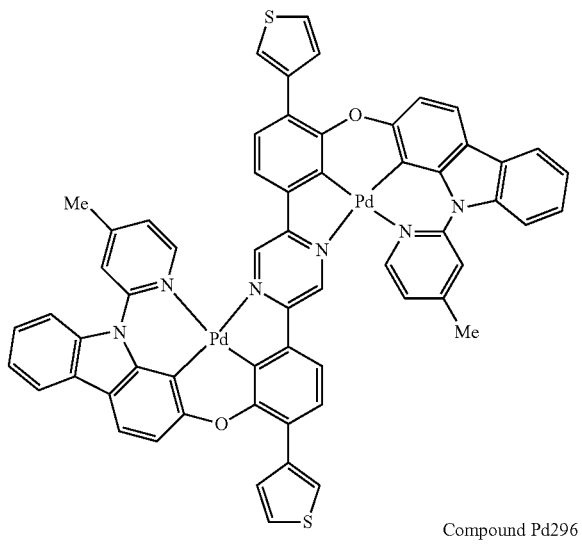
Compound Pd296
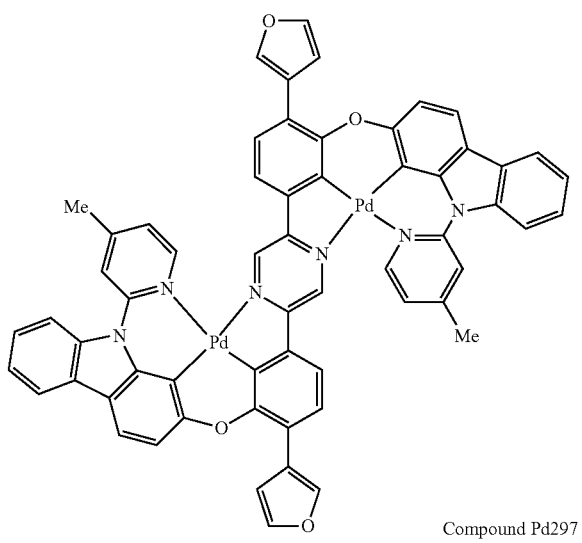
Compound Pd297
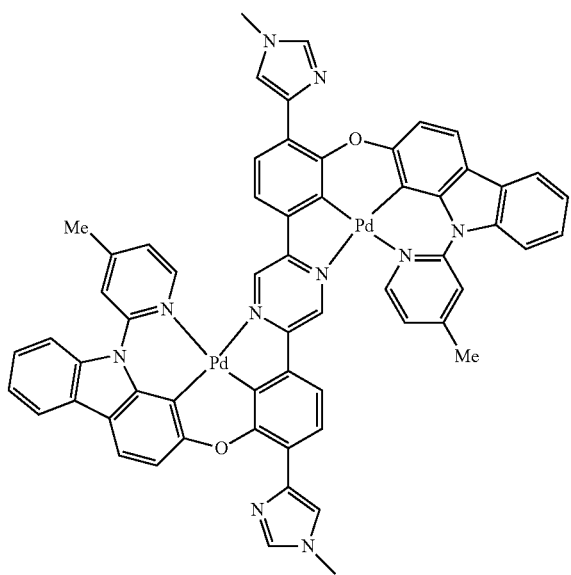
-continued
Compound Pd298
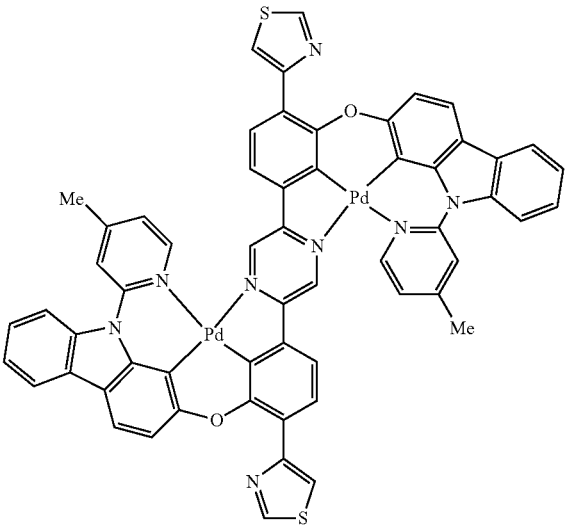
Compound Pd299
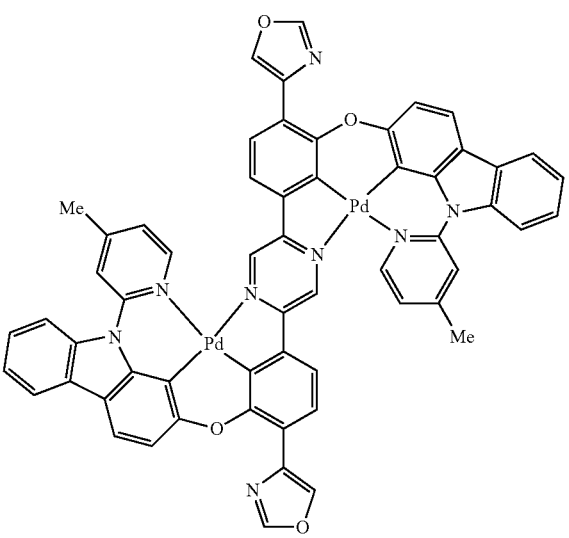
Compound Pd300
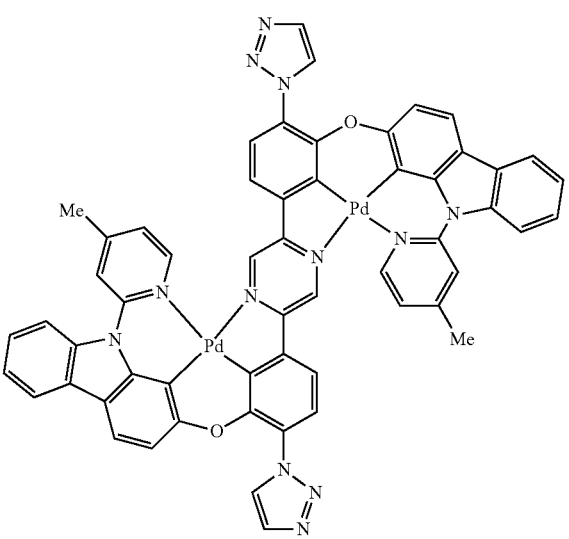

Compound Pd301
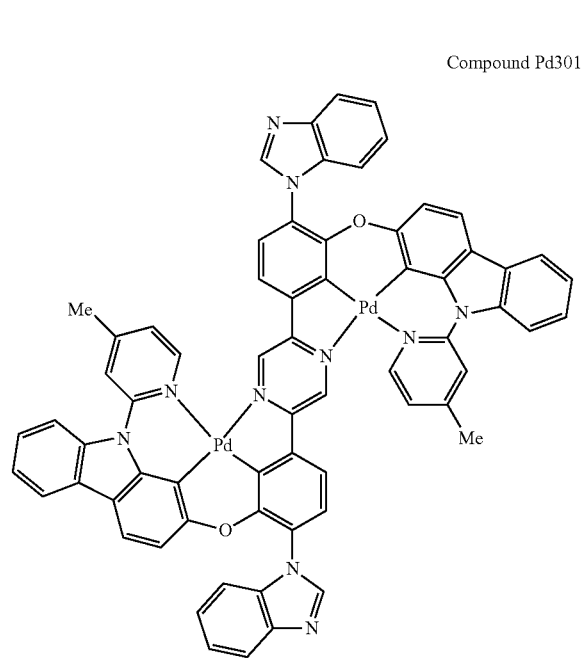
Compound Pd303
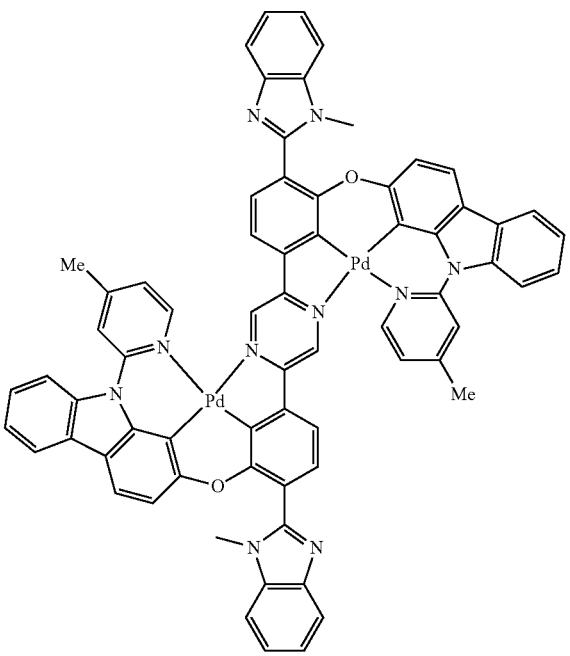
Compound Pd302
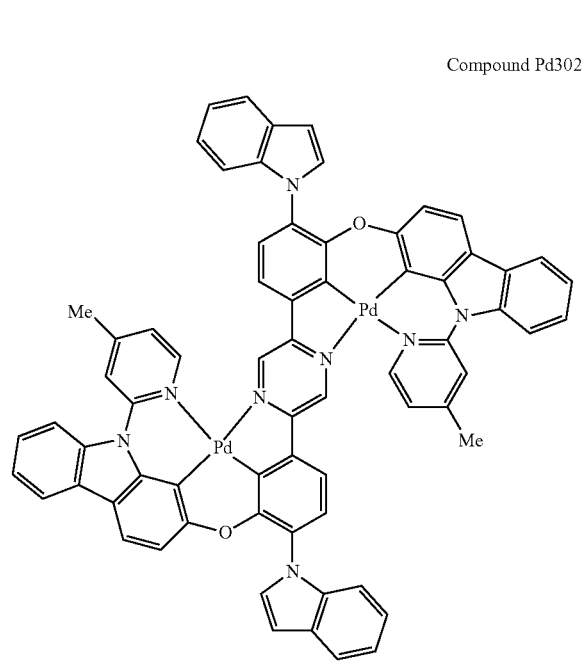
Compound Pd304
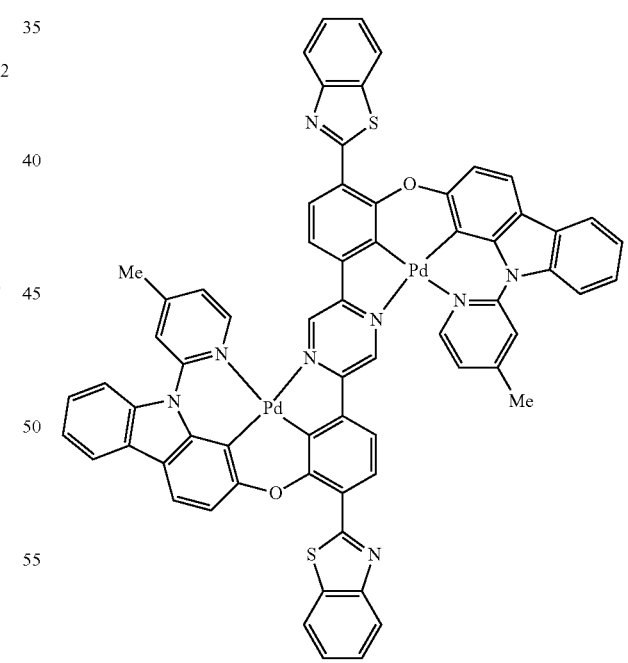

Compound Pd305
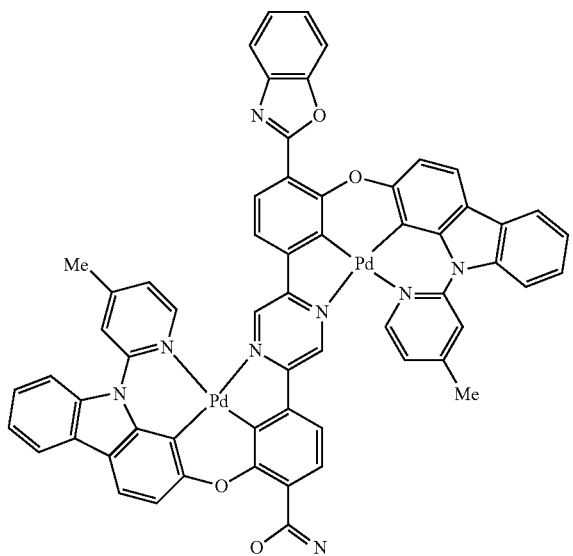
Compound Pd306
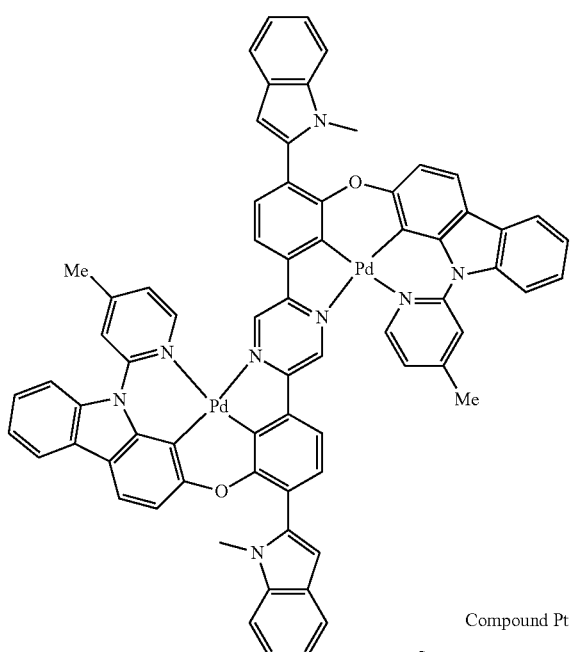
Compound Pt1
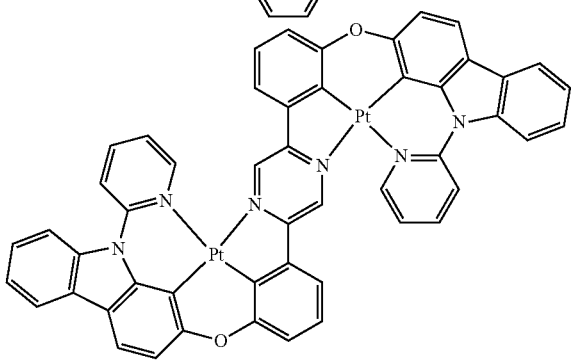
Compound Pt2
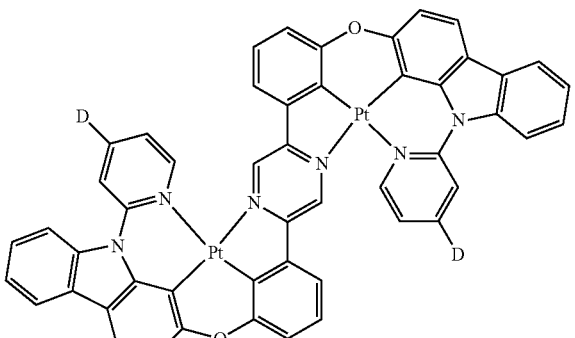
Compound Pt3
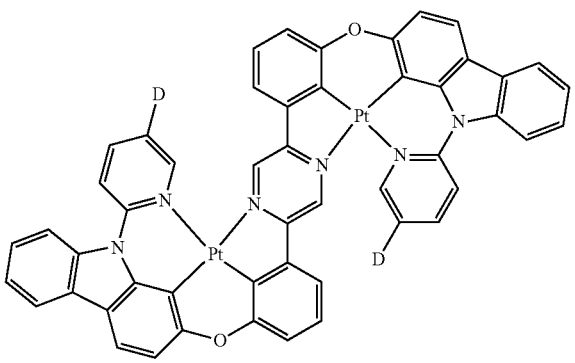
Compound Pt4
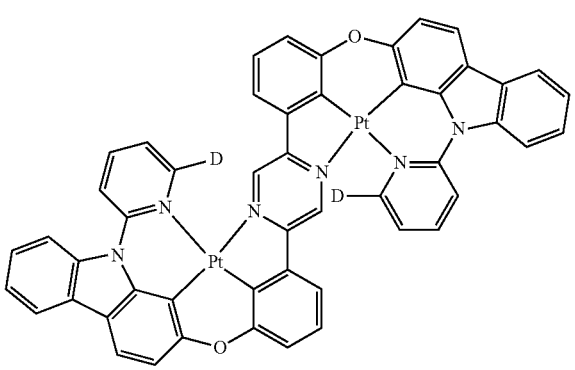
Compound Pt5
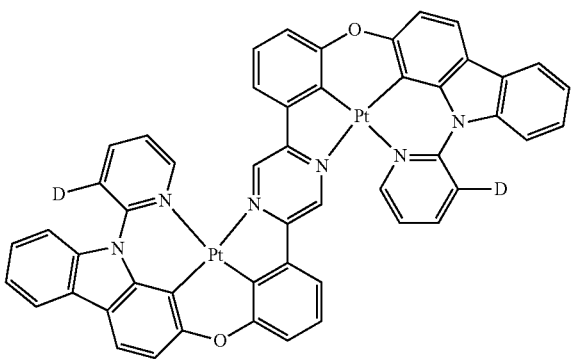

Compound Pt6
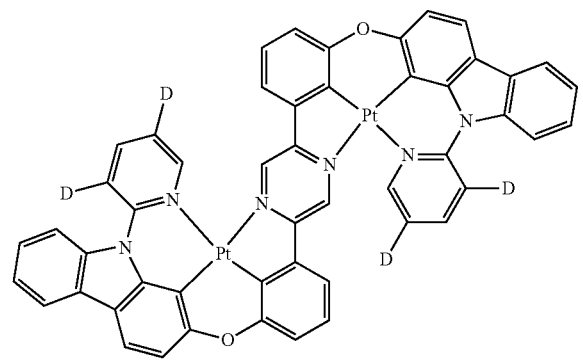
Compound Pt7
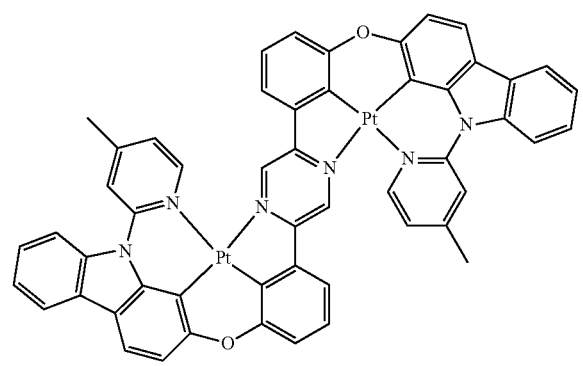
Compound Pt8
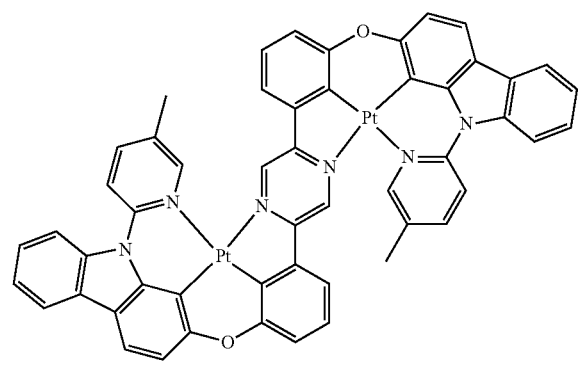
Compound Pt9
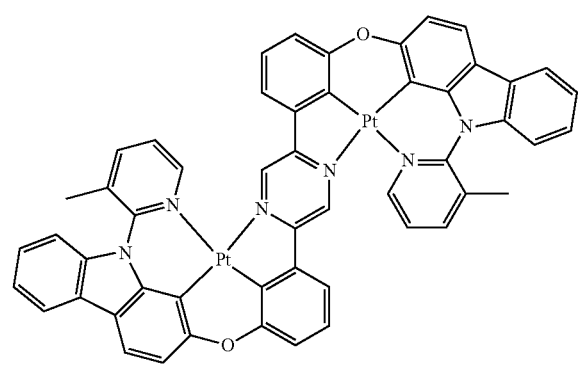
Compound Pt10
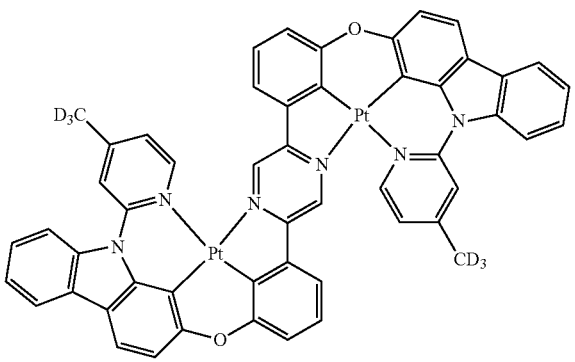
Compound Pt11
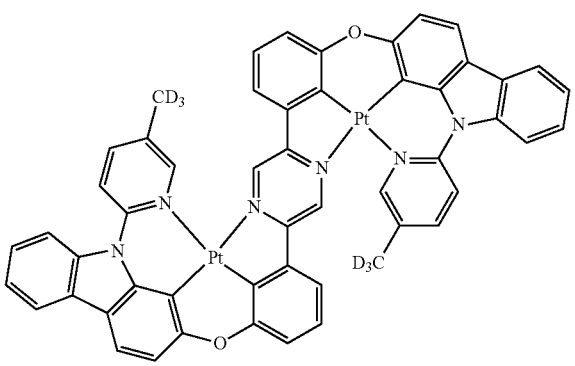
Compound Pt12
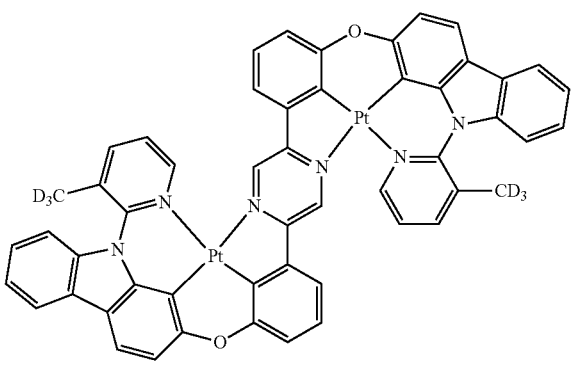
Compound Pt13
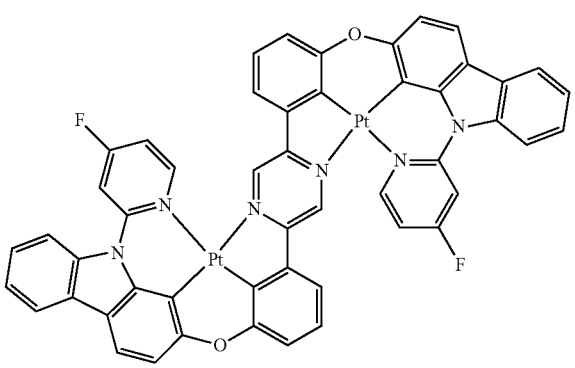

Compound Pt14
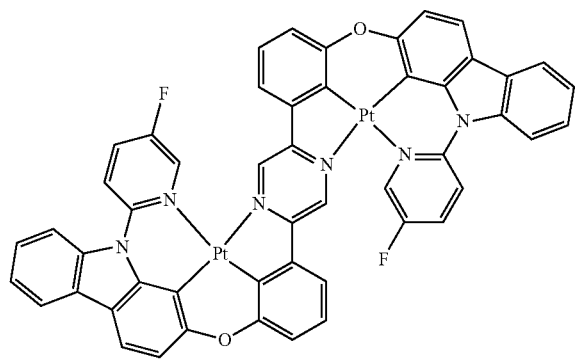
Compound Pt18
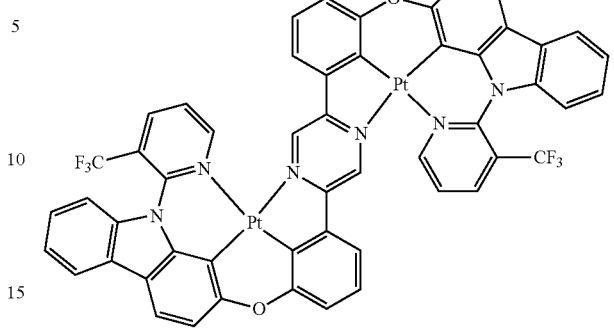
Compound Pt15
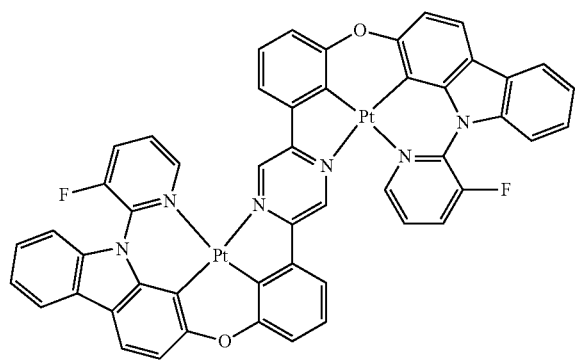
Compound Pt19
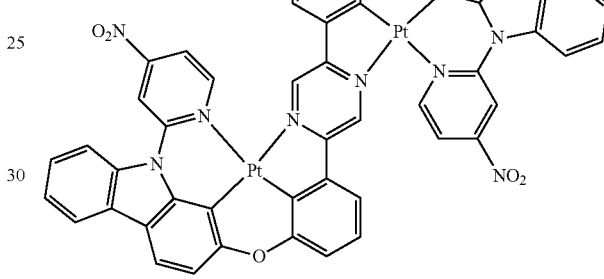
Compound Pt16
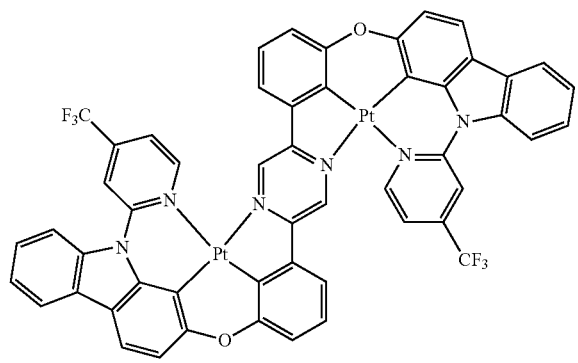
Compound Pt20
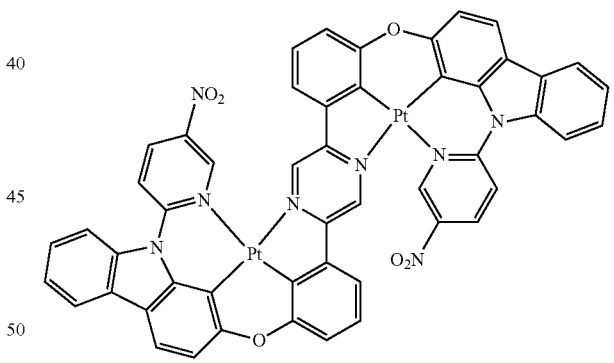
Compound Pt17
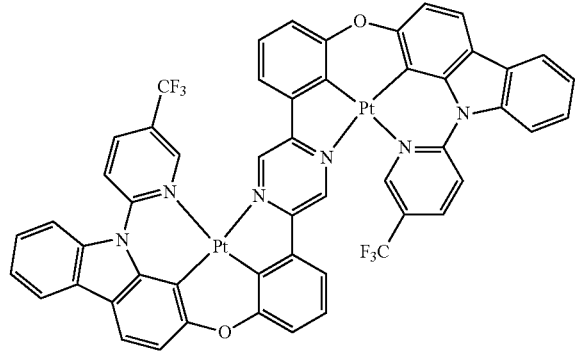
Compound Pt21
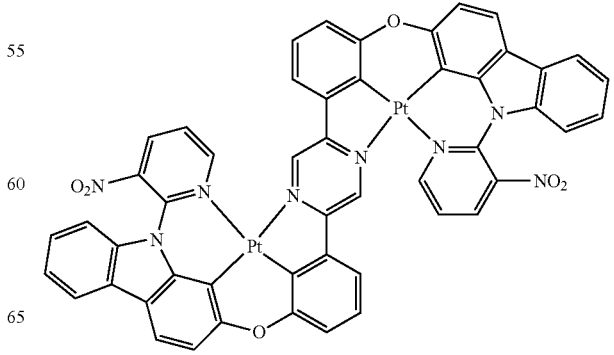

101
-continued
Compound Pt22
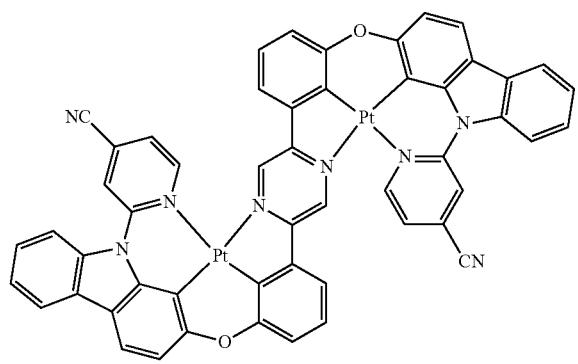
Compound Pt23
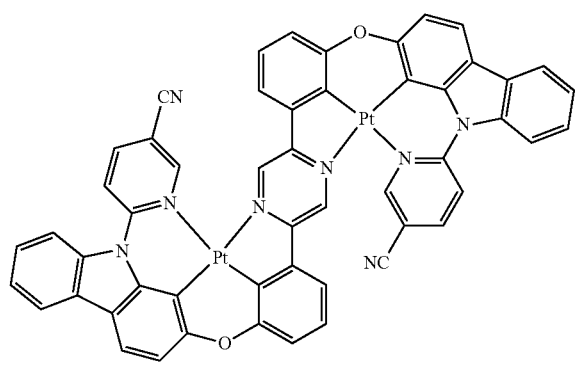
Compound Pt24
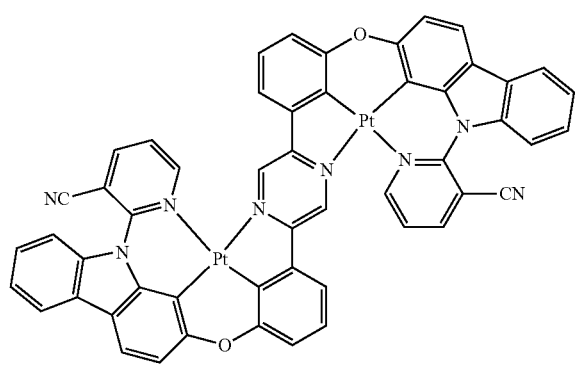
Compound Pt25
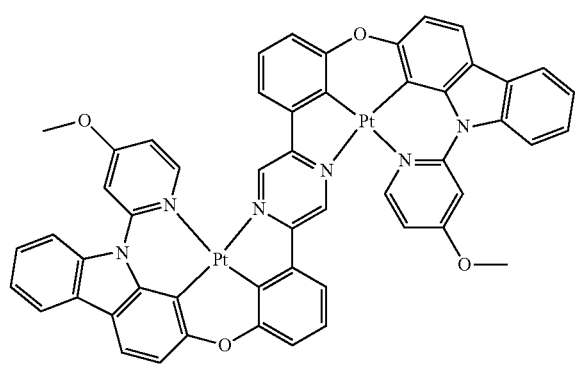
102
-continued
Compound Pt26
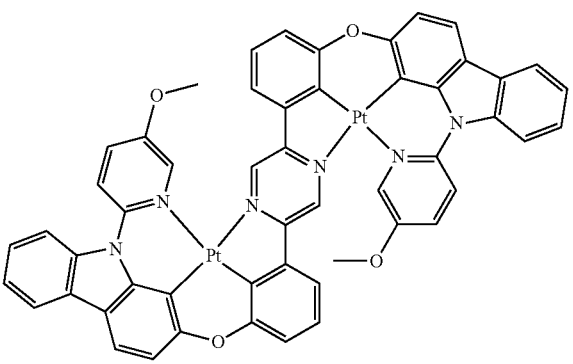
Compound Pt27
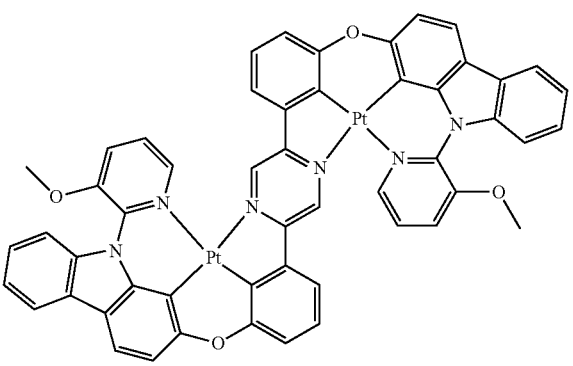
Compound Pt28
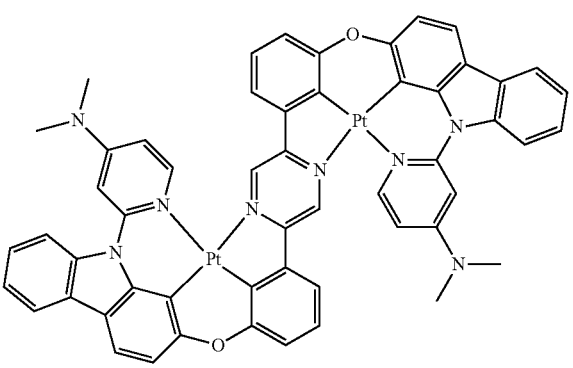
Compound Pt29
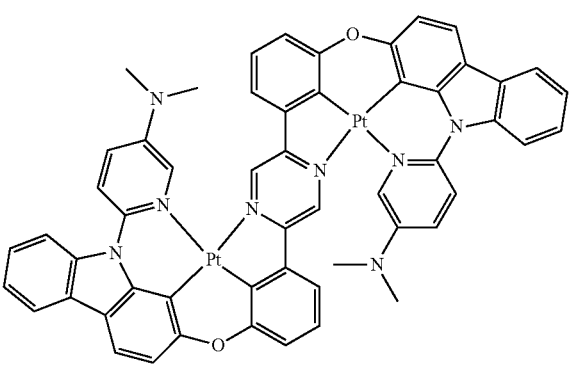

Compound Pt30
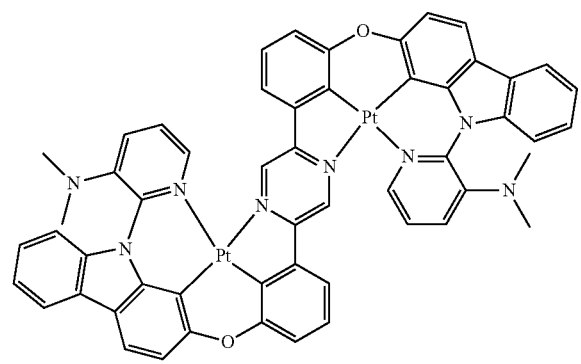
Compound Pt34
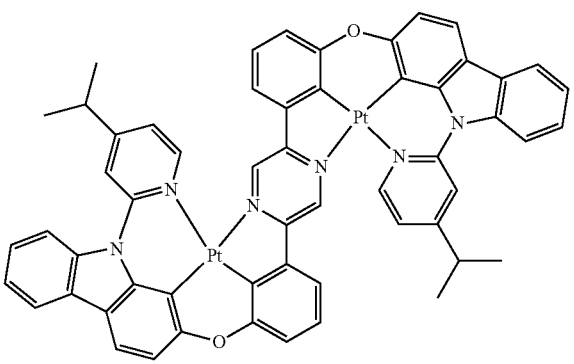
Compound Pt31
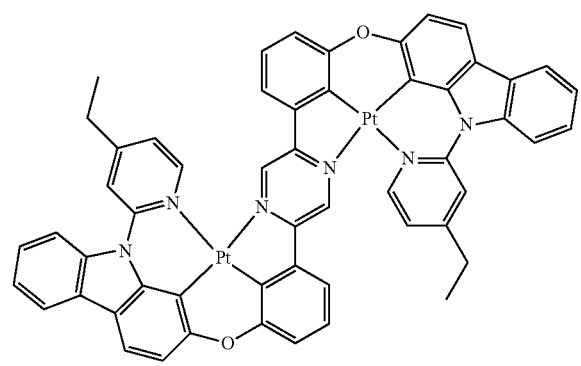
Compound Pt35
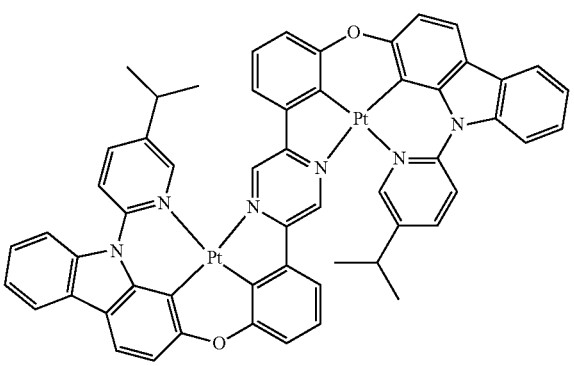
Compound Pt32
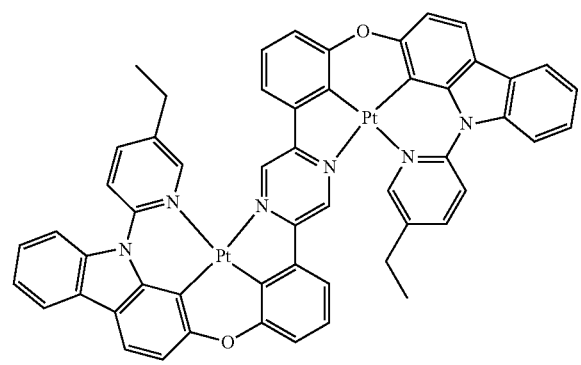
Compound Pt36
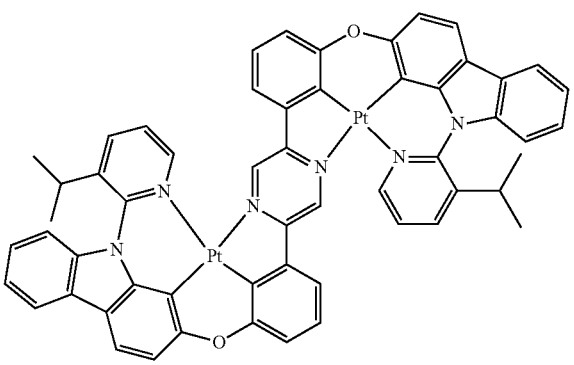
Compound Pt33
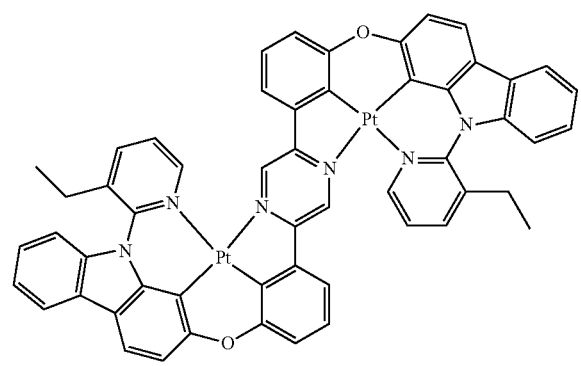
Compound Pt37
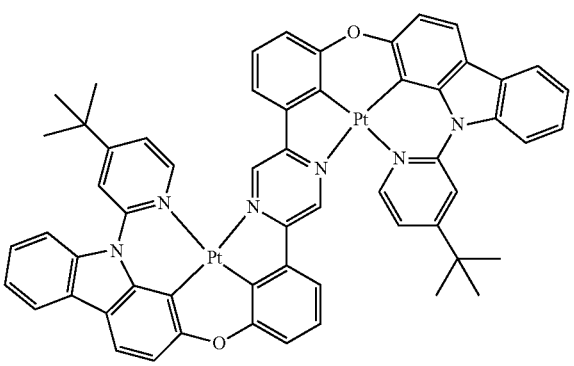

Compound Pt38
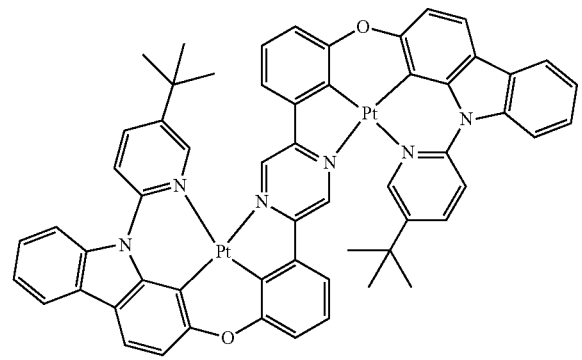
Compound Pt39
Compound Pt40
Compound Pt41
Compound Pt42
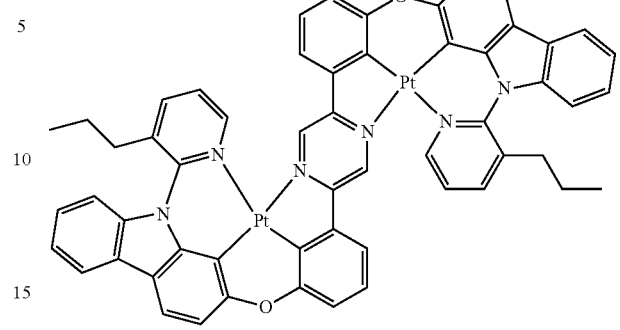
Compound Pt43
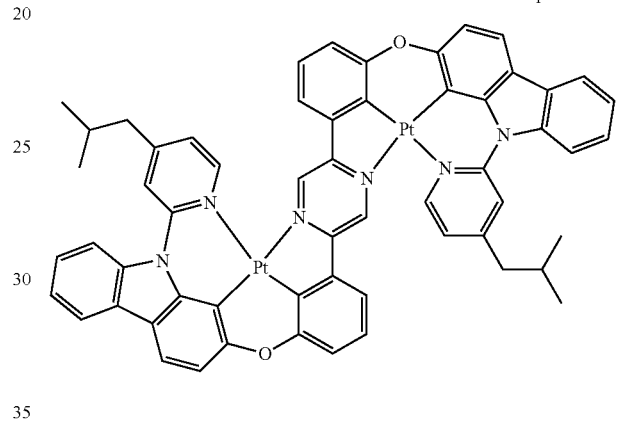
Compound Pt44
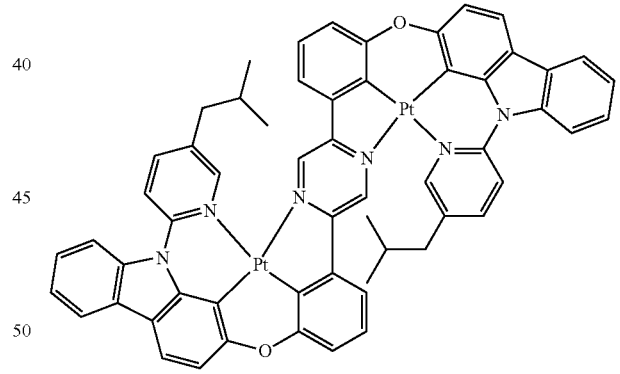
Compound Pt45
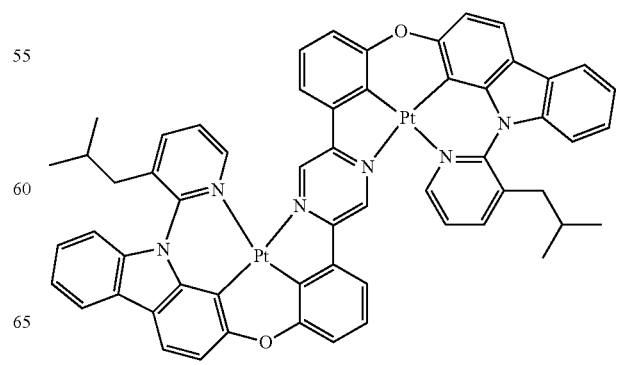

Compound Pt46
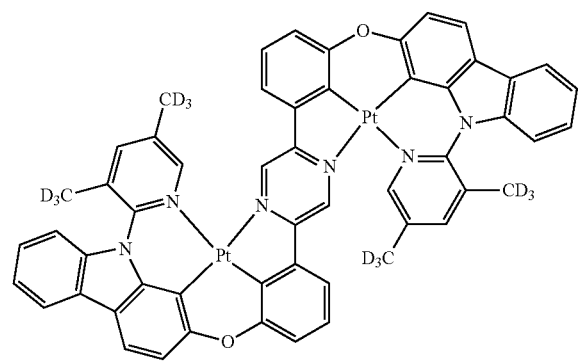
Compound Pt47
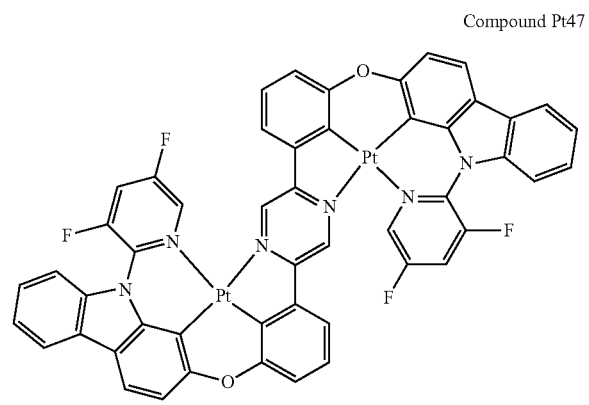
Compound Pt48
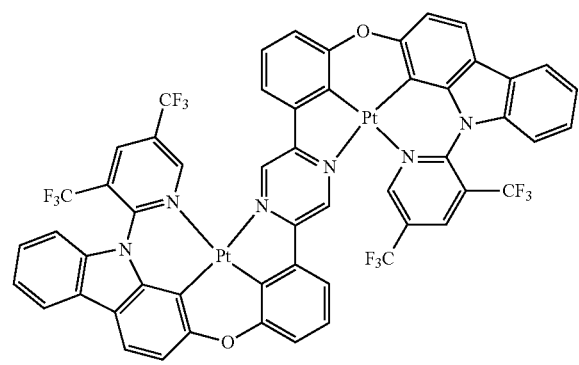
Compound Pt49
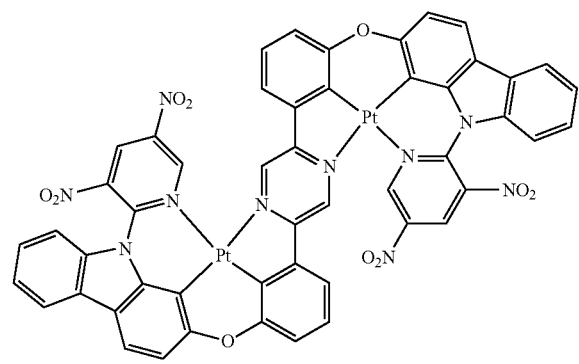
Compound Pt50
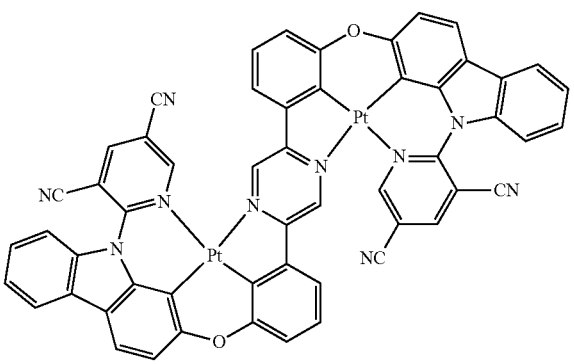
Compound Pt51
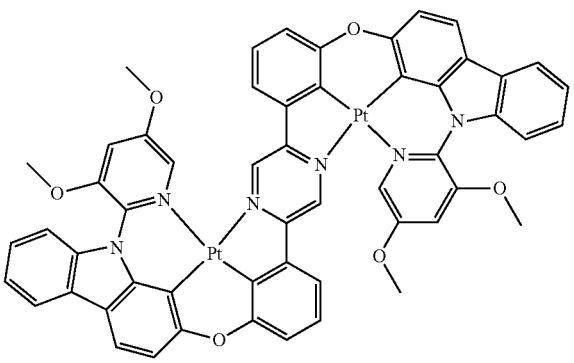
Compound Pt52
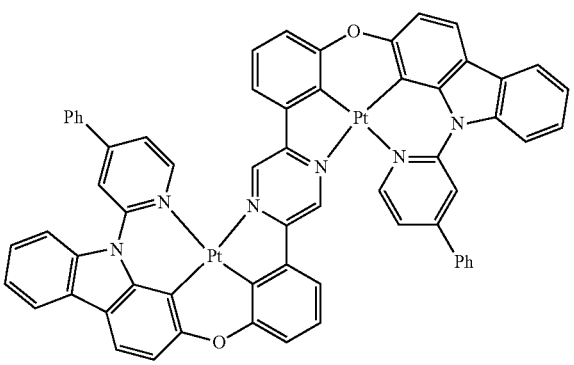
Compound Pt53
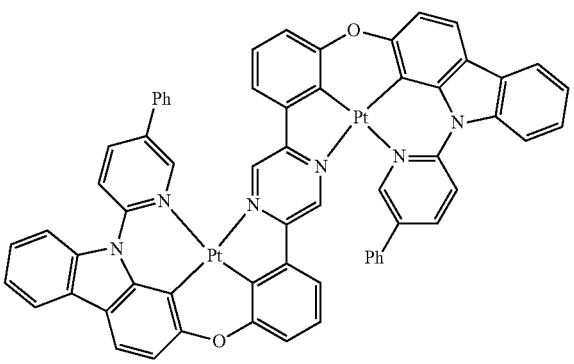

Compound Pt54
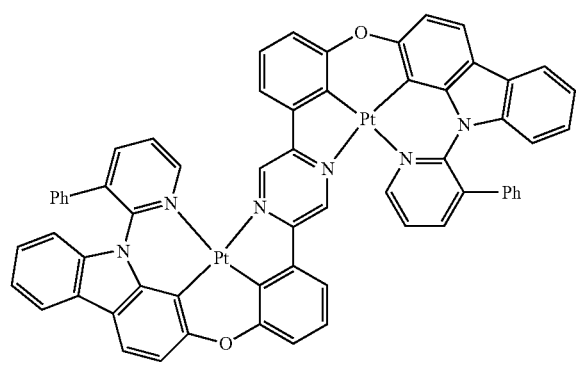
Compound Pt58
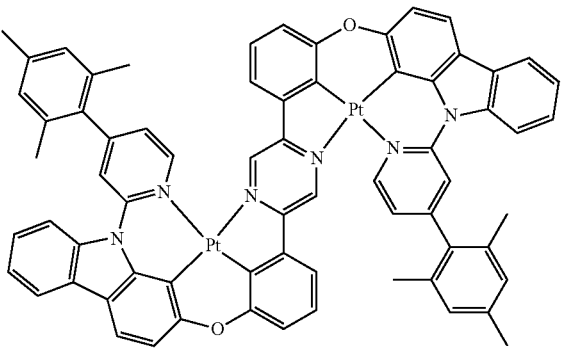
Compound Pt55
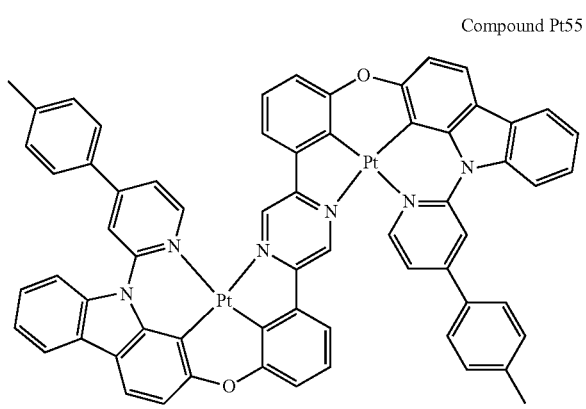
Compound Pt59
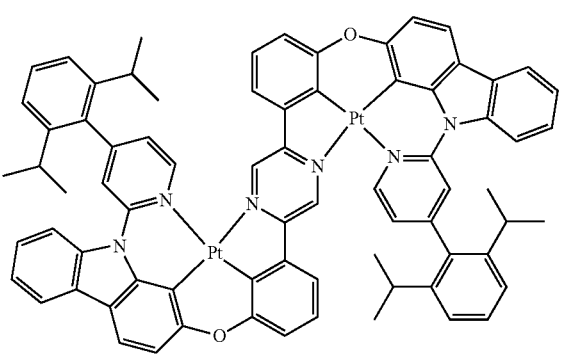
Compound Pt56
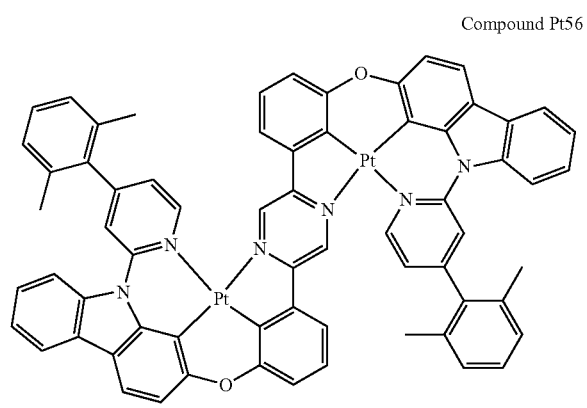
Compound Pt60
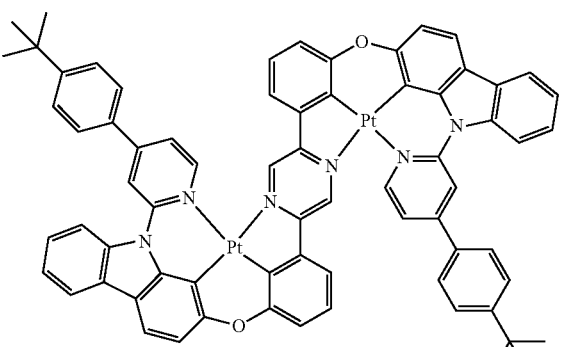
Compound Pt57
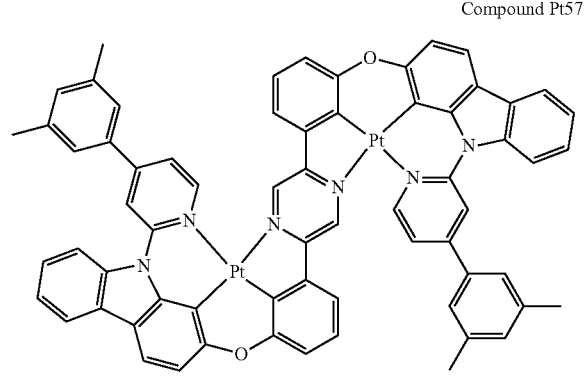
Compound Pt61

Compound Pt62
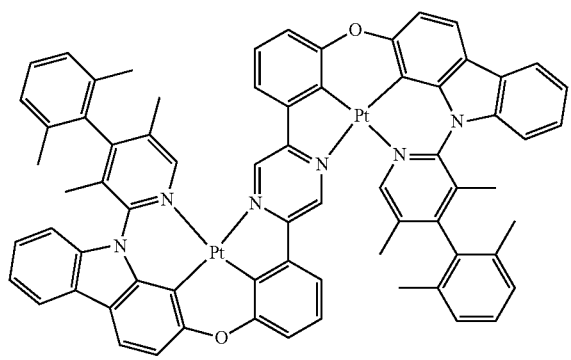
Compound Pt66
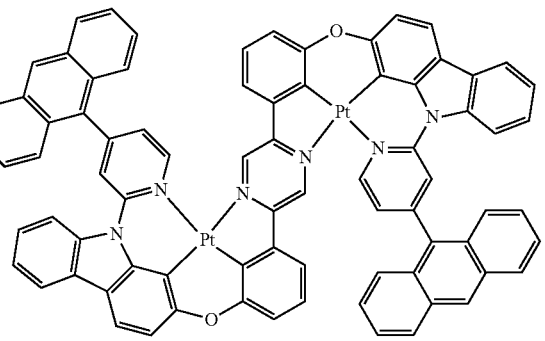
Compound Pt63
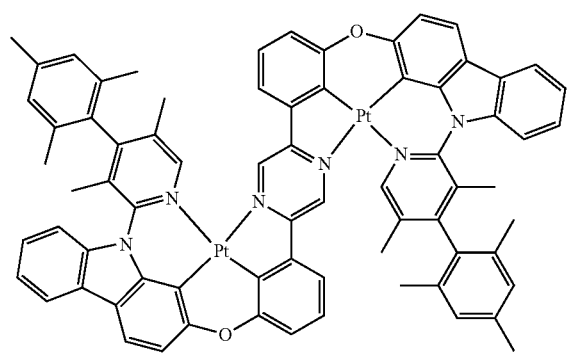
Compound Pt67
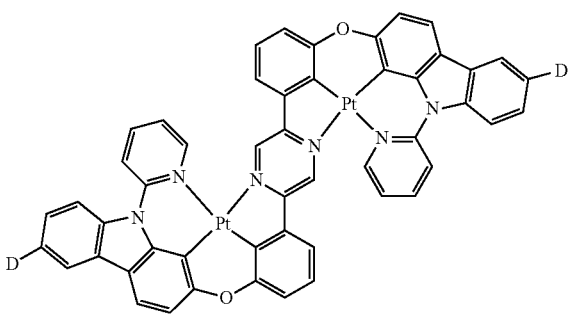
Compound Pt64
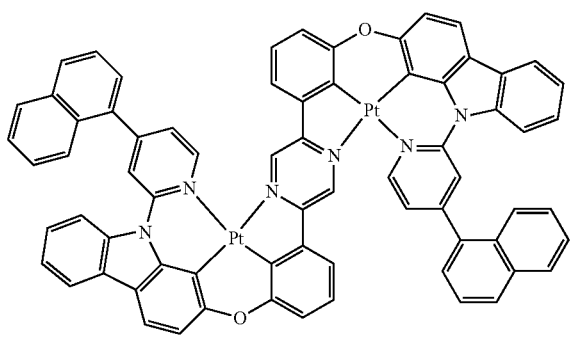
Compound Pt68
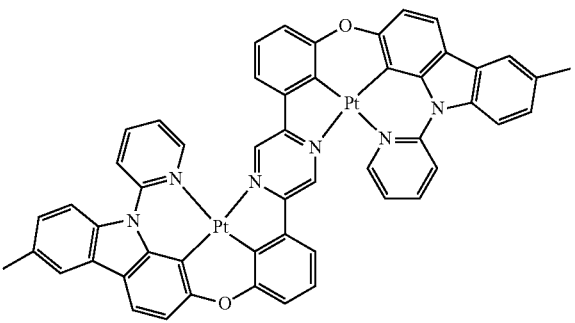
Compound Pt5
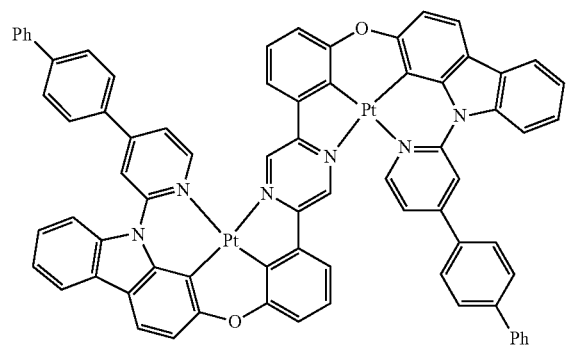
Compound Pt69
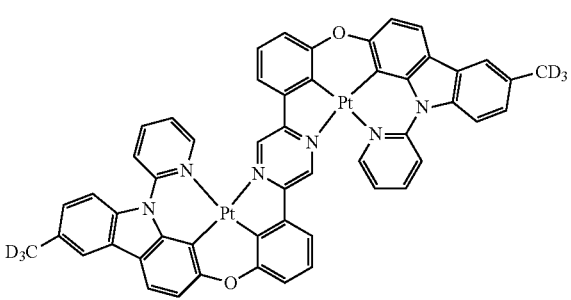

Compound Pt70
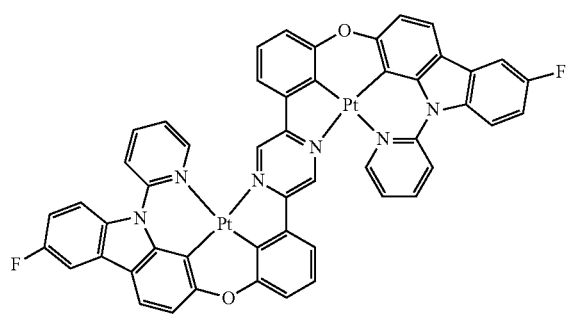
Compound Pt71
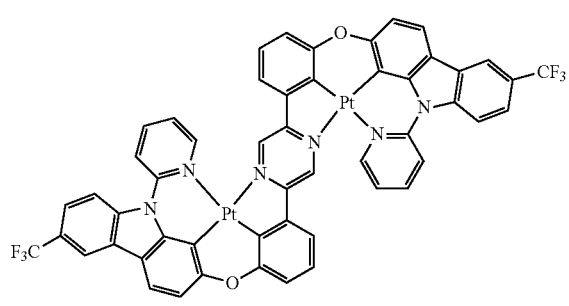
Compound Pt72
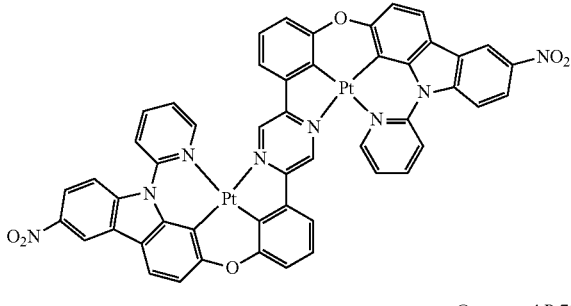
Compound Pt73
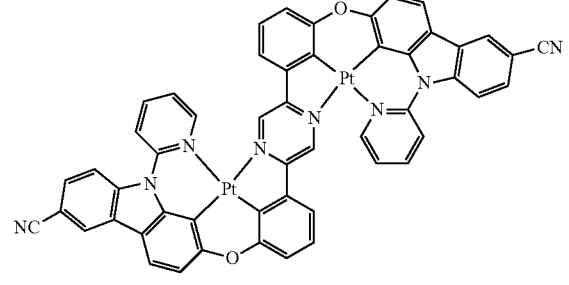
Compound Pt74
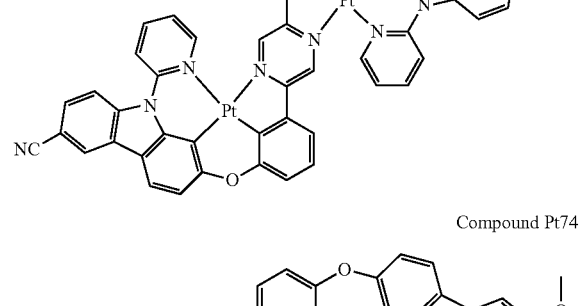
Compound Pt75
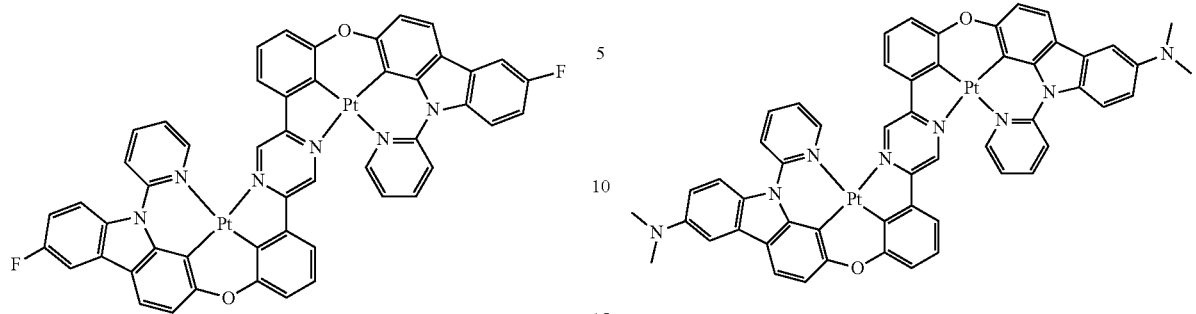
Compound Pt76
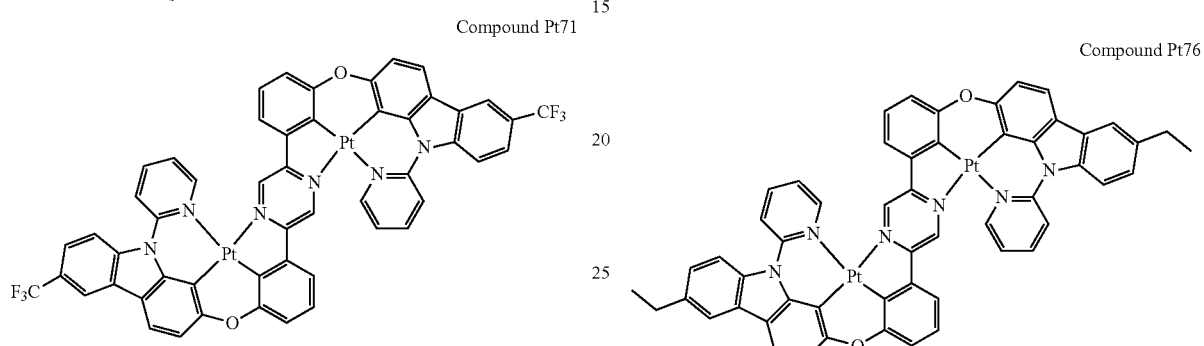
Compound Pt77
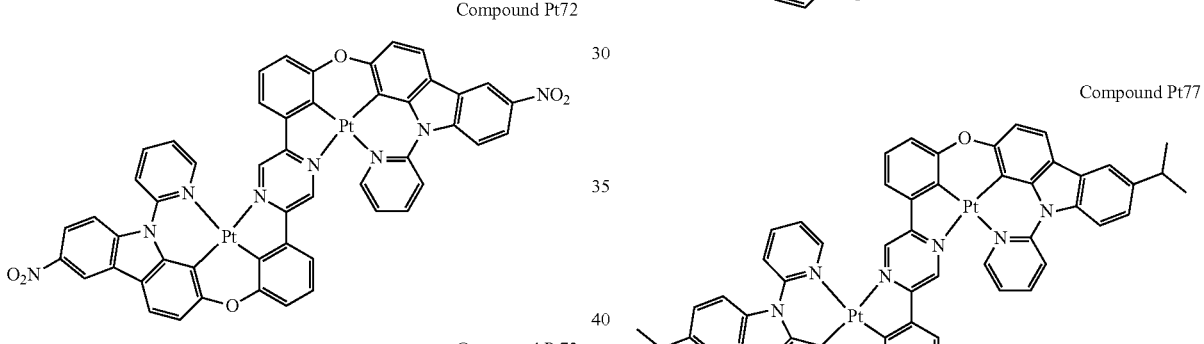
Compound Pt78
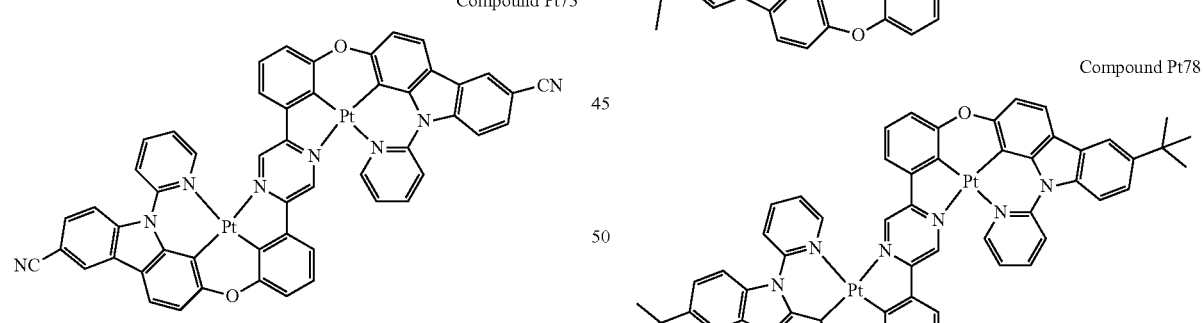
Compound Pt79
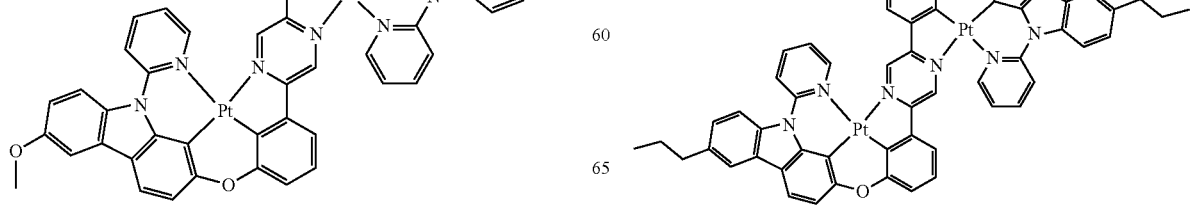

Compound Pt80
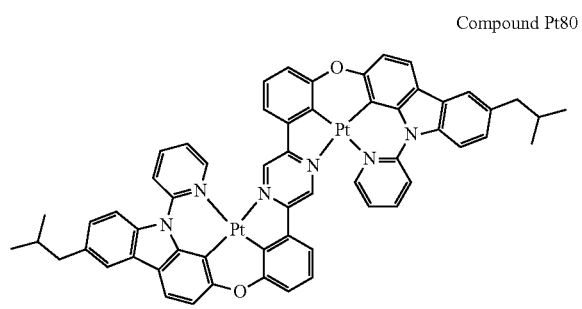
Compound Pt81
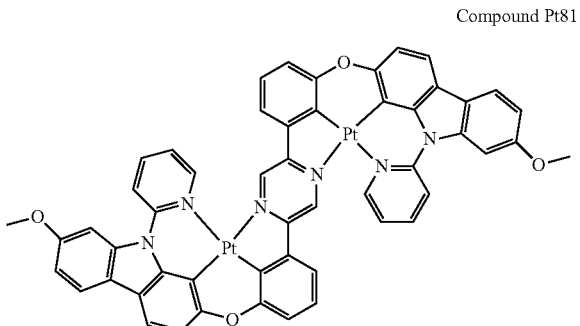
Compound Pt82
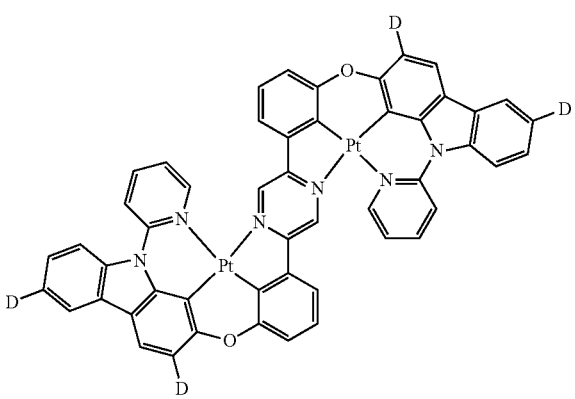
Compound Pt83
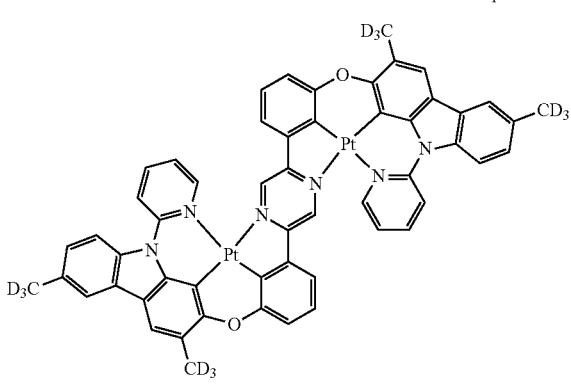
Compound Pt84
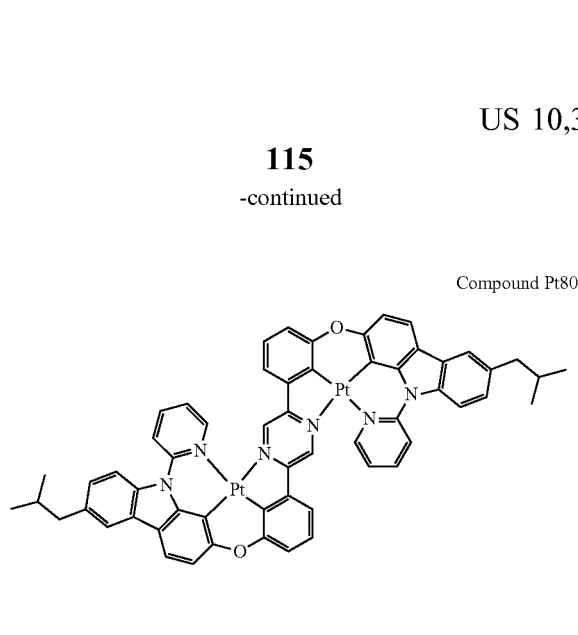
Compound Pt85
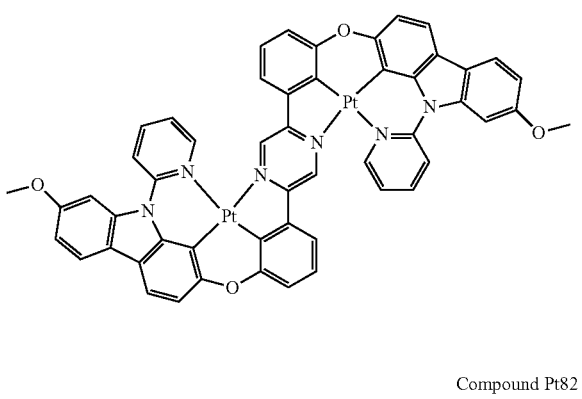
Compound Pt86
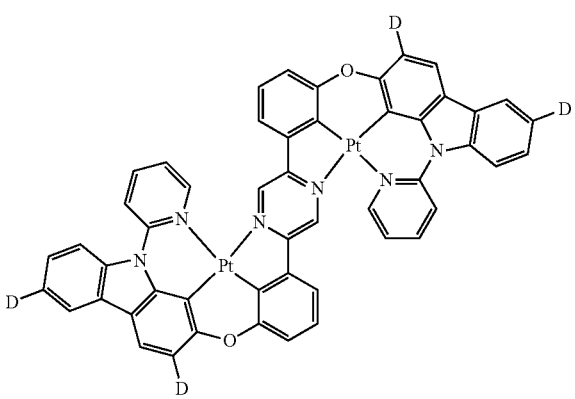
Compound Pt87
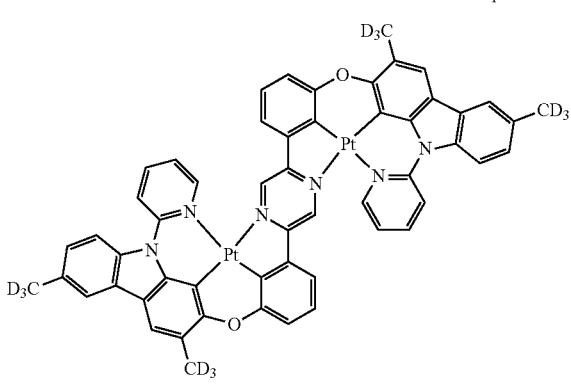

Compound Pt88
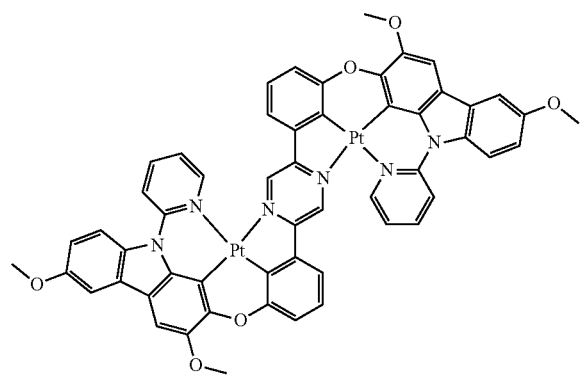
Compound Pt92
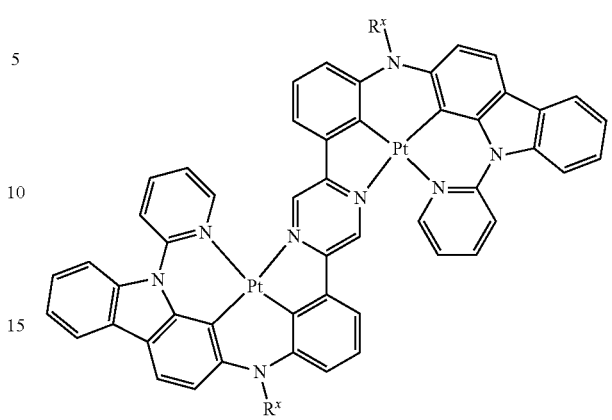
Compound Pt89
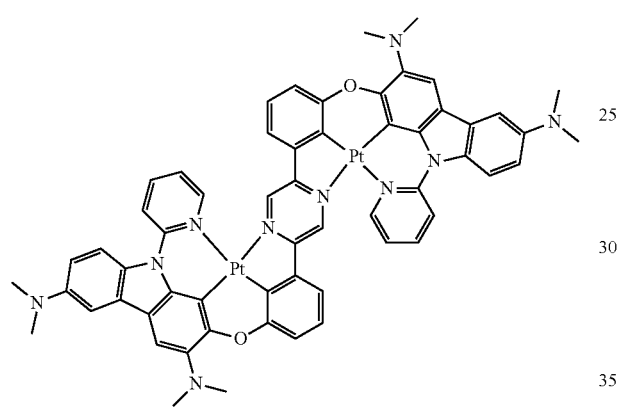
Compound Pt93
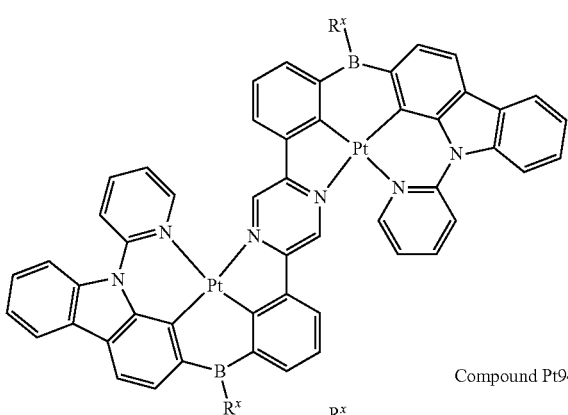
Compound Pt90
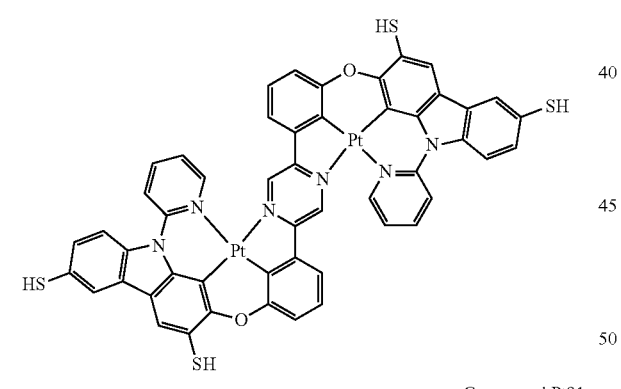
Compound Pt94
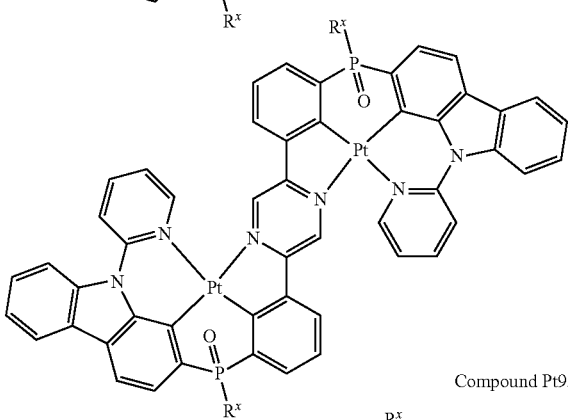
Compound Pt91
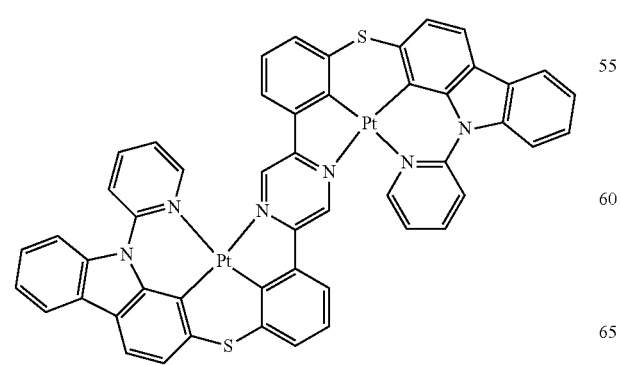
Compound Pt95

Compound Pt96
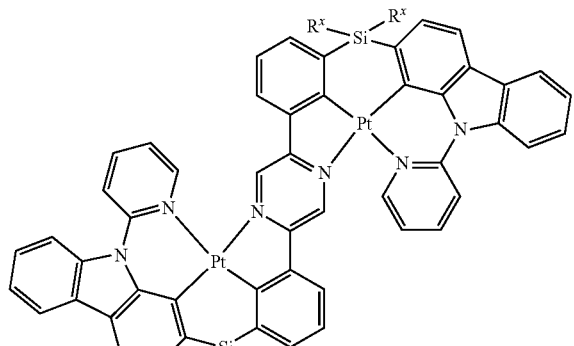
Compound Pt97
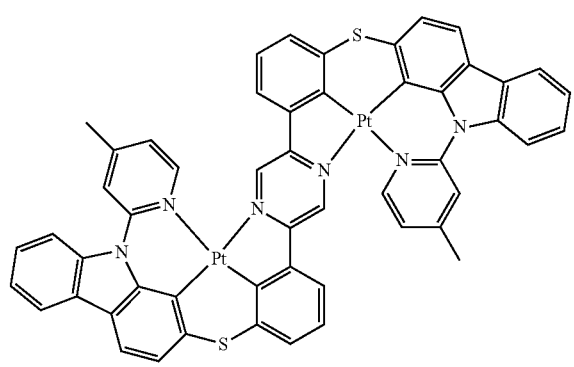
Compound Pt98
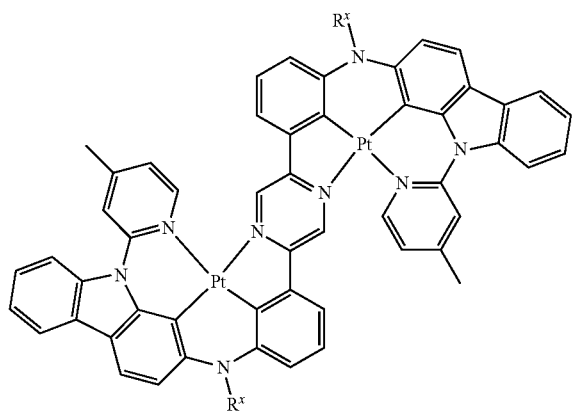
Compound Pt99
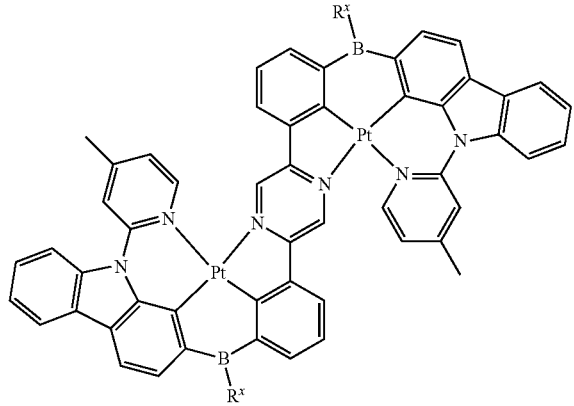
Compound Pt100
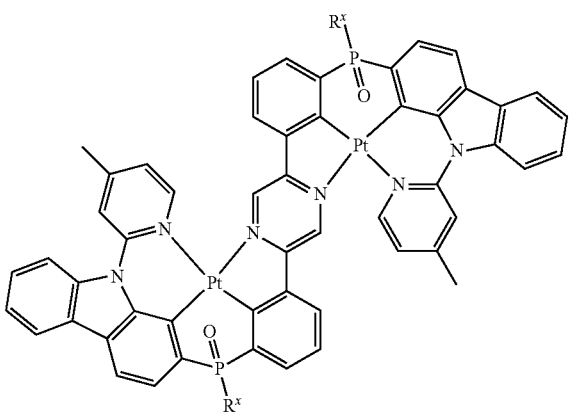
Compound Pt101
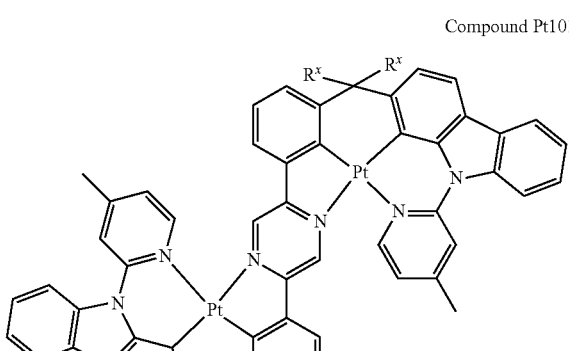
Compound Pt102
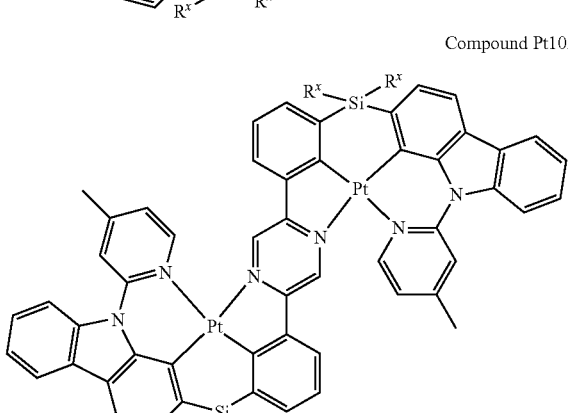
Compound Pt103
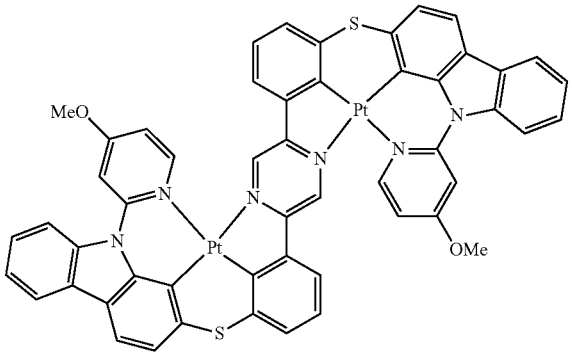

Compound Pt104
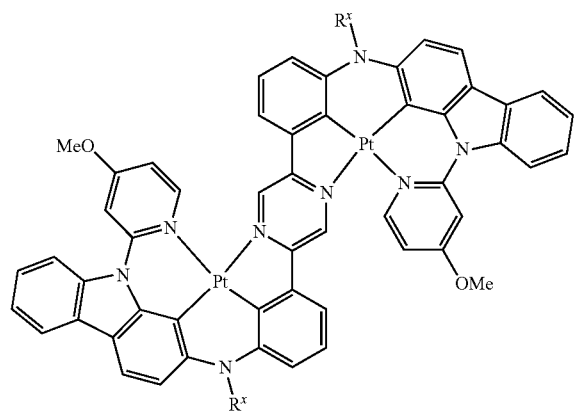
Compound Pt108
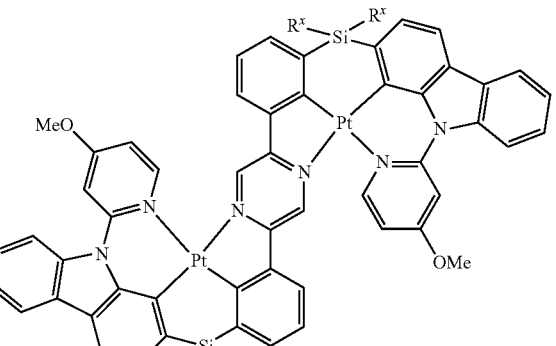
Compound Pt105
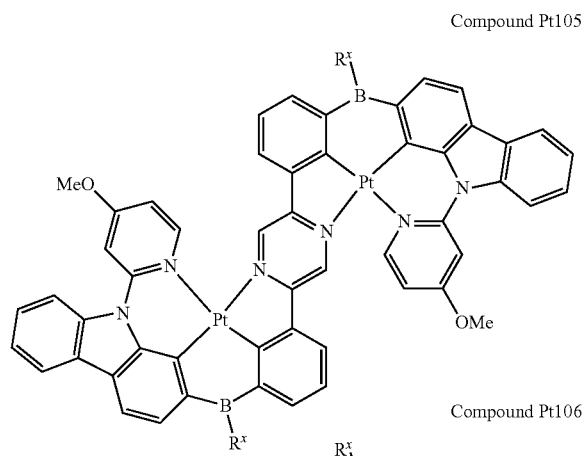
Compound Pt109
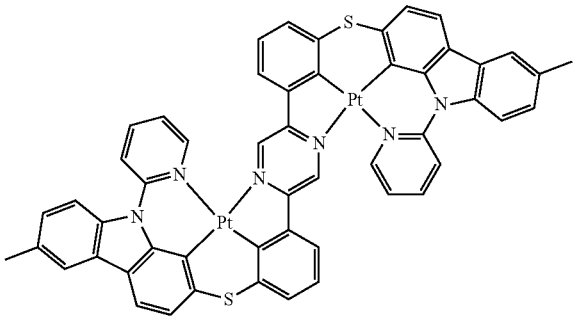
Compound Pt106
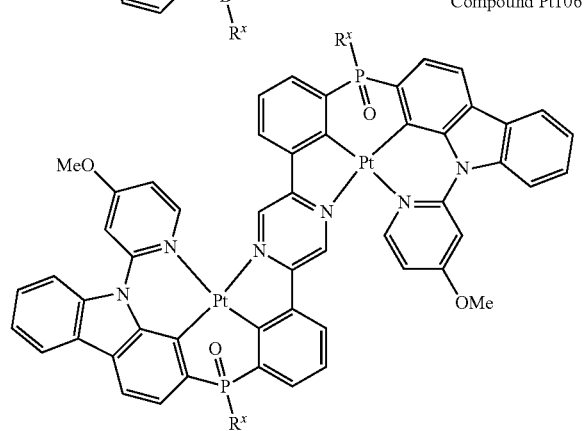
Compound Pt110
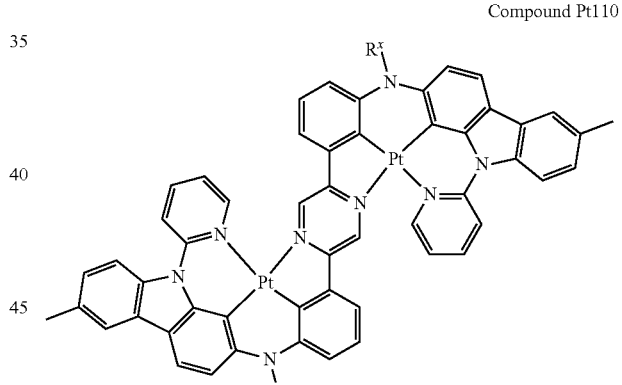
Compound Pt107
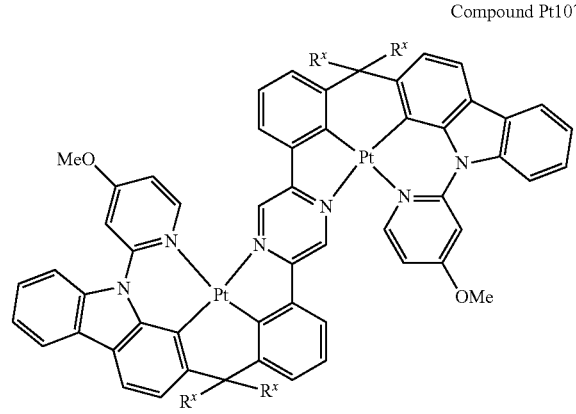
Compound Pt111
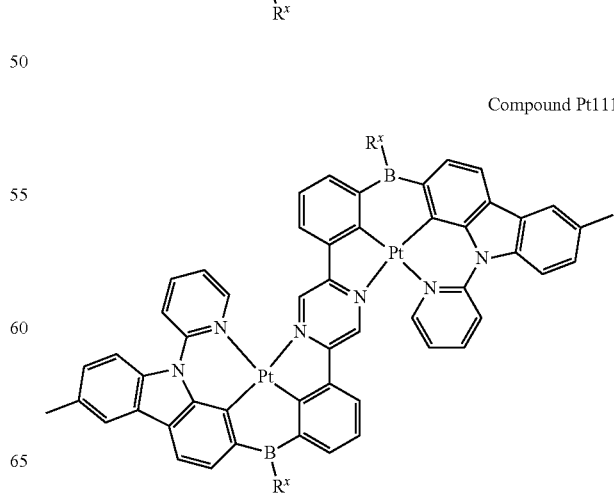

Compound Pt112
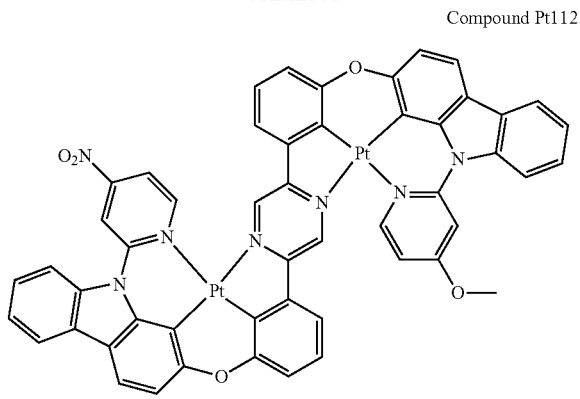
Compound Pt113
Compound Pt114
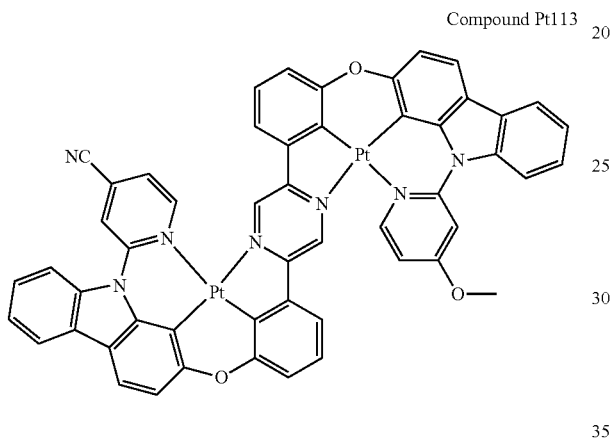
Compound Pt115
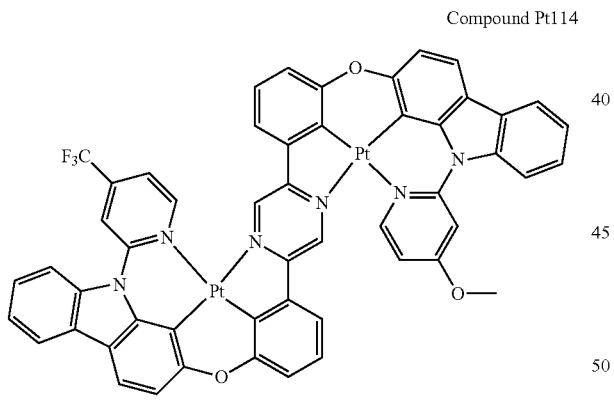
Compound Pt116
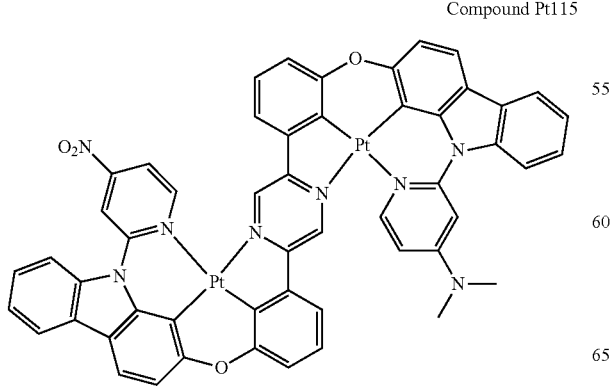
Compound Pt117
Compound Pt118
Compound Pt119

Compound Pt120
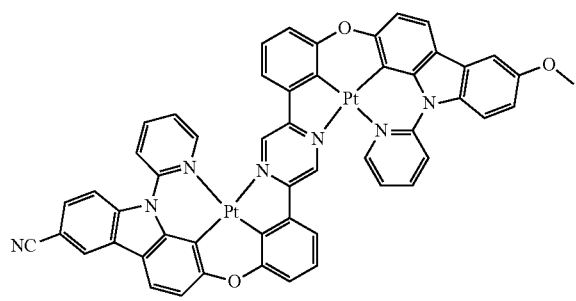
Compound Pt121
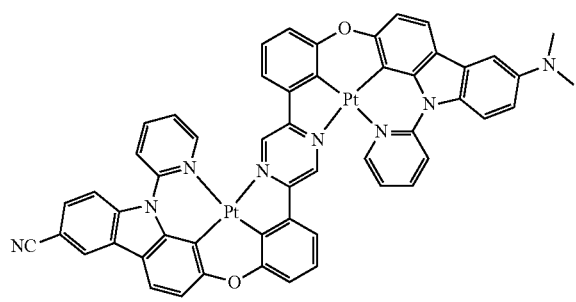
Compound Pt122
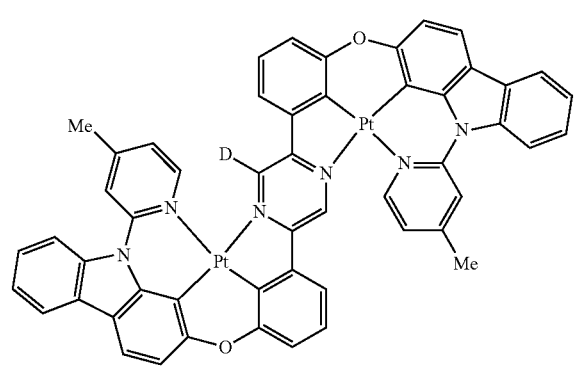
Compound Pt123
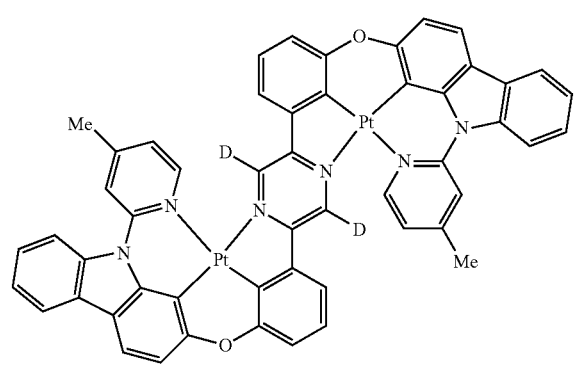
Compound Pt124
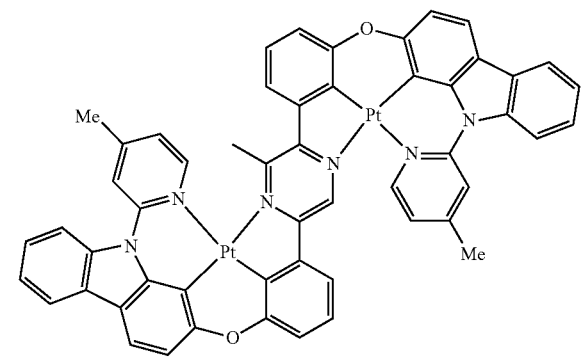
Compound Pt125
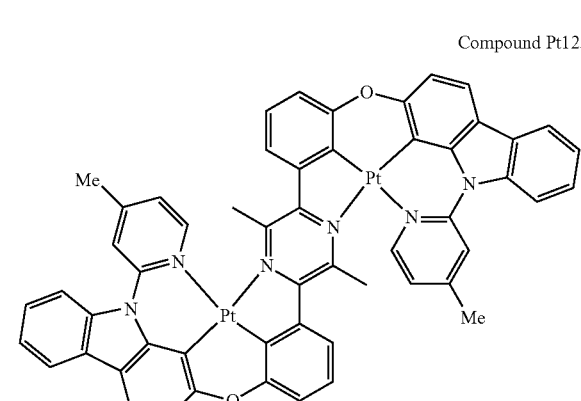
Compound Pt126
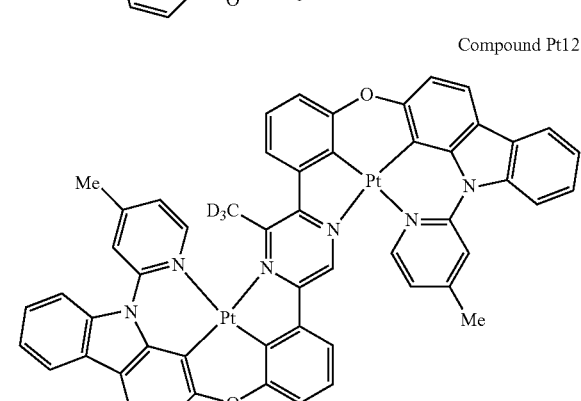
Compound Pt127
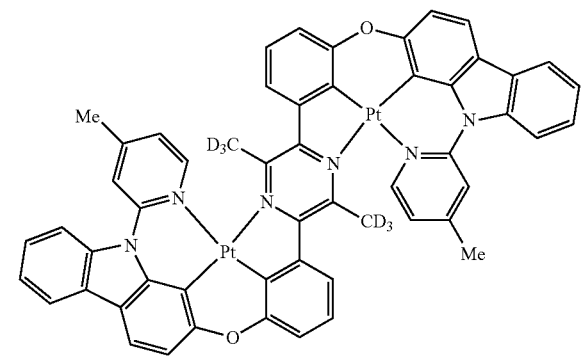

Compound Pt128
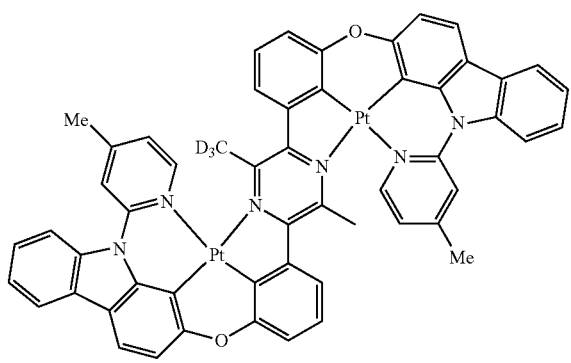
Compound Pt132
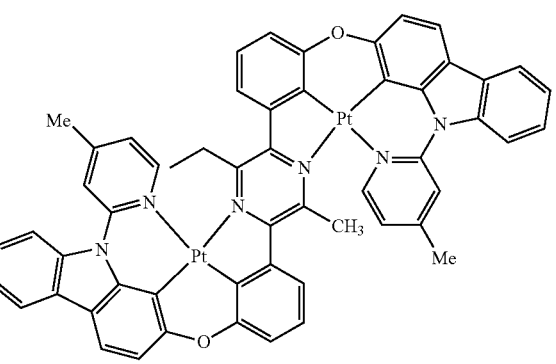
Compound Pt129
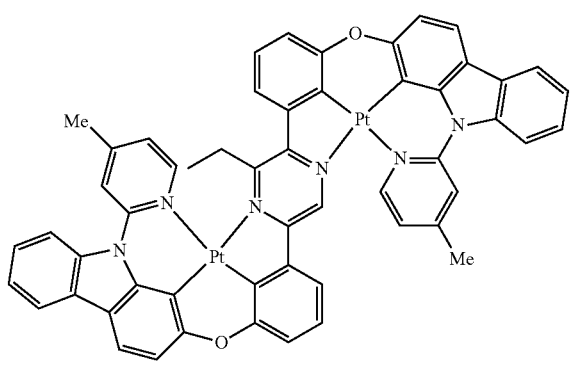
Compound Pt133
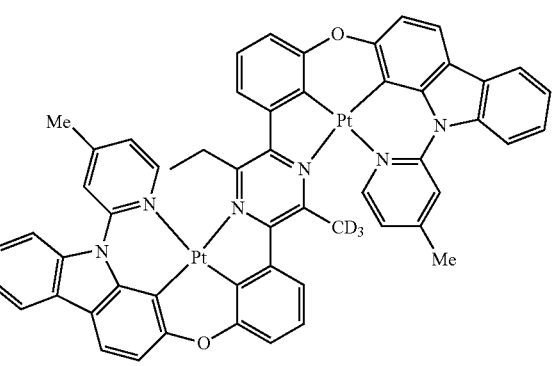
Compound Pt130
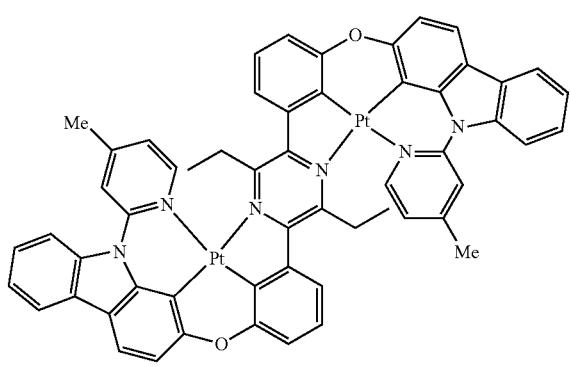
Compound Pt134
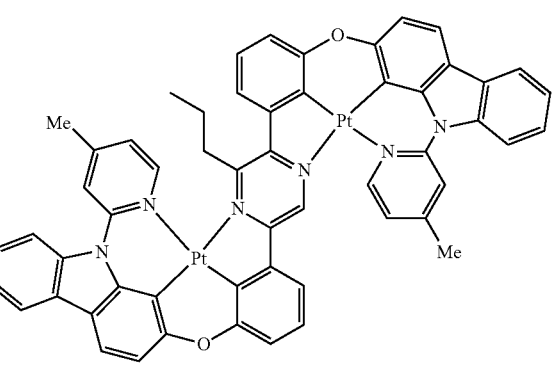
Compound Pt131
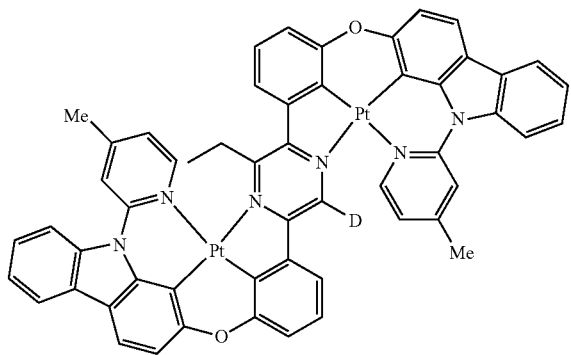
Compound Pt135
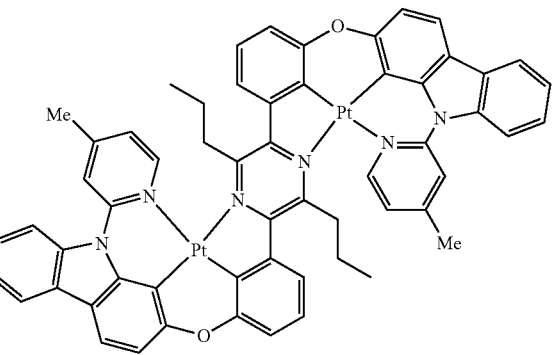

Compound Pt136
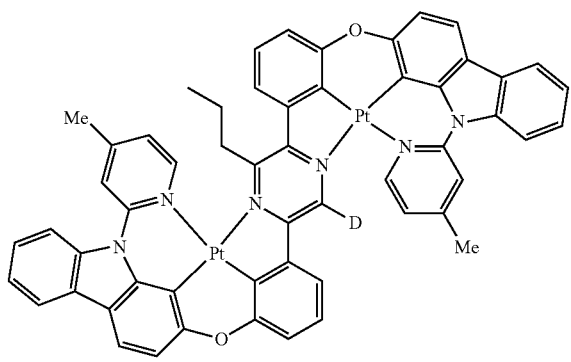
Compound Pt140
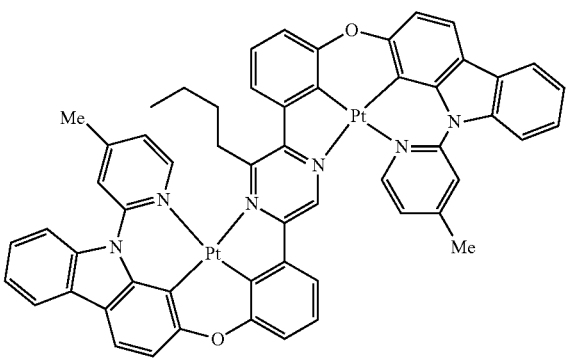
Compound Pt137
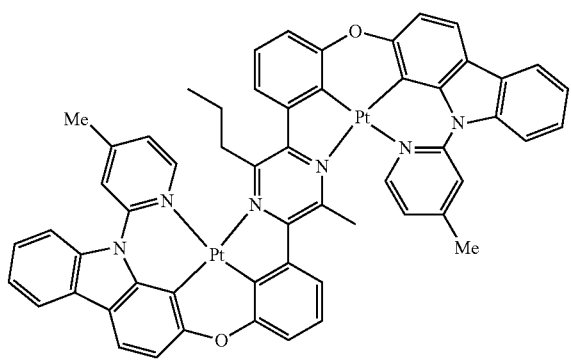
Compound Pt141
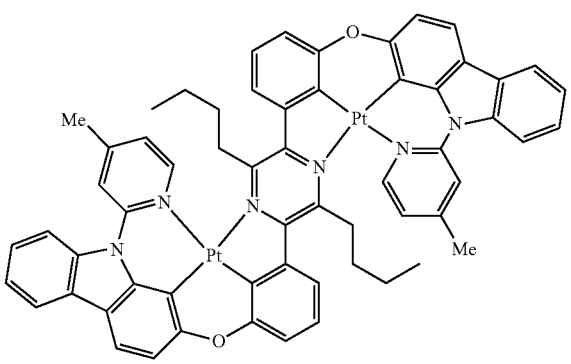
Compound Pt138
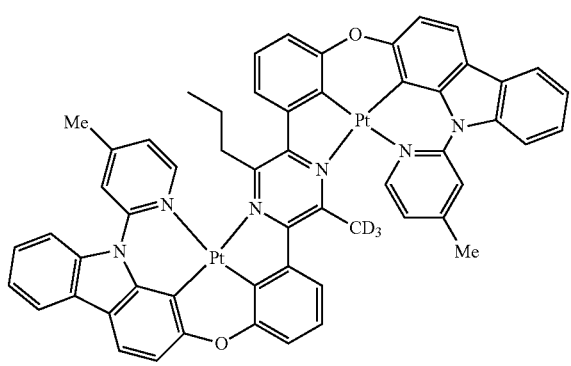
Compound Pt142
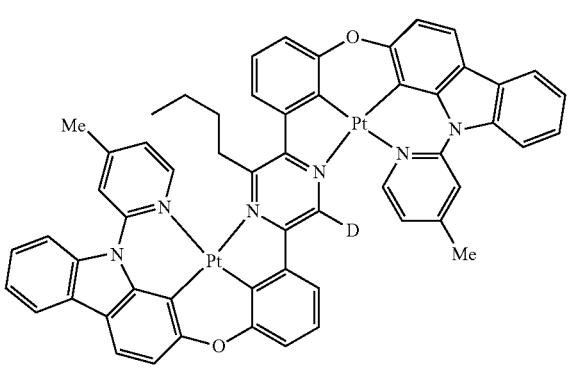
Compound Pt139
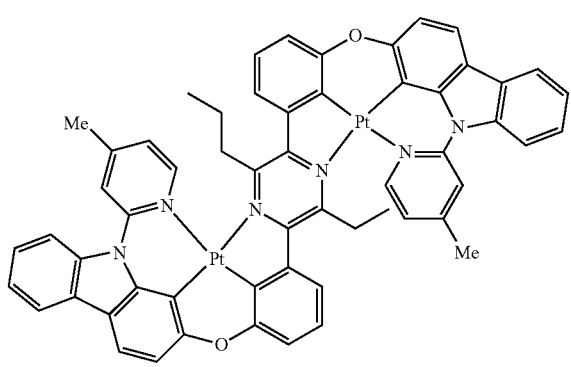
Compound Pt143
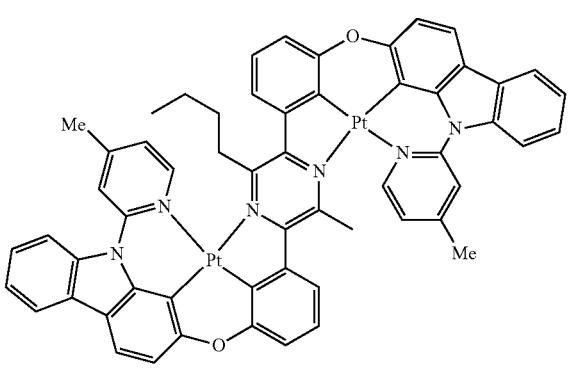

Compound Pt144
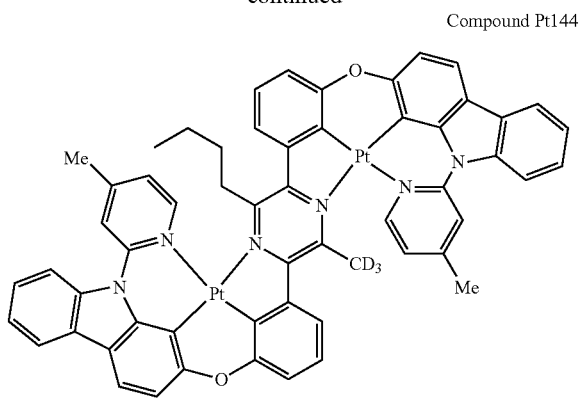
Compound Pt148
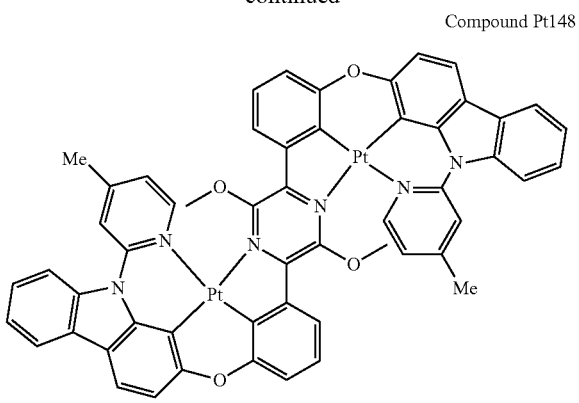
Compound Pt145
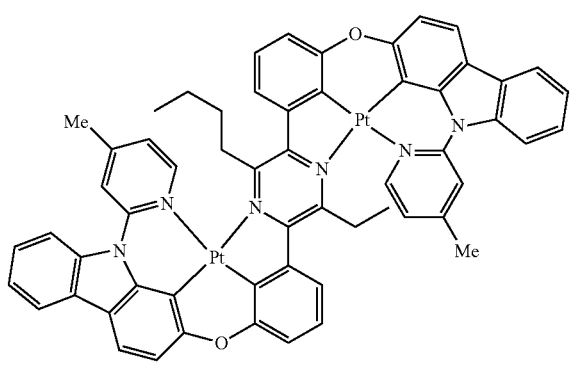
Compound Pt149
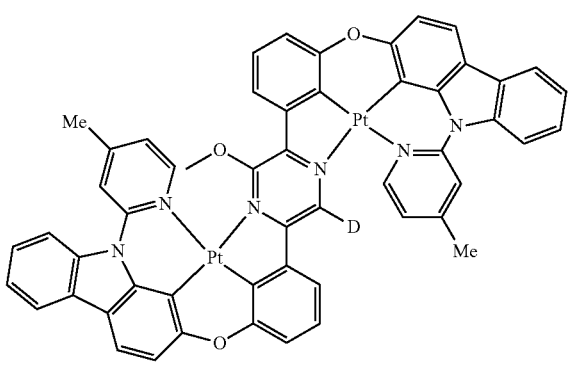
Compound Pt146
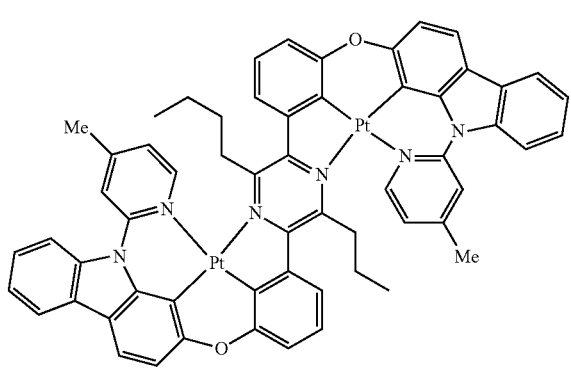
Compound Pt150
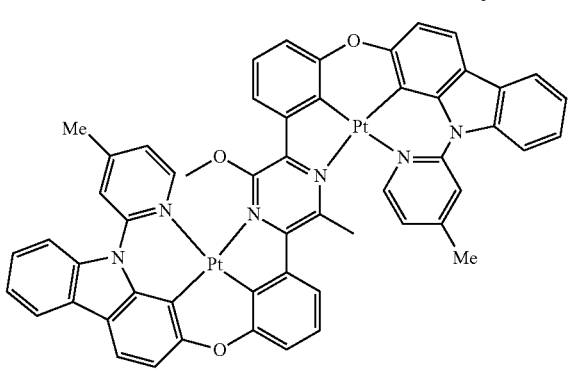
Compound Pt147
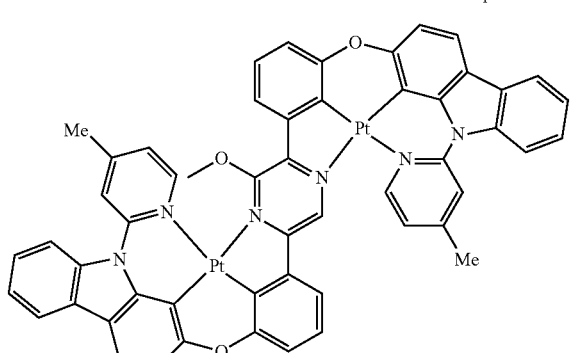
Compound Pt151
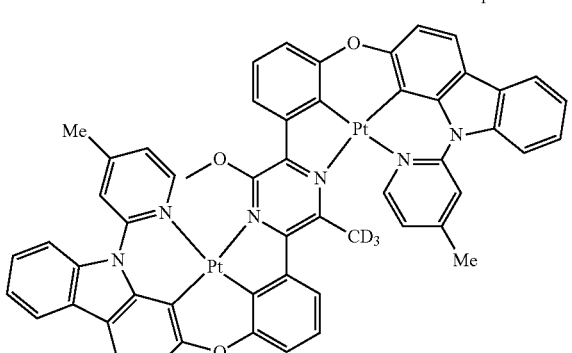

Compound Pt152
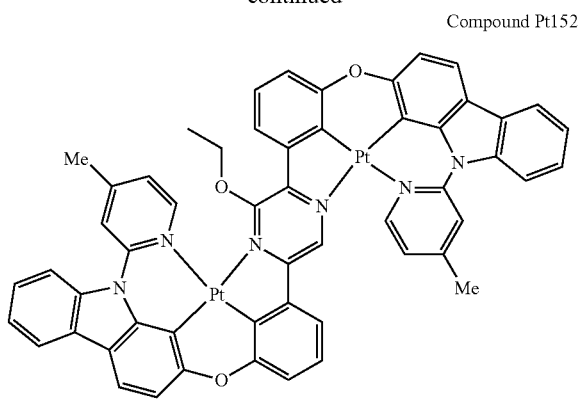
Compound Pt156
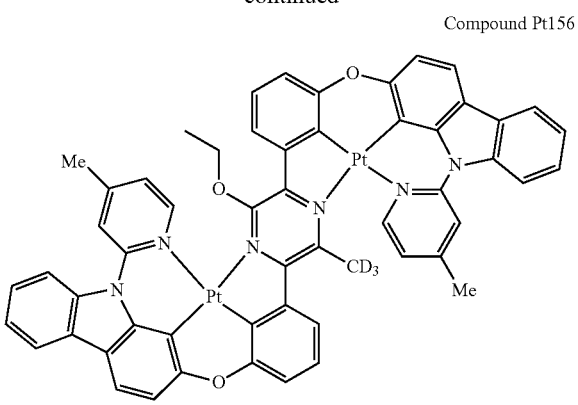
Compound Pt153
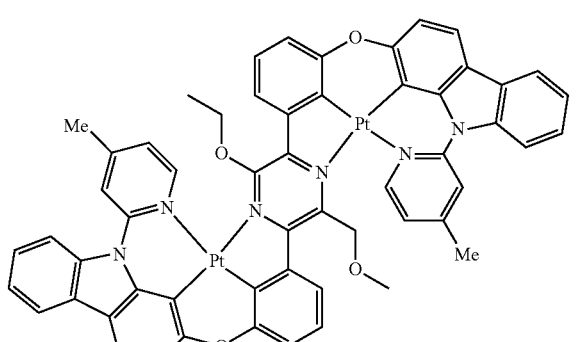
Compound Pt157
Compound Pt154
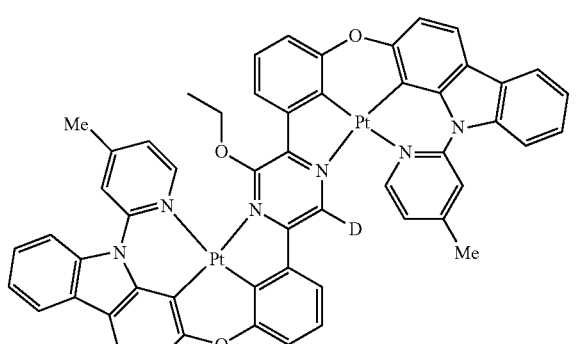
Compound Pt158
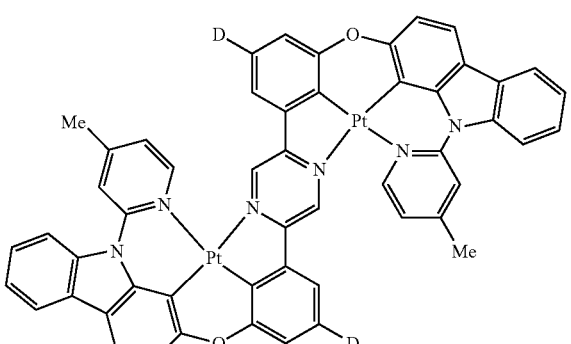
Compound Pt155
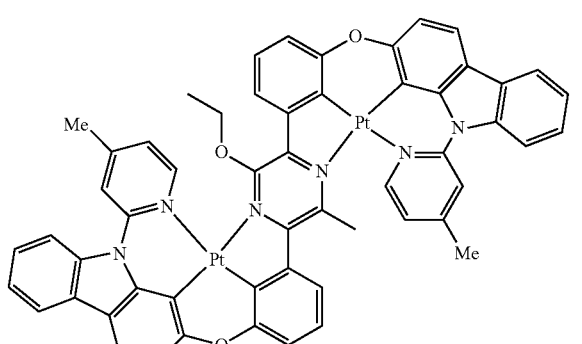
Compound Pt159
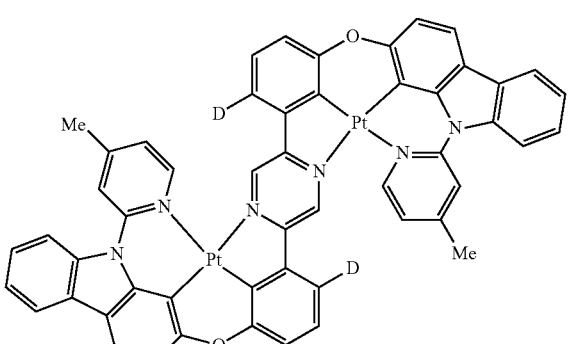

-continued
Compound Pt160
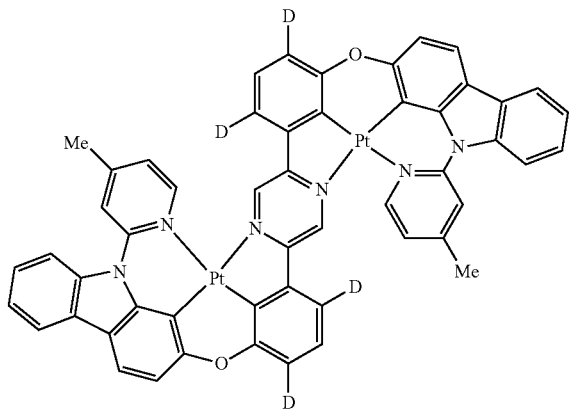
Compound Pt161
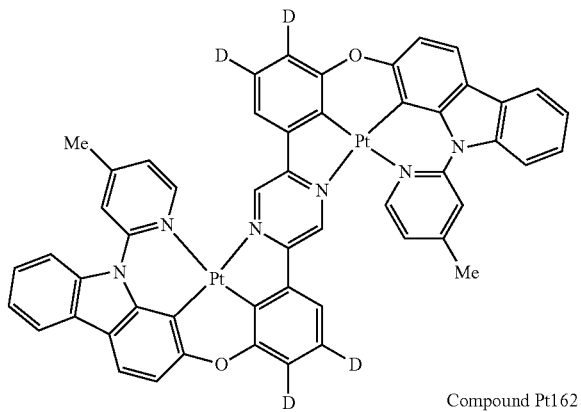
Compound Pt162
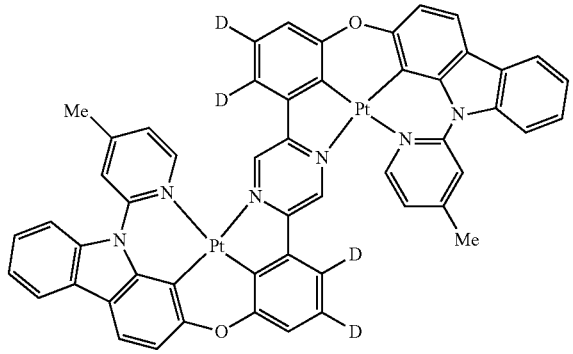
Compound Pt163
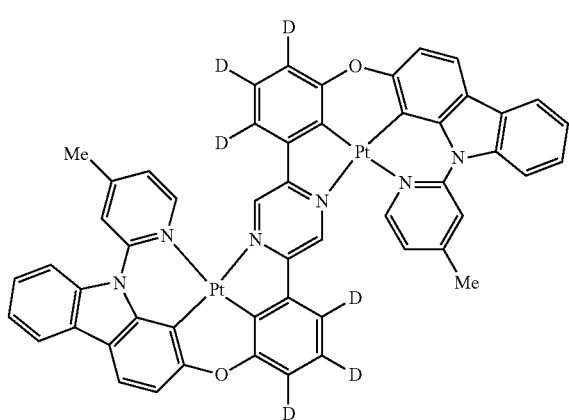
-continued
Compound Pt164
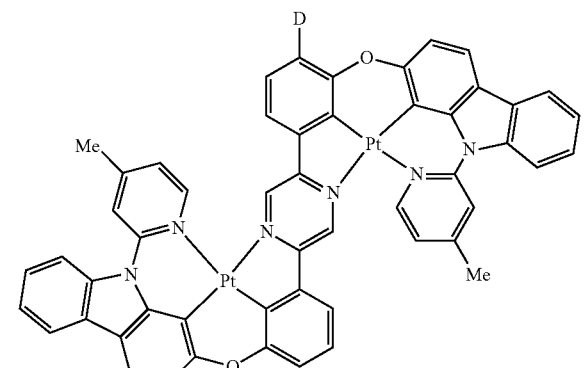
Compound Pt165
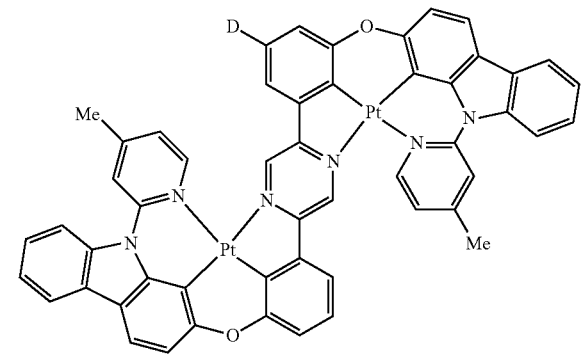
Compound Pt166
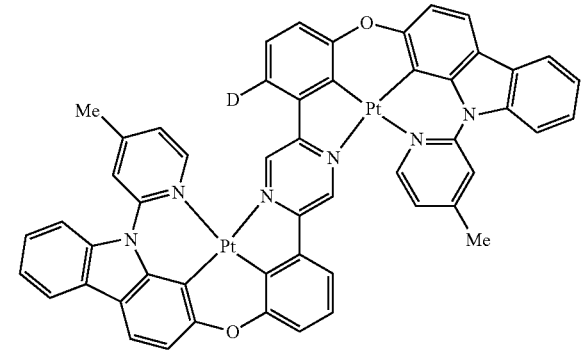
Compound Pt167
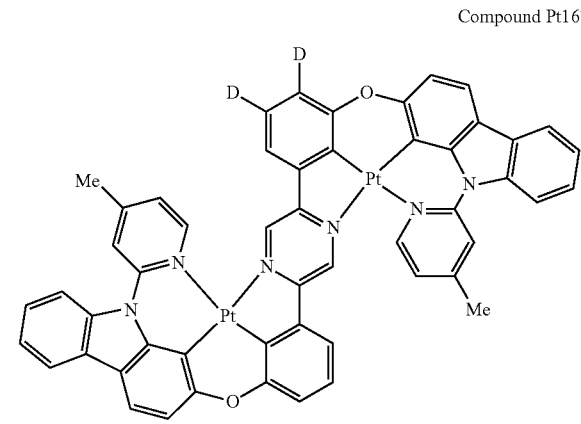

Compound Pt168
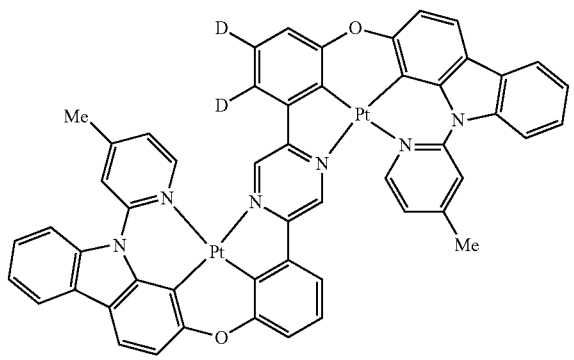
Compound Pt169
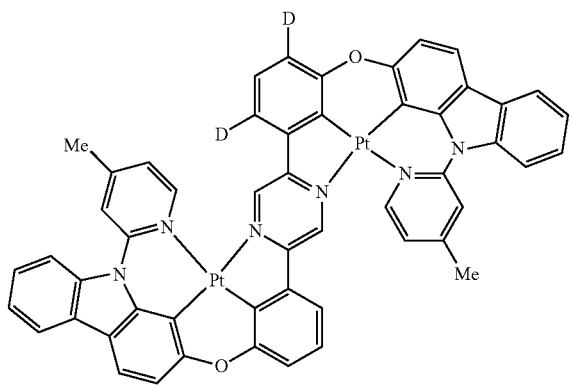
Compound Pt170
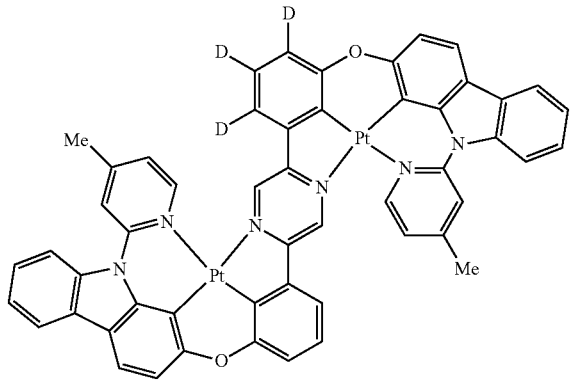
Compound Pt171
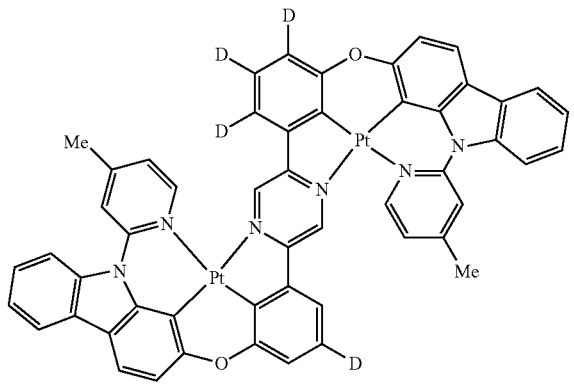
Compound Pt172
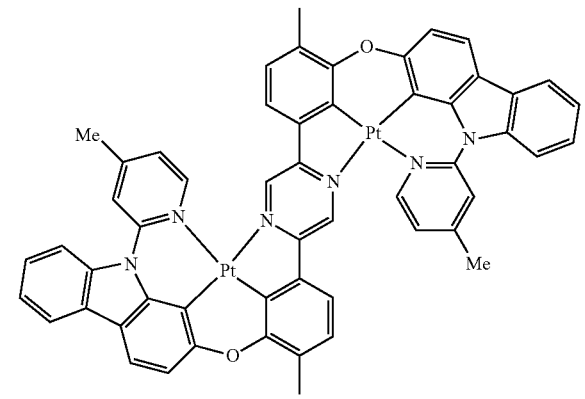
Compound Pt173
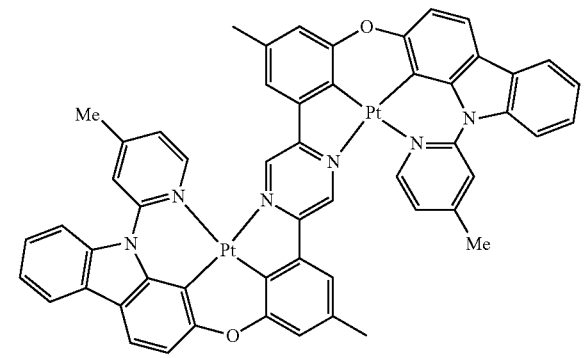
Compound Pt174
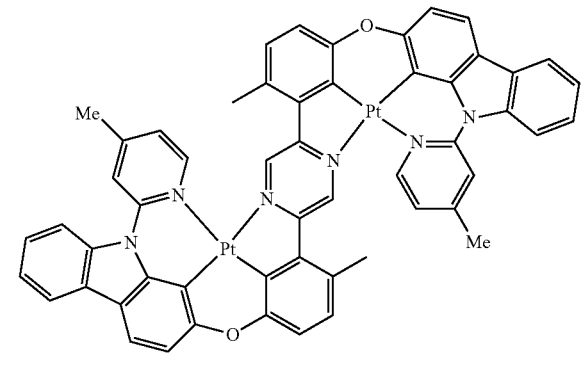
Compound Pt175
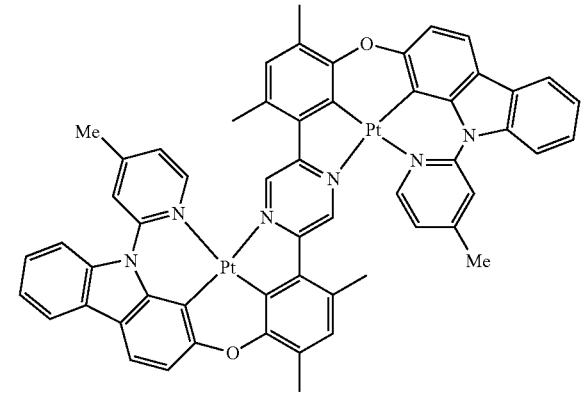

Compound Pt176
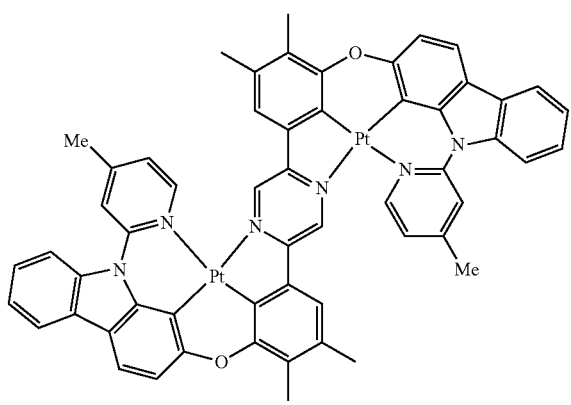
Compound Pt177
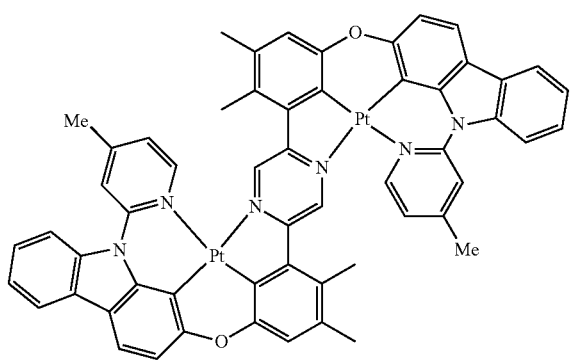
Compound Pt178
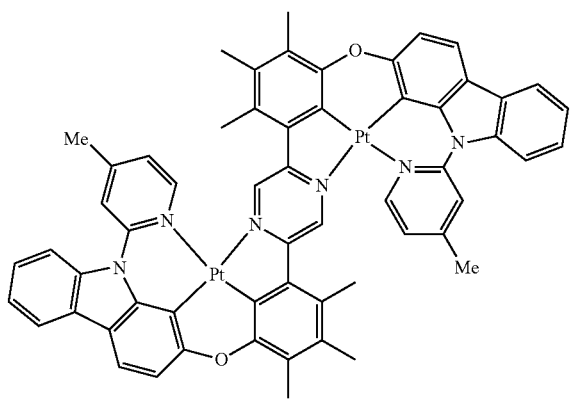
Compound Pt179
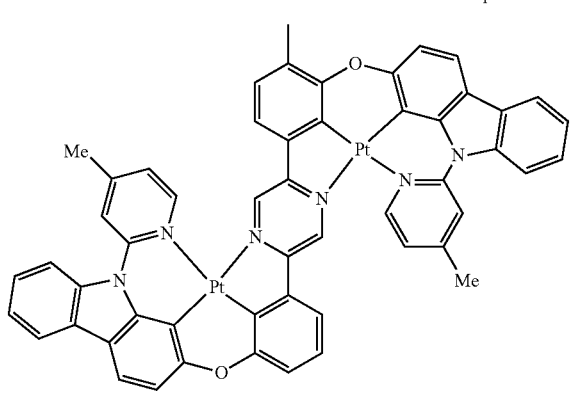
Compound Pt180
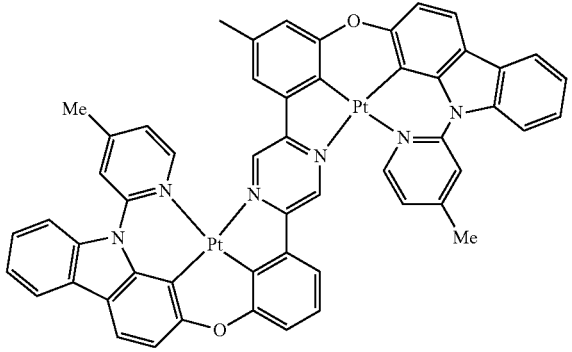
Compound Pt181
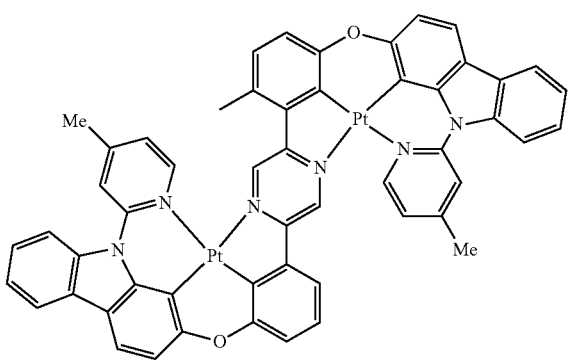
Compound Pt182
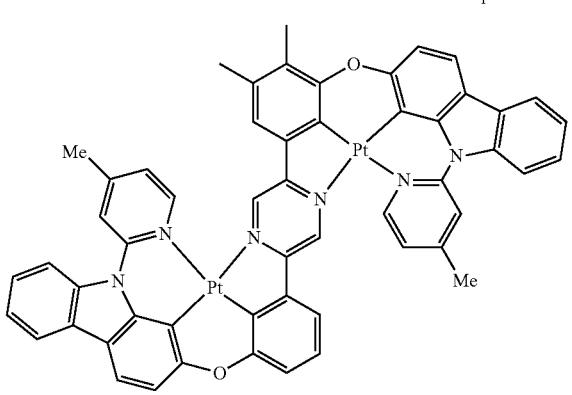
Compound Pt183
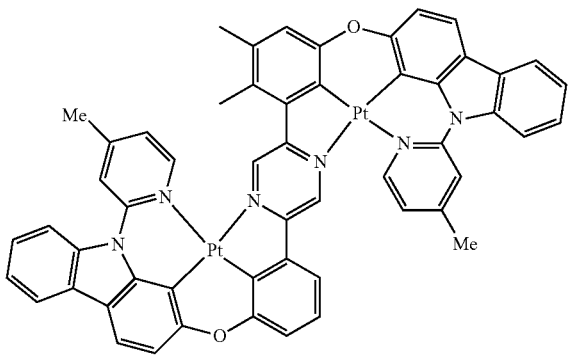

Compound Pt184
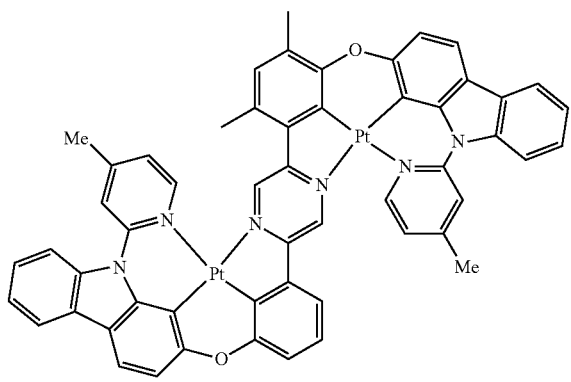
Compound Pt185
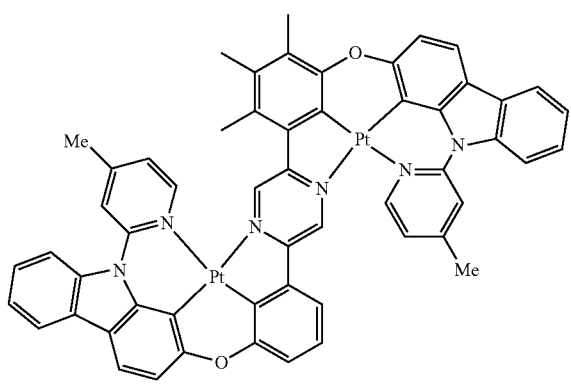
Compound Pt186
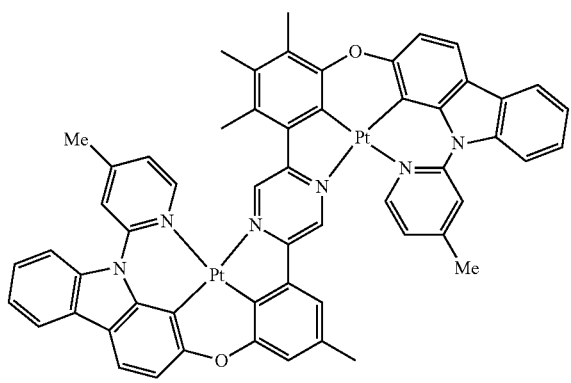
Compound Pt187
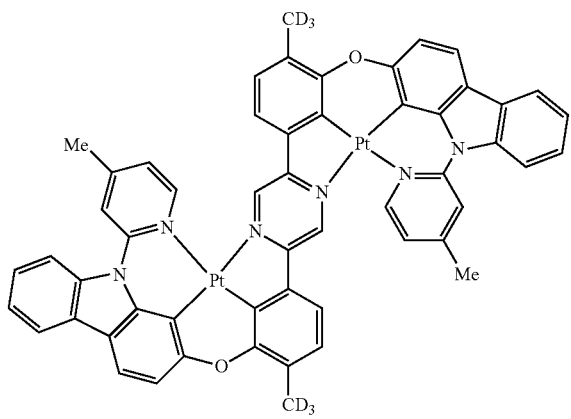
Compound Pt188
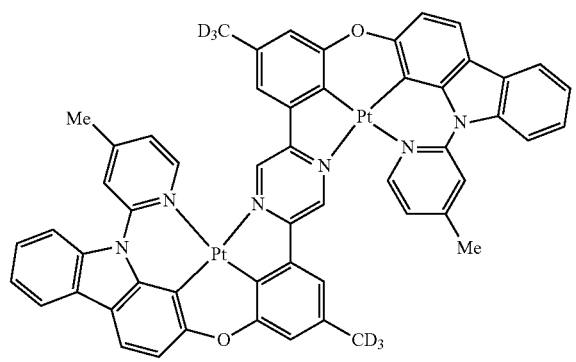
Compound Pt189
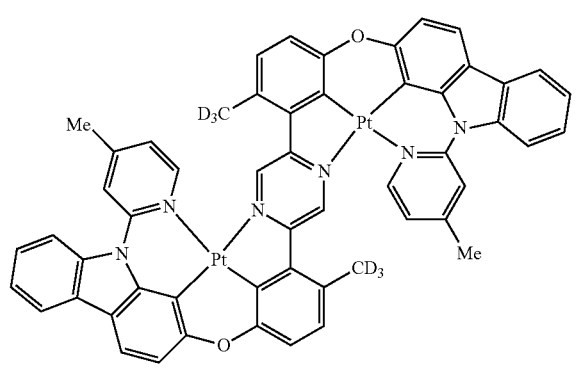
Compound Pt190
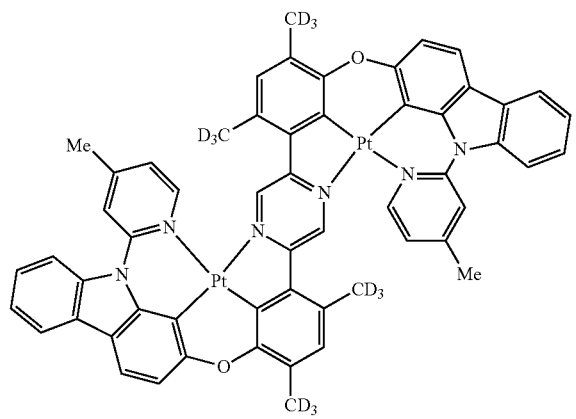
Compound Pt191
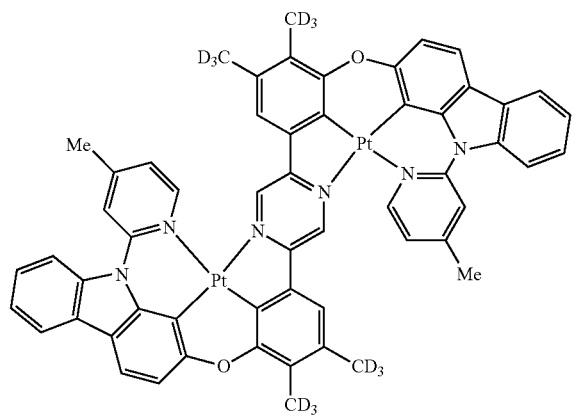

Compound Pt192
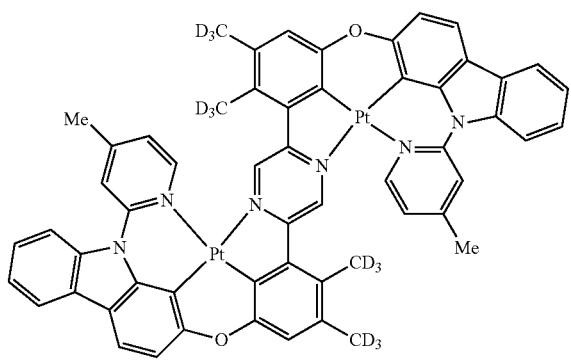
Compound Pt196
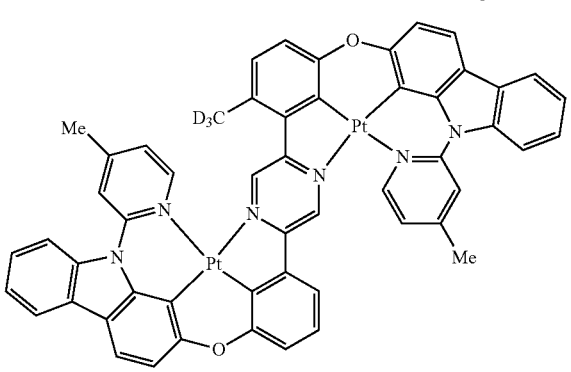
Compound Pt193
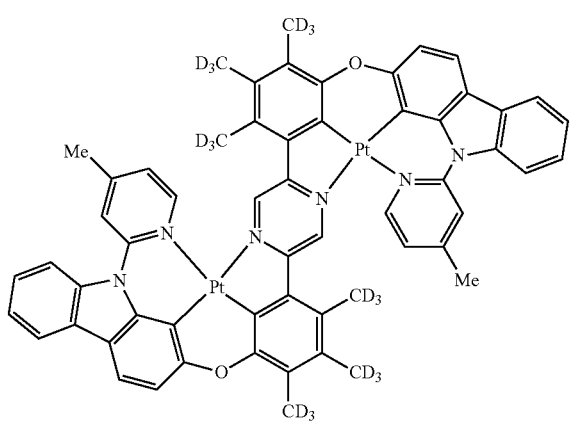
Compound Pt197
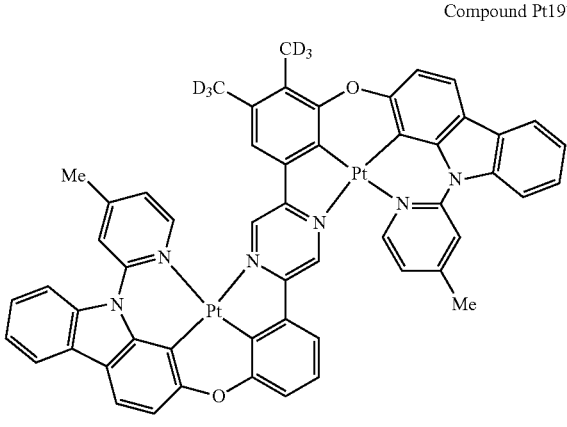
Compound Pt194
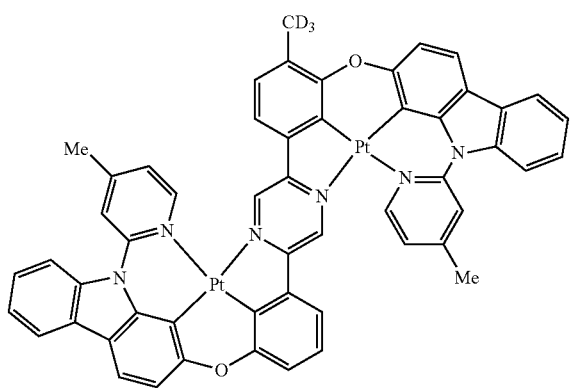
Compound Pt198
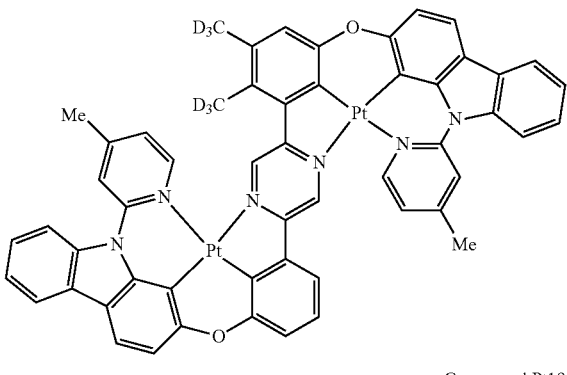
Compound Pt195
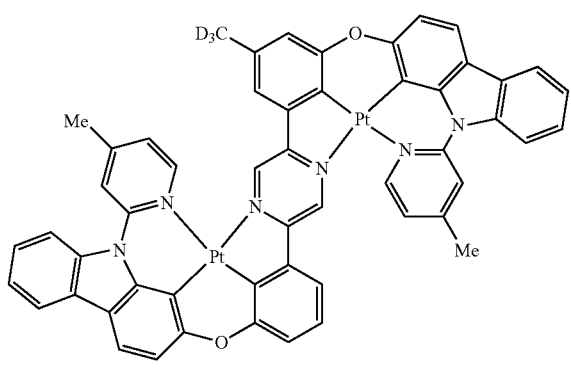
Compound Pt199
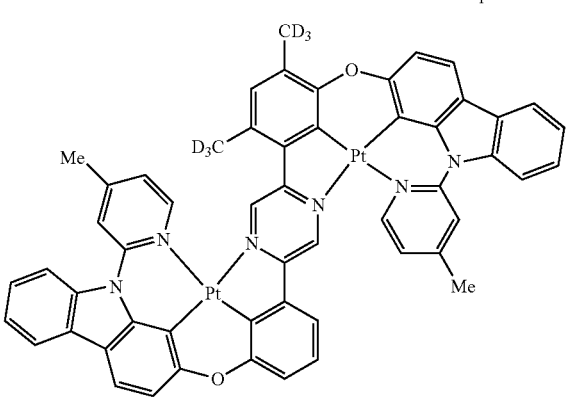

Compound Pt200
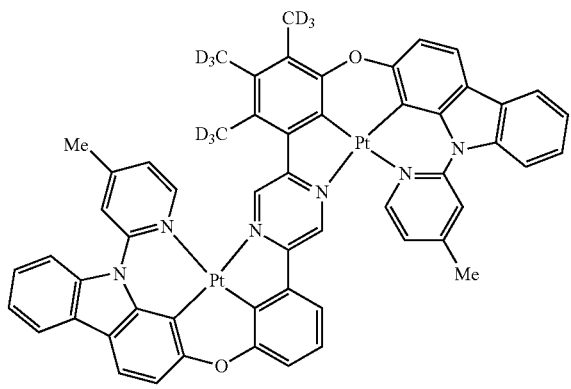
Compound Pt201
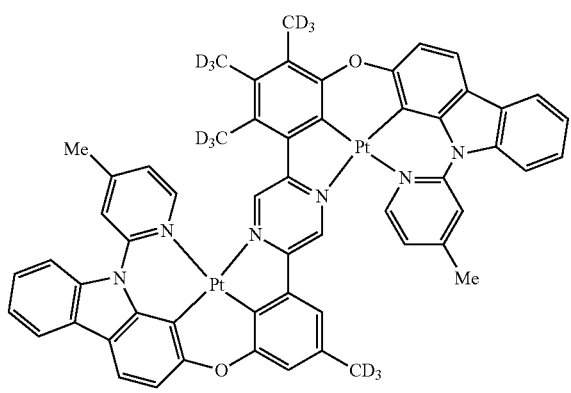
Compound Pt202
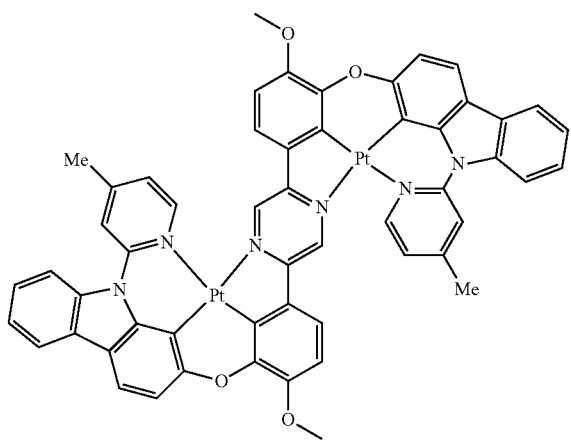
Compound Pt203
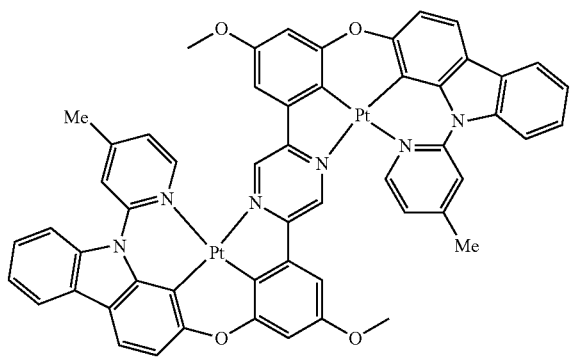
Compound Pt204
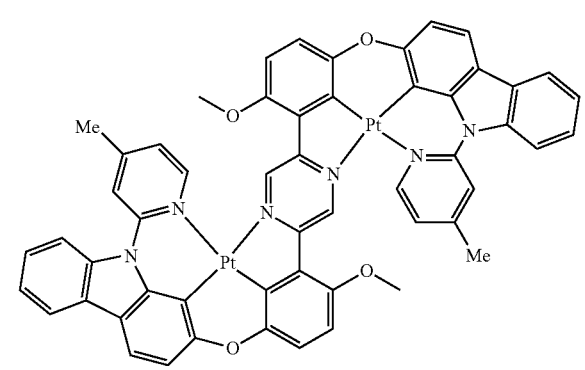
Compound Pt205
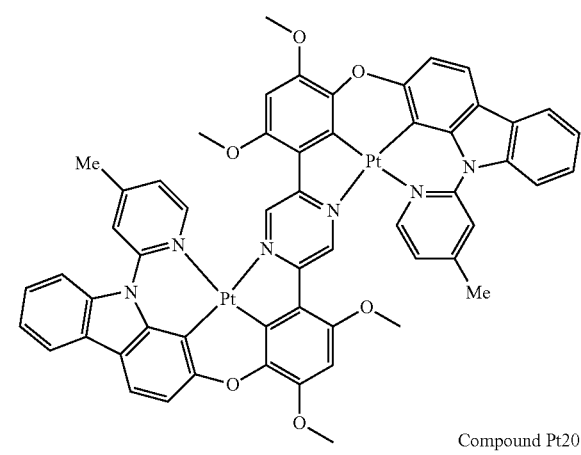
Compound Pt206
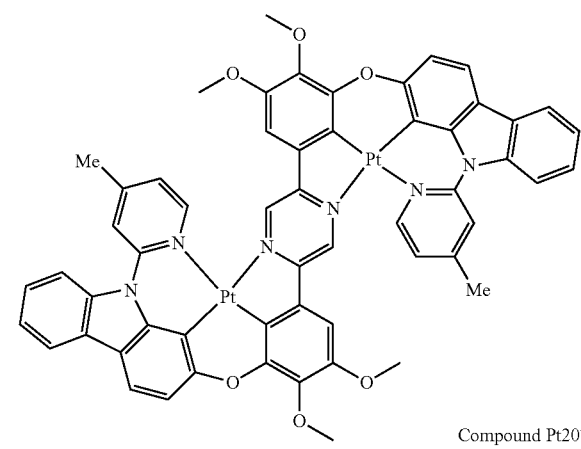
Compound Pt207
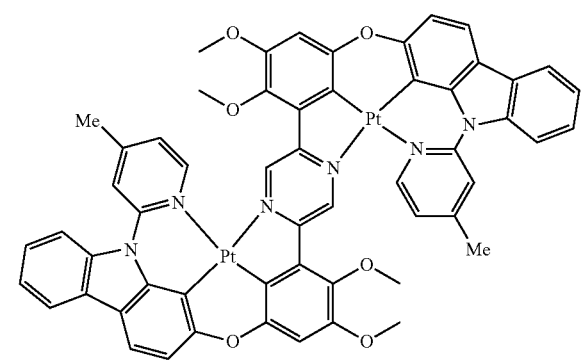

-continued
Compound Pt208
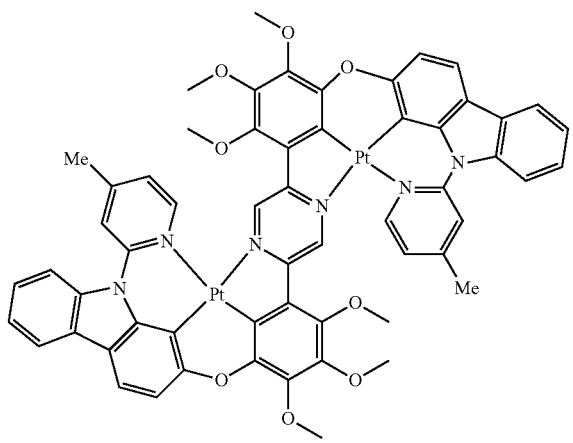
Compound Pt212
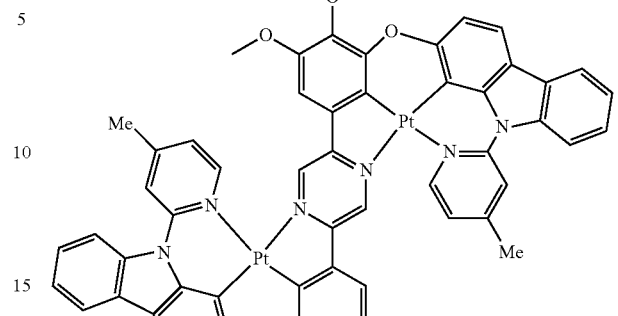
Compound Pt209
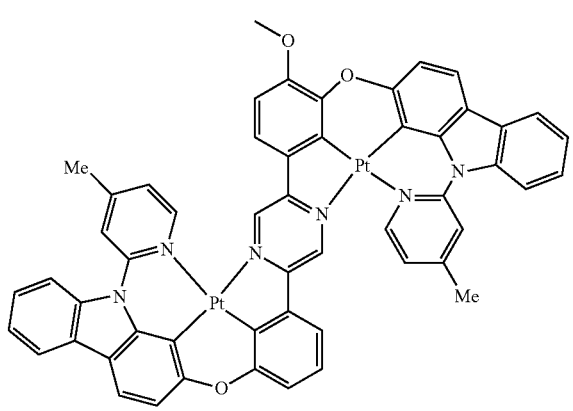
Compound Pt213
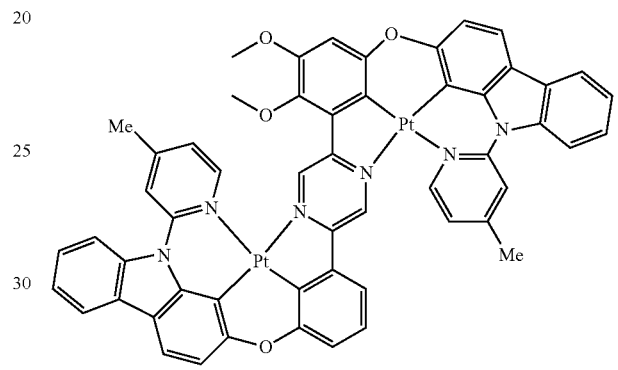
Compound Pt210
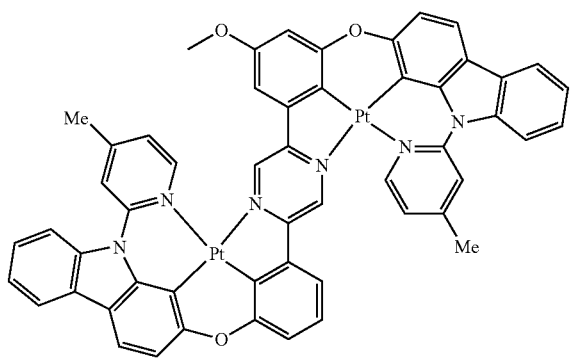
Compound Pt214
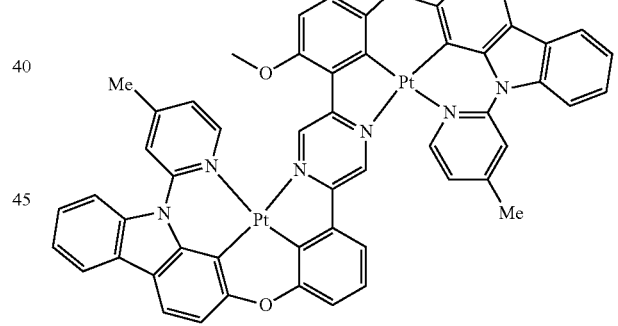
Compound Pt211
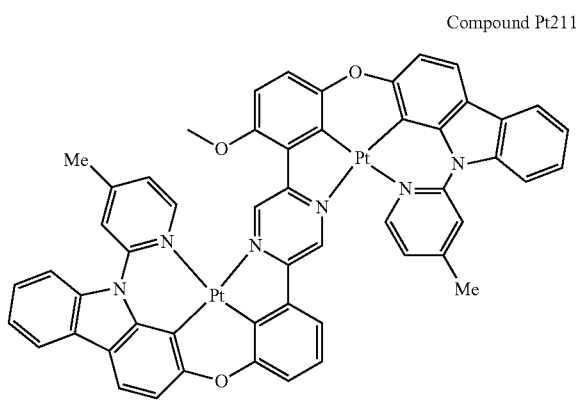
Compound Pt215
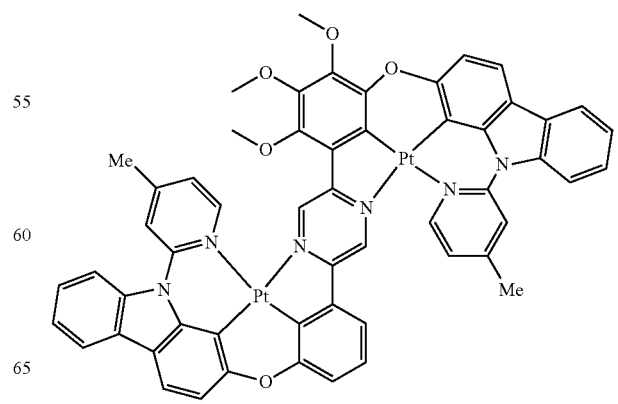

-continued
Compound Pt216
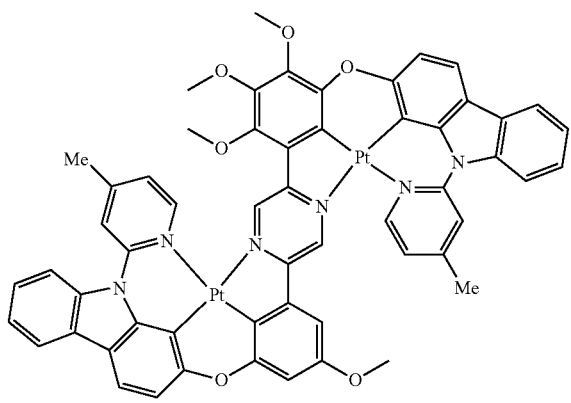
Compound Pt217
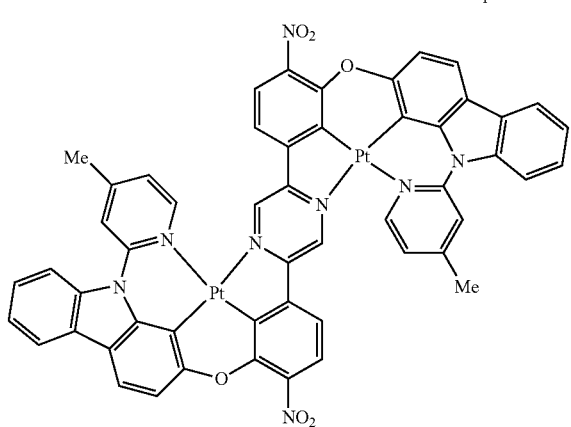
Compound Pt218
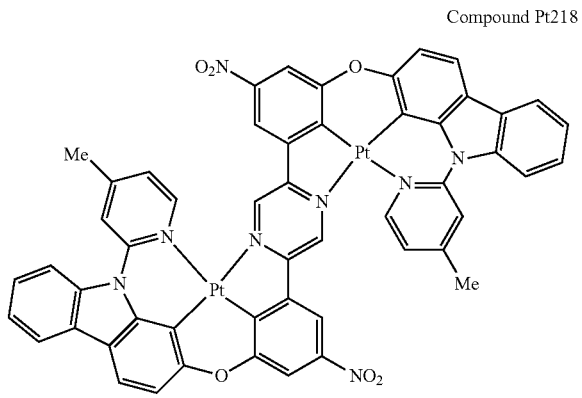
Compound Pt219
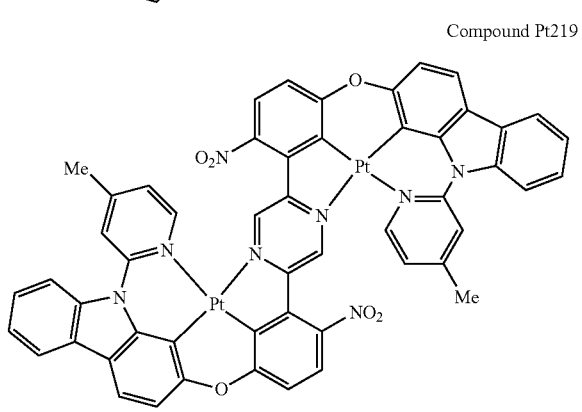
-continued
Compound Pt220
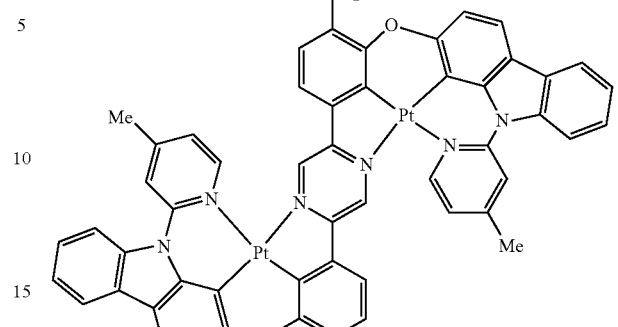
Compound Pt221
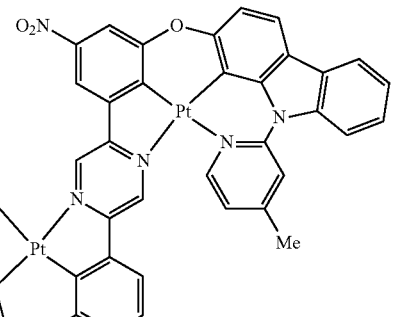
Compound Pt222
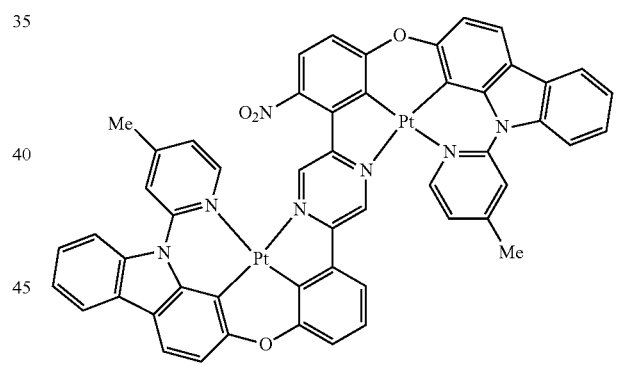
Compound Pt223
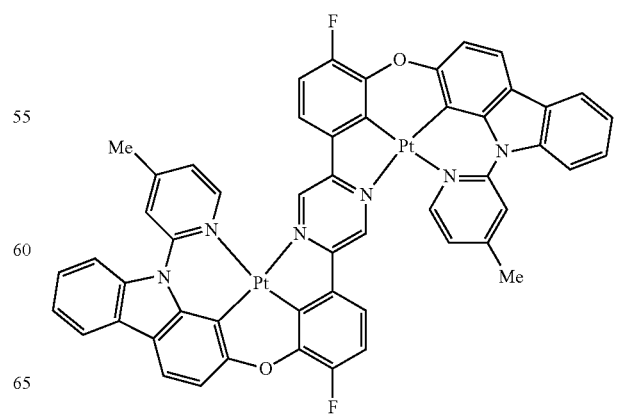

-continued
Compound Pt224
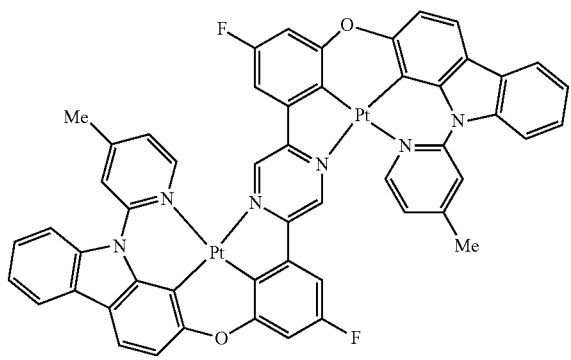
Compound Pt225
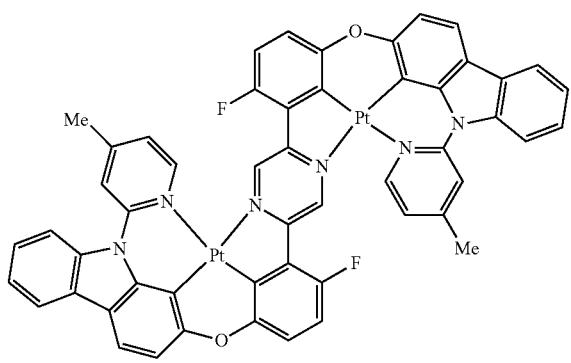
Compound Pt226
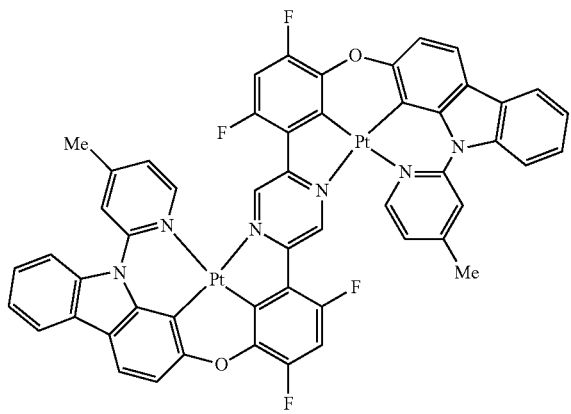
Compound Pt227
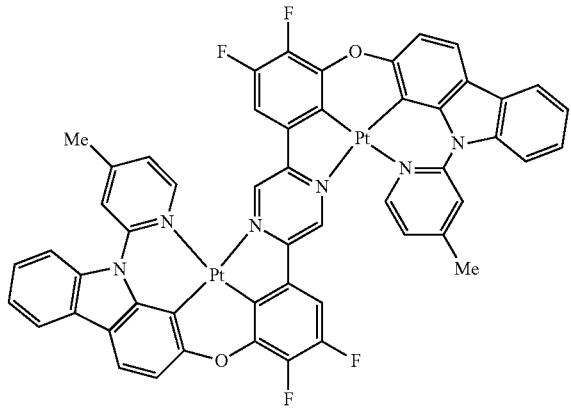
-continued
Compound Pt228
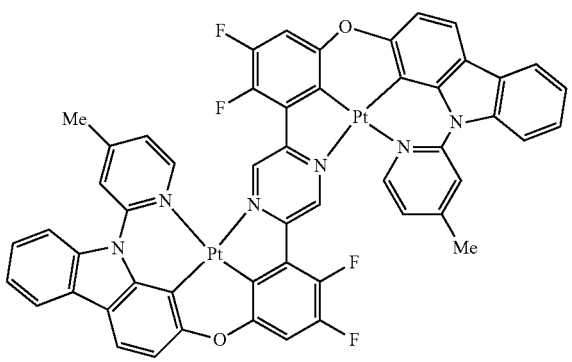
Compound Pt229
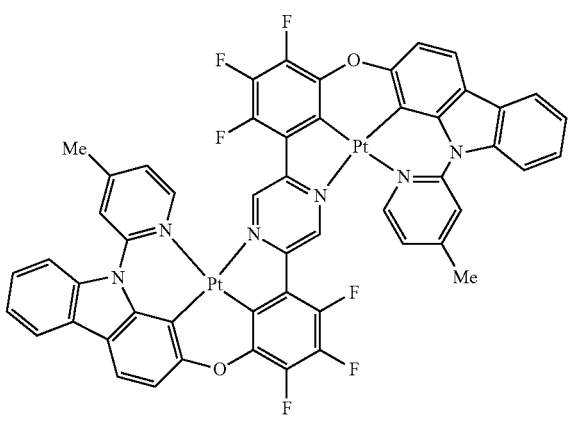
Compound Pt230
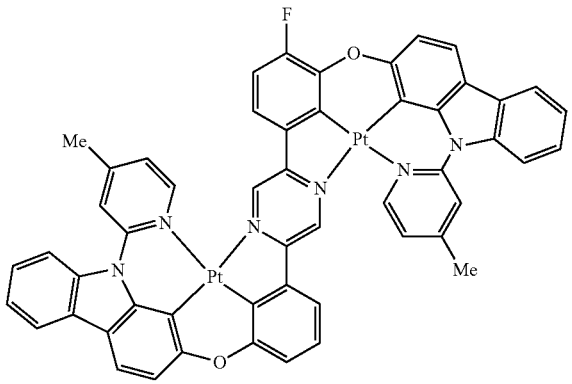
Compound Pt231
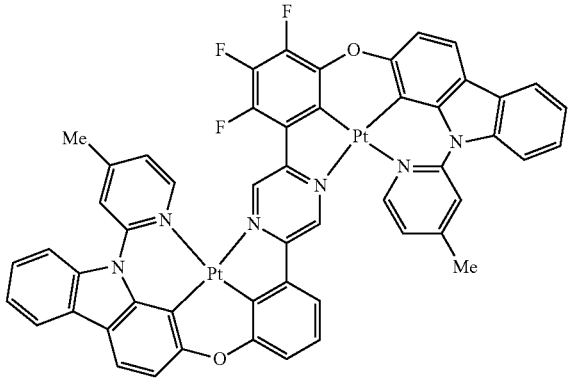

Compound Pt232
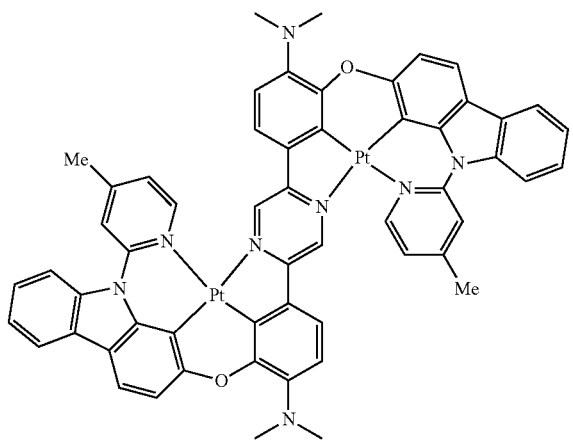
Compound Pt233
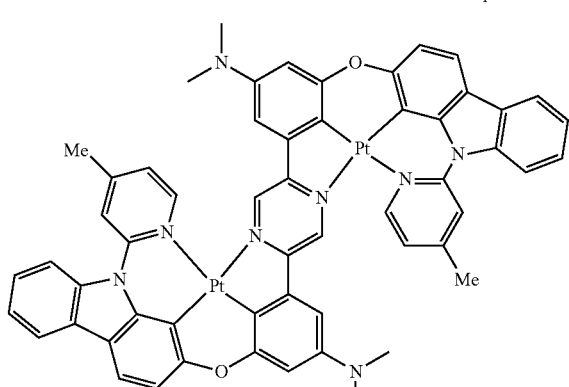
Compound Pt234
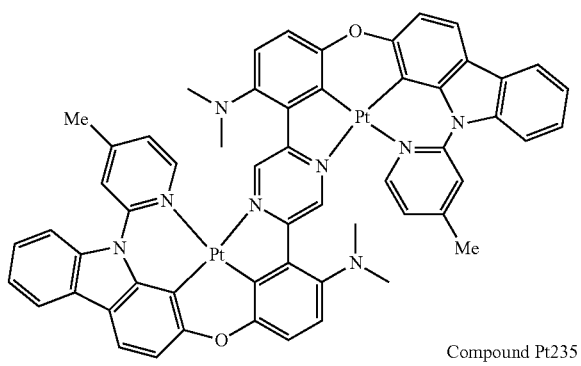
Compound Pt235
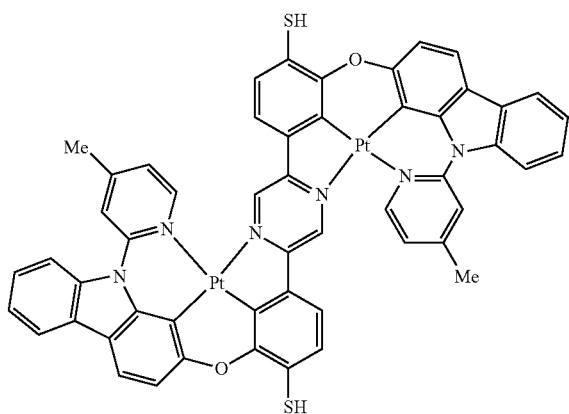
Compound Pt236
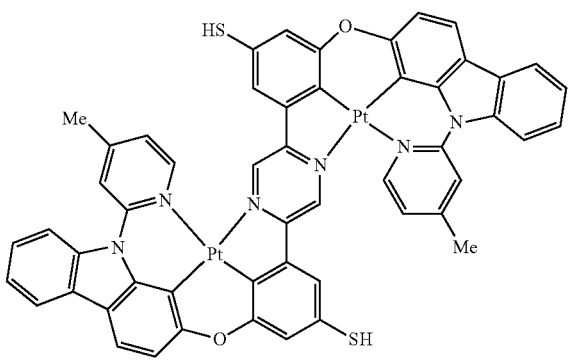
Compound Pt237
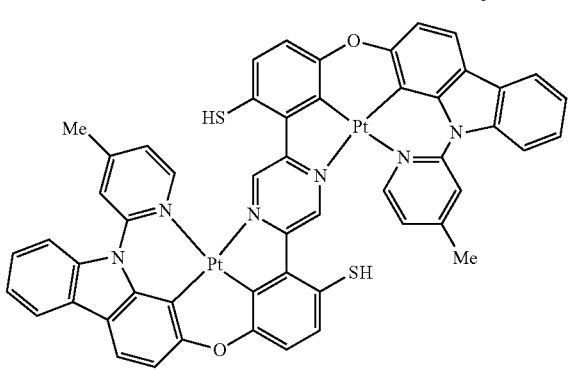
Compound Pt238
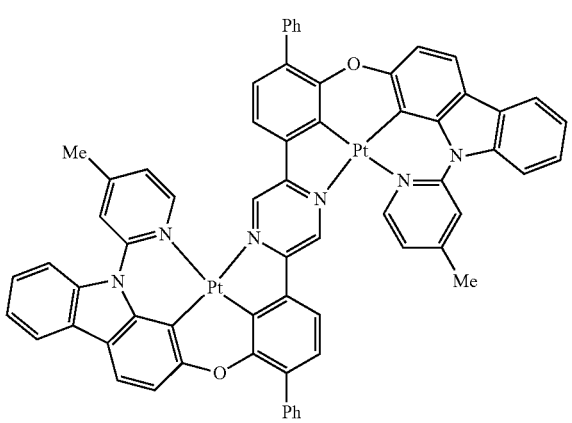
Compound Pt239
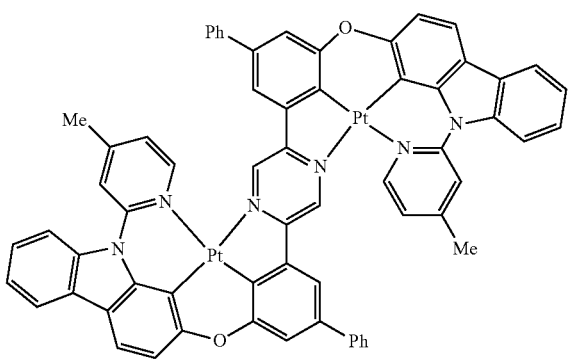

Compound Pt240
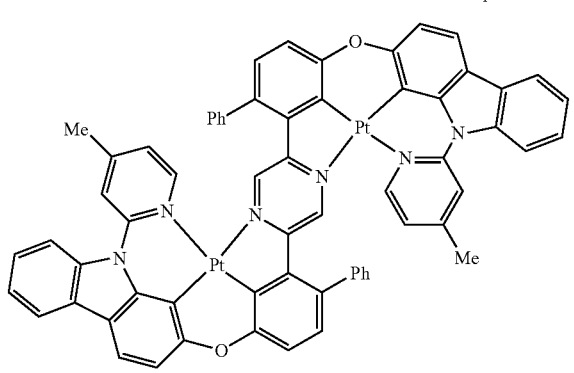
Compound Pt244
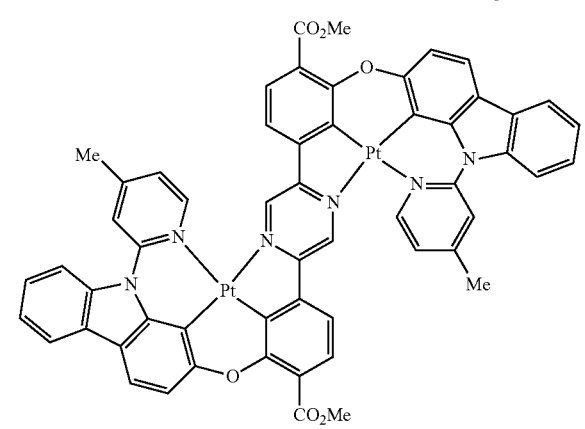
Compound Pt241
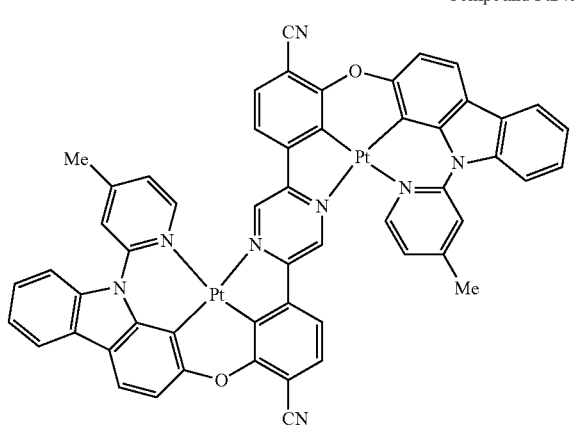
Compound Pt245
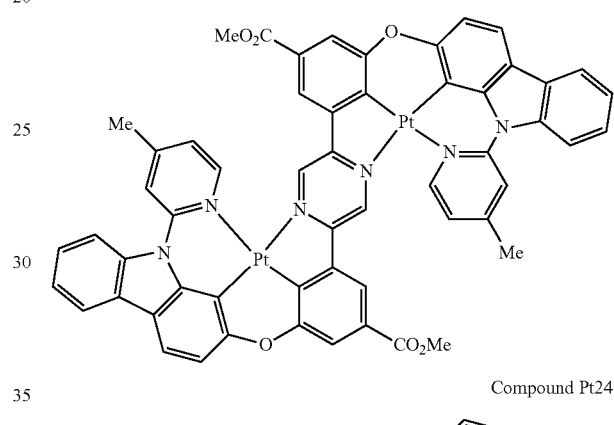
Compound Pt242
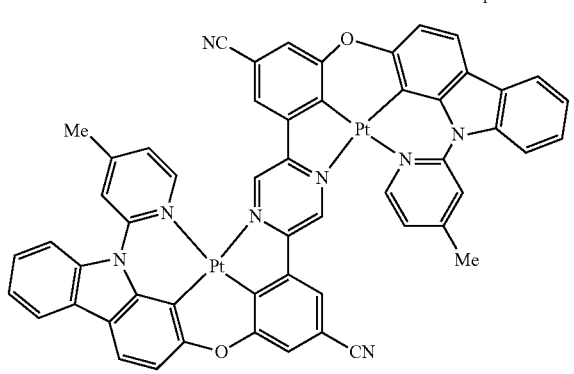
Compound Pt246
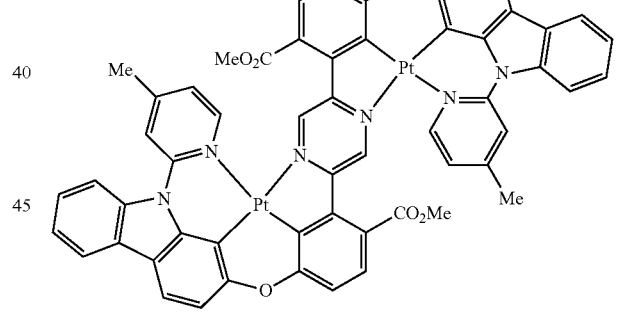
Compound Pt243
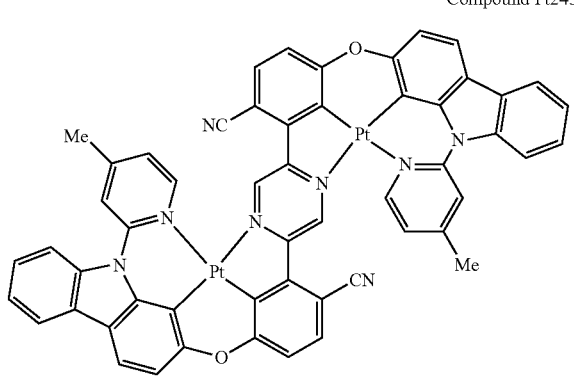
Compound Pt247
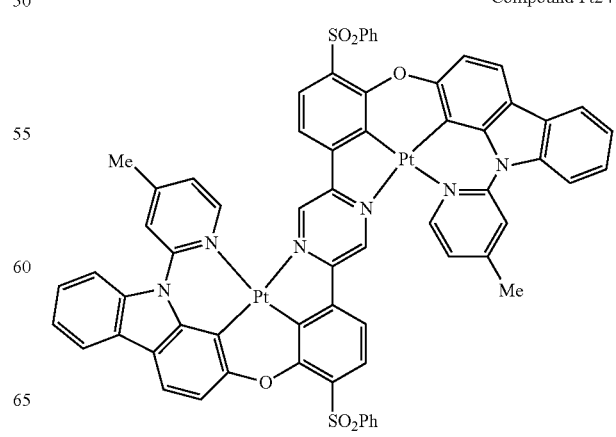

-continued
Compound Pt248
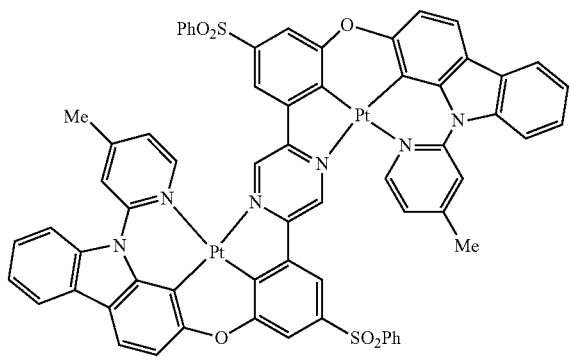
Compound Pt249
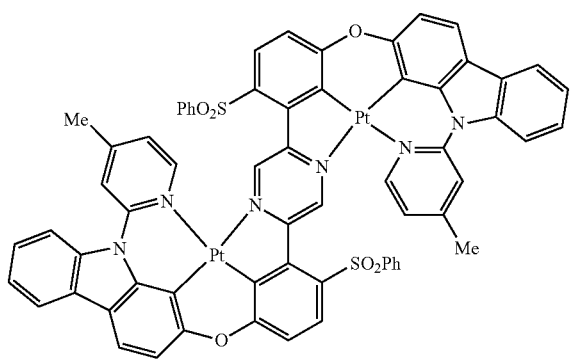
Compound Pt250
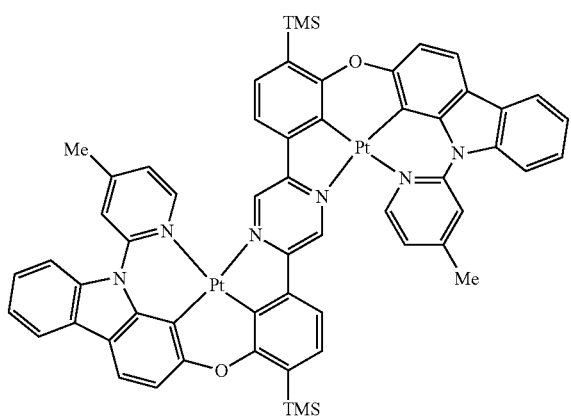
Compound Pt251
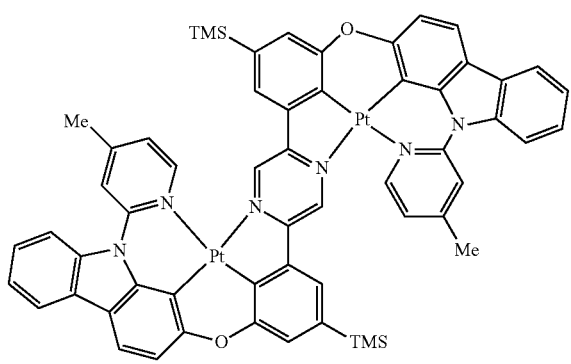
-continued
Compound Pt252
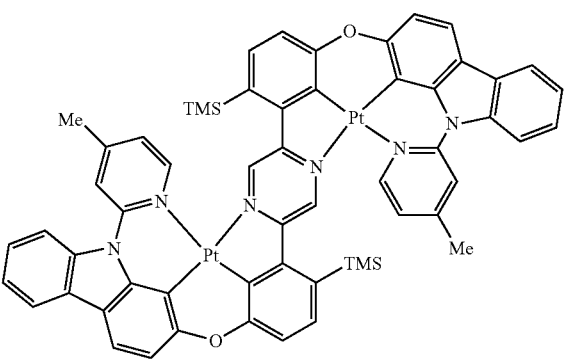
Compound Pt253
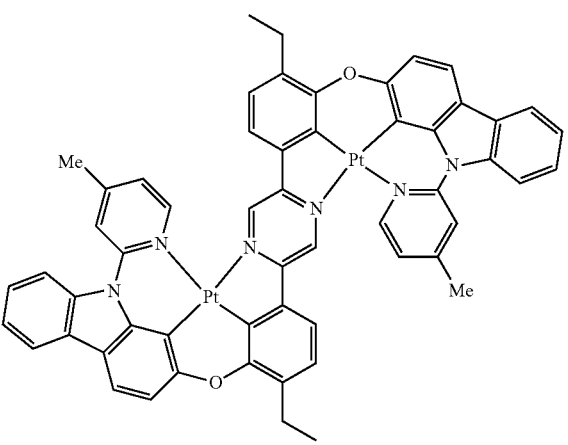
Compound Pt254
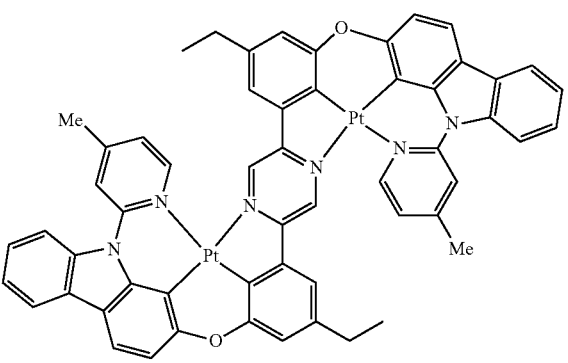
Compound Pt255
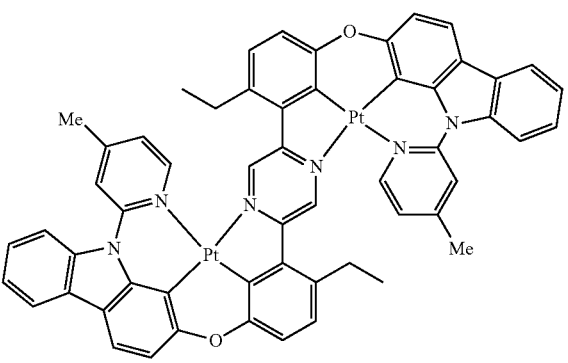

Compound Pt256
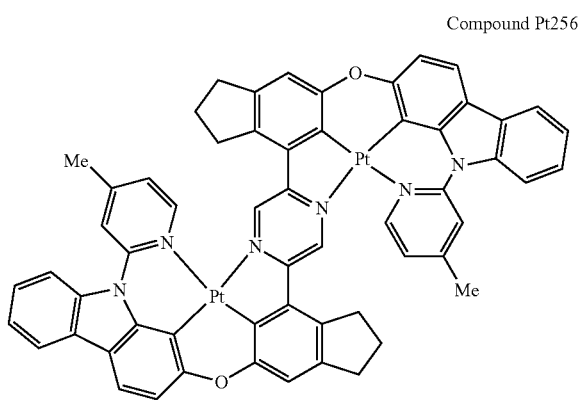
Compound Pt257
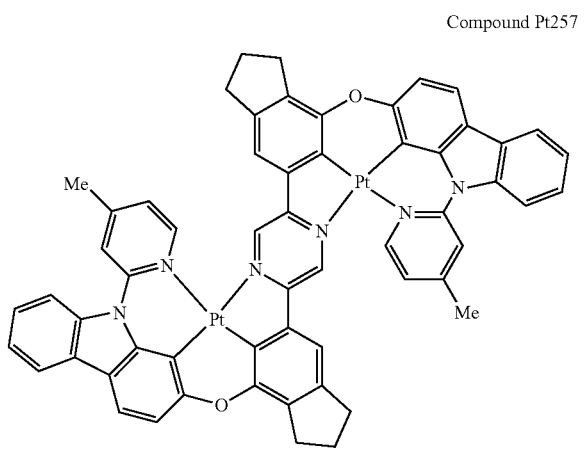
Compound Pt258
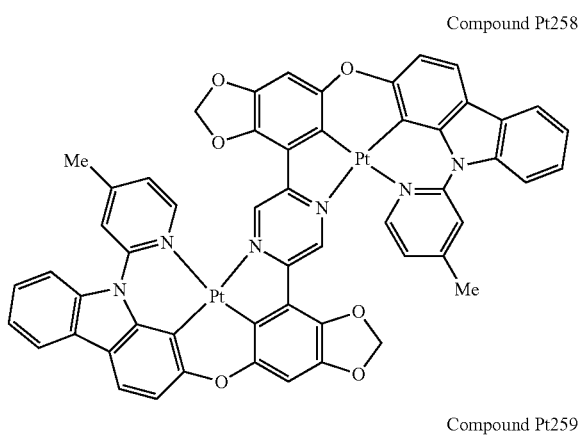
Compound Pt259
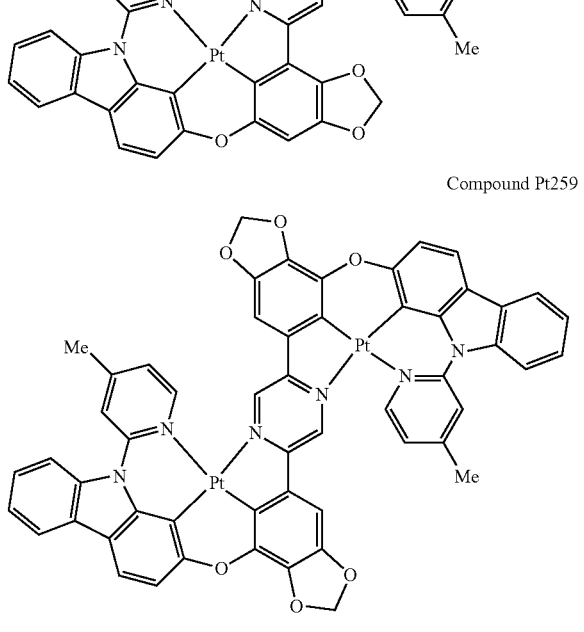
Compound Pt260
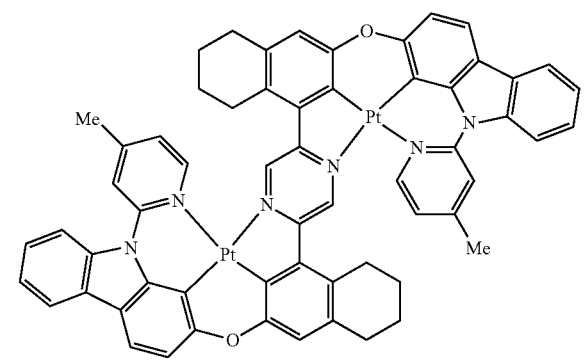
Compound Pt261
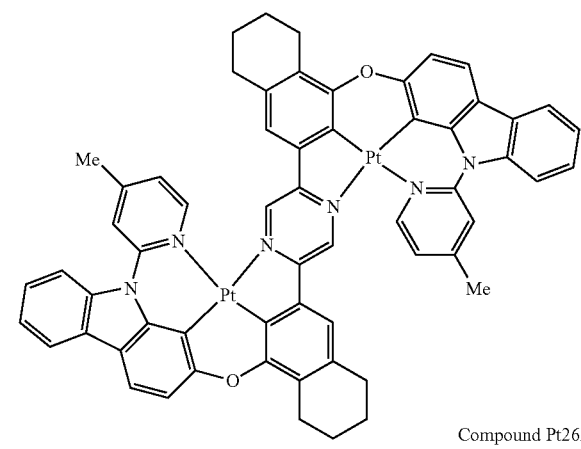
Compound Pt262
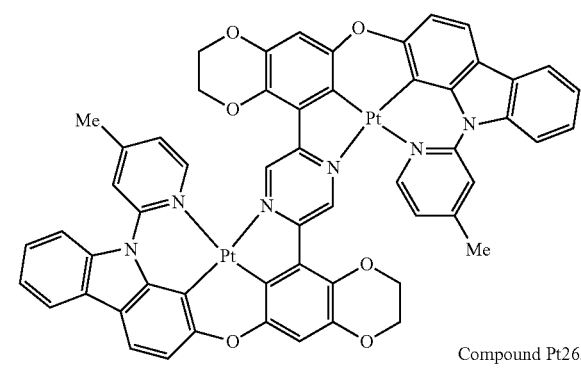
Compound Pt263
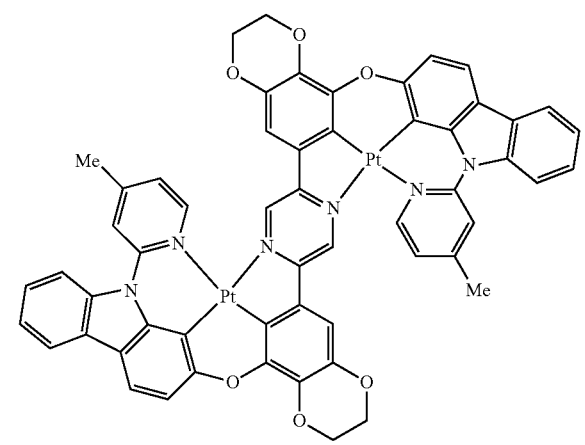

Compound Pt264
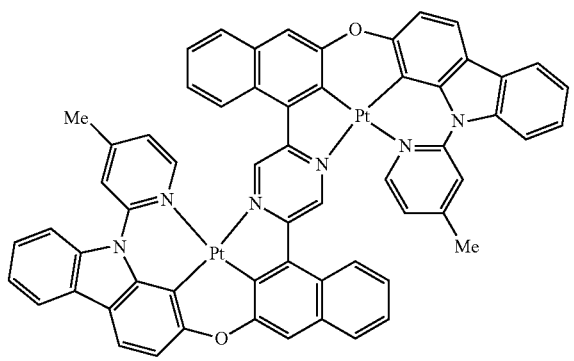
Compound Pt265
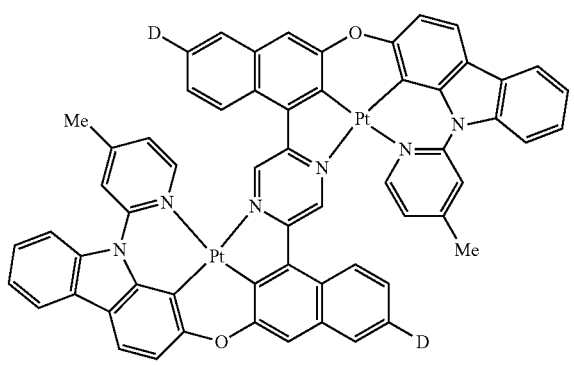
Compound Pt266
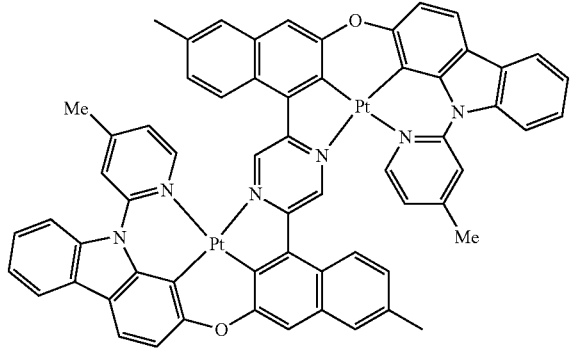
Compound Pt267
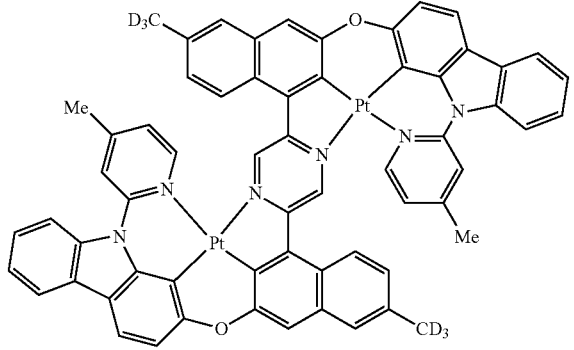
Compound Pt268
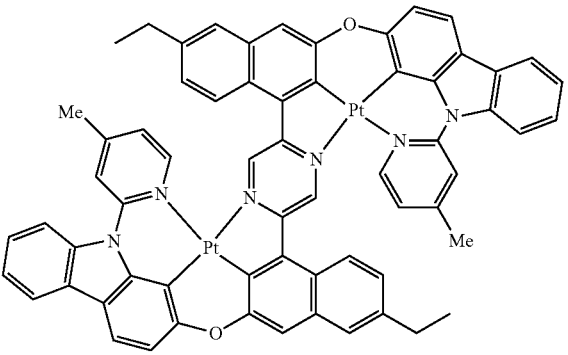
Compound Pt269
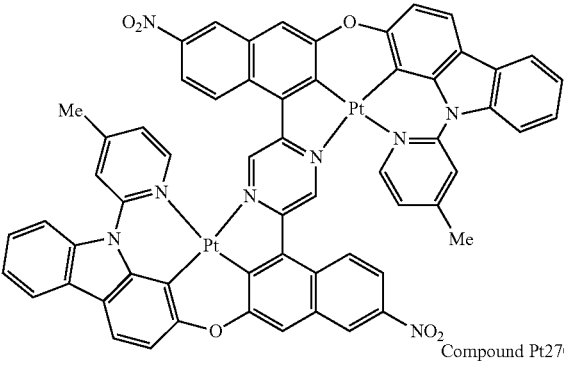
Compound Pt270
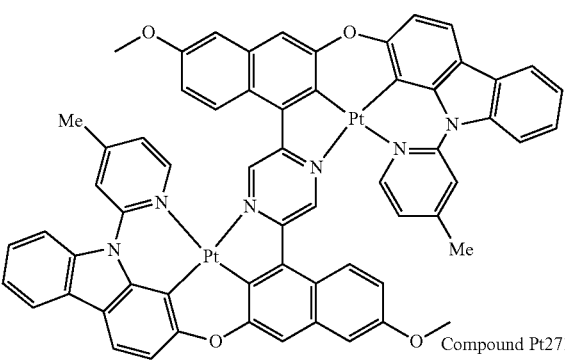
Compound Pt271
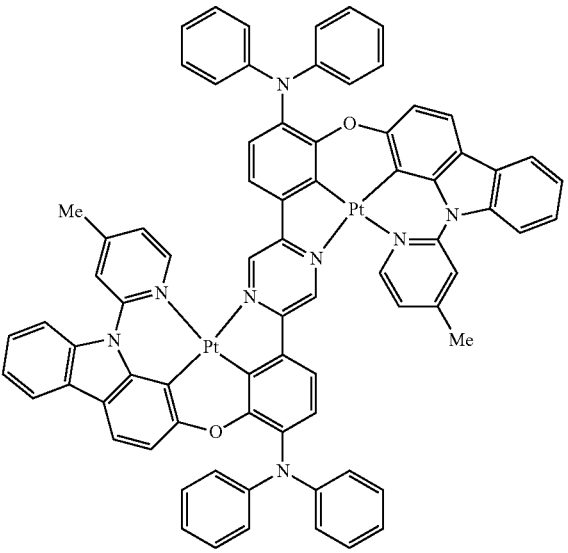

Compound Pt272
Compound Pt273
Compound Pt274
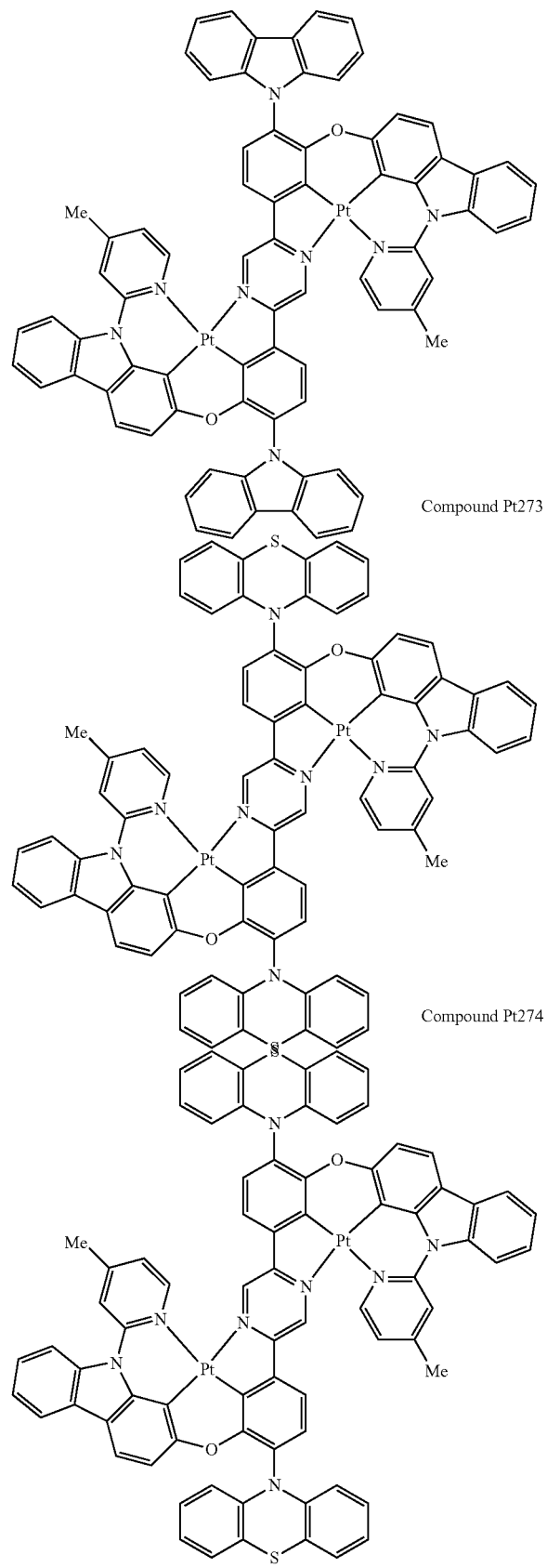
Compound Pt275
Compound Pt276
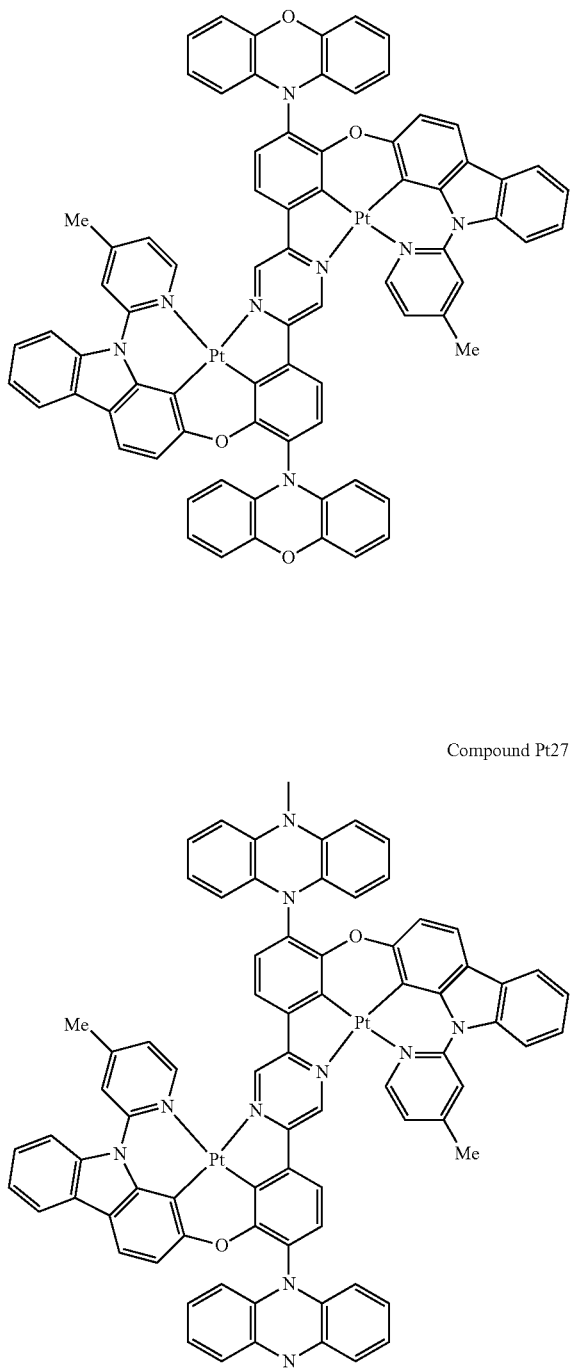

Compound Pt277
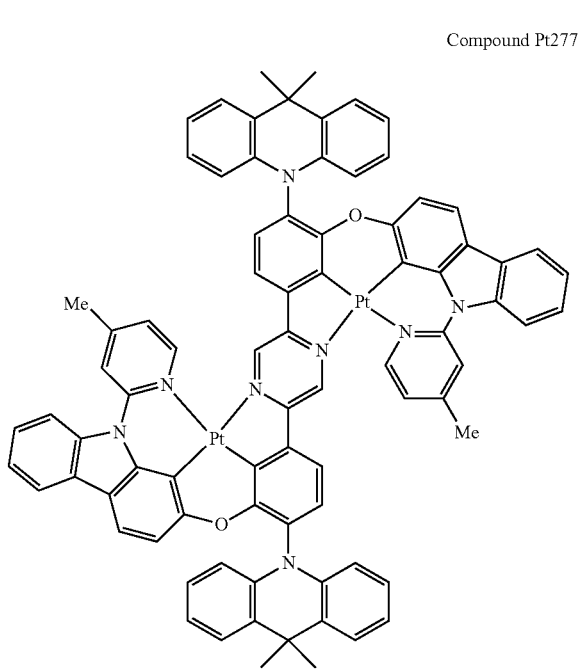
Compound Pt279
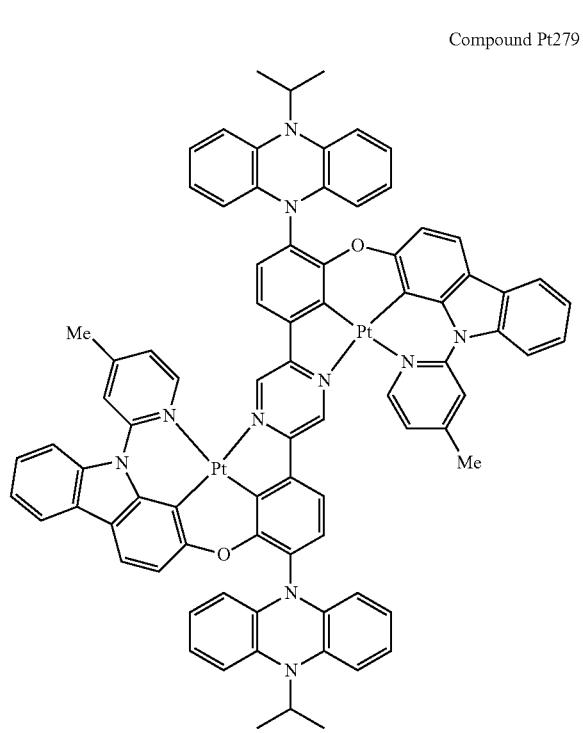
Compound Pt278
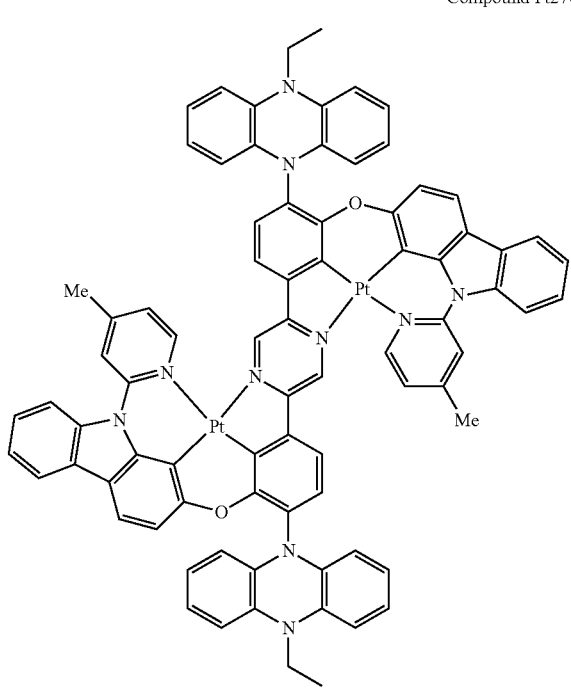
Compound Pt280
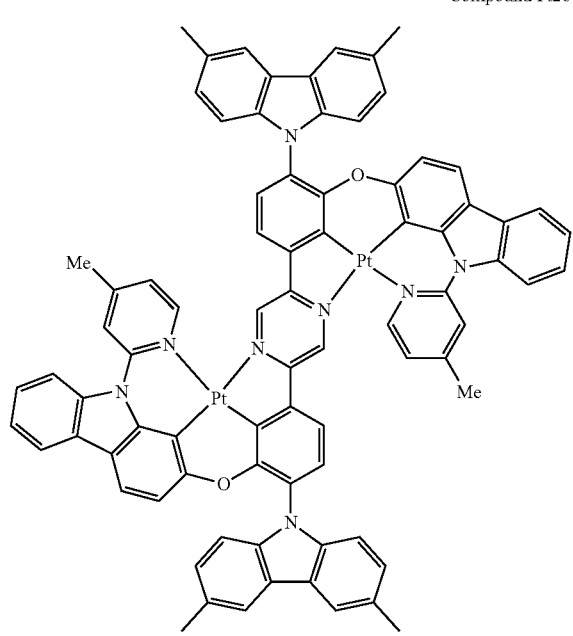

Compound Pt281
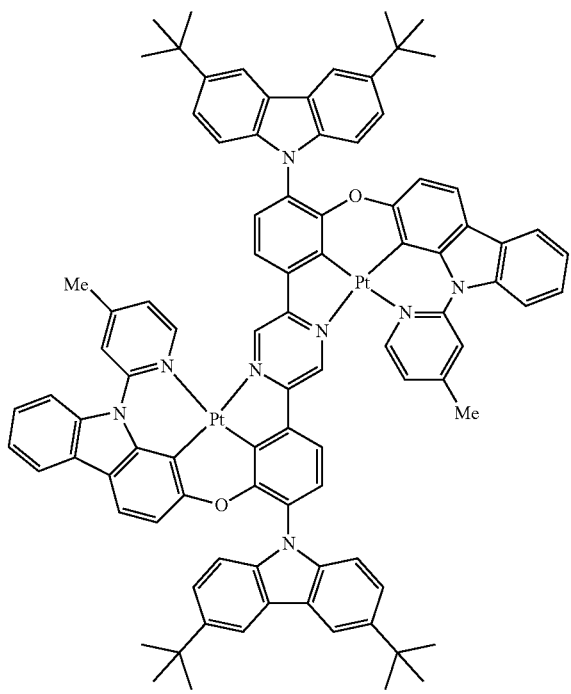
Compound Pt282
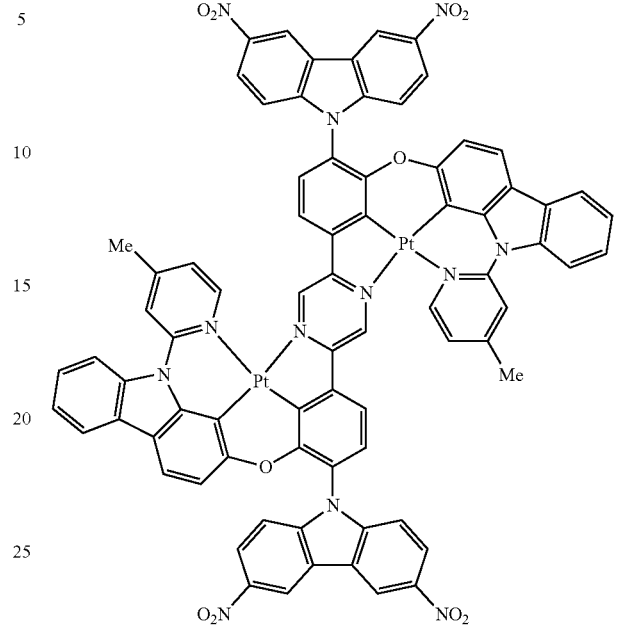
Compound Pt283
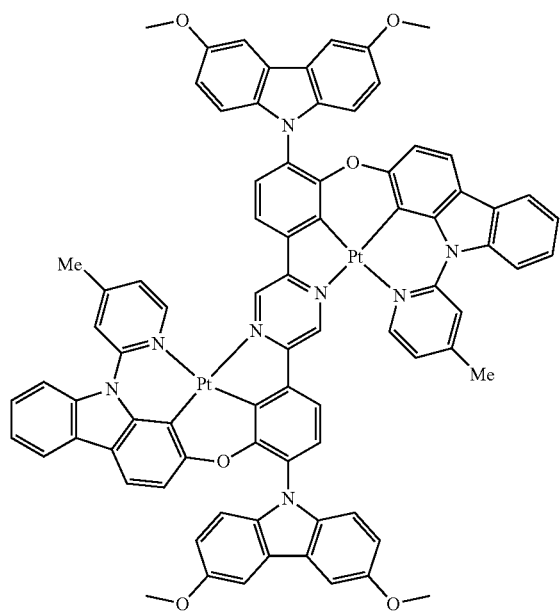
Compound Pt284
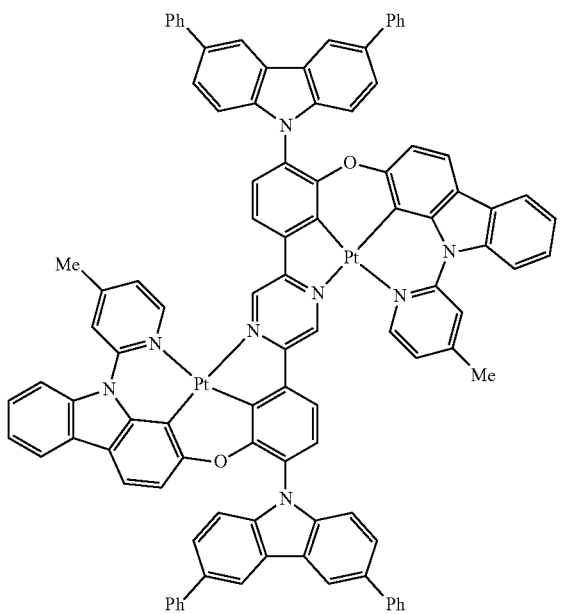

-continued
Compound Pt285
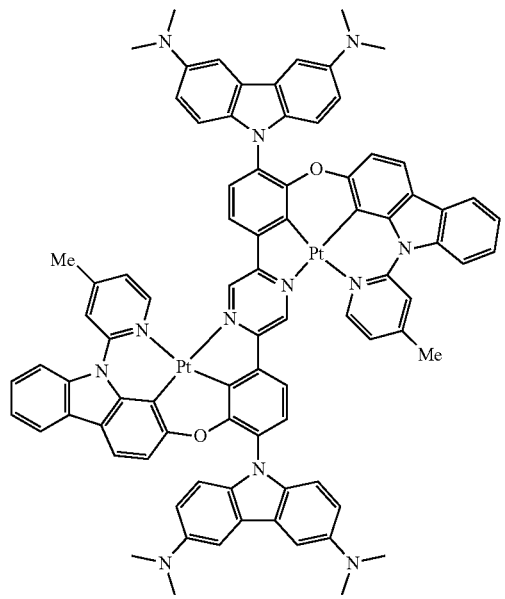
Compound Pt286
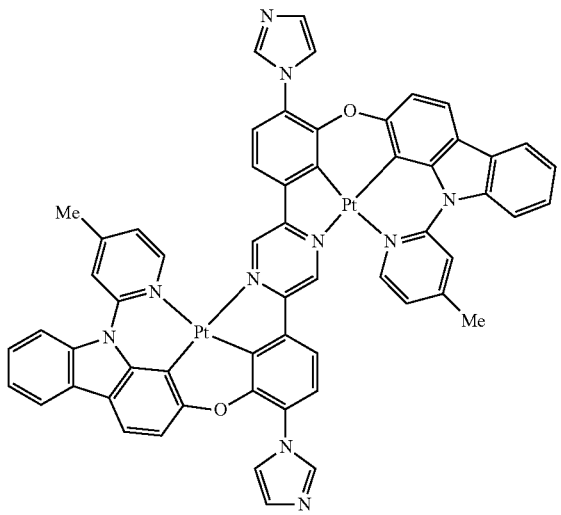
Compound Pt287
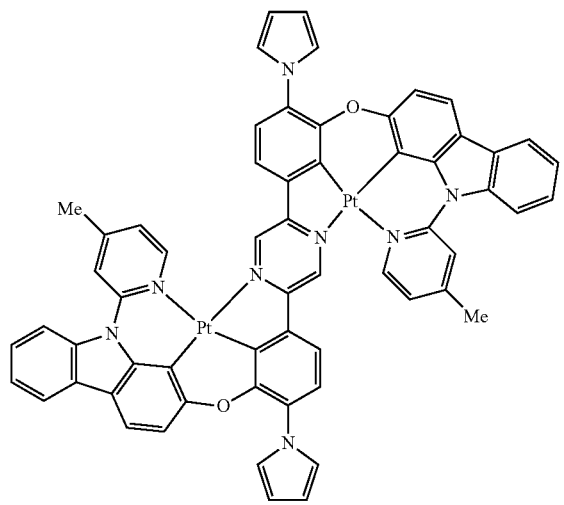
Compound Pt288
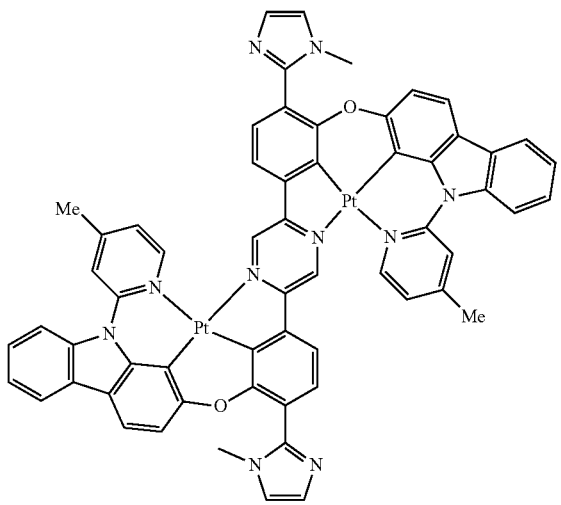
Compound Pt289
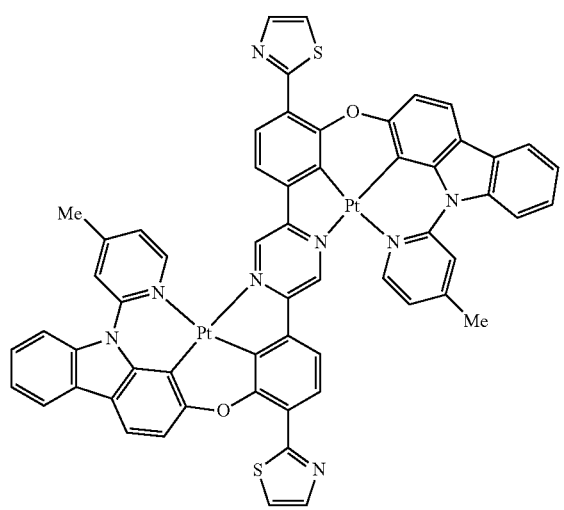
Compound Pt290
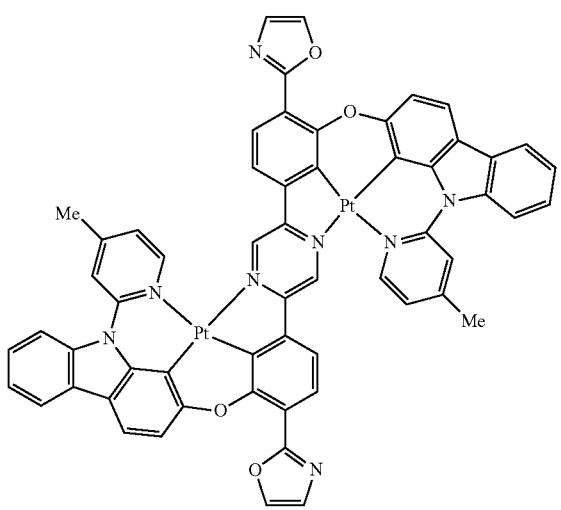

-continued
Compound Pt291
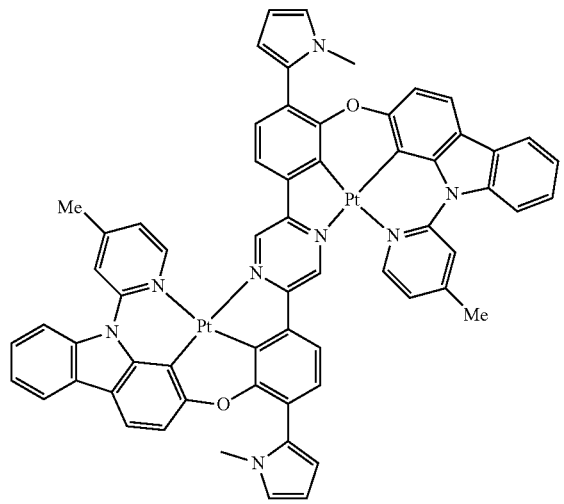
Compound Pt292
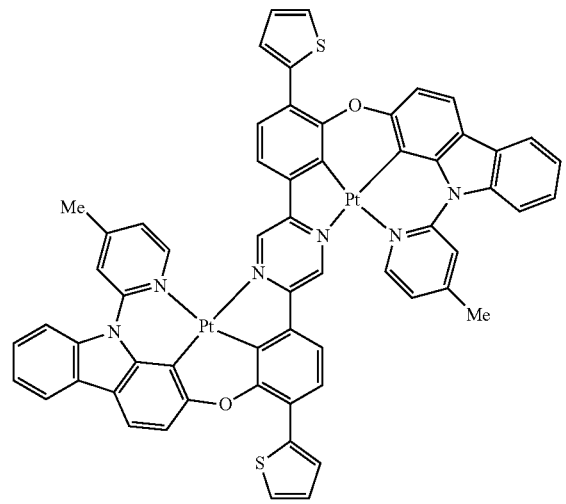
Compound Pt293
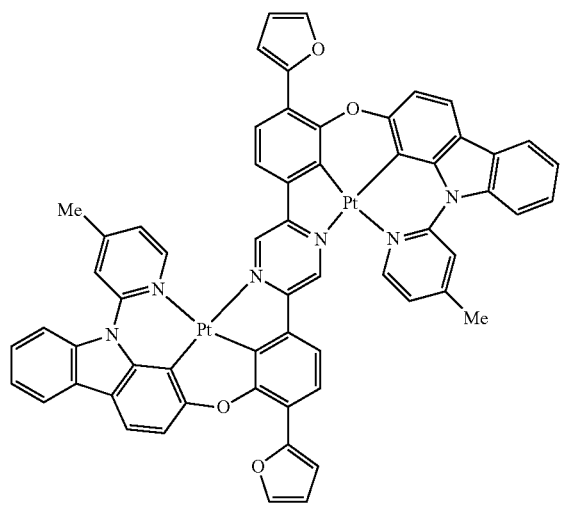
Compound Pt294
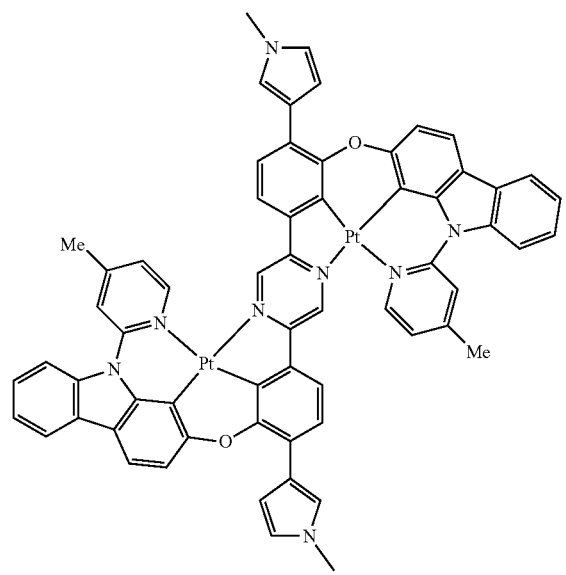
Compound Pt295
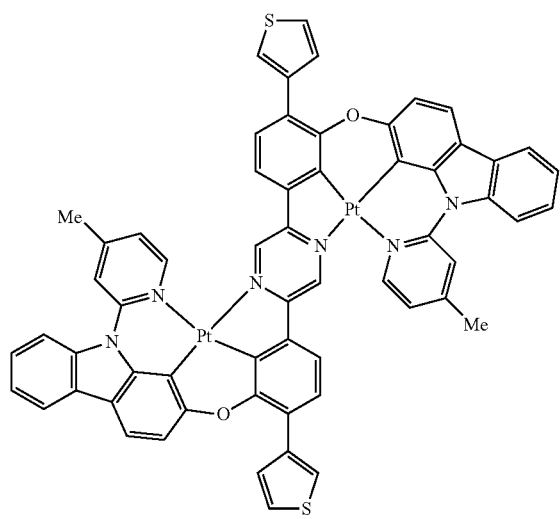
Compound Pt296
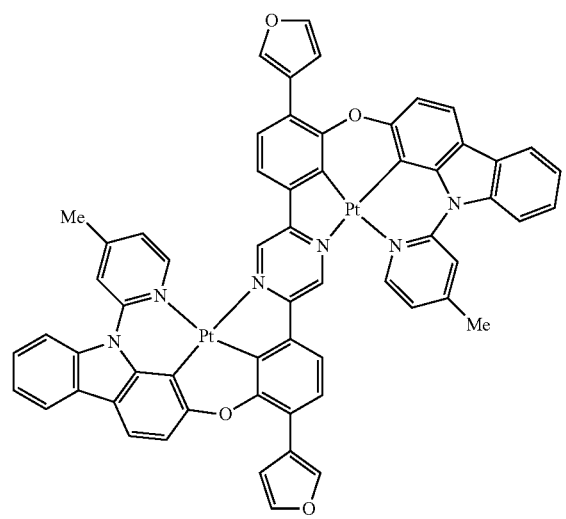

-continued
Compound Pt297
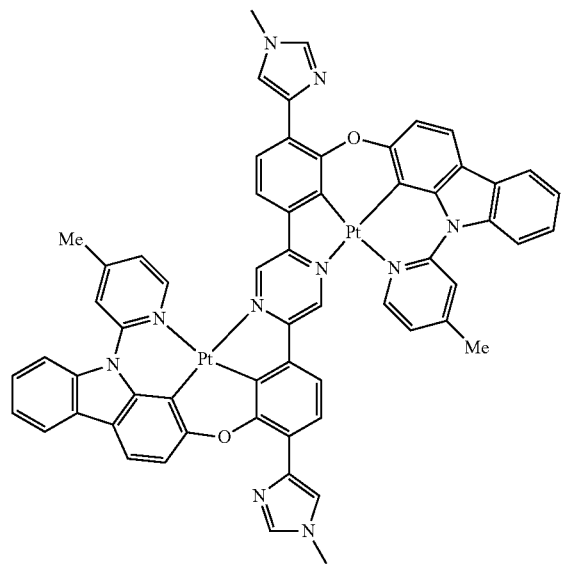
Compound Pt298
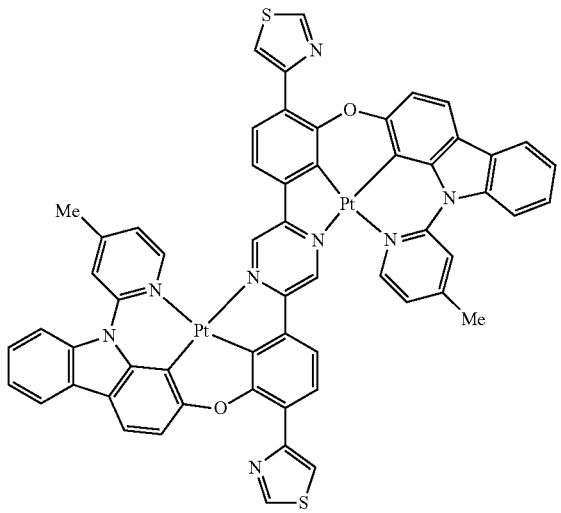
Compound Pt299
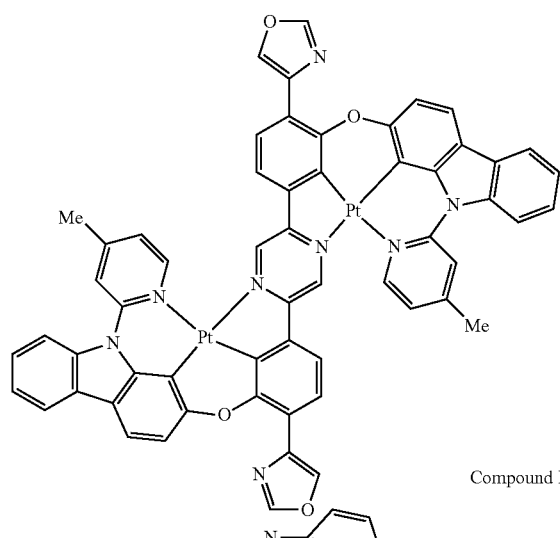
Compound Pt300
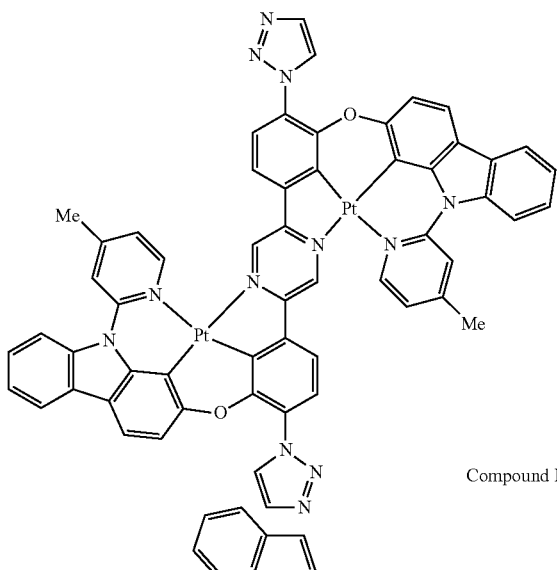
Compound Pt301
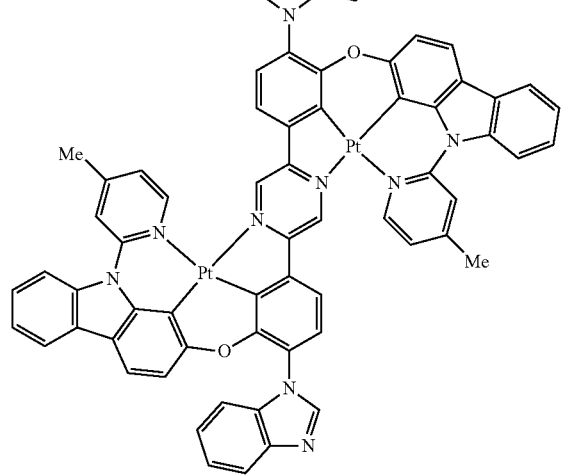
Compound Pt302
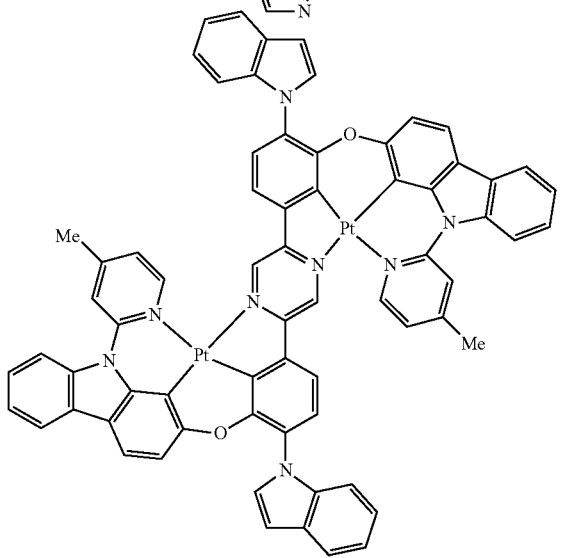

-continued
Compound Pt303
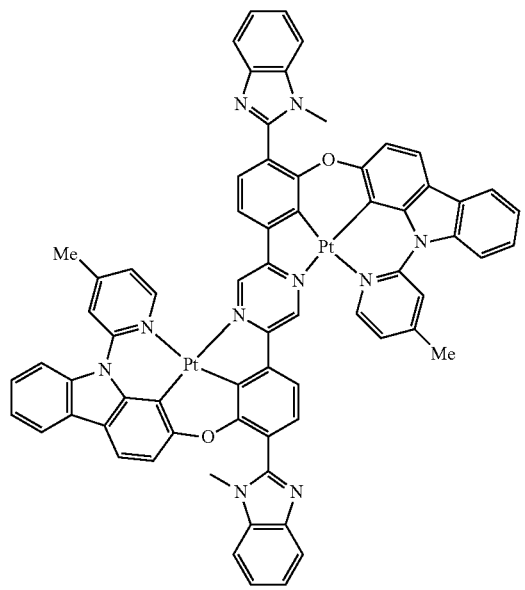
Compound Pt304
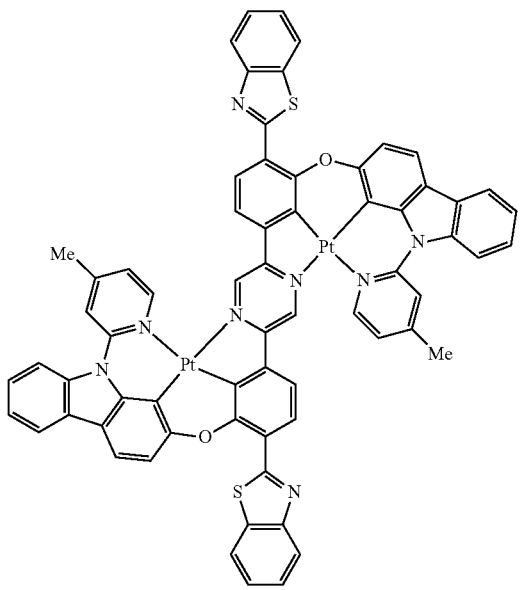
Compound Pt305
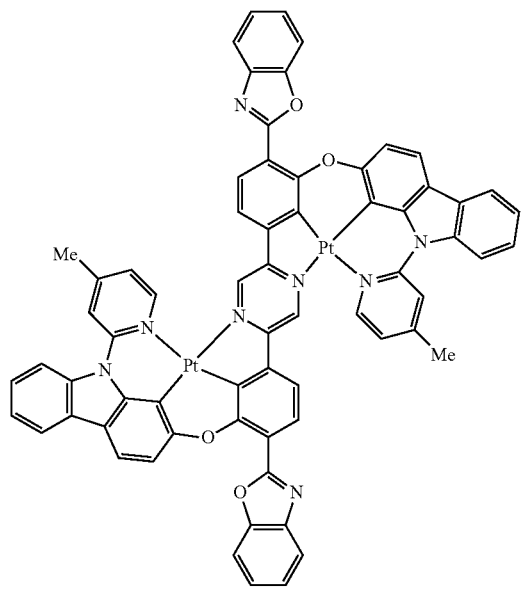
Compound Pt306
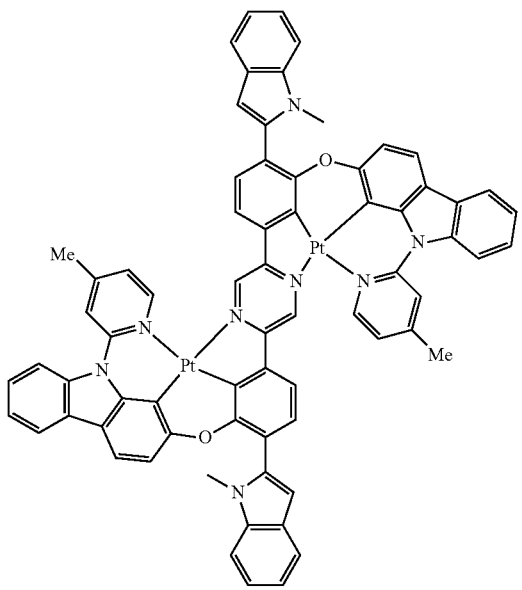
Compound PdPt1
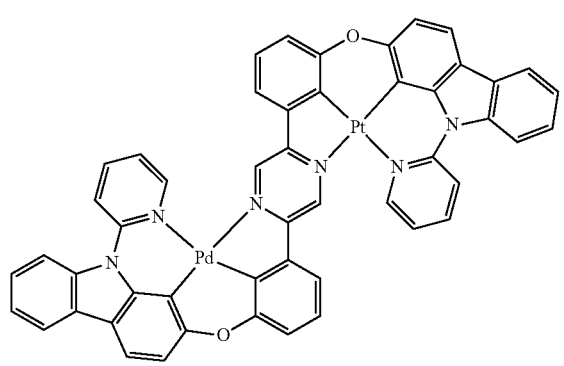
Compound PdPt2
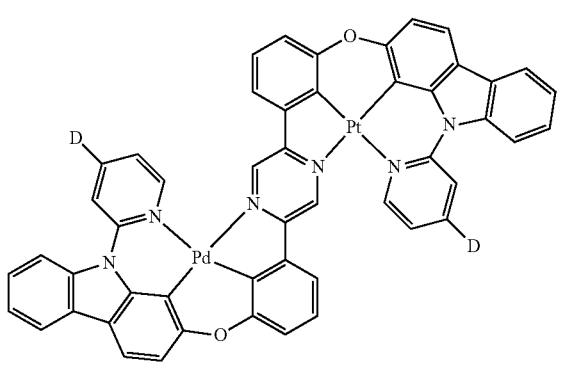

-continued
Compound PdPt3
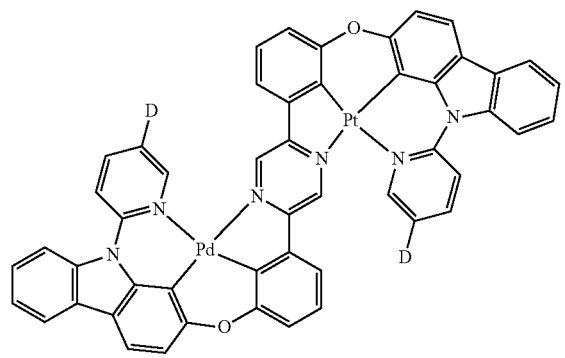
Compound PdPt4
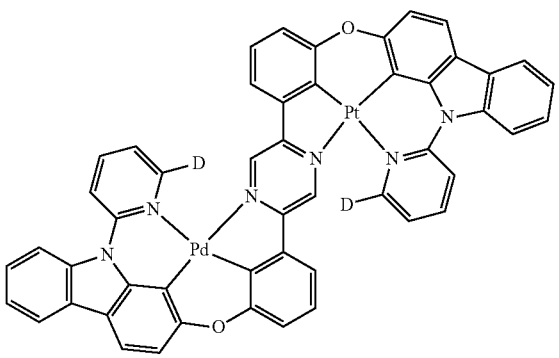
Compound PdPt5
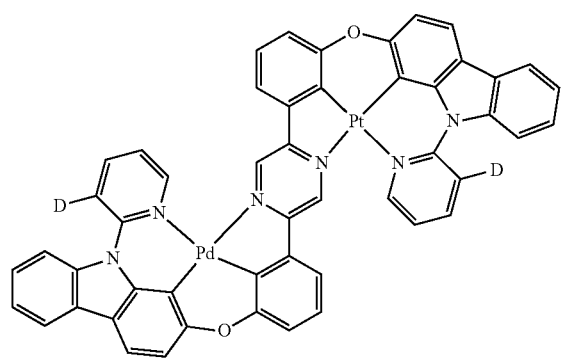
Compound PdPt6
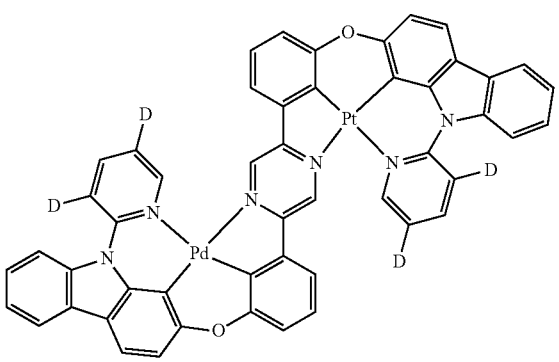
Compound PdPt7
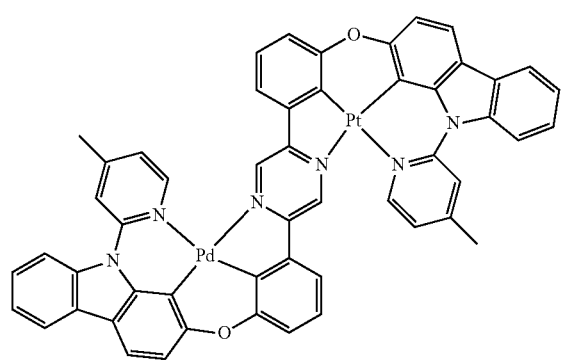
Compound PdPt8
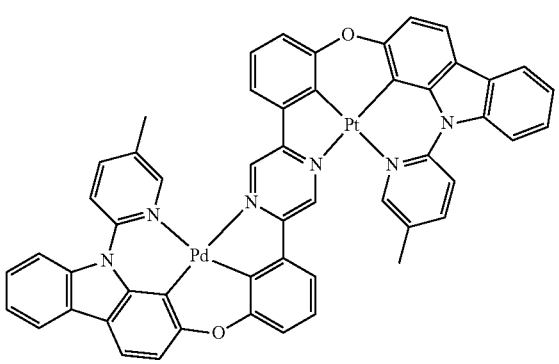
Compound PdPt9
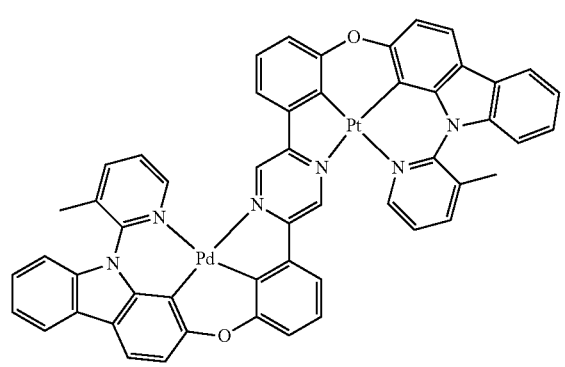
Compound PdPt10
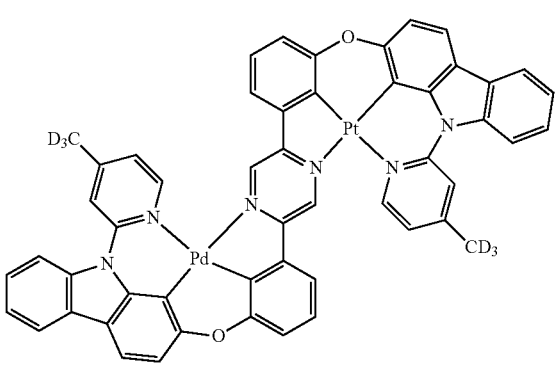

-continued
Compound PdPt11
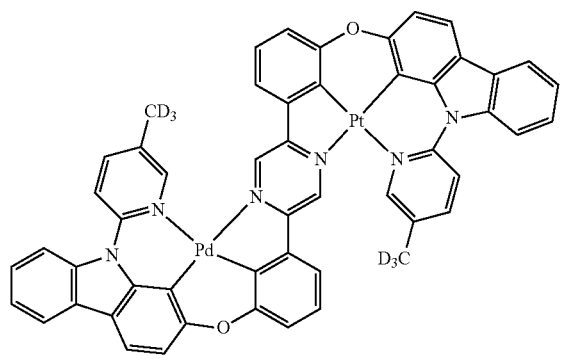
Compound PdPt12
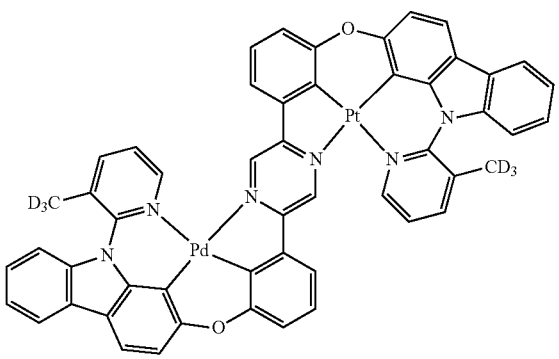
Compound PdPt13
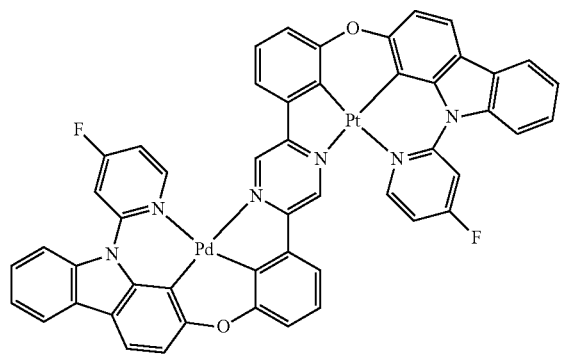
Compound PdPt14
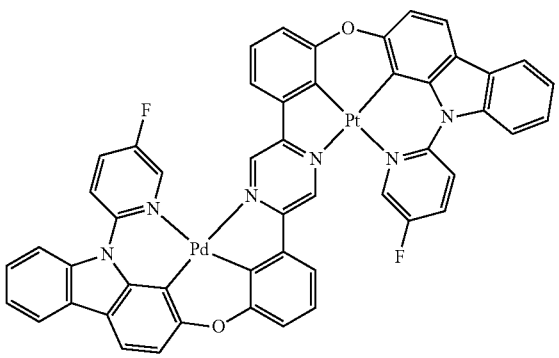
Compound PdPt15
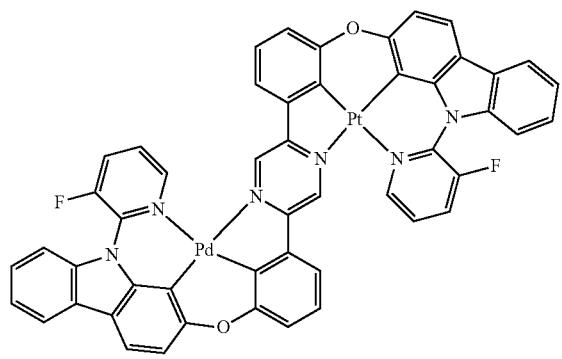
Compound PdPt16
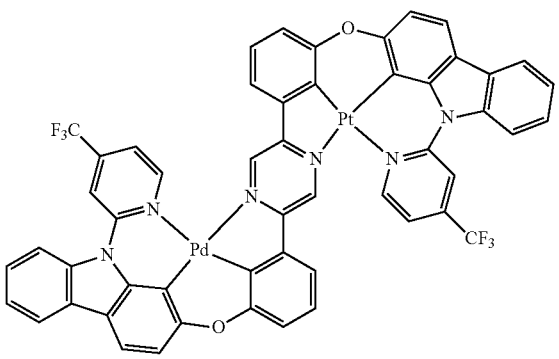
Compound PdPt17
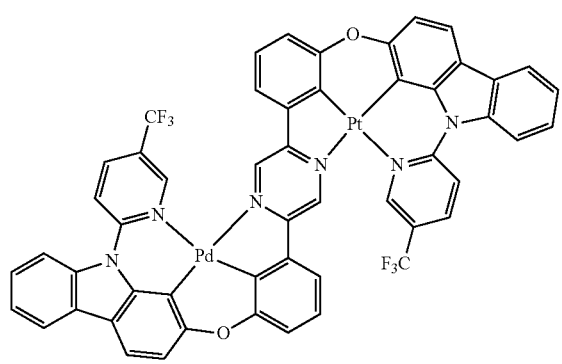
Compound PdPt18
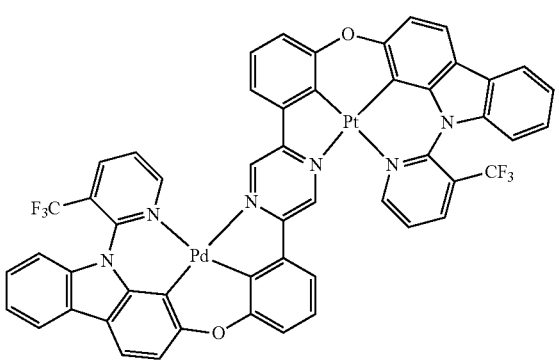

-continued
Compound PdPt19
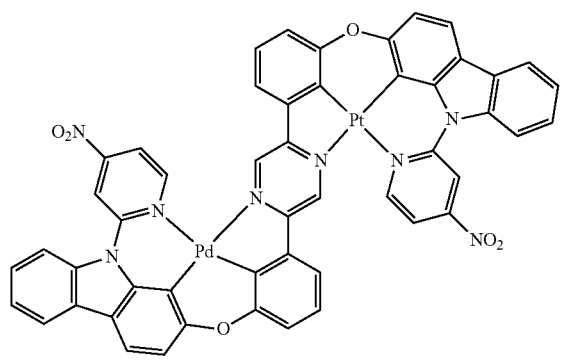
Compound PdPt20
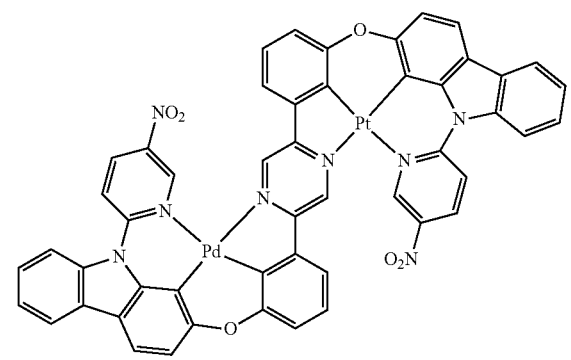
Compound PdPt21
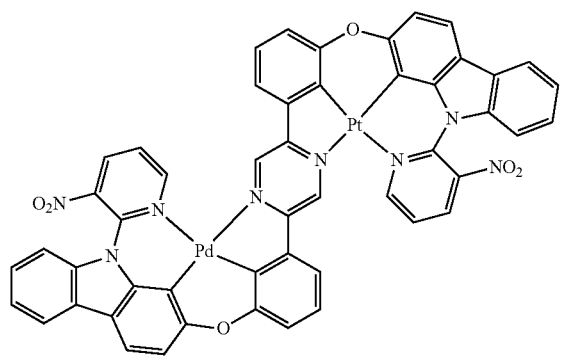
Compound PdPt22
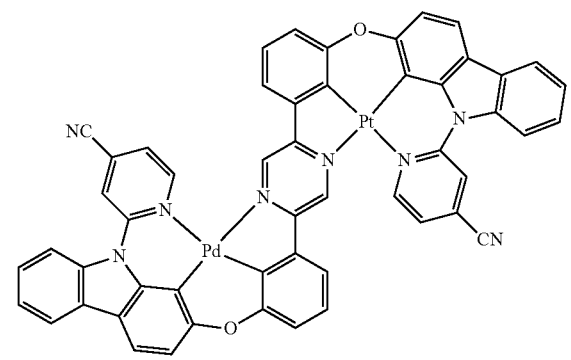
Compound PdPt23
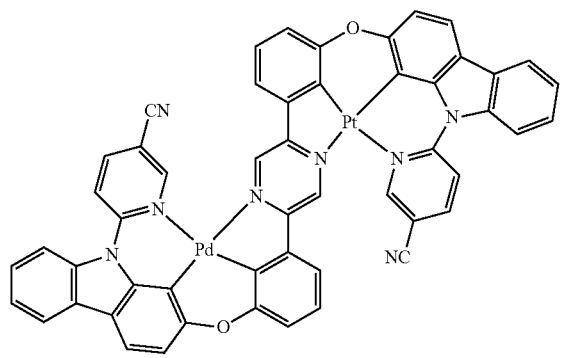
Compound PdPt24
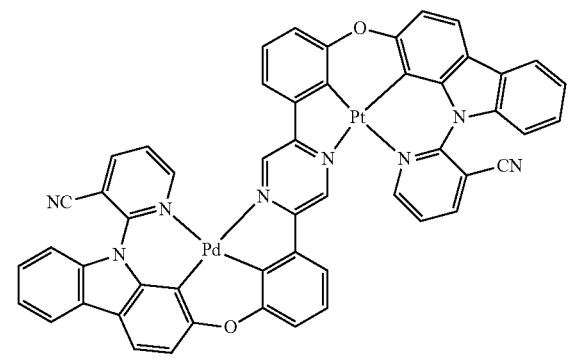
Compound PdPt25
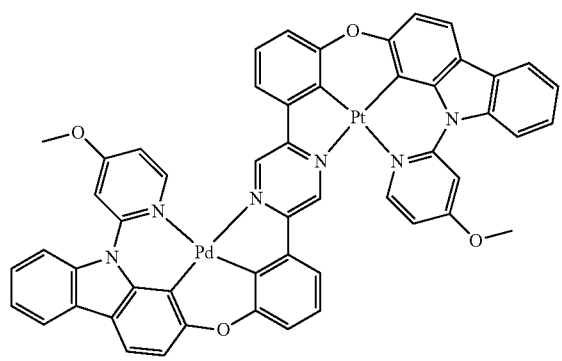
Compound PdPt26
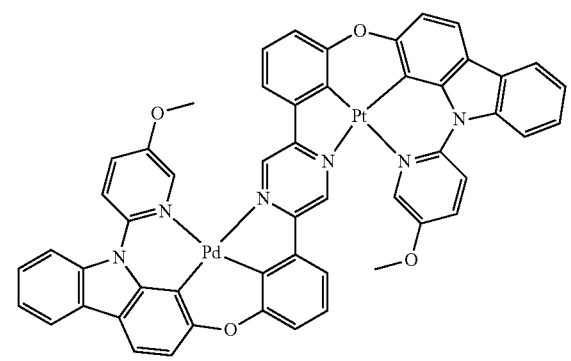

-continued
Compound PdPt27
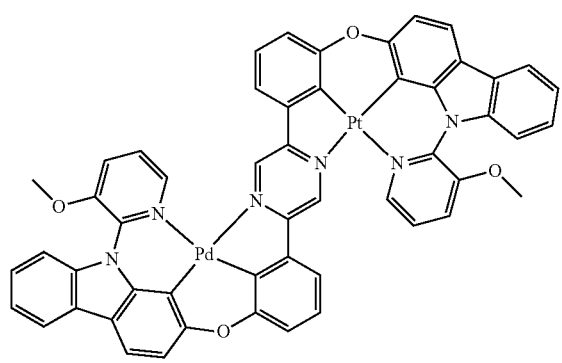
Compound PdPt28
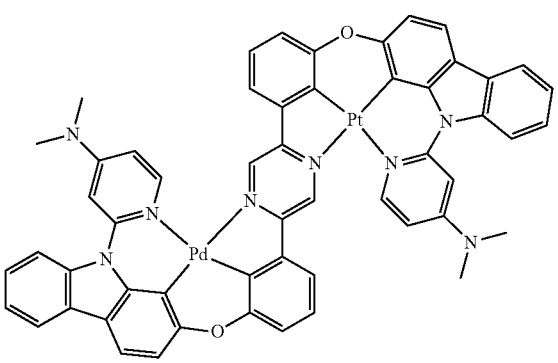
Compound PdPt29
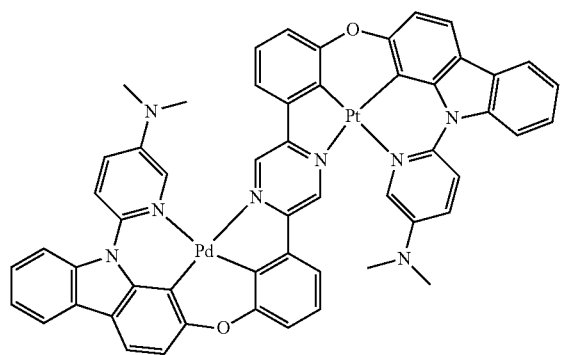
Compound PdPt30
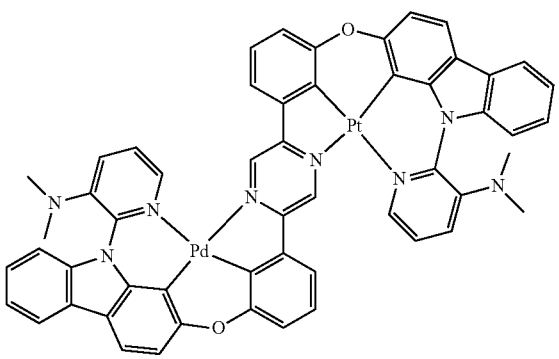
Compound PdPt31
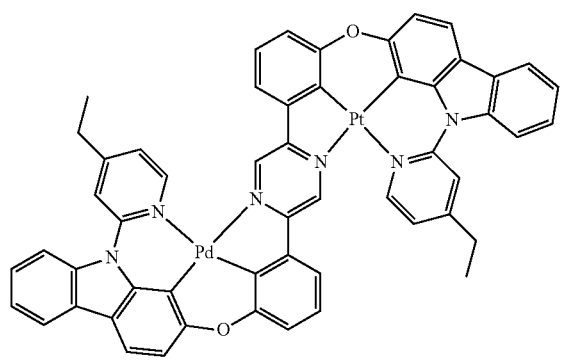
Compound PdPt32
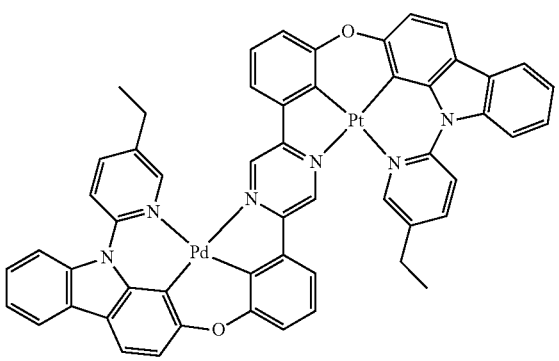
Compound PdPt33
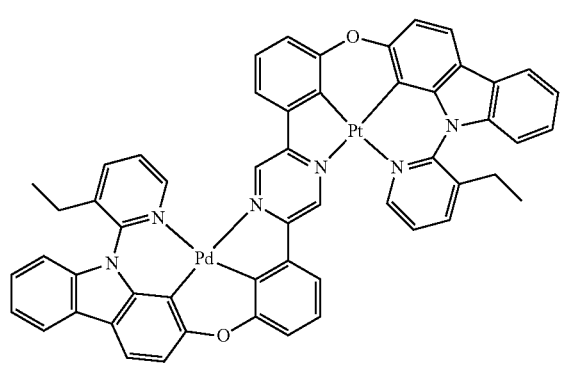
Compound PdPt34
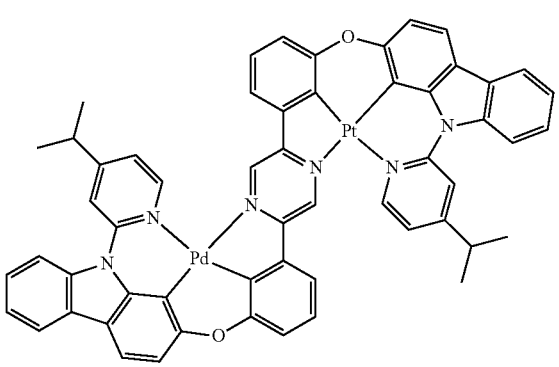

-continued
Compound PdPt35
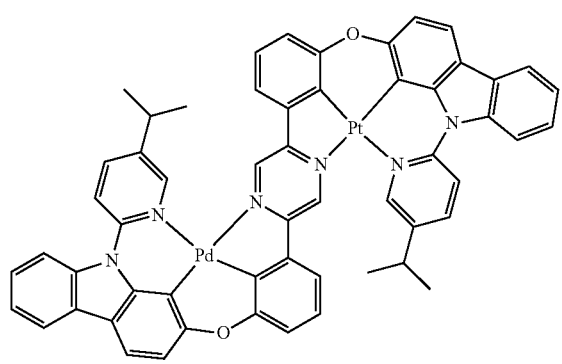
Compound PdPt36
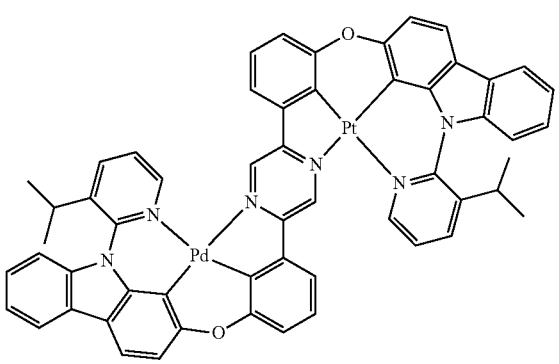
Compound PdPt37
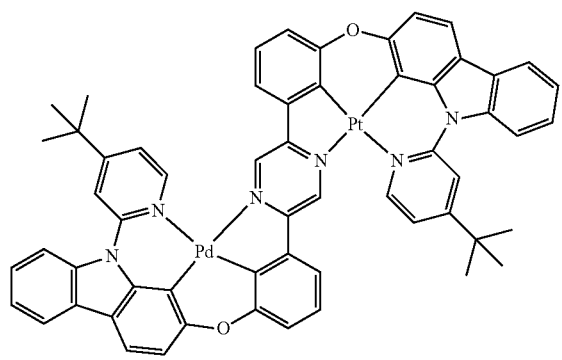
Compound PdPt38
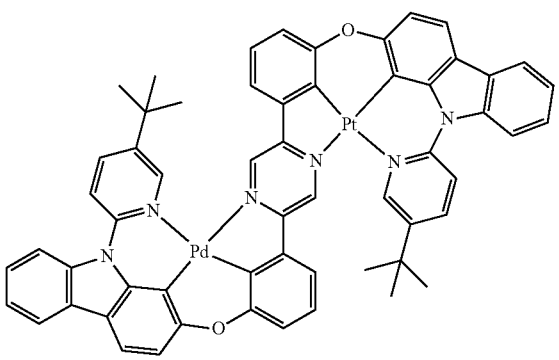
Compound PdPt39
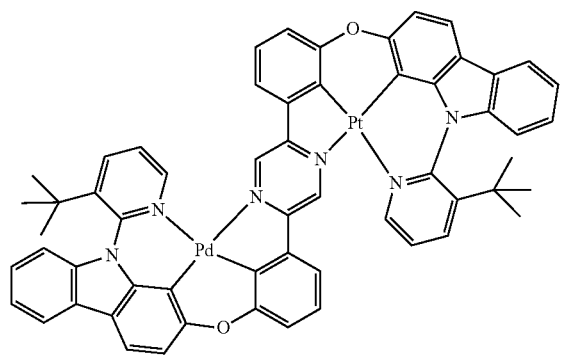
Compound PdPt40
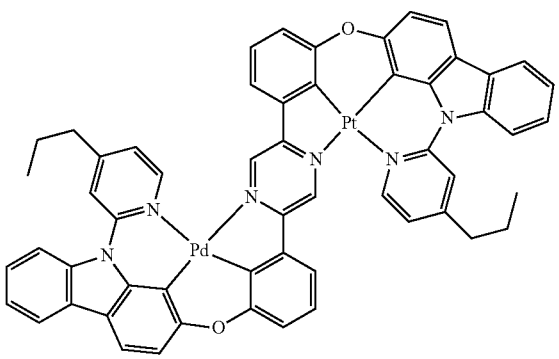
Compound PdPt41
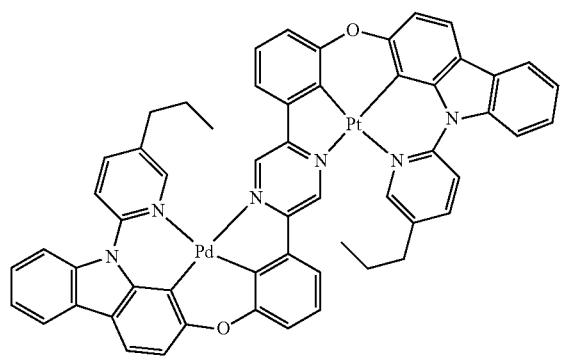
Compound PdPt42
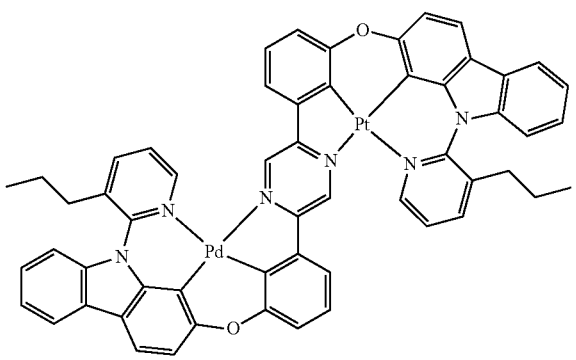

Compound PdPt43
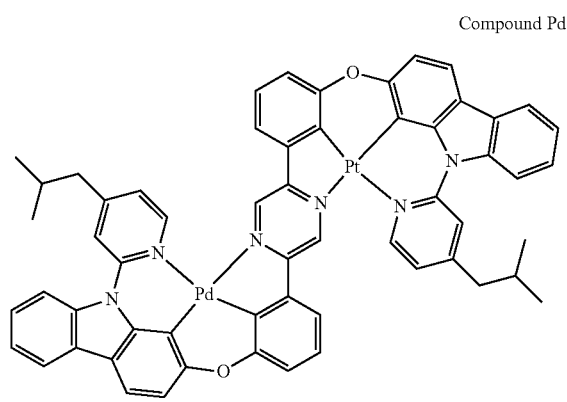
Compound PdPt44
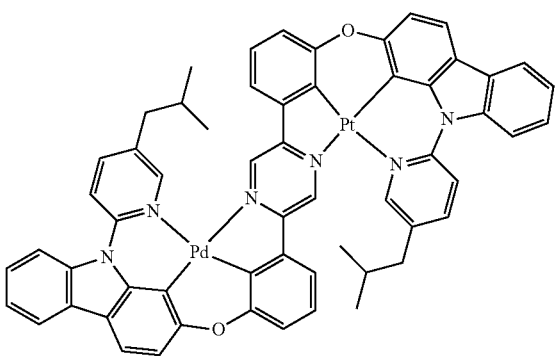
Compound PdPt45
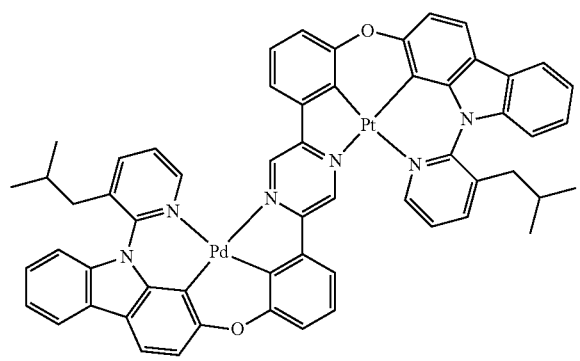
Compound PdPt46
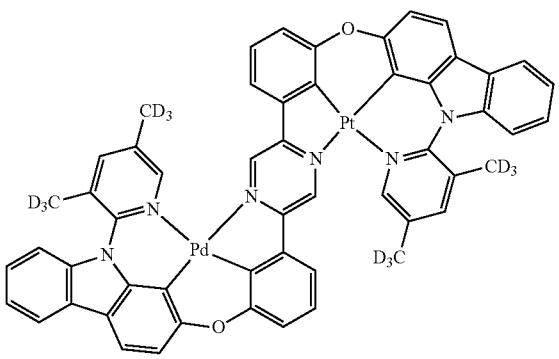
Compound PdPt47
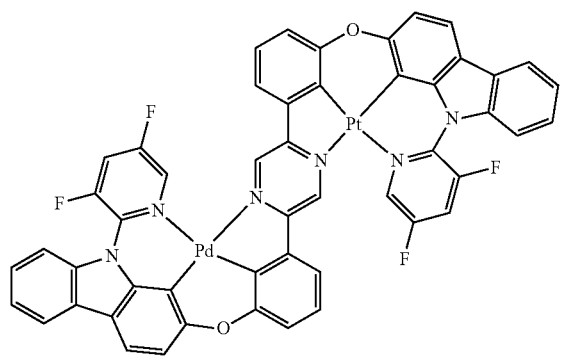
Compound PdPt48
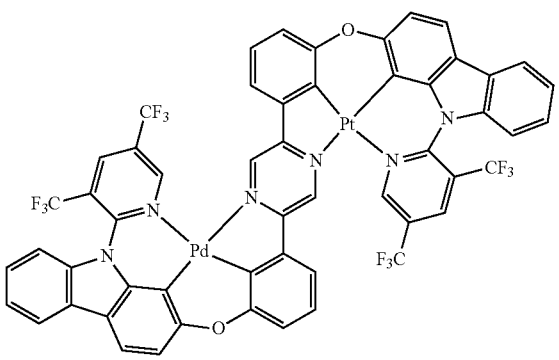
Compound PdPt49
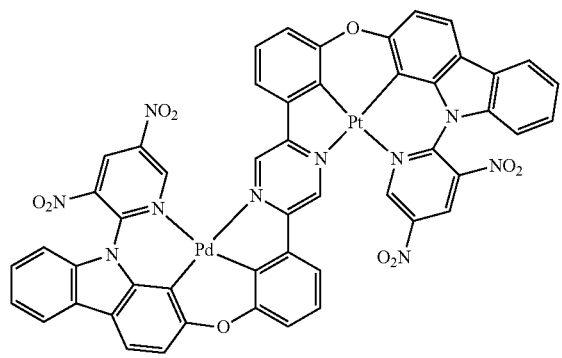
Compound PdPt50
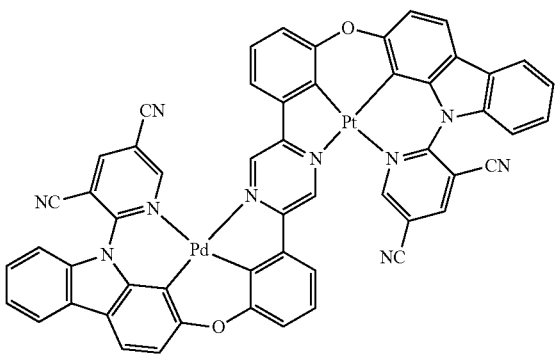

Compound PdPt51
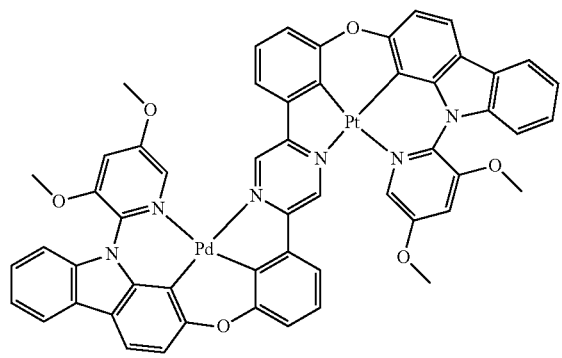
Compound PdPt52
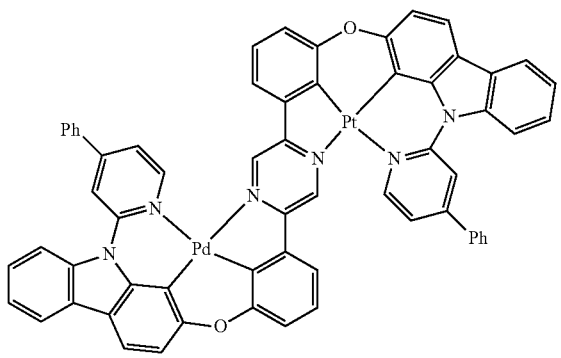
Compound PdPt53
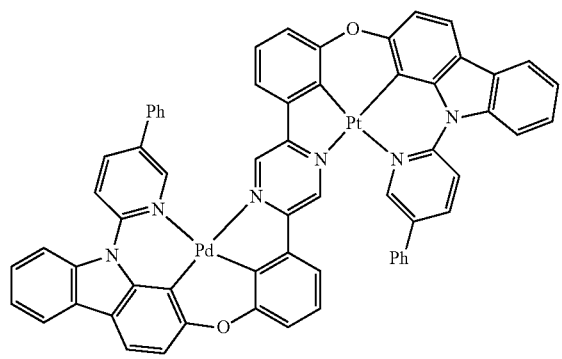
Compound PdPt54
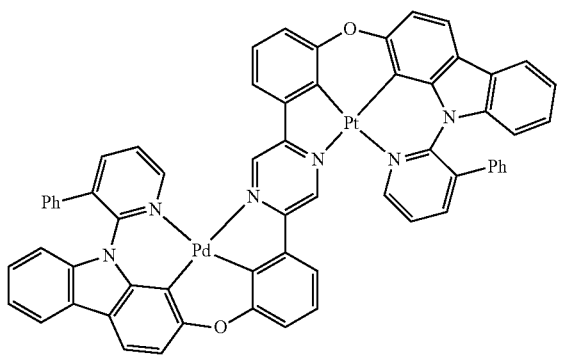
Compound PdPt55
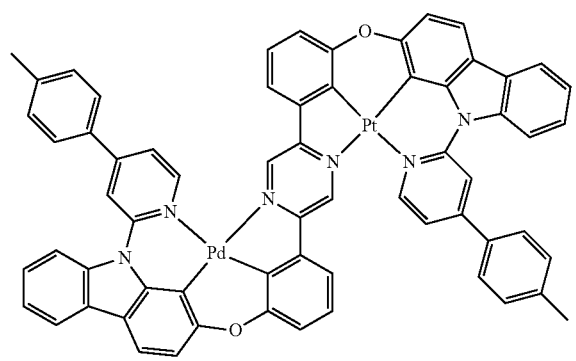
Compound PdPt56
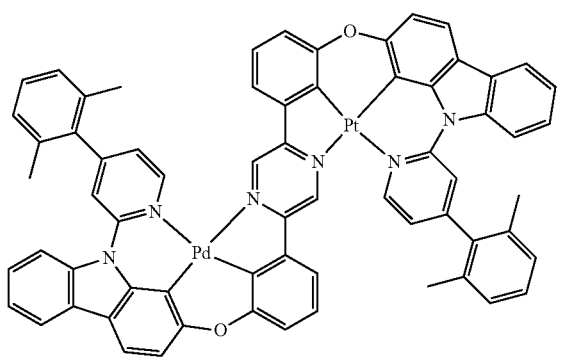
Compound PdPt57
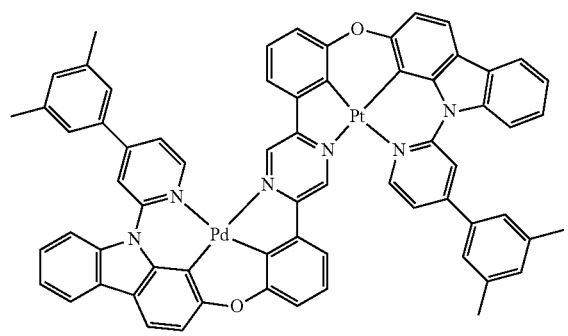
Compound PdPt58
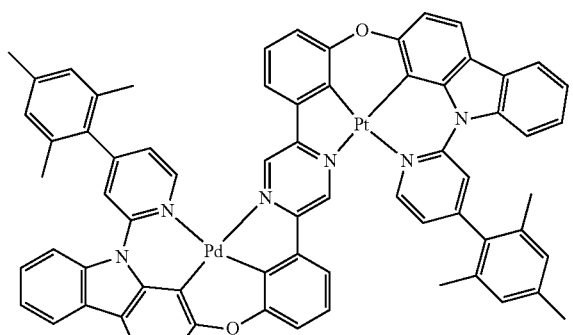

-continued
Compound PdPt59
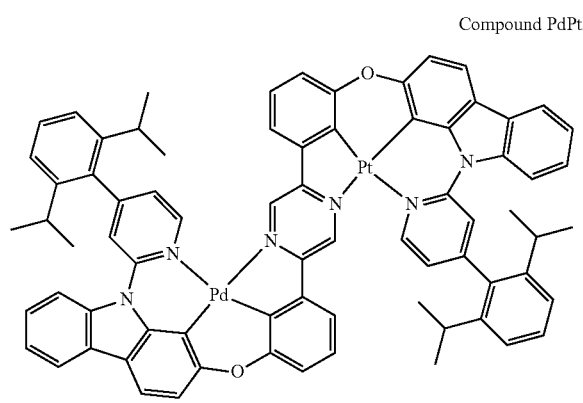
Compound PdPt60
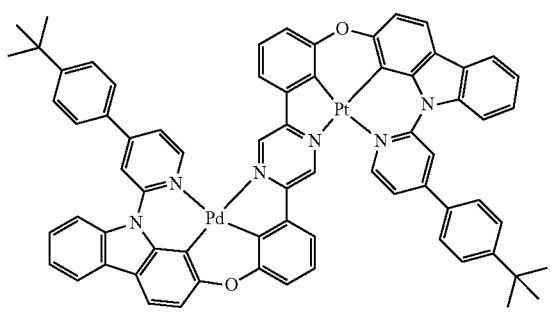
Compound PdPt61
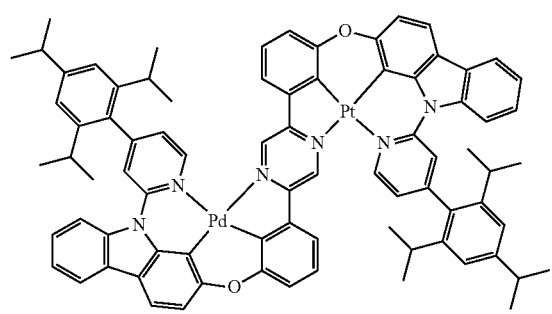
Compound PdPt62
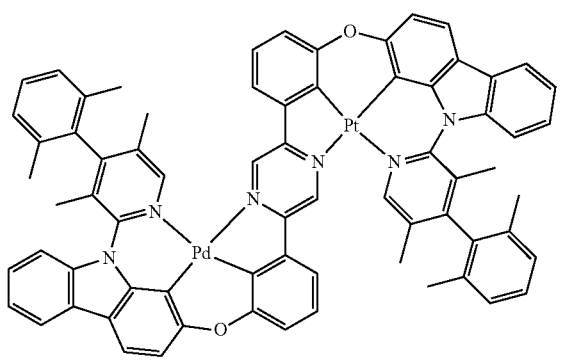
Compound PdPt63
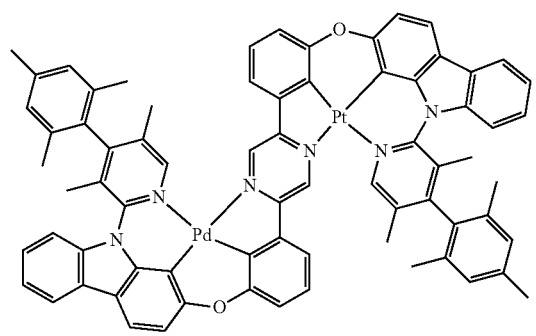
Compound PdPt64
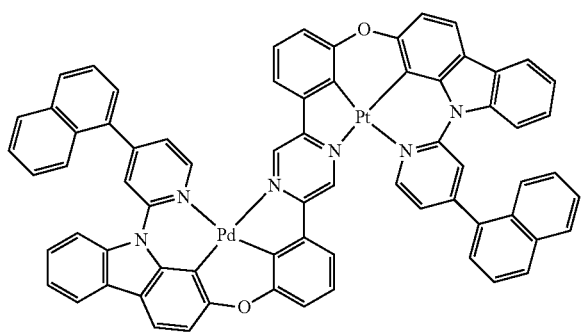
Compound PdPt5
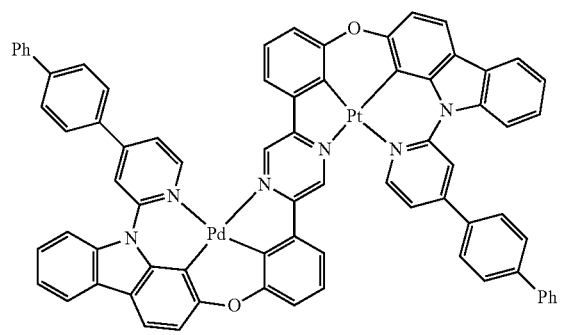
Compound PdPt66
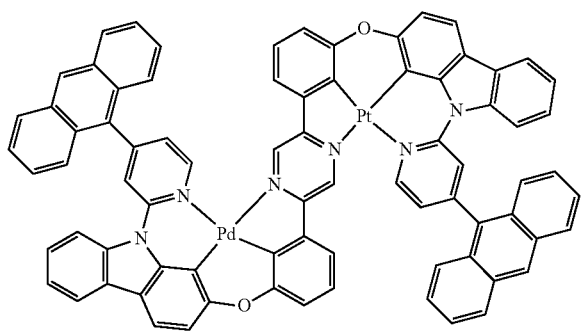

-continued
Compound PdPt67
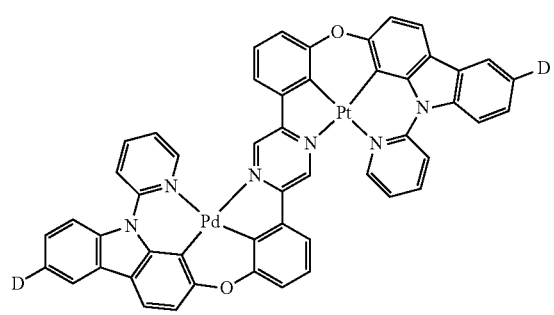
Compound PdPt68
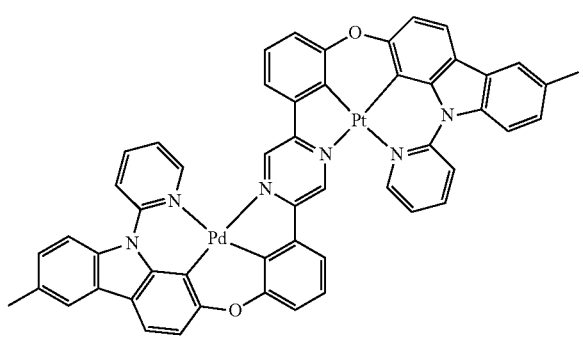
Compound PdPt69
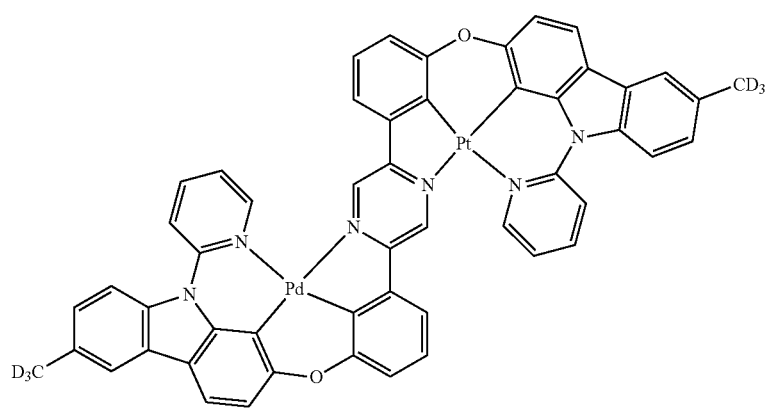
Compound PdPt70
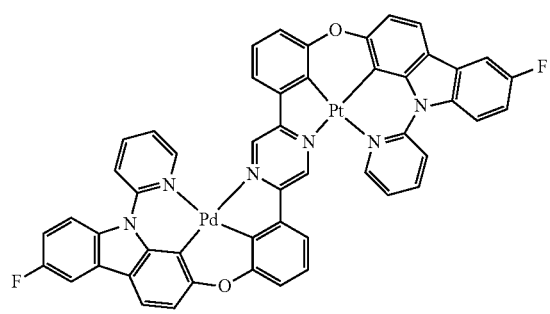
Compound PdPt71
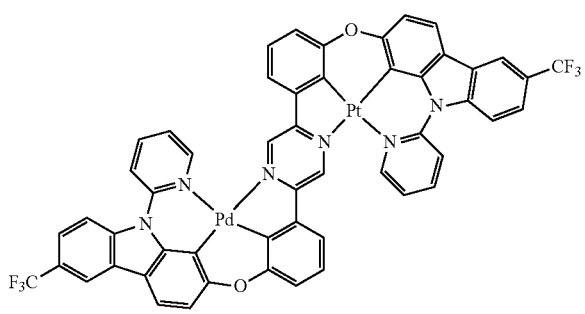
Compound PdPt72
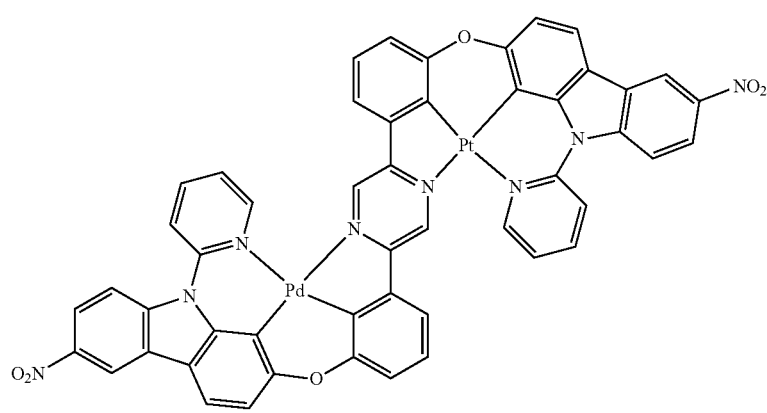

Compound PdPt73
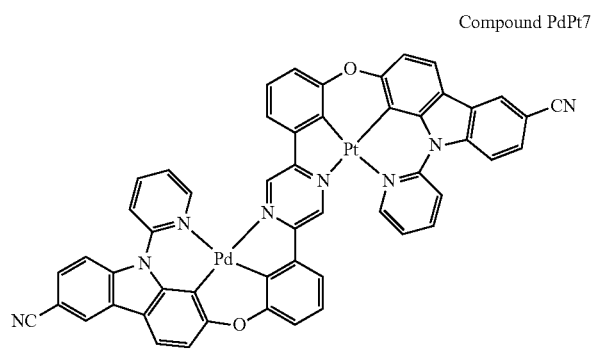
Compound PdPt74
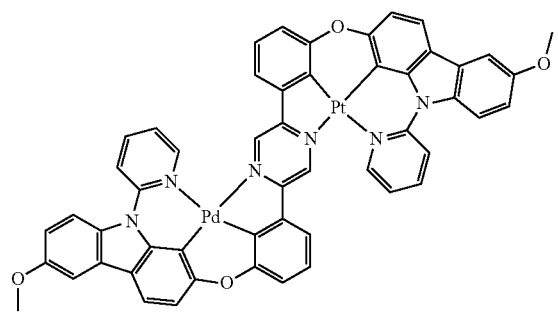
Compound PdPt75
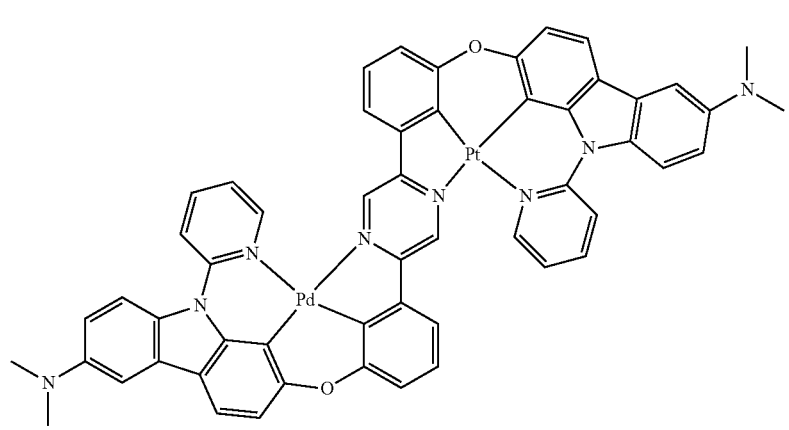
Compound PdPt76
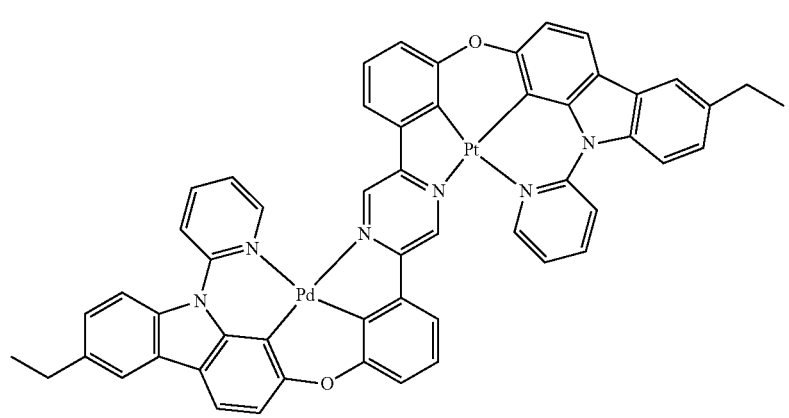
Compound PdPt77
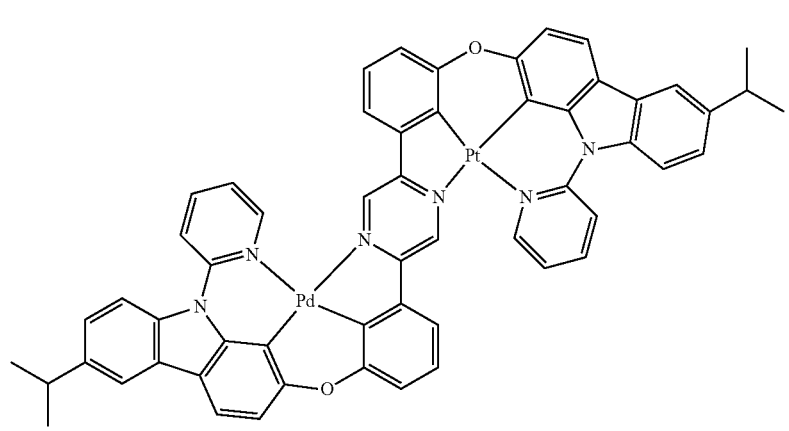

-continued
Compound PdPt78
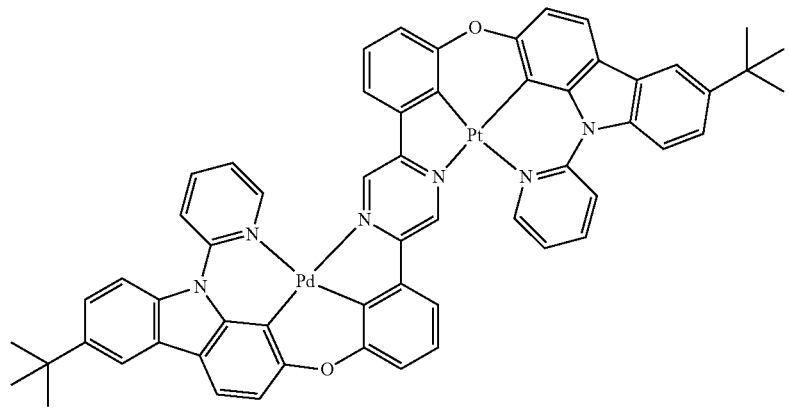
Compound PdPt79
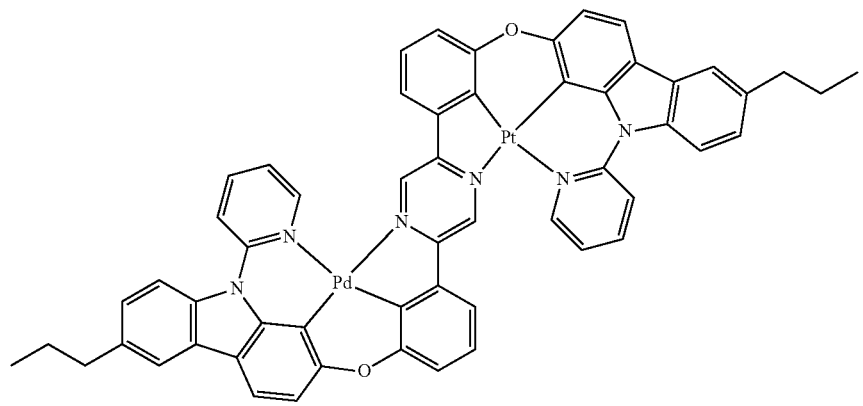
Compound PdPt80
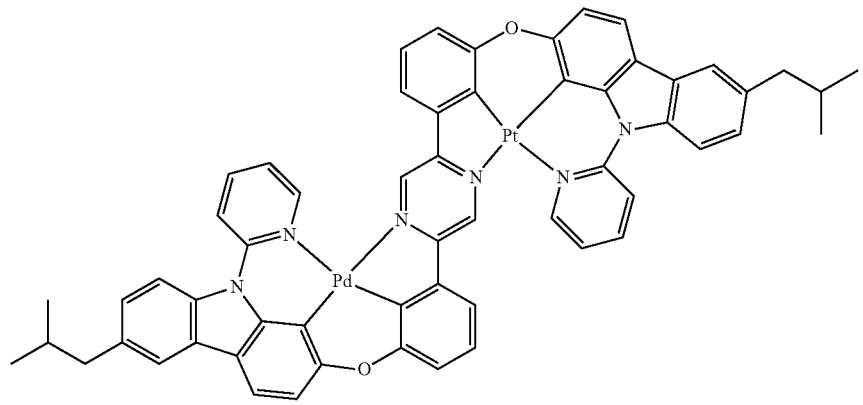
Compound PdPt81
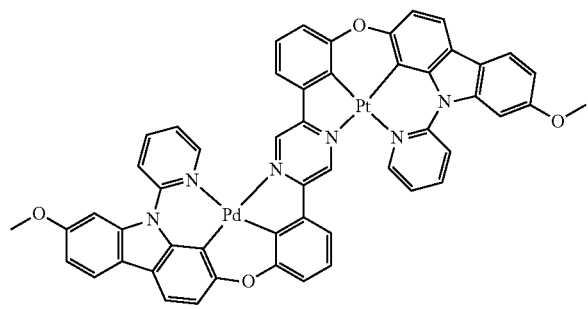
Compound PdPt82
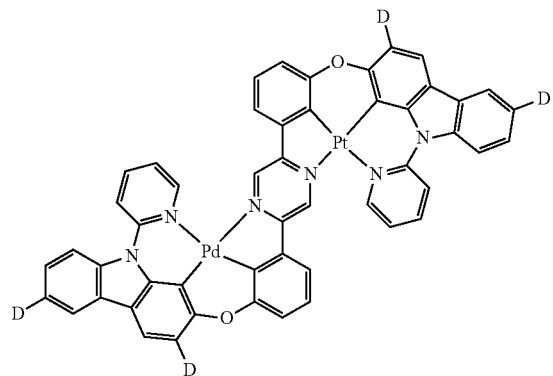

Compound PdPt83
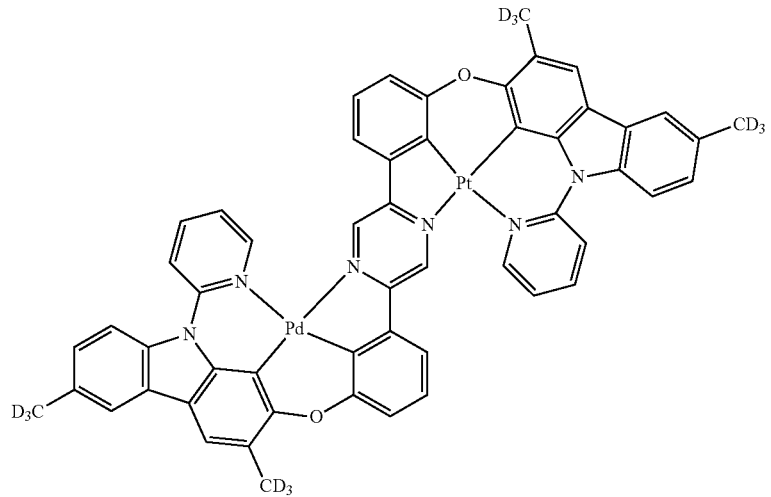
Compound PdPt84
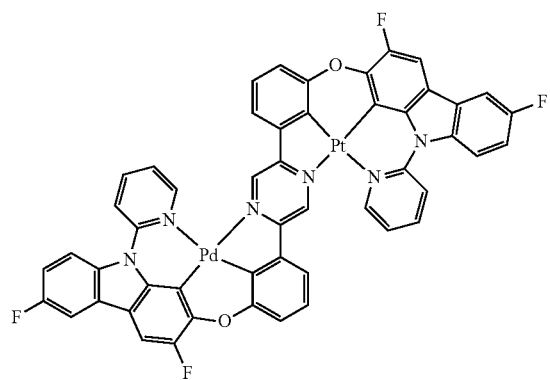
Compound PdPt85
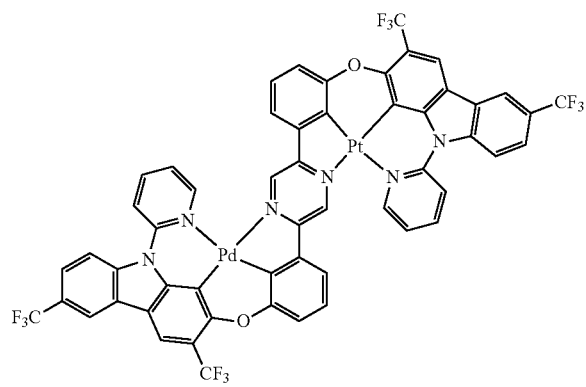
Compound PdPt86
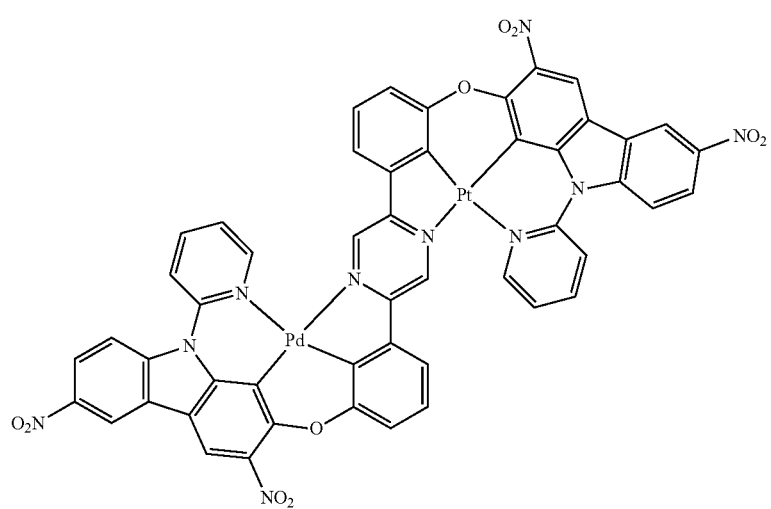

-continued
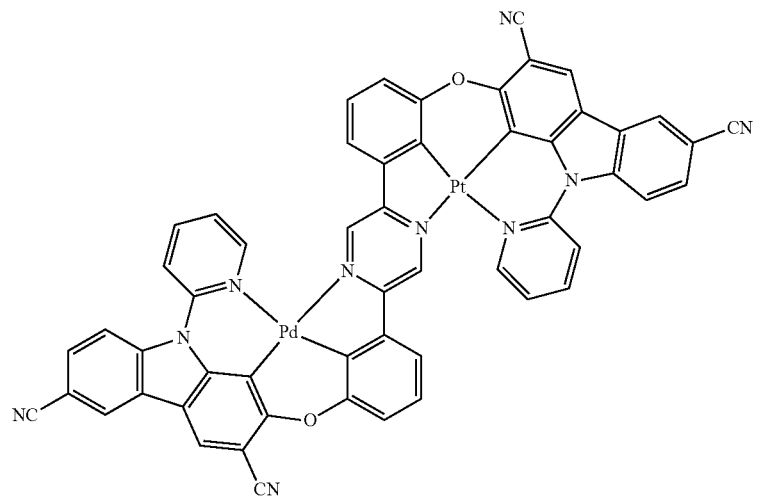
Compound PdPt87
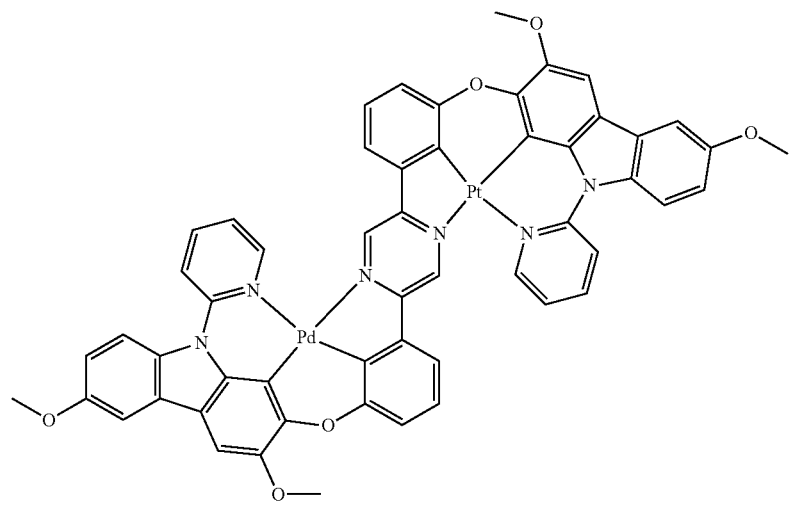
Compound PdPt88
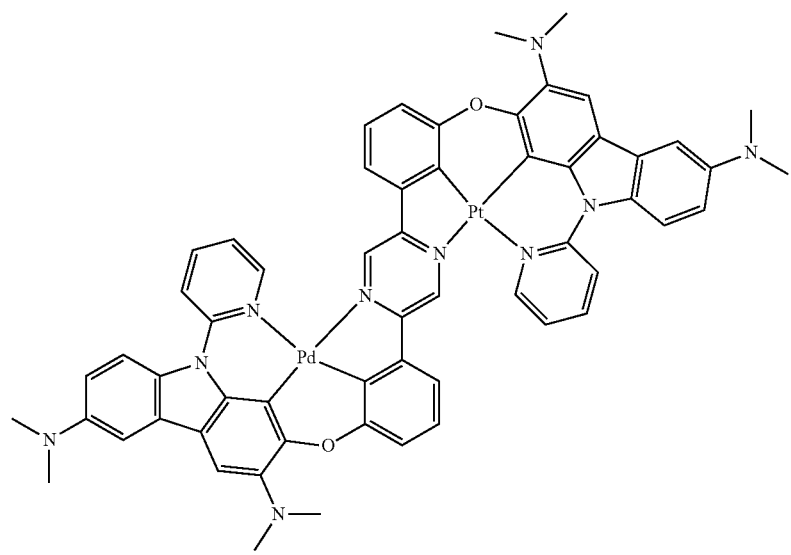
Compound PdPt89

Compound PdPt90
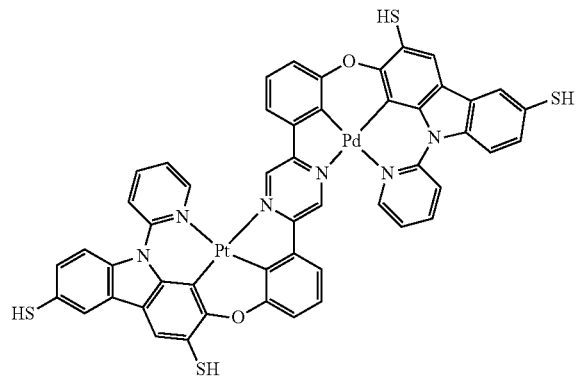
Compound PdPt91
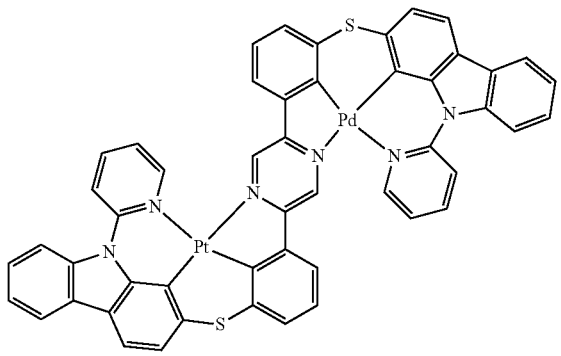
Compound PdPt92
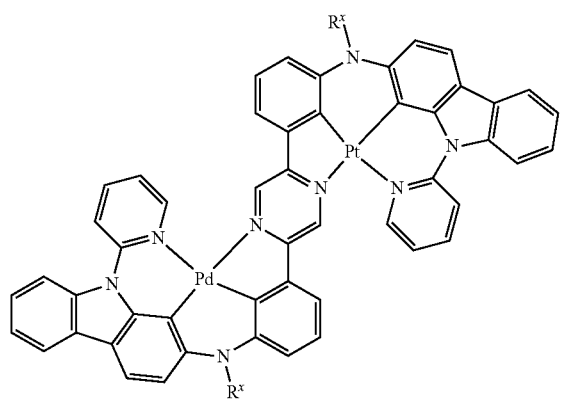
Compound PdPt93
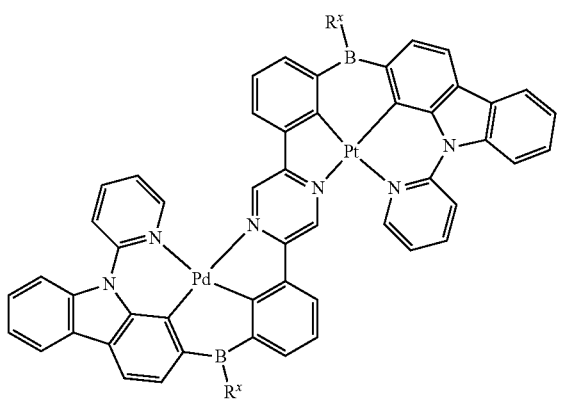
Compound PdPt94
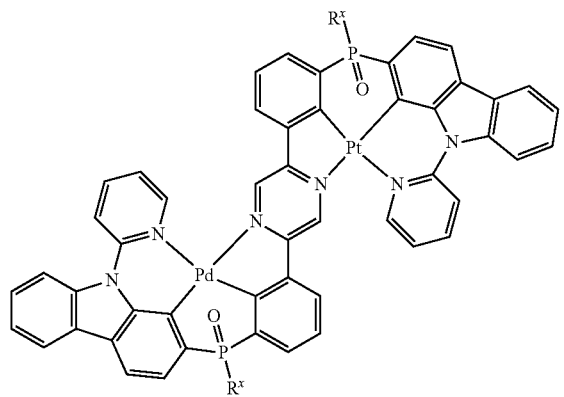
Compound PdPt95
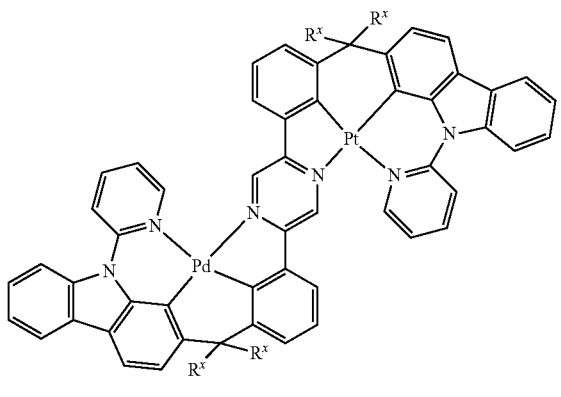
Compound PdPt96
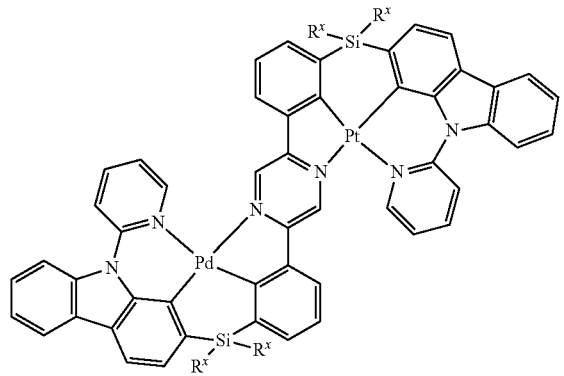
Compound PdPt97
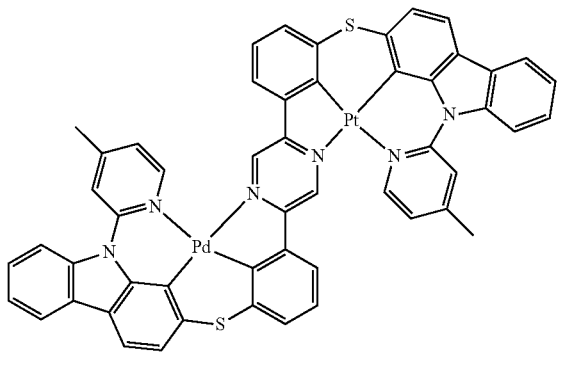

-continued
Compound PdPt98
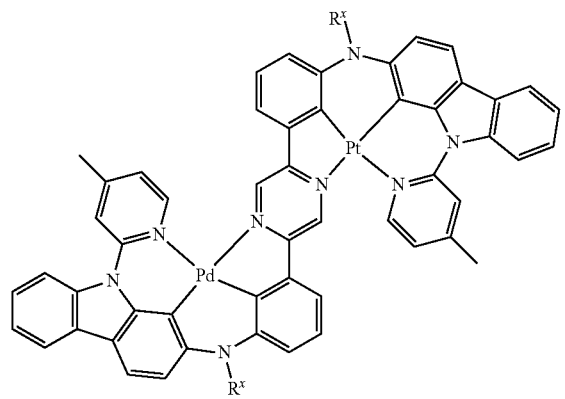
Compound PdPt99
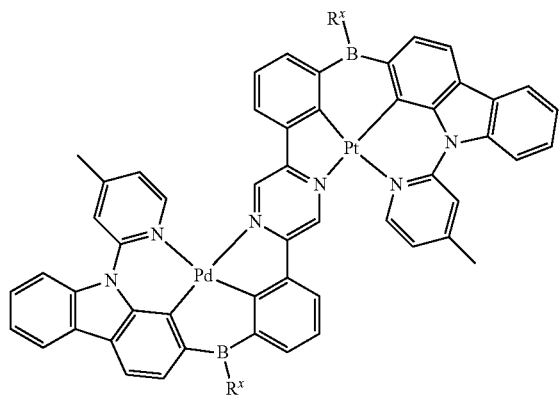
Compound PdPt100
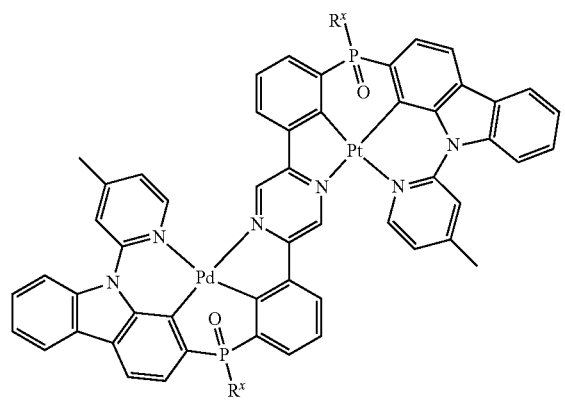
Compound PdPt101
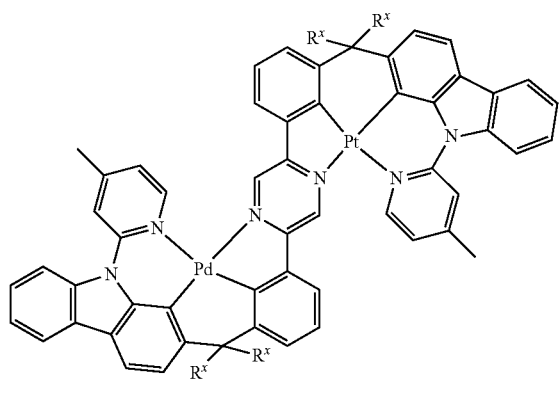
Compound PdPt102
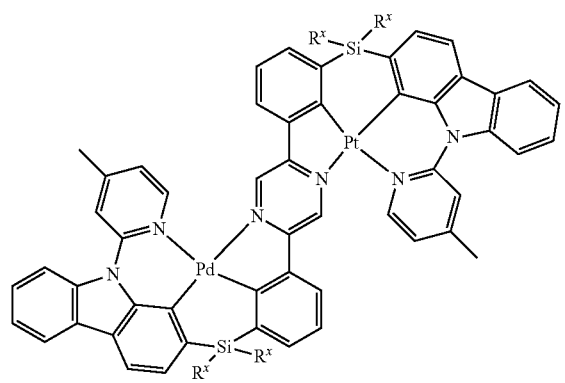
Compound PdPt103
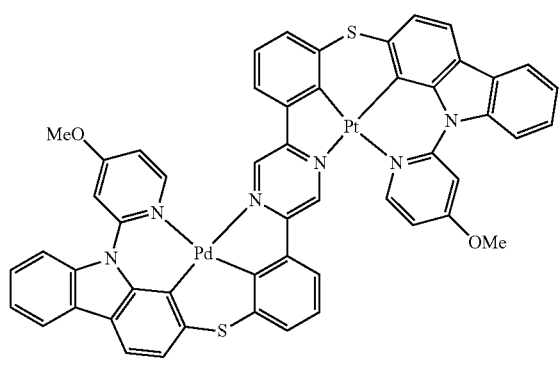
Compound PdPt104
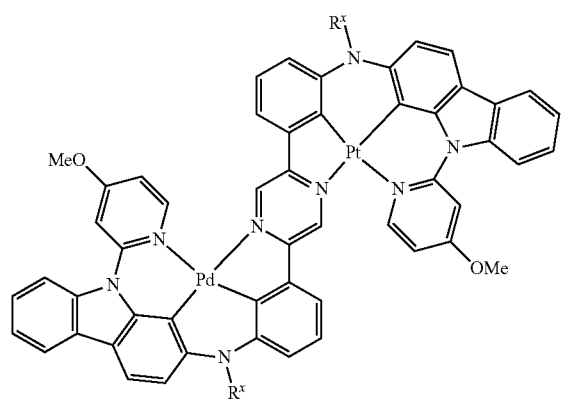
Compound PdPt105
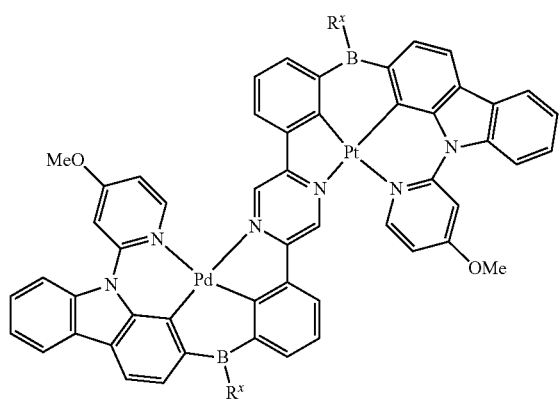

-continued
Compound Pt106
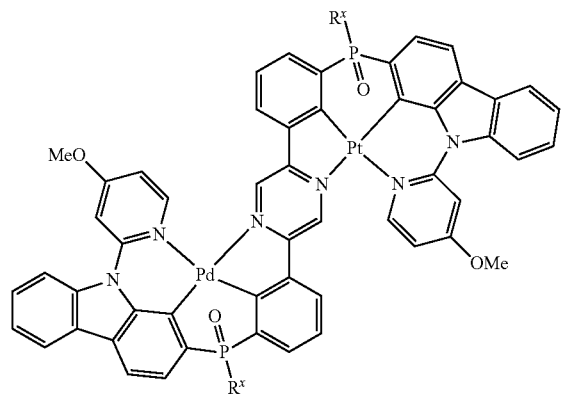
Compound Pt107
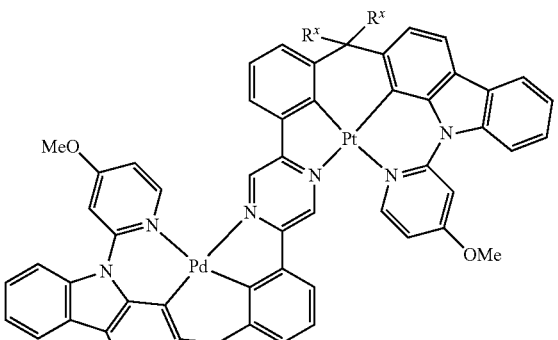
Compound Pt108
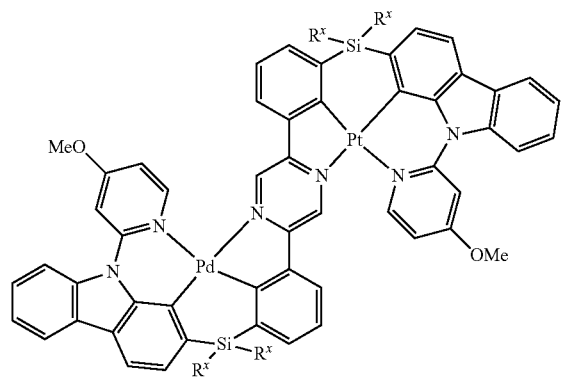
Compound PdPt109
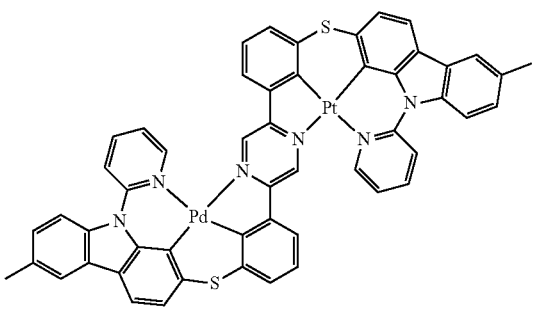
Compound PdPt110
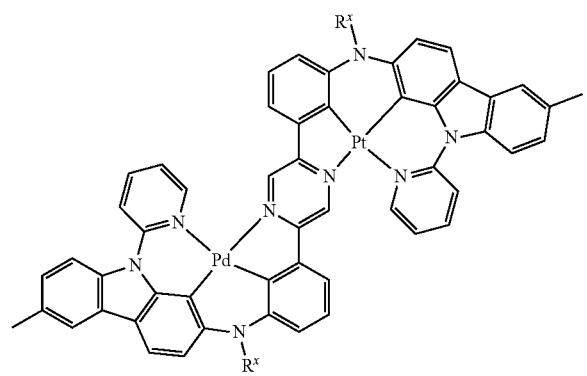
Compound PdPt111
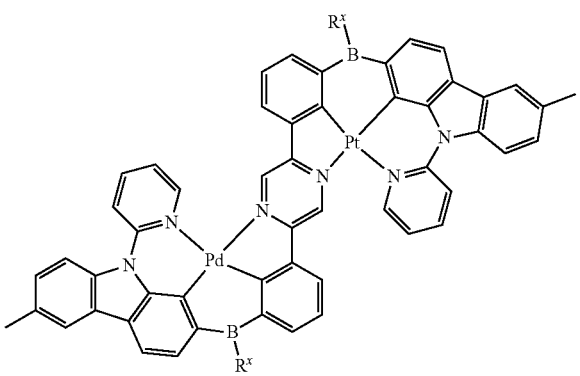
Compound PdPt112
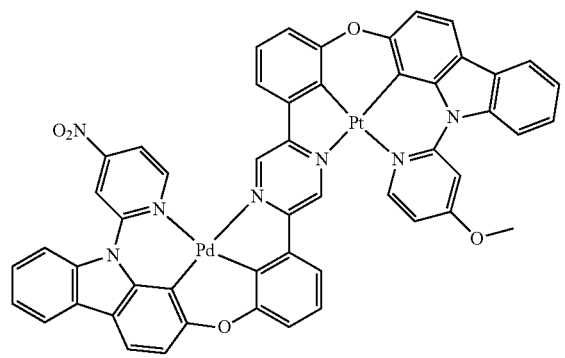
Compound PdPt113
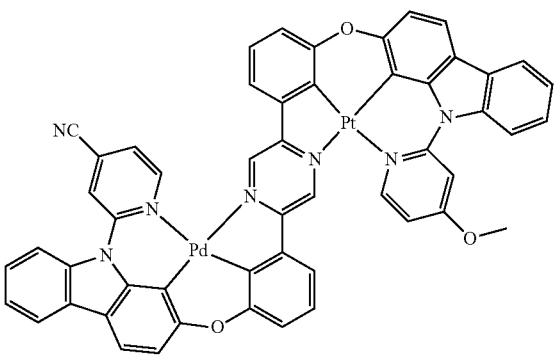

-continued
Compound PdPt114
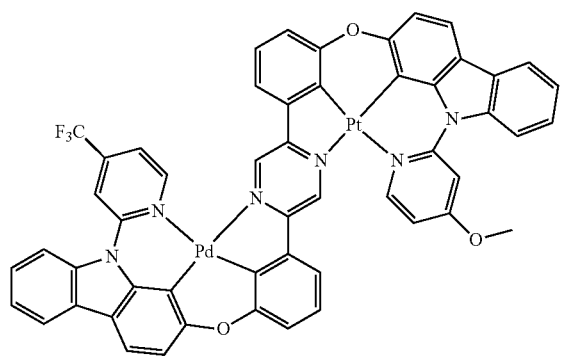
Compound PdPt115
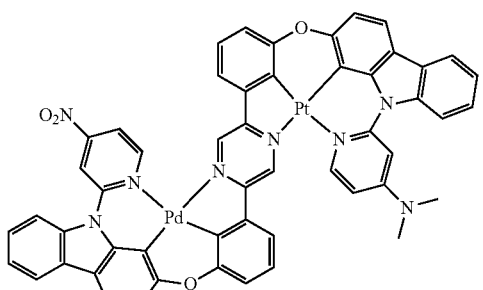
Compound PdPt116
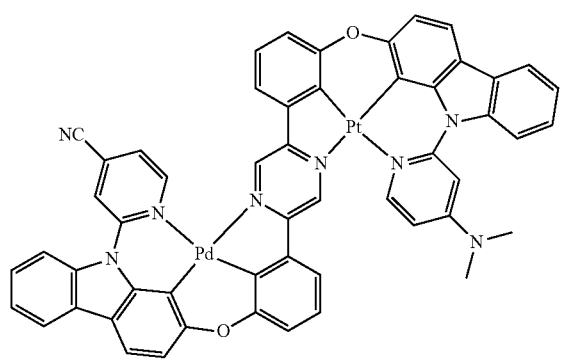
Compound PdPt117
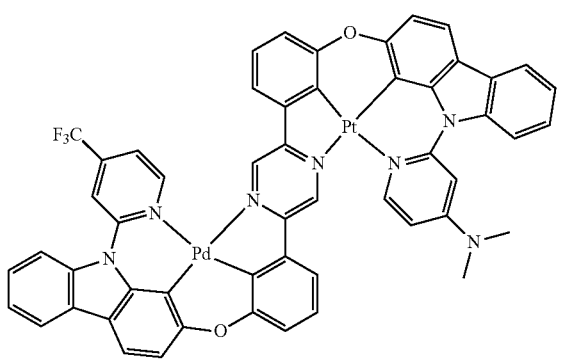
Compound PdPt118
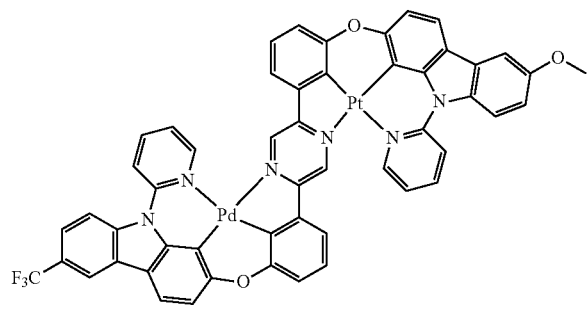
Compound PdPt119
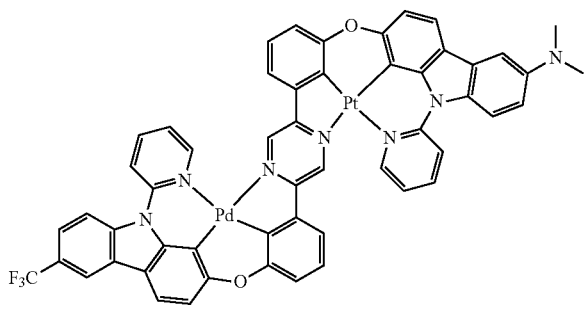
Compound PdPt120
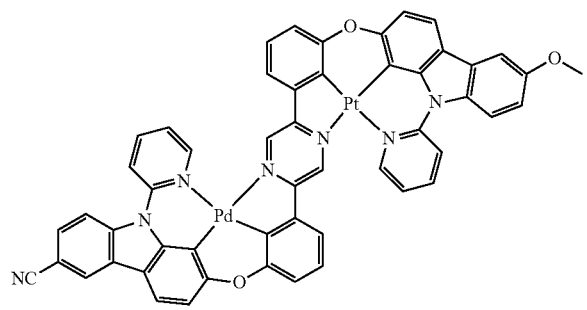
Compound PdPt121
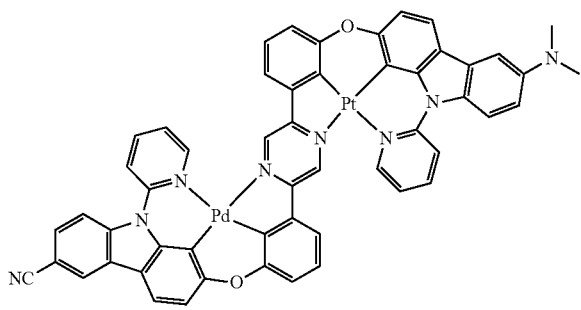

-continued
Compound PdPt122
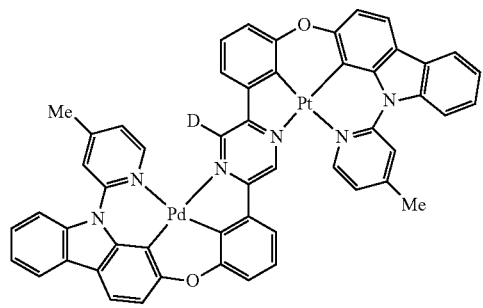
Compound PdPt123
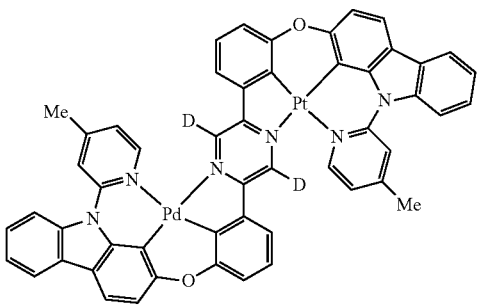
Compound PdPt124
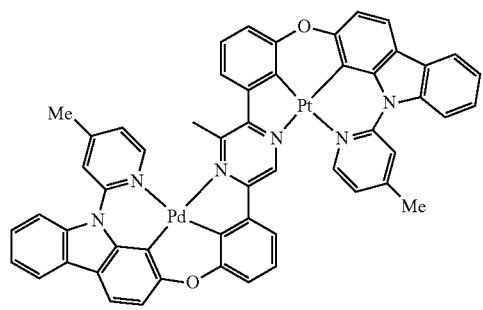
Compound PdPt125
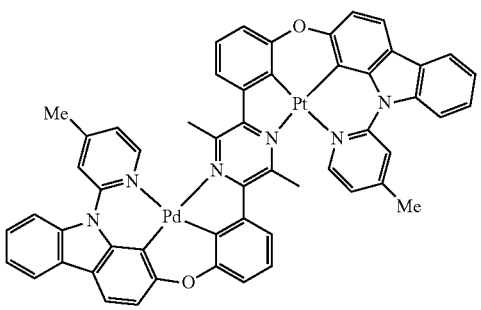
Compound PdPt126
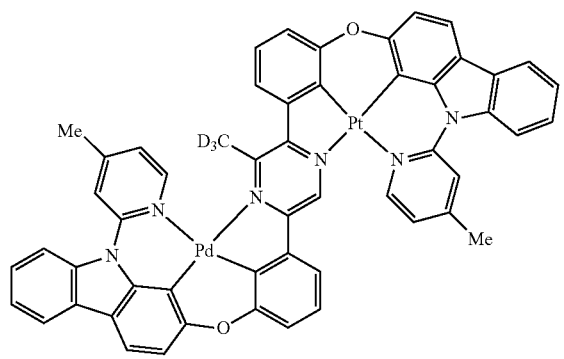
Compound PdPt127
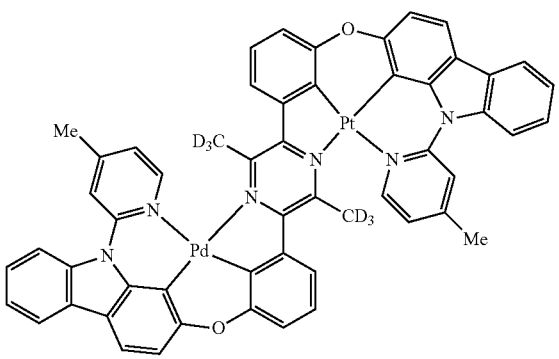
Compound PdPt128
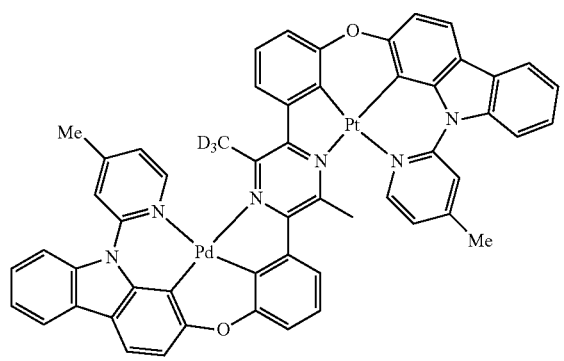
Compound PdPt129
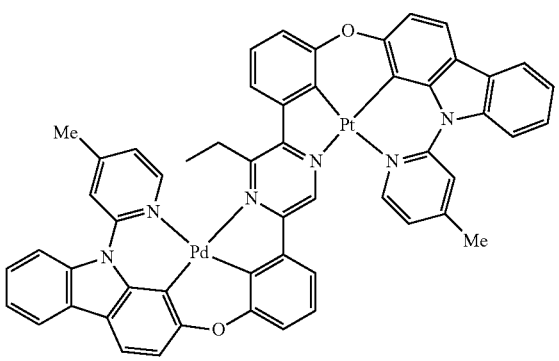

-continued
Compound PdPt130
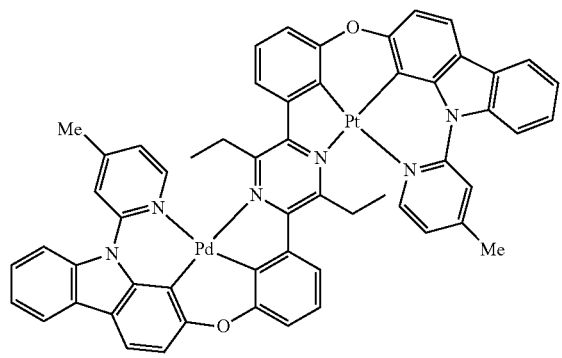
Compound PdPt131
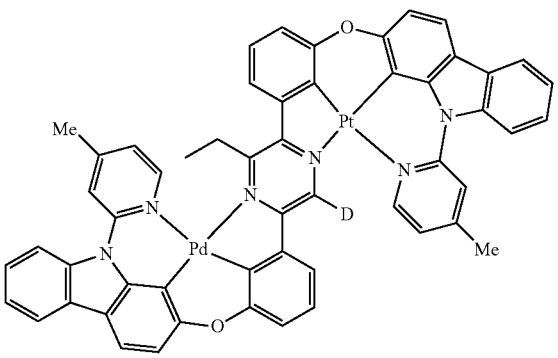
Compound PdPt132
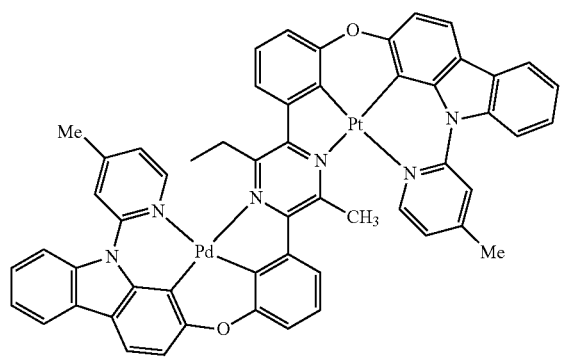
Compound PdPt133
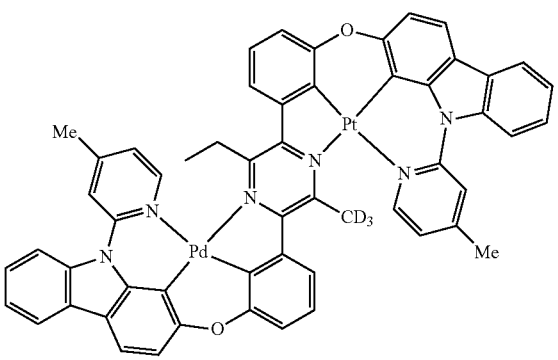
Compound PdPt134
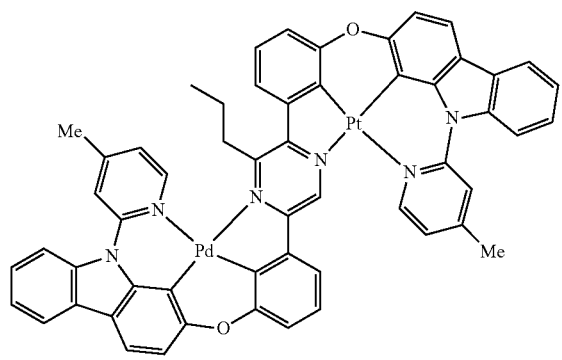
Compound PdPt135
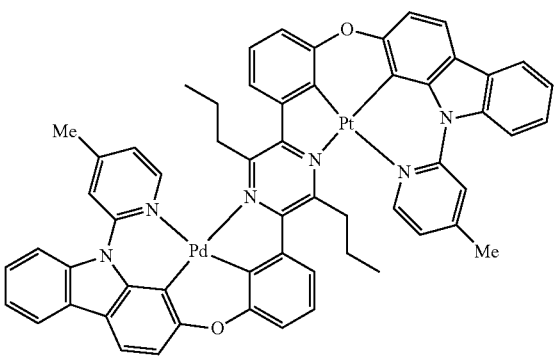
Compound PdPt136
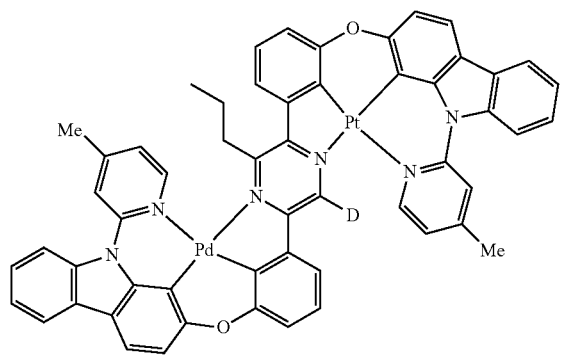
Compound PdPt137
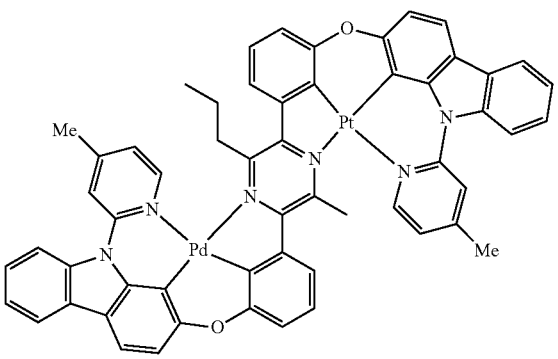

Compound PdPt138
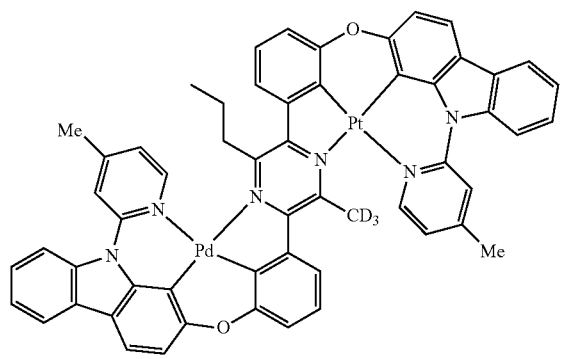
Compound PdPt140
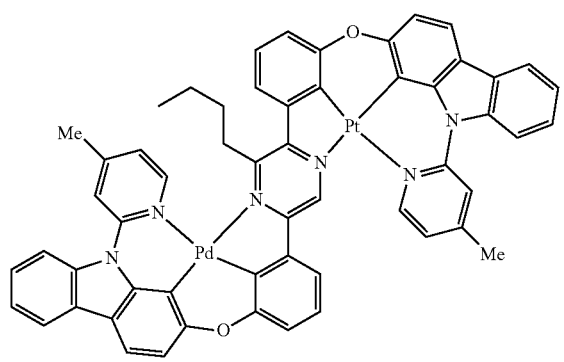
Compound PdPt142
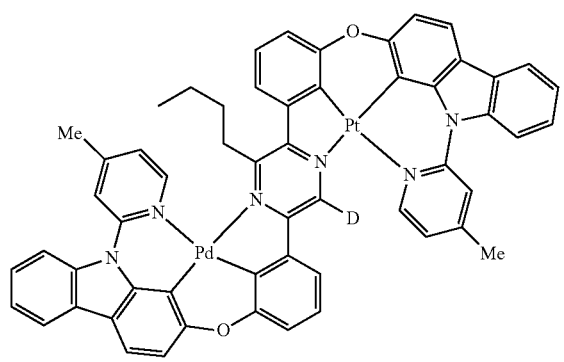
Compound PdPt144
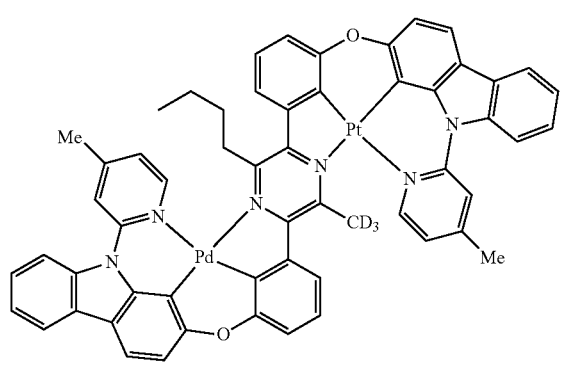
Compound PdPt139
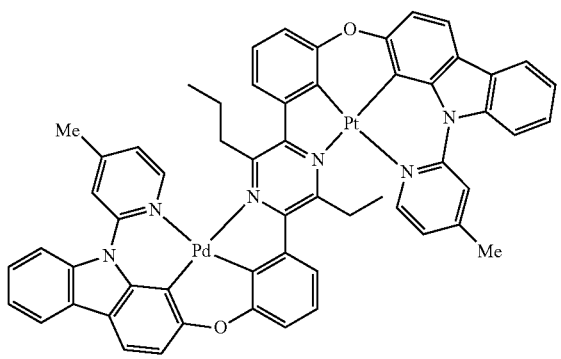
Compound PdPt141
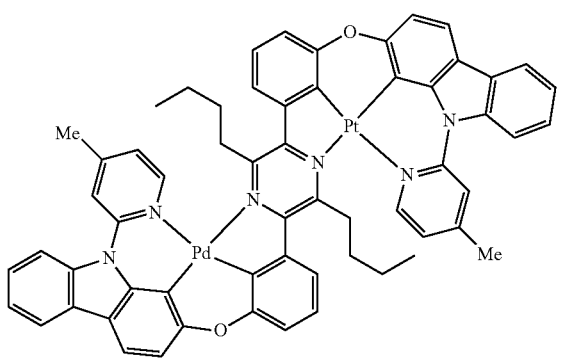
Compound PdPt143
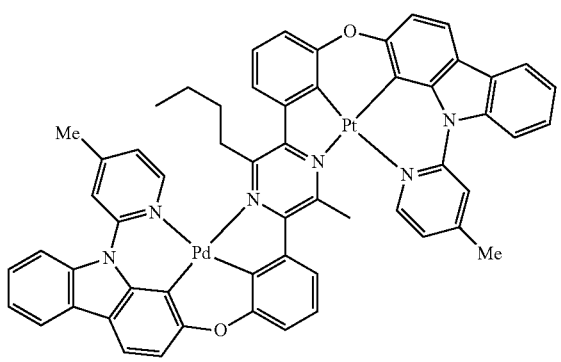
Compound PdPt145
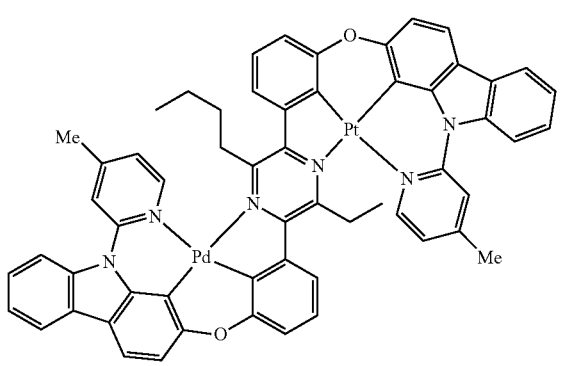

-continued
Compound PdPt146
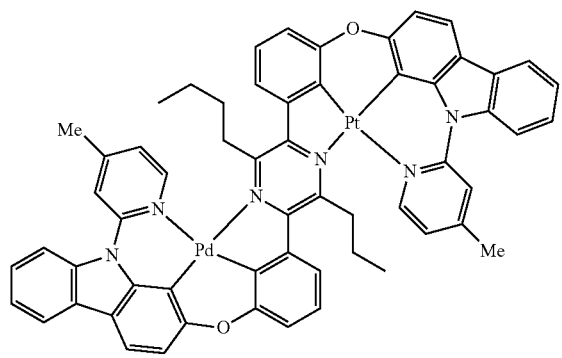
Compound PdPt147
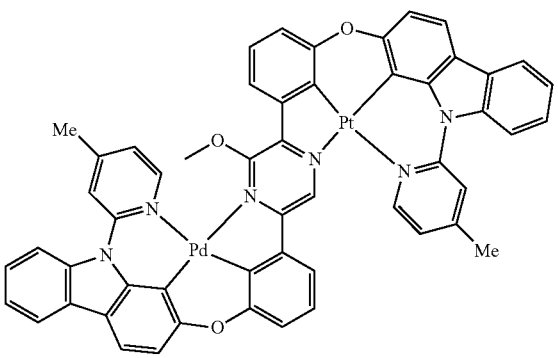
Compound PdPt148
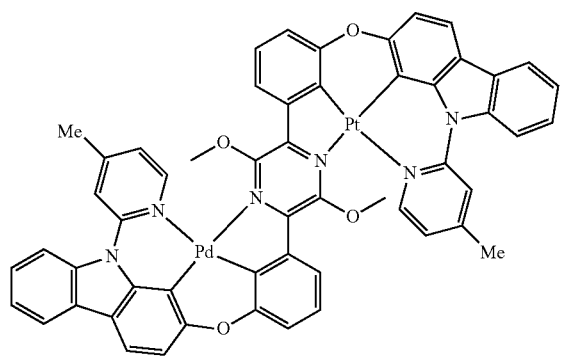
Compound PdPt149
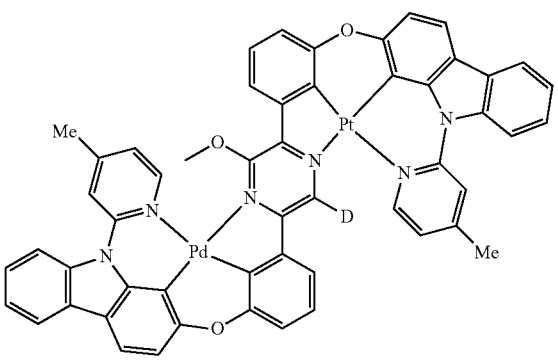
Compound PdPt150
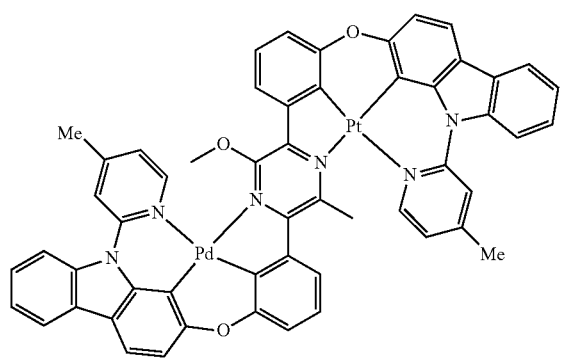
Compound PdPt151
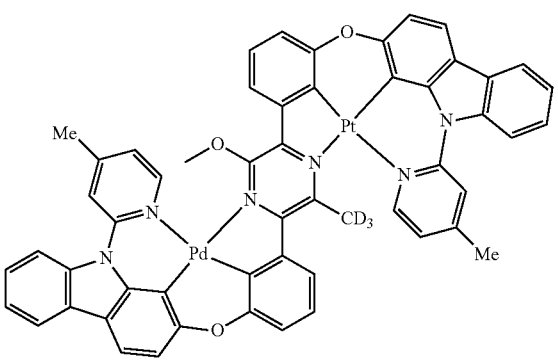
Compound PdPt152
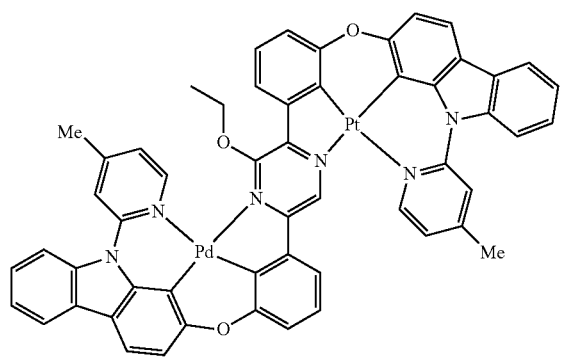
Compound PdPt153
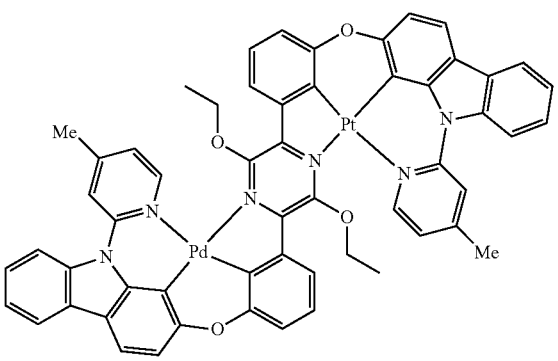

-continued
Compound PdPt154
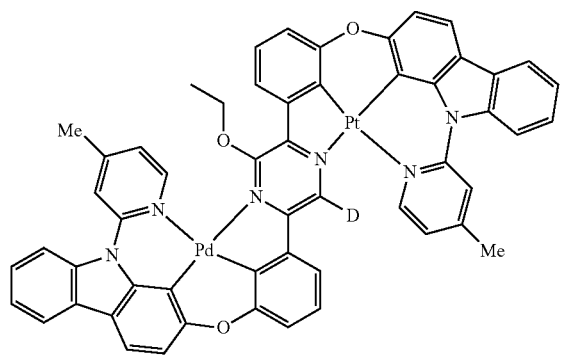
Compound PdPt155
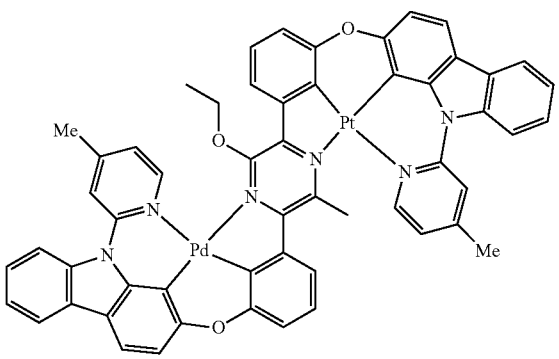
Compound PdPt156
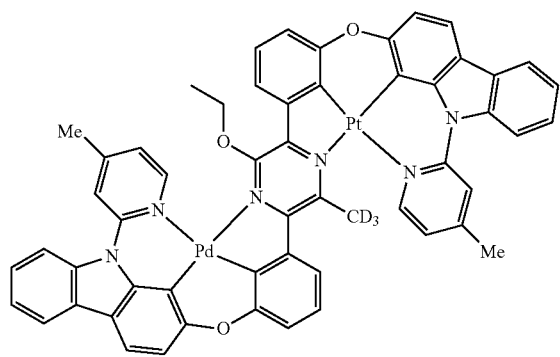
Compound PdPt157
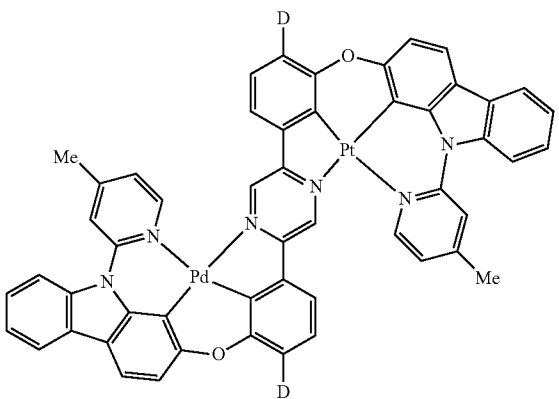
Compound PdPt158
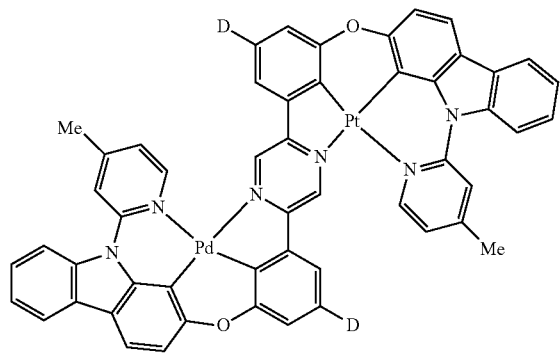
Compound PdPt159
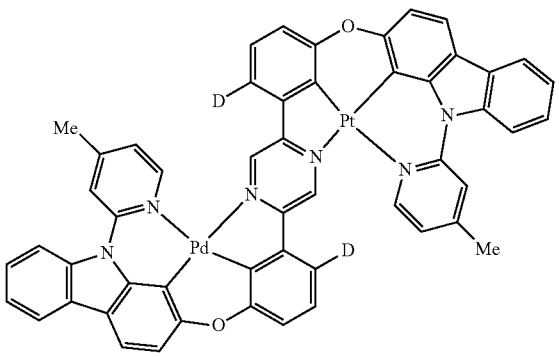
Compound PdPt160
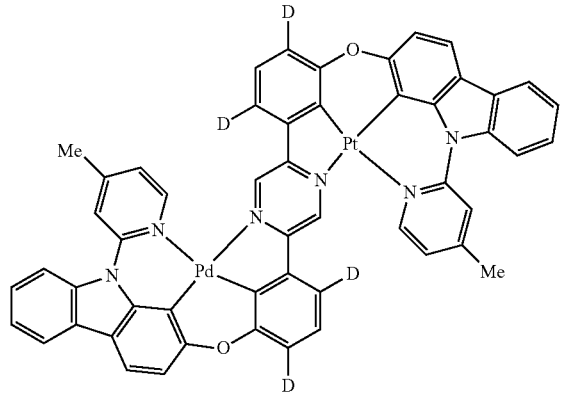
Compound PdPt161
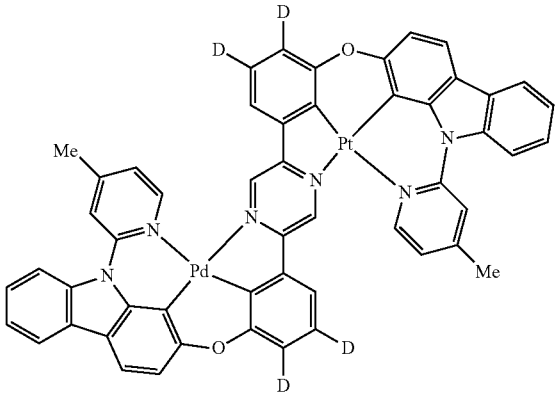

-continued
Compound PdPt162
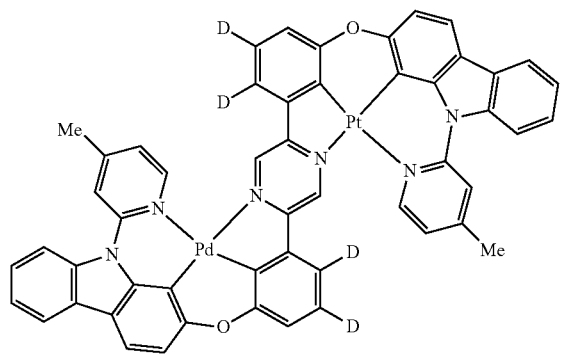
Compound PdPt163
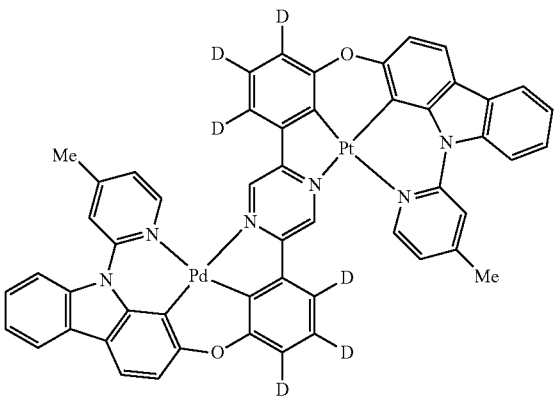
Compound PdPt164
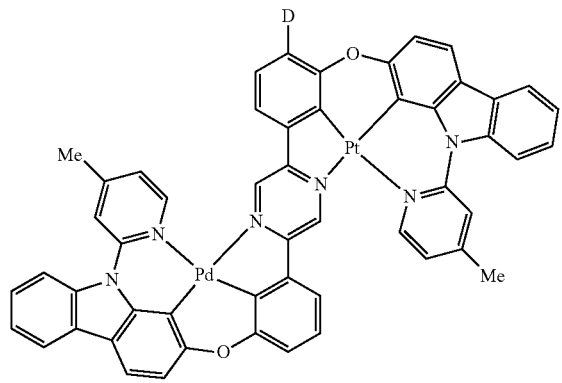
Compound PdPt165
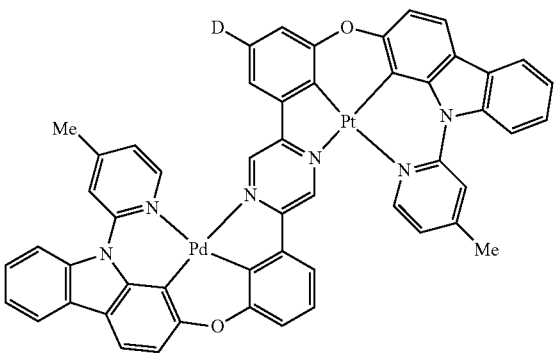
Compound PdPt166
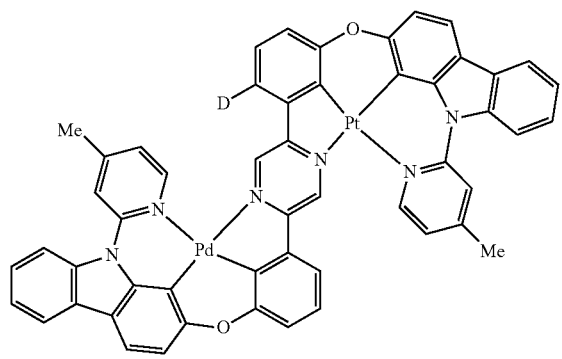
Compound PdPt167
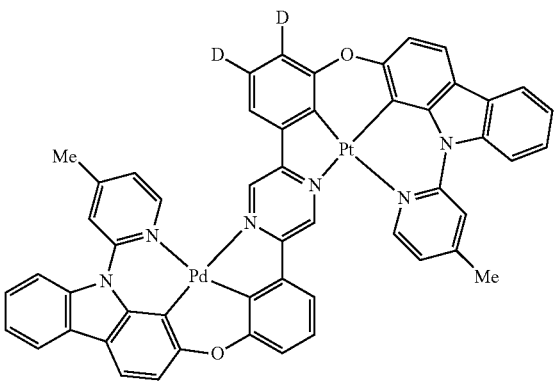
Compound PdPt168
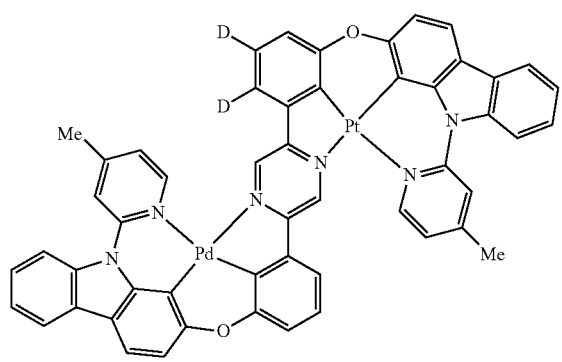
Compound PdPt169
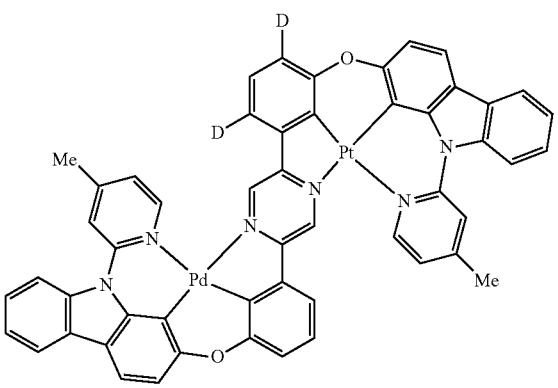

-continued
Compound PdPt170
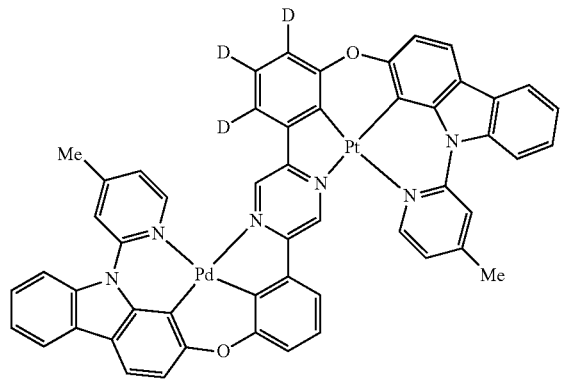
Compound PdPt171
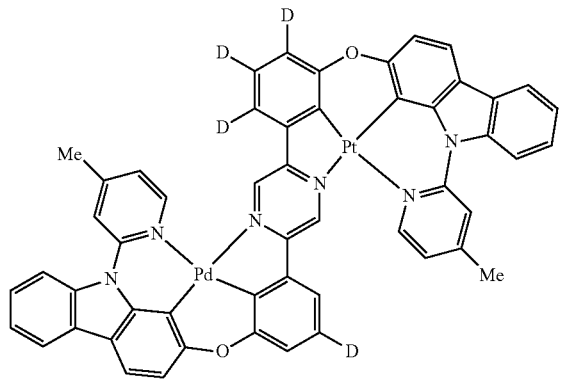
Compound PdPt172
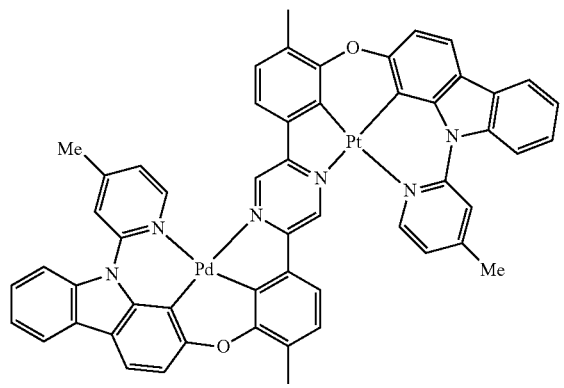
Compound PdPt173
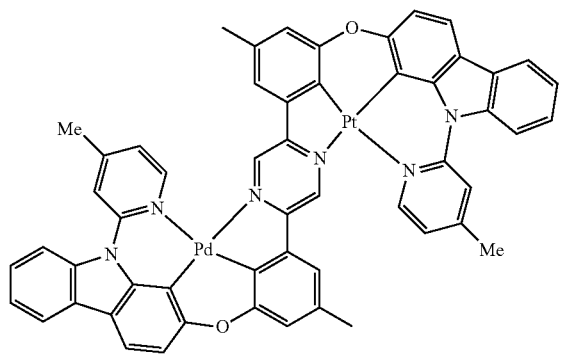
Compound PdPt174
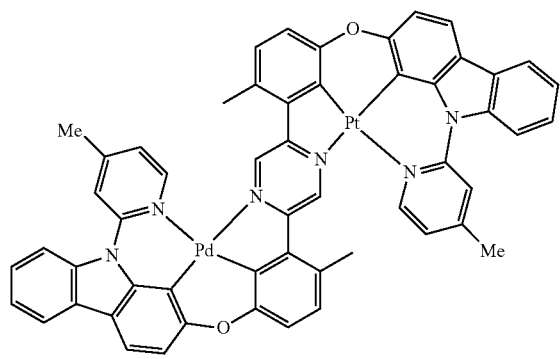
Compound PdPt175
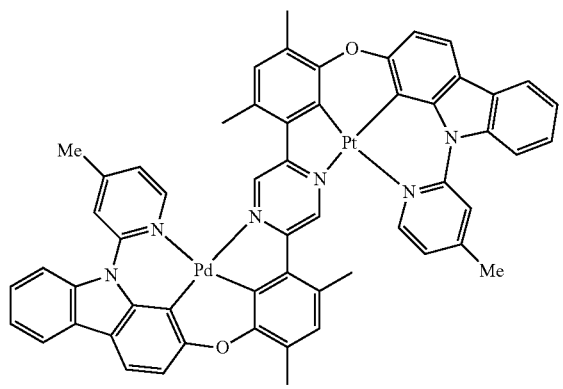
Compound PdPt176
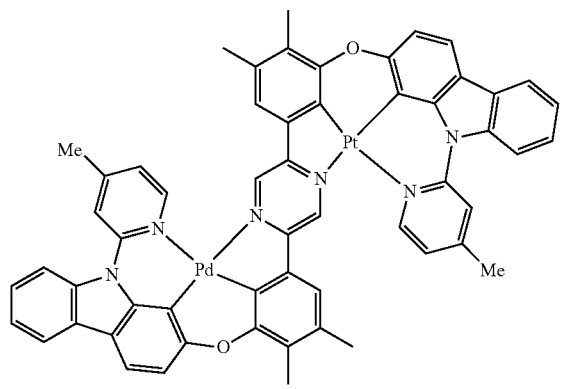
Compound PdPt177
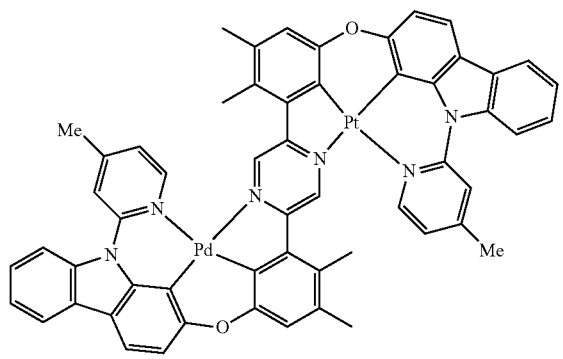

-continued
Compound PdPt178
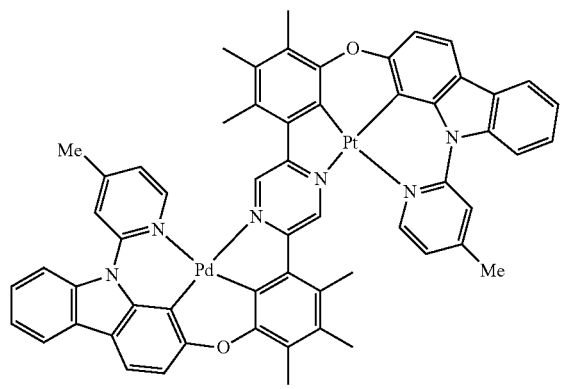
Compound PdPt179
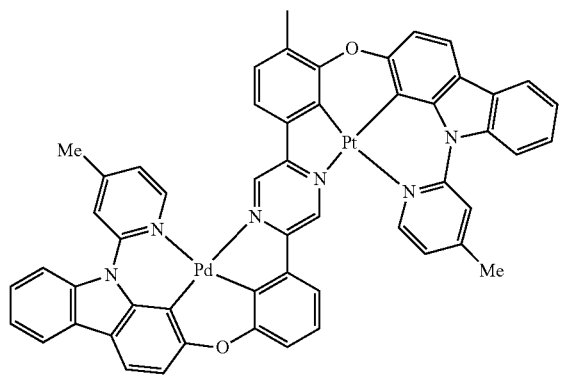
Compound PdPt180
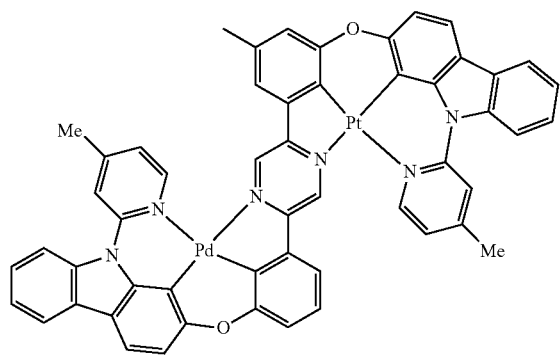
Compound PdPt181
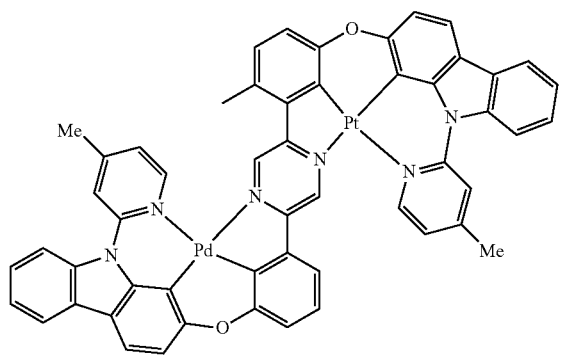
Compound PdPt182
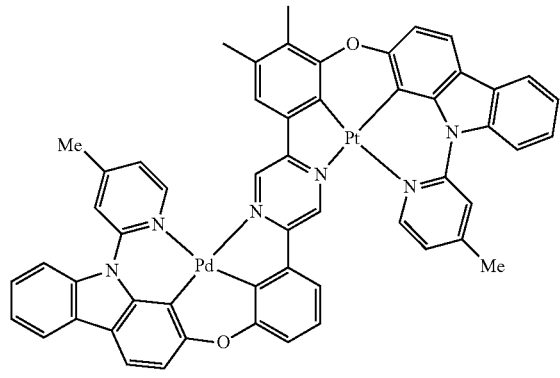
Compound PdPt183
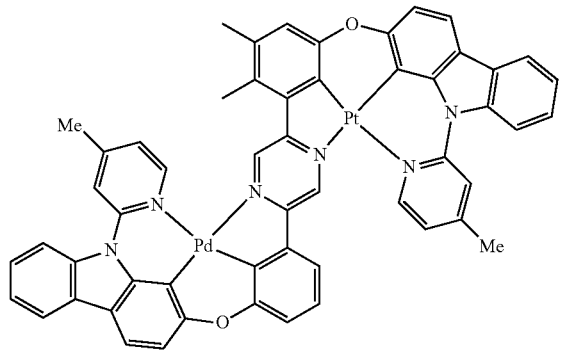
Compound PdPt184
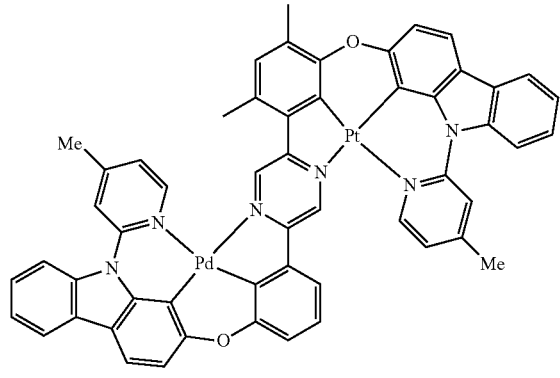
Compound PdPt185
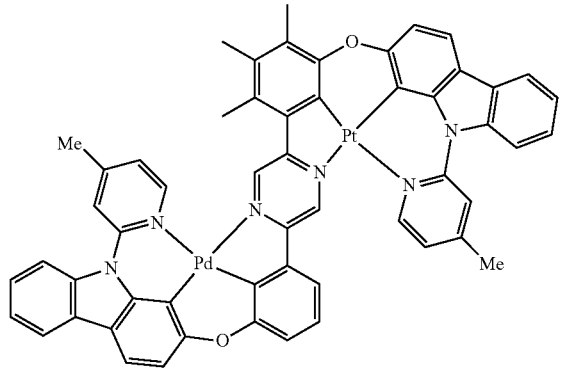

-continued
Compound PdPt186
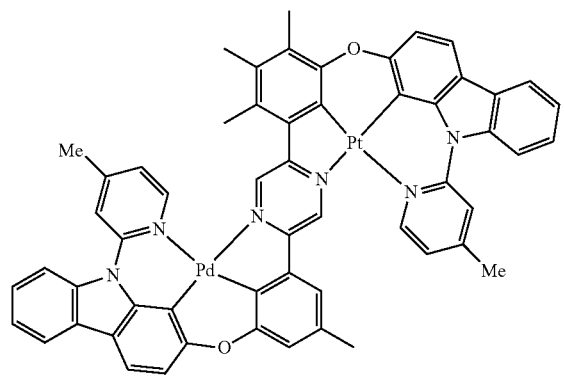
Compound PdPt187
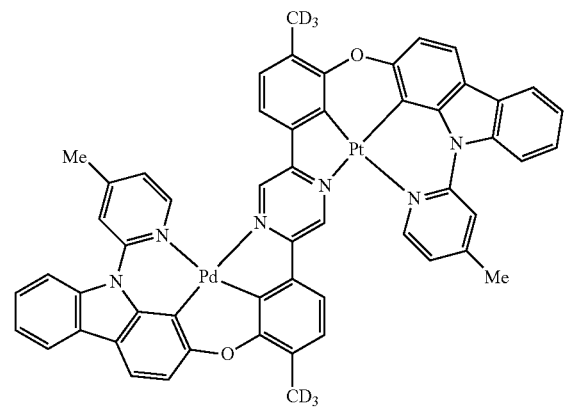
Compound PdPt188
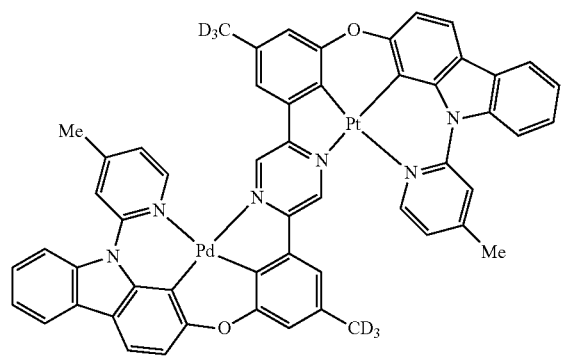
Compound PdPt189
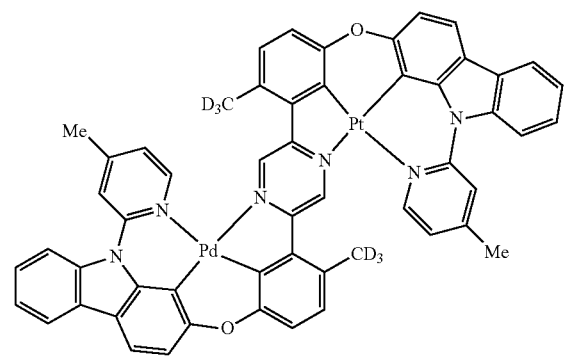
Compound PdPt190
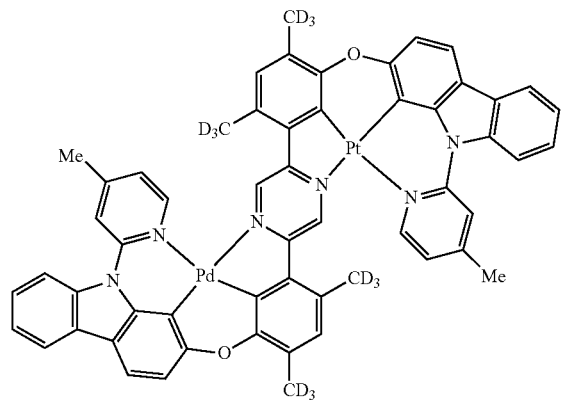
Compound PdPt191
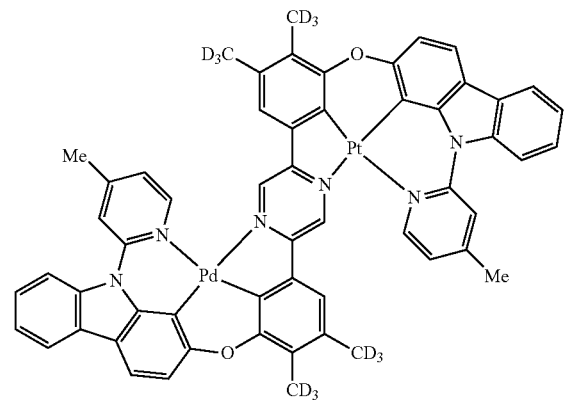
Compound PdPt192
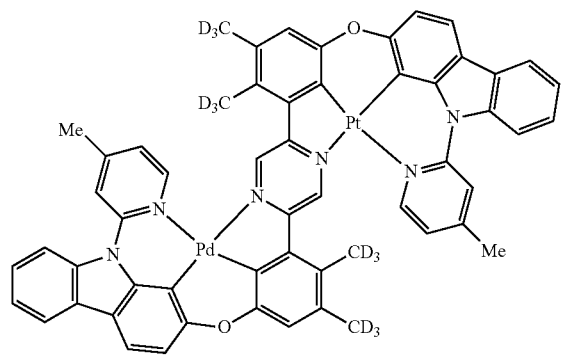
Compound PdPt193
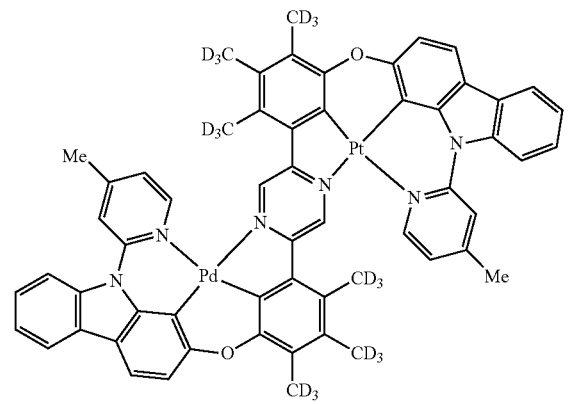

-continued
Compound PdPt194
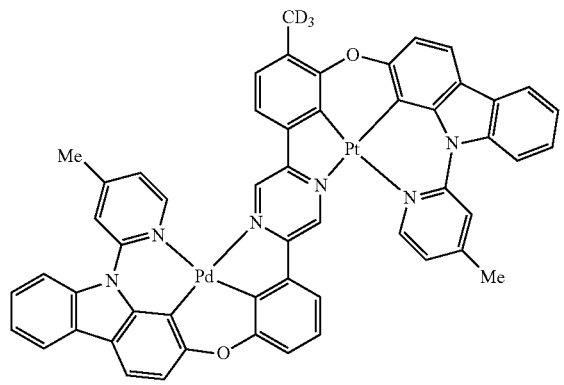
Compound PdPt196
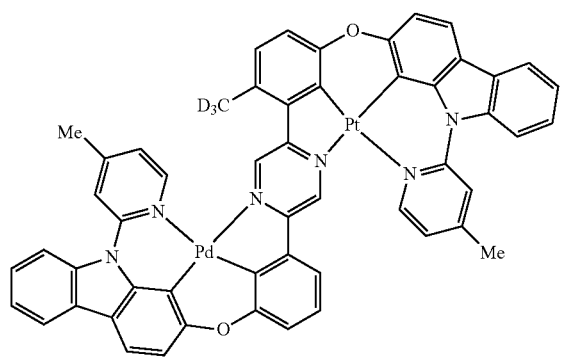
Compound PdPt198
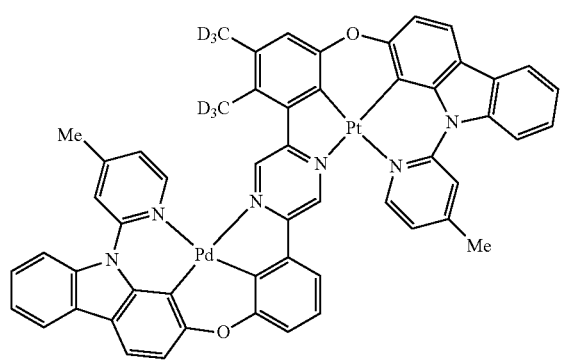
Compound PdPt200
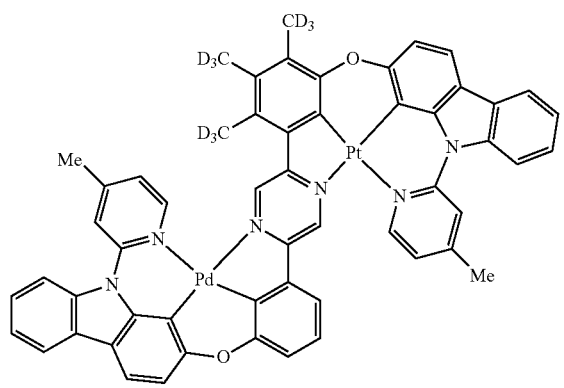
Compound PdPt195
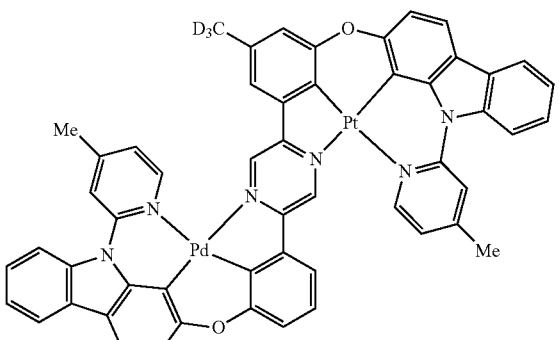
Compound PdPt197
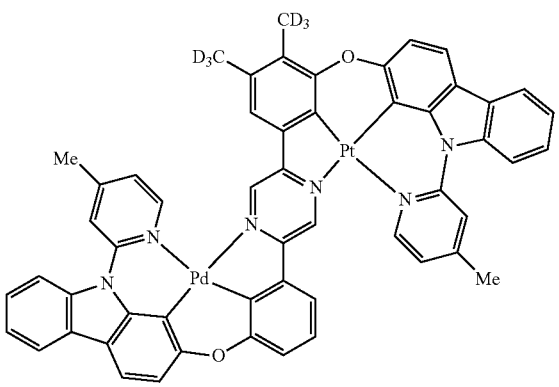
Compound PdPt199
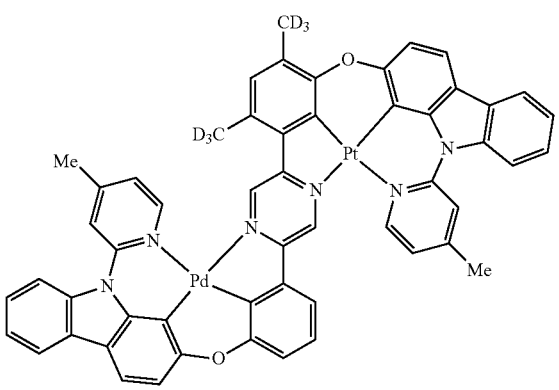
Compound PdPt201
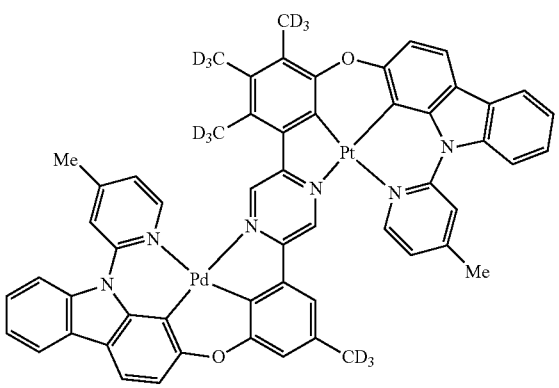

-continued
Compound PdPt202
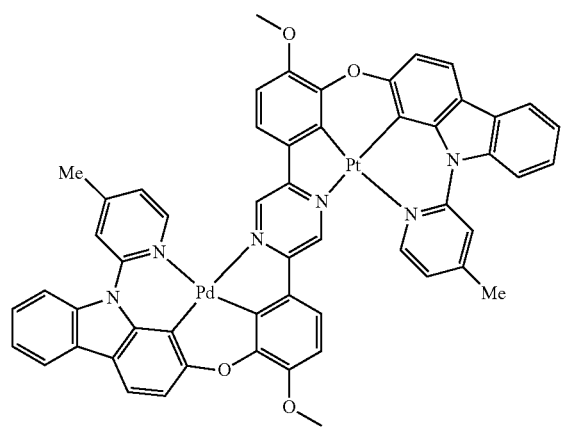
Compound PdPt203
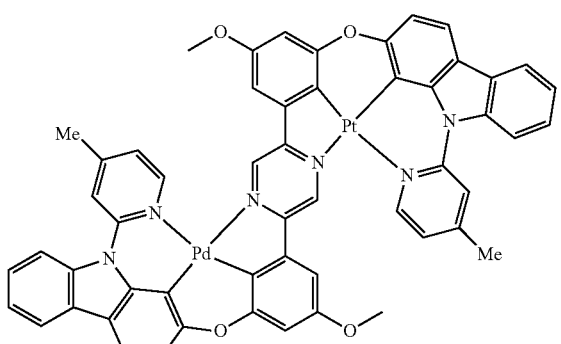
Compound PdPt204
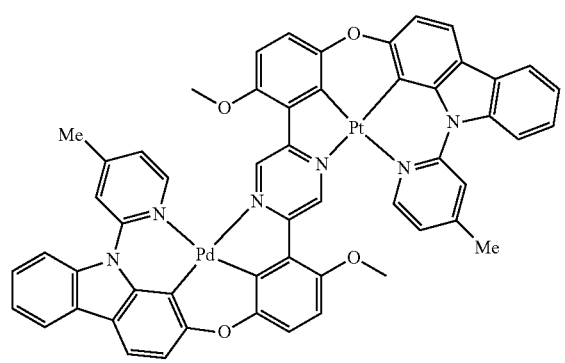
Compound PdPt205
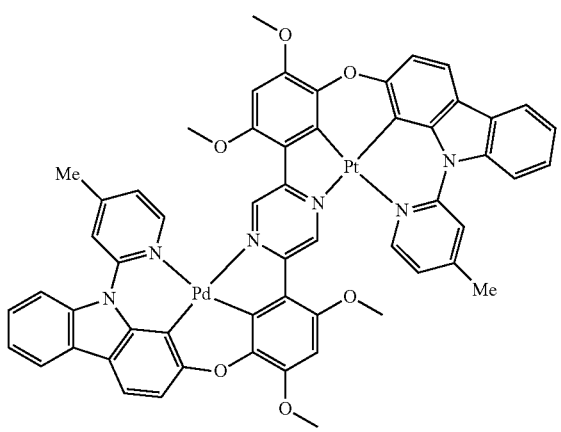
Compound PdPt206
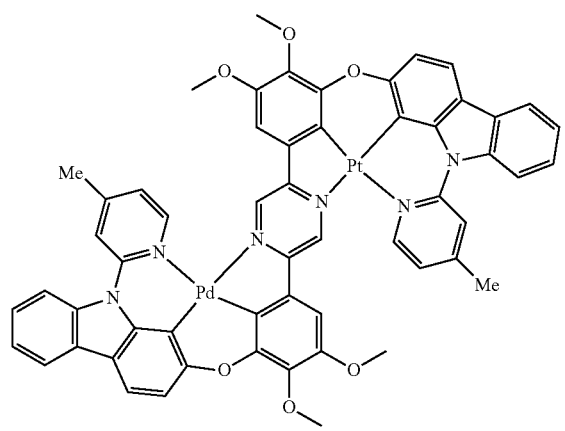
Compound PdPt207
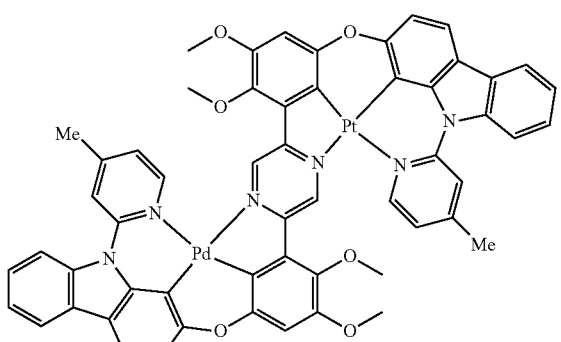

-continued
Compound PdPt208
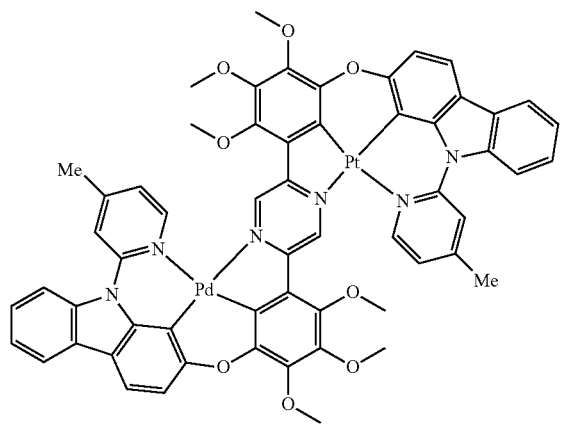
Compound PdPt209
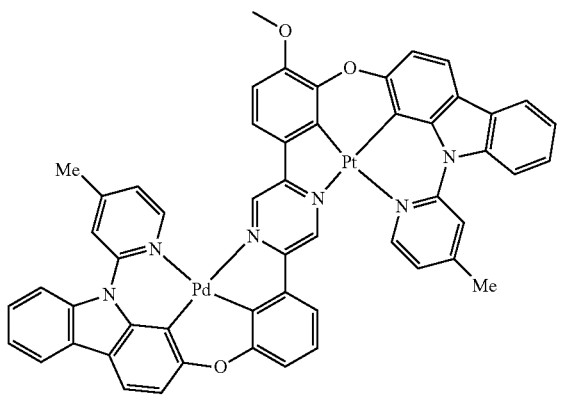
Compound PdPt210
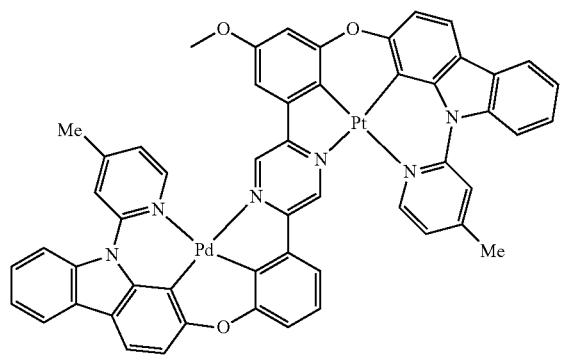
Compound PdPt211
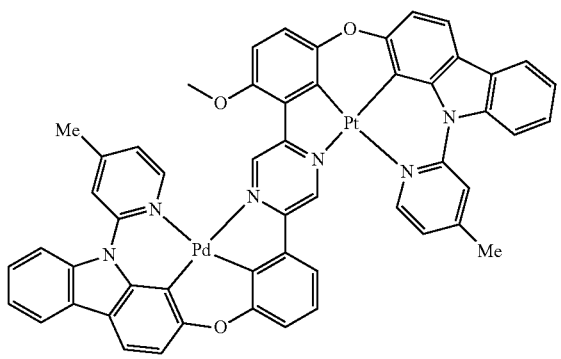
Compound PdPt212
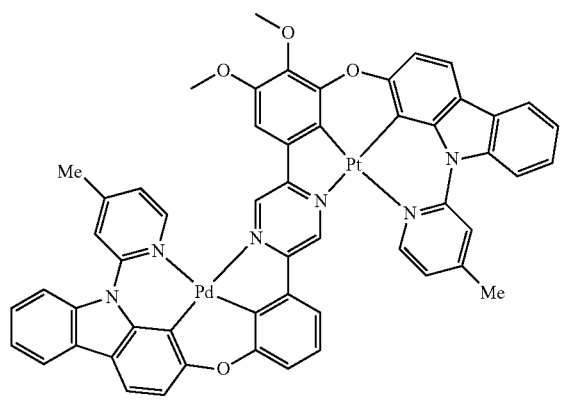
Compound PdPt213
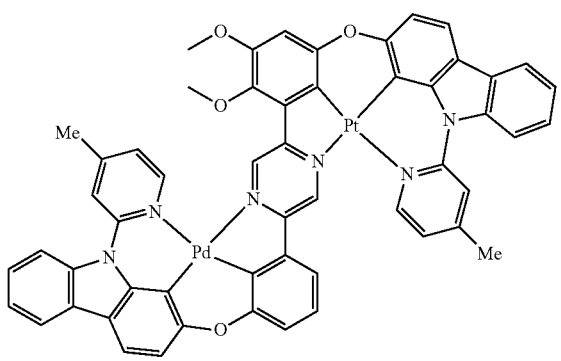
Compound PdPt214
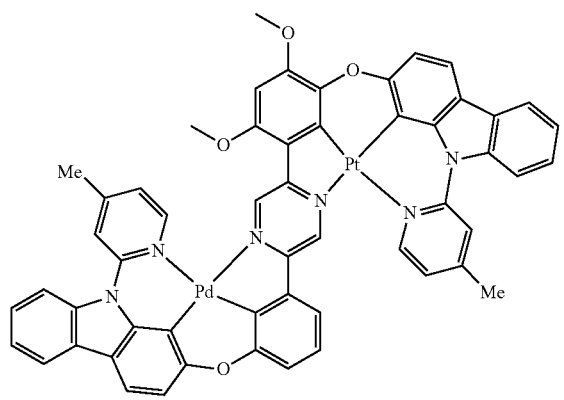
Compound PdPt215
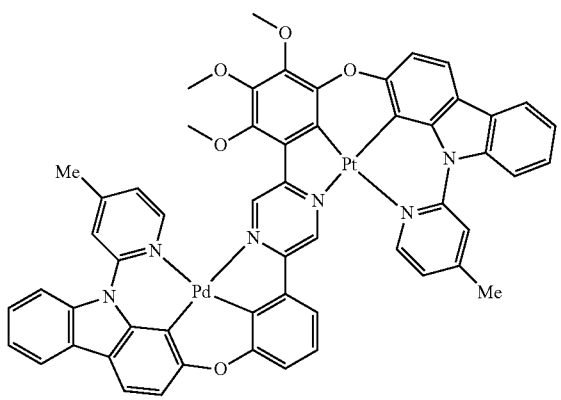

-continued
Compound PdPt216
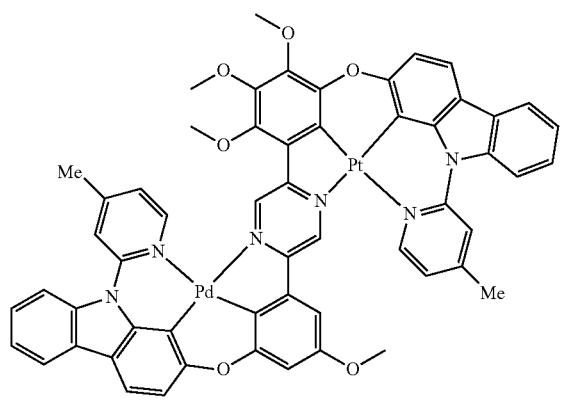
Compound PdPt218
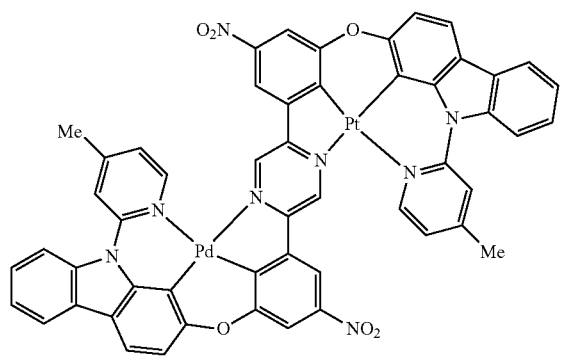
Compound PdPt220
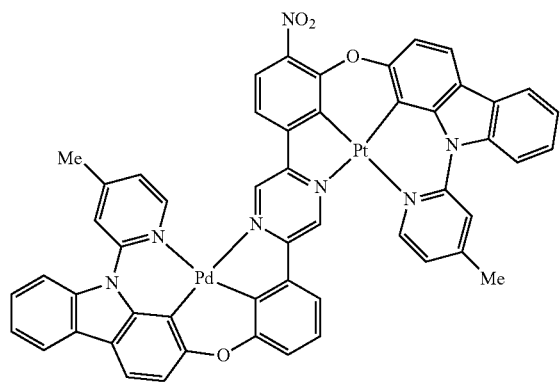
Compound PdPt222
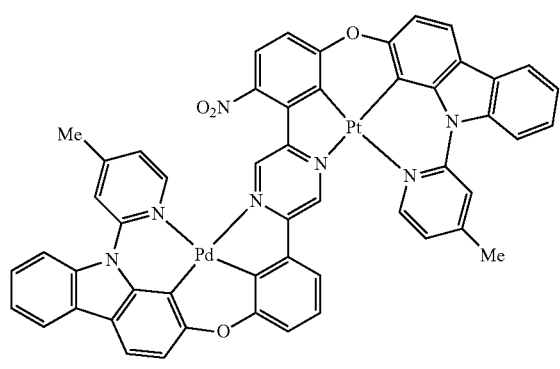
Compound PdPt217
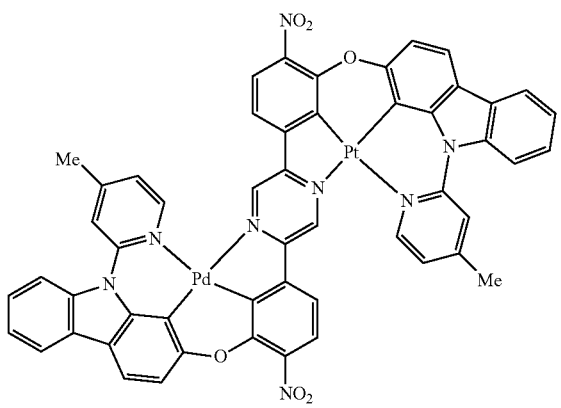
Compound PdPt219
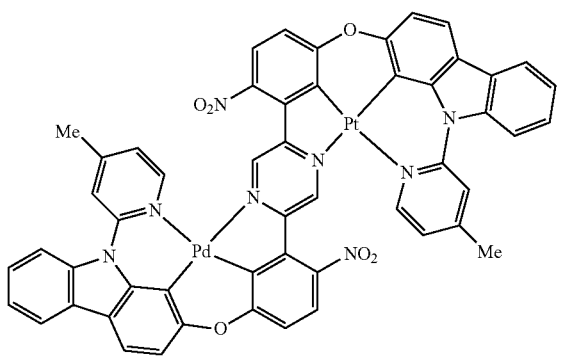
Compound PdPt221
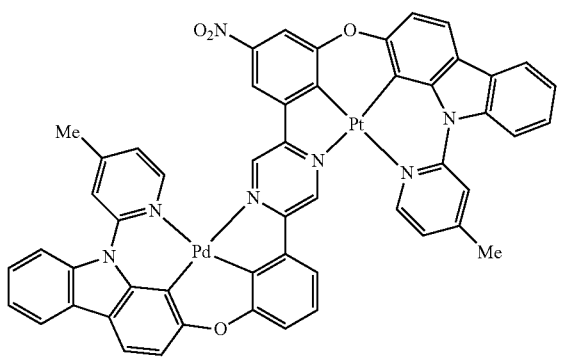
Compound PdPt223
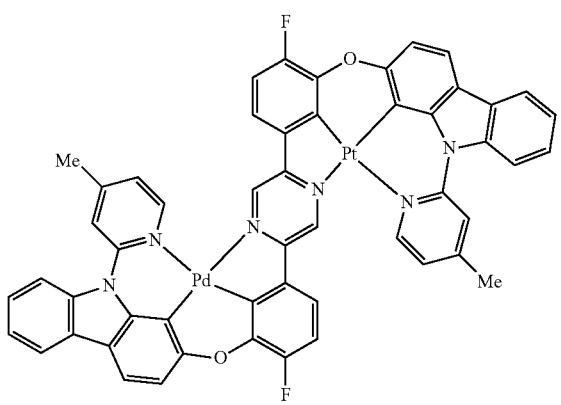

-continued
Compound PdPt224
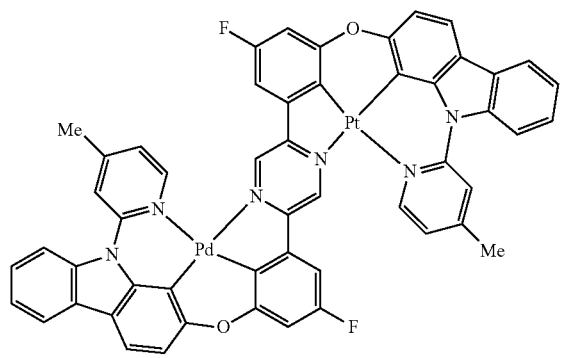
Compound PdPt225
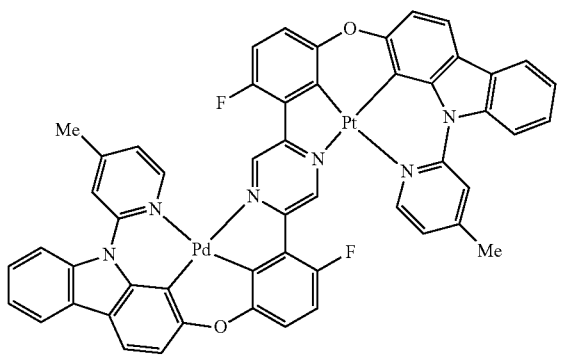
Compound PdPt226
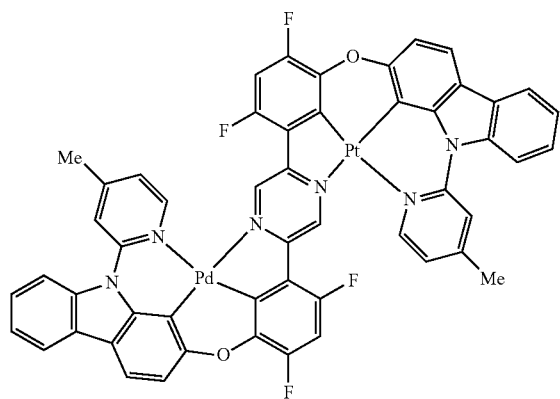
Compound PdPt227
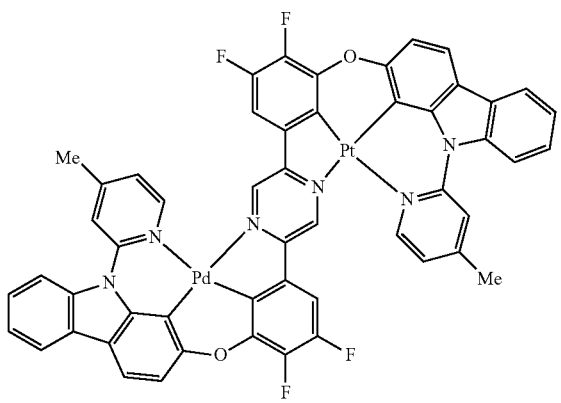
Compound PdPt228
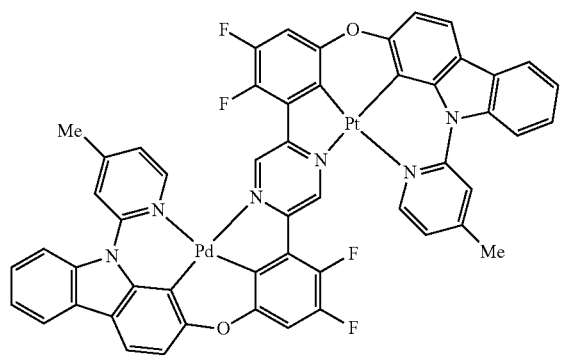
Compound PdPt229
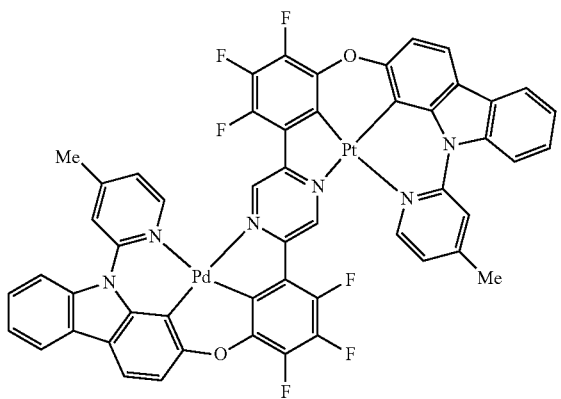
Compound PdPt230
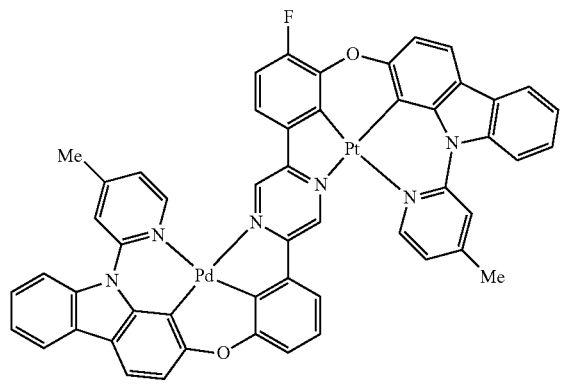
Compound PdPt231
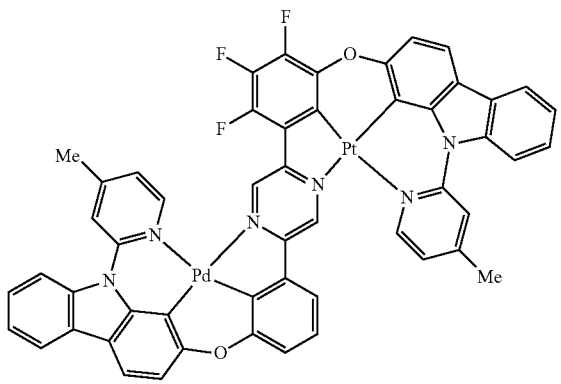

-continued
Compound PdPt232
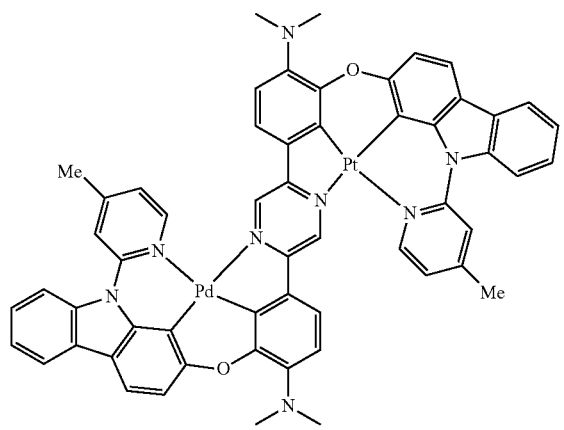
Compound PdPt233
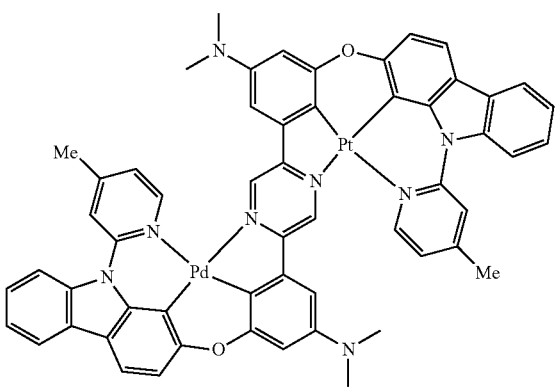
Compound PdPt234
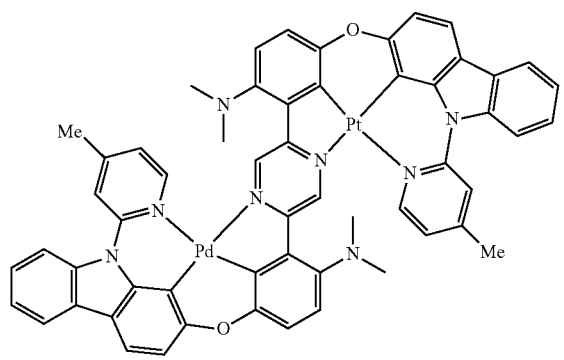
Compound PdPt235
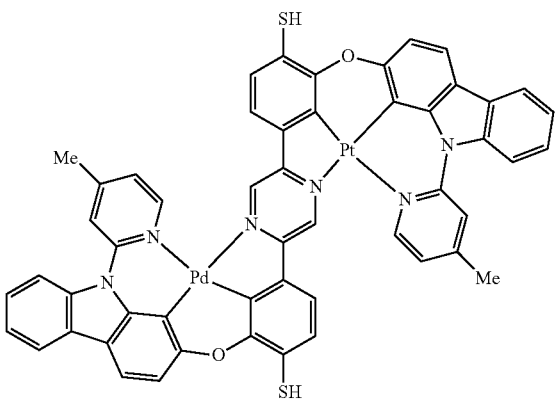
Compound PdPt236
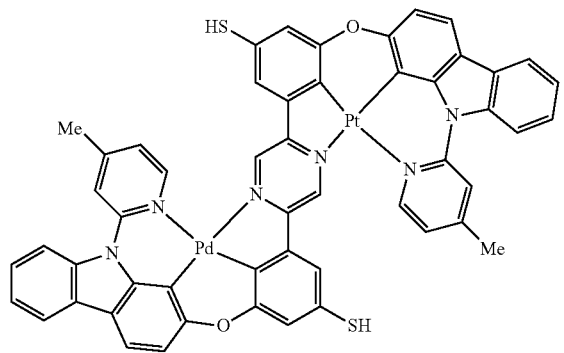
Compound PdPt237
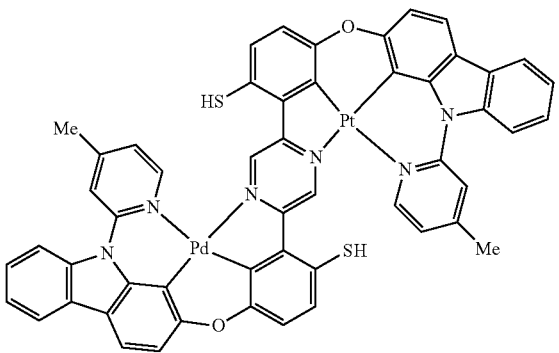
Compound PdPt238
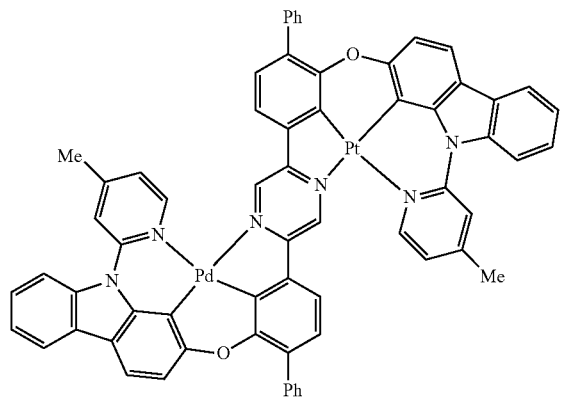
Compound PdPt239
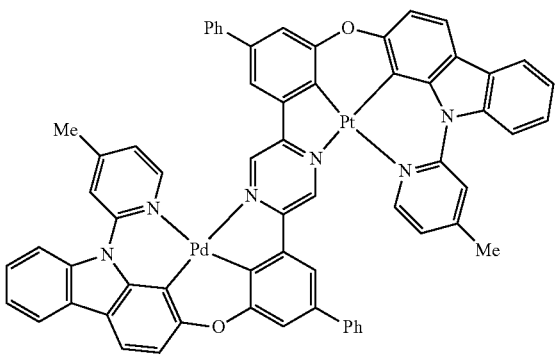

-continued
Compound PdPt240
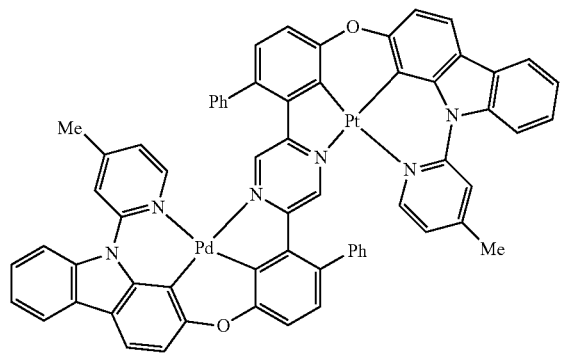
Compound PdPt241
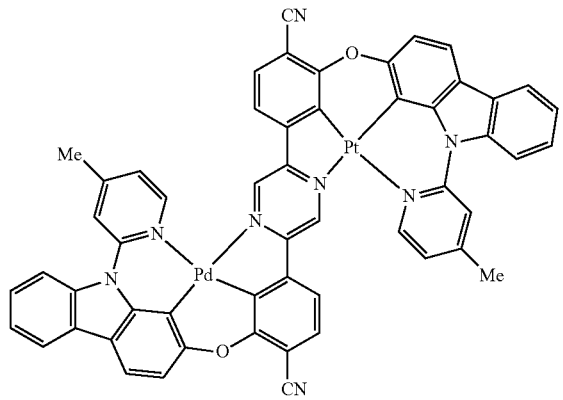
Compound PdPt242
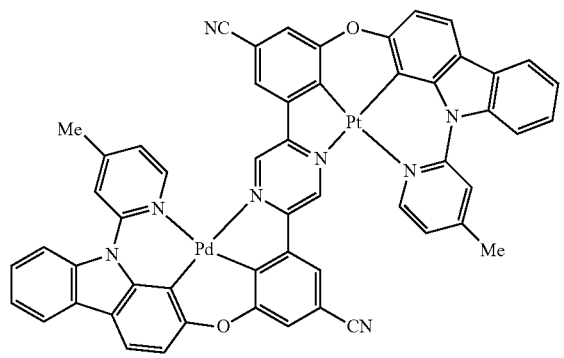
Compound PdPt243
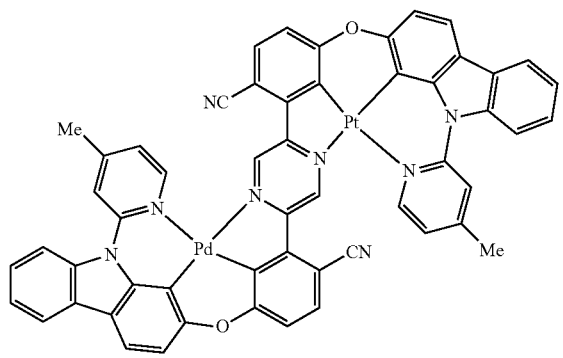
Compound PdPt244
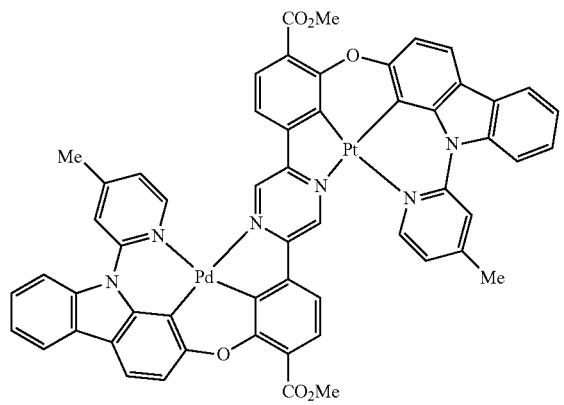
Compound PdPt245
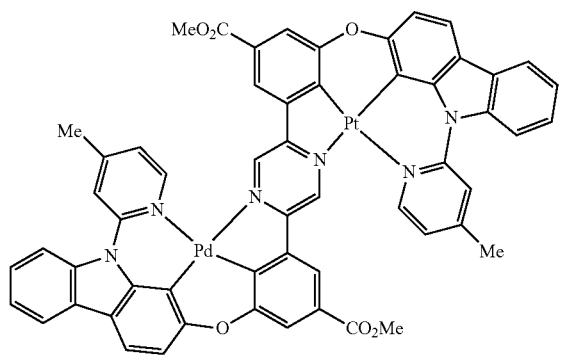
Compound PdPt246
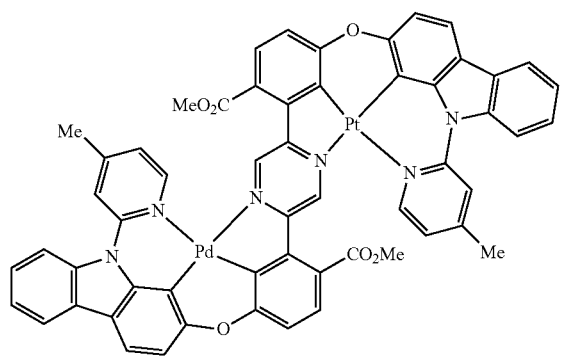
Compound PdPt247
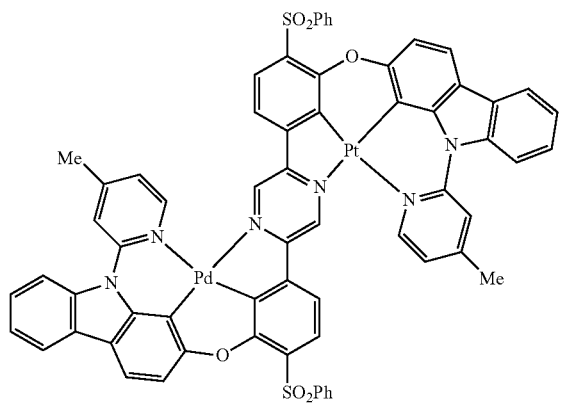

-continued
Compound PdPt248
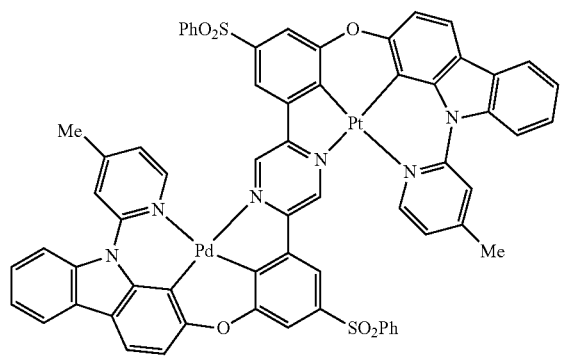
Compound PdPt249
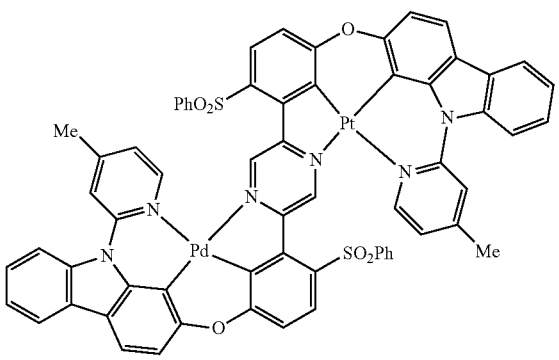
Compound PdPt250
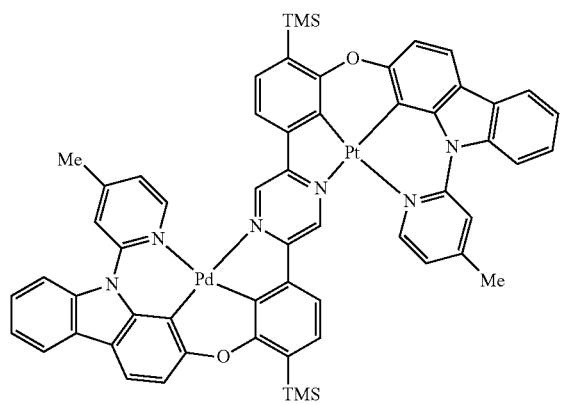
Compound PdPt251
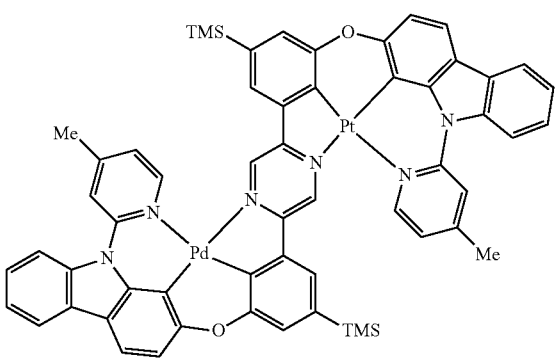
Compound PdPt252
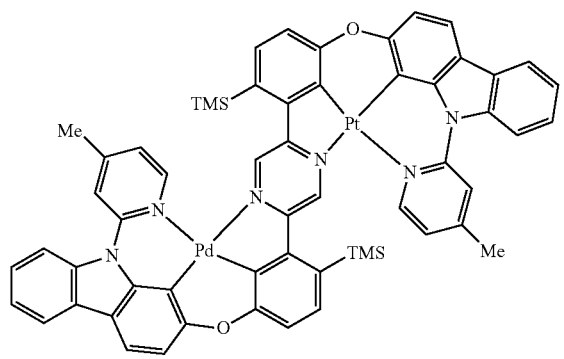
Compound PdPt253
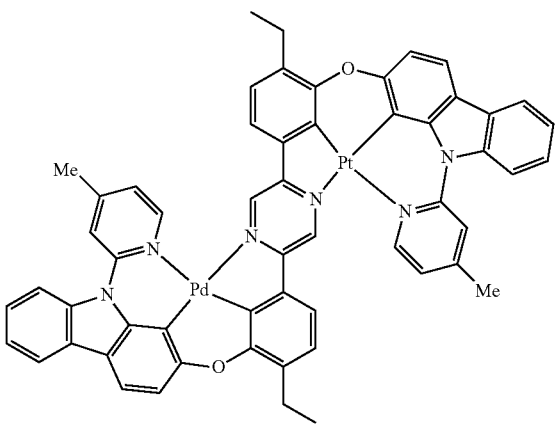
Compound PdPt254
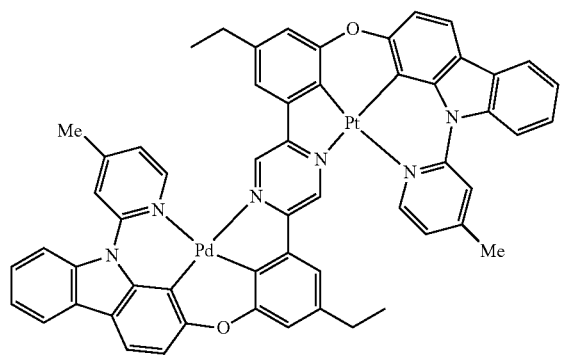
Compound PdPt255
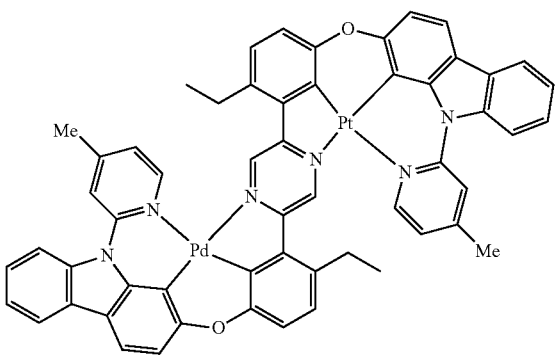

Compound PdPt256
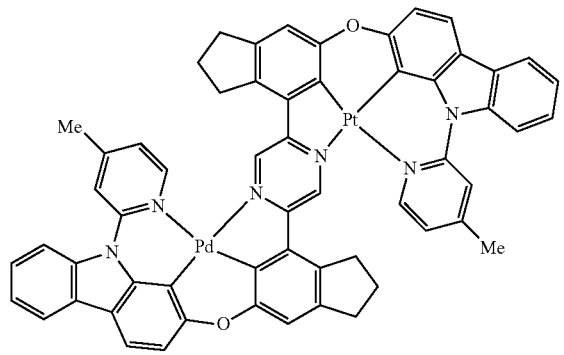
Compound PdPt257
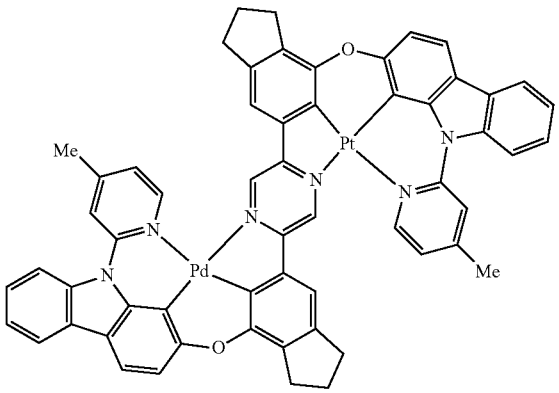
Compound PdPt258
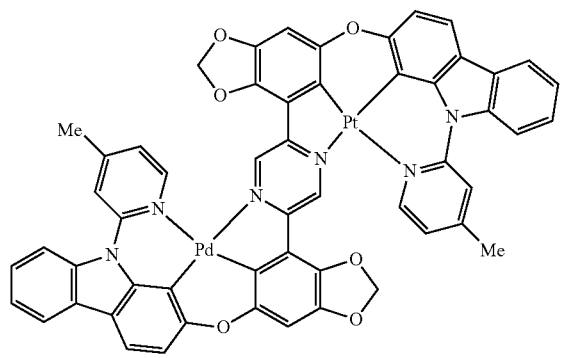
Compound PdPt259
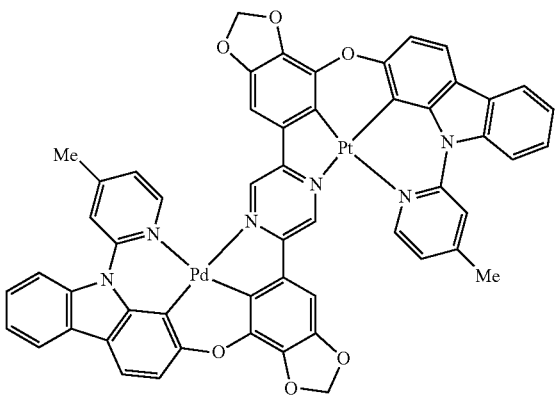
Compound PdPt260
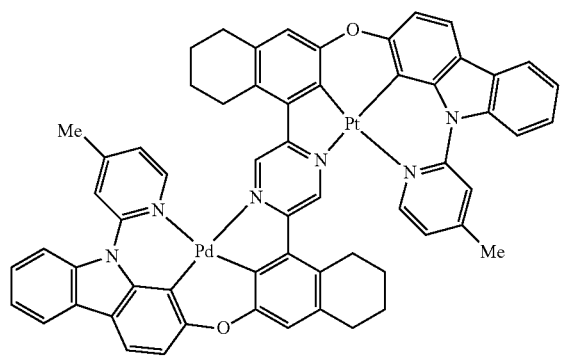
Compound PdPt261
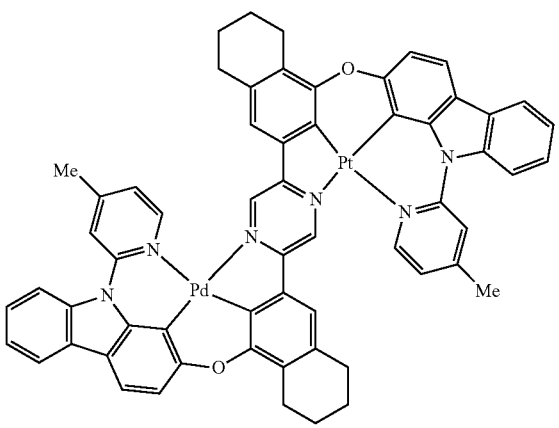

-continued
Compound PdPt262
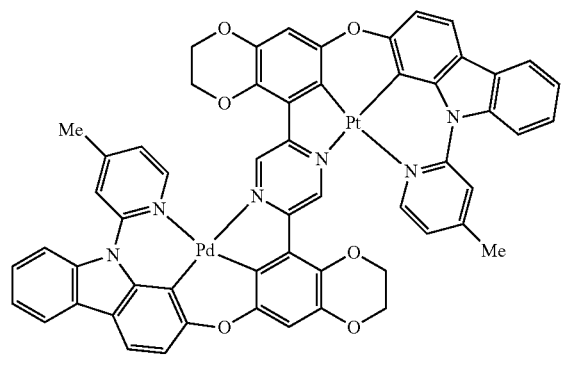
Compound PdPt263
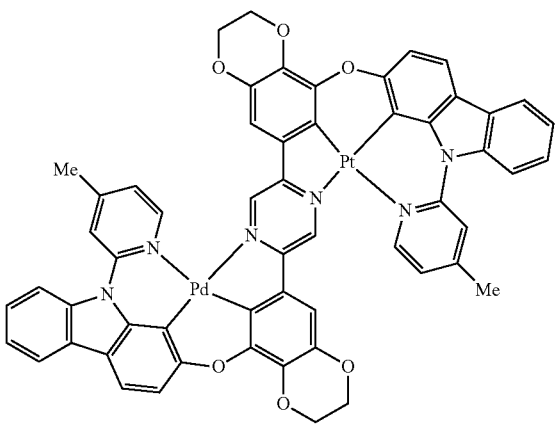
Compound PdPt264
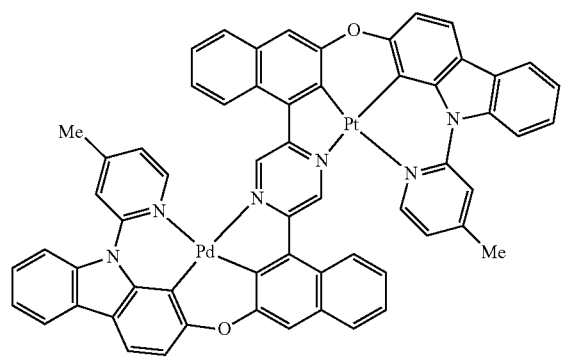
Compound PdPt265
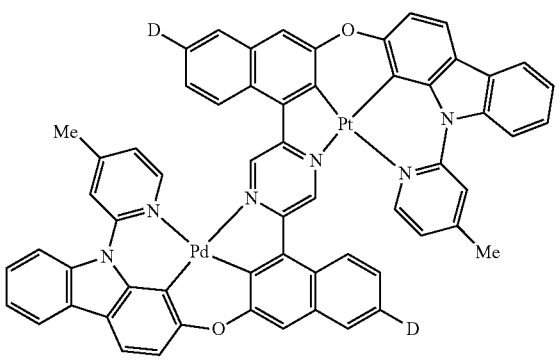
Compound PdPt266
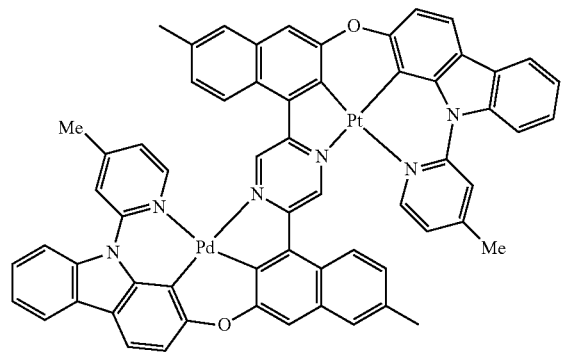
Compound PdPt267
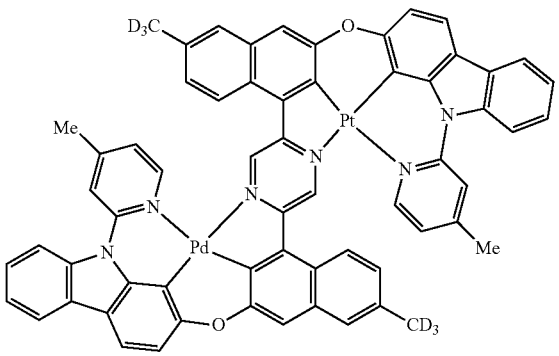
Compound PdPt268
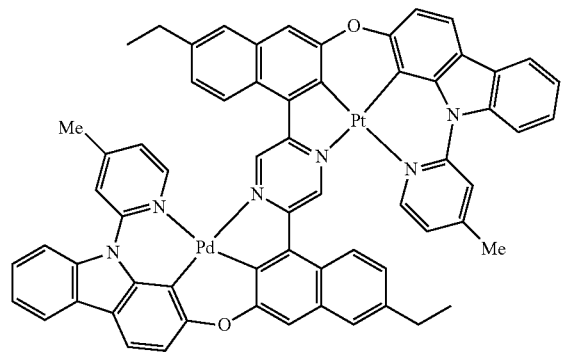
Compound PdPt269
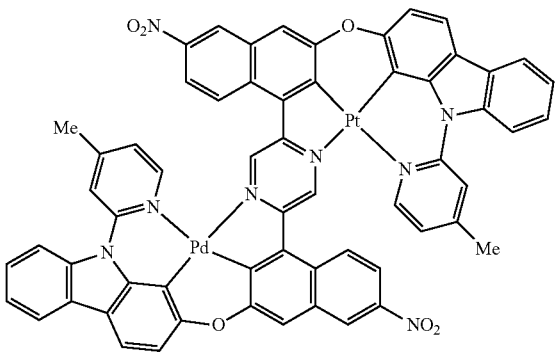

-continued
Compound PdPt270
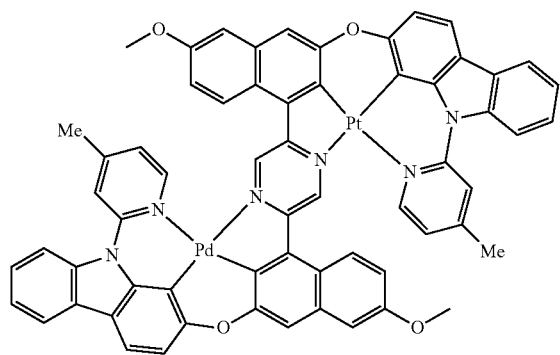
Compound PdPt271
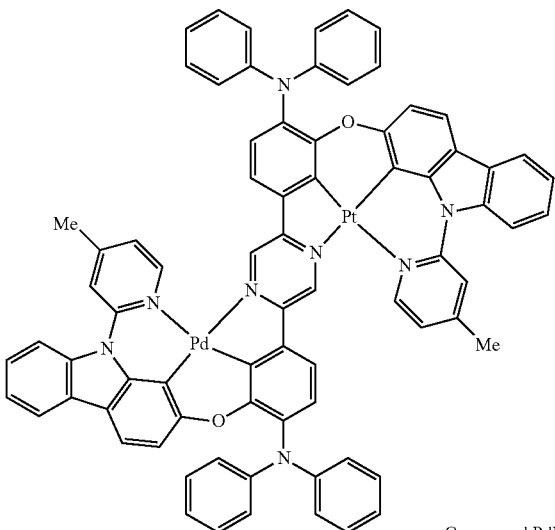
Compound PdPt272
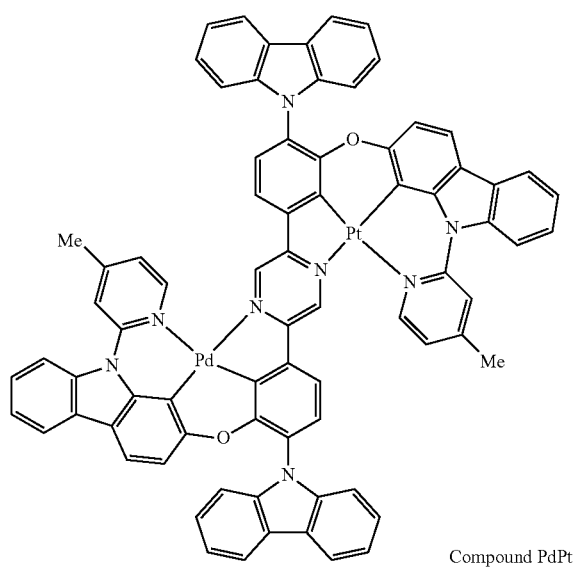
Compound PdPt273
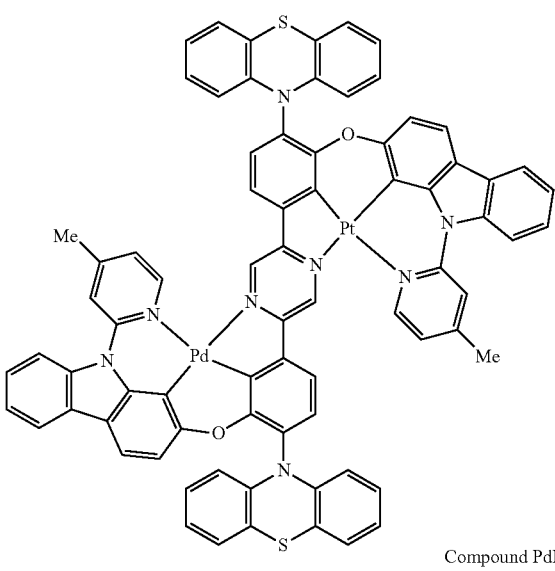
Compound PdPt274
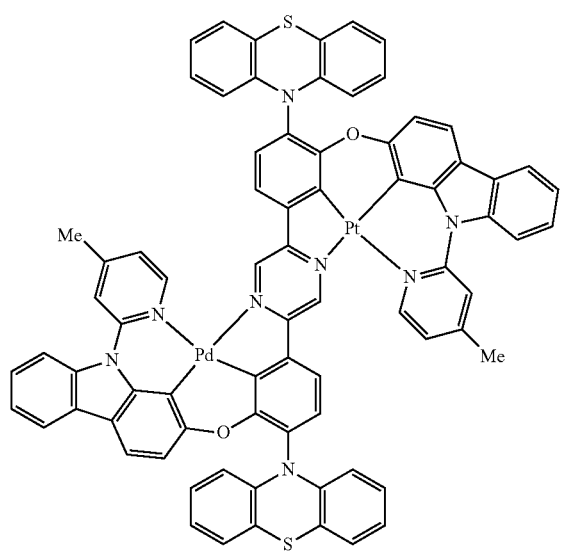
Compound PdPt275
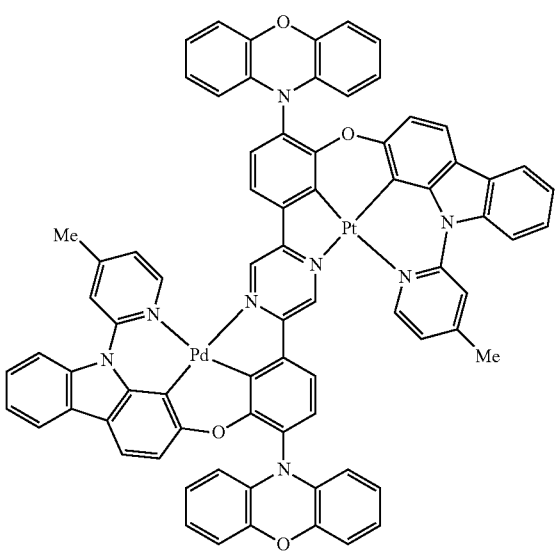

Compound PdPt276
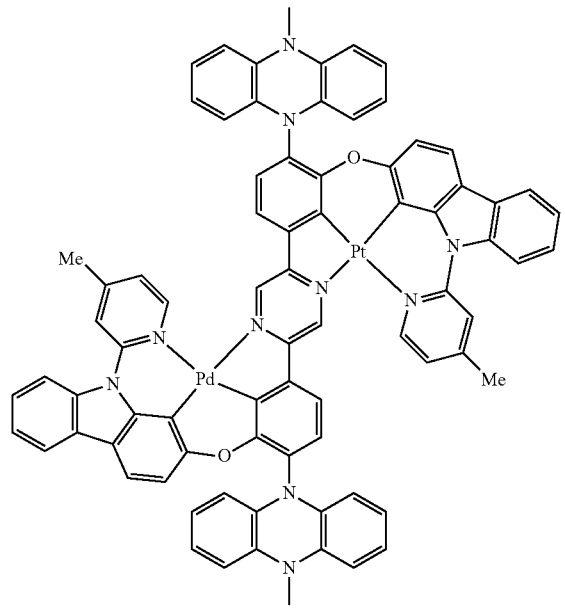
Compound PdPt277
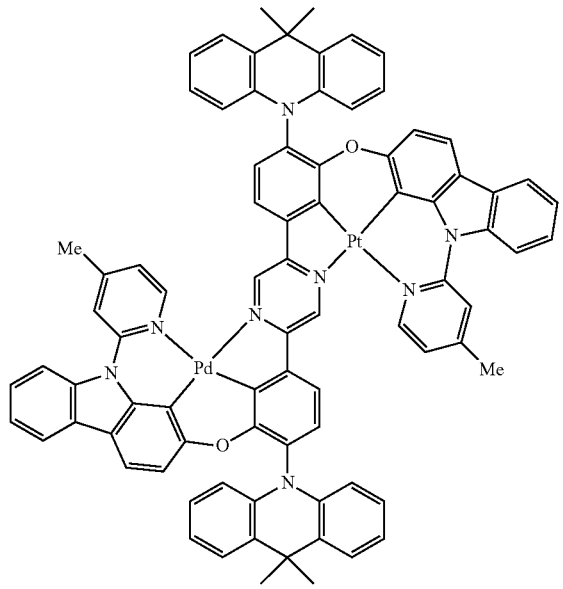
Compound PdPt278
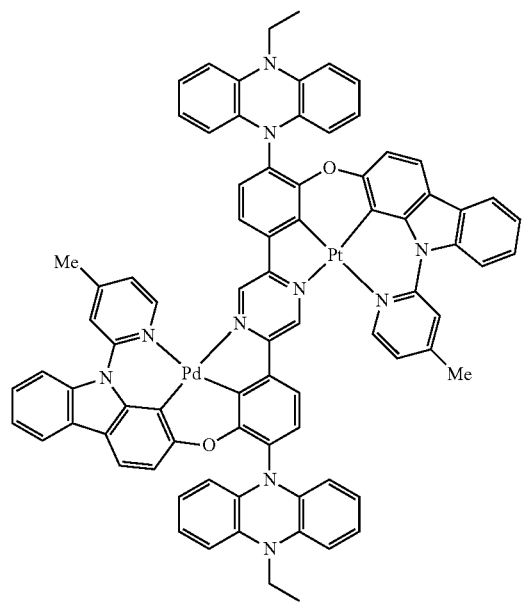
Compound PdPt279
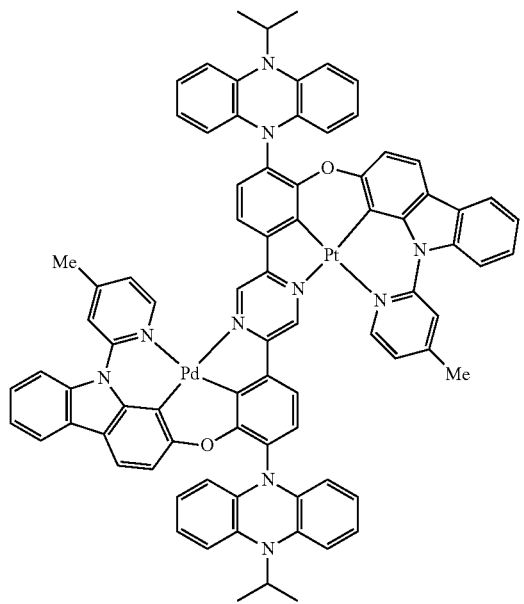

Compound PdPt280
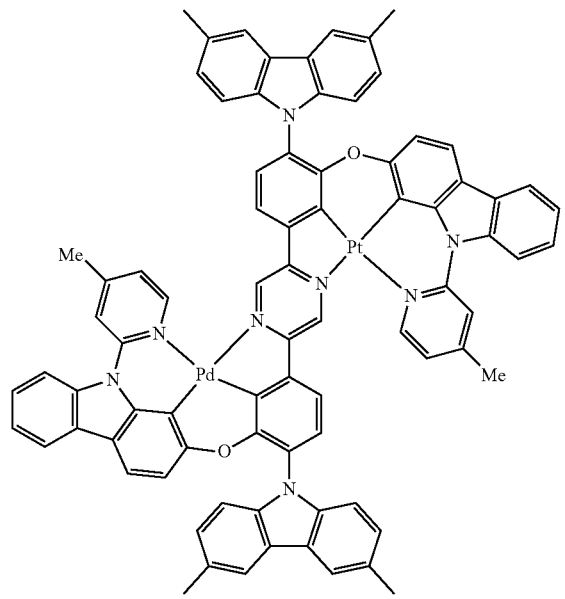
Compound PdPt281
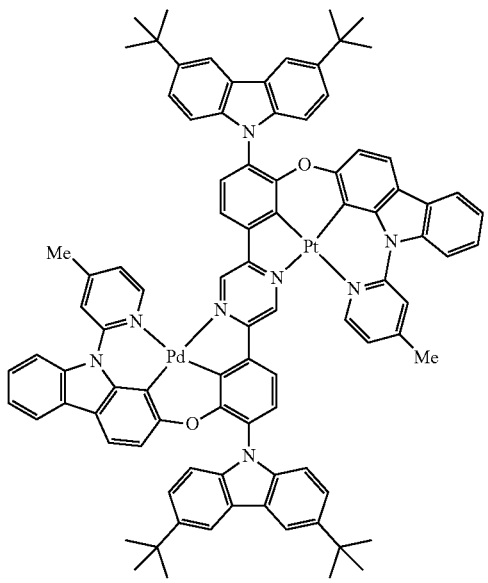
Compound PdPt282
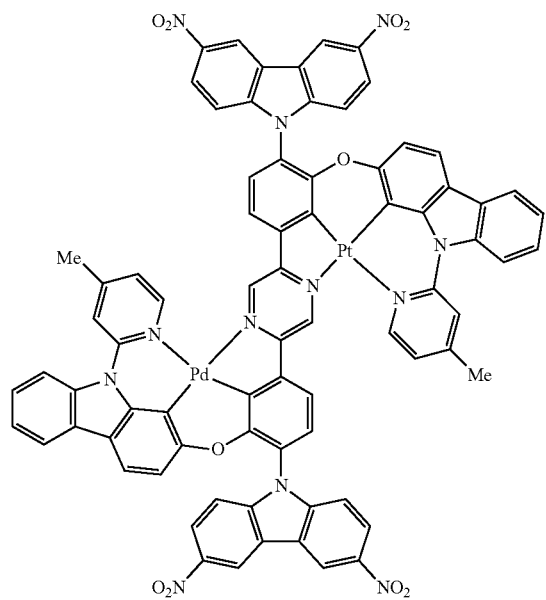
Compound PdPt283
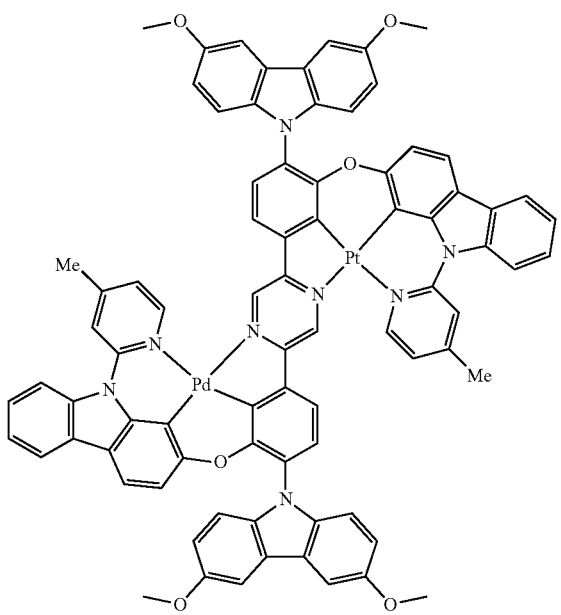

Compound PdPt284
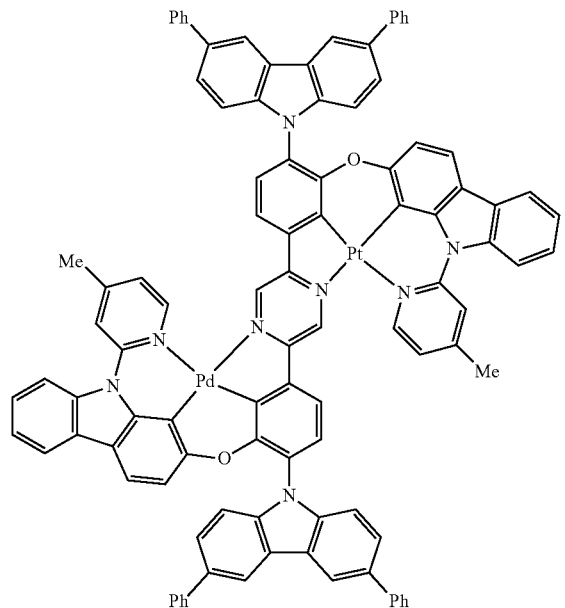
Compound PdPt285
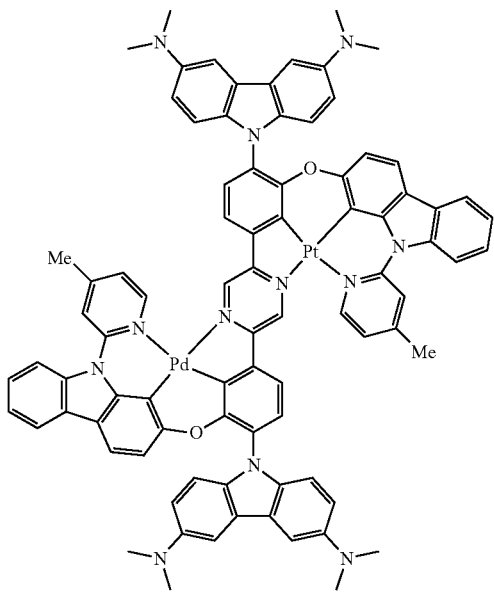
Compound PdPt286
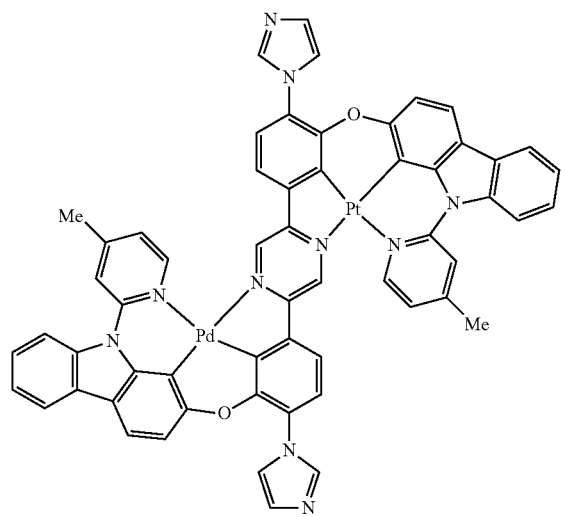
Compound PdPt287
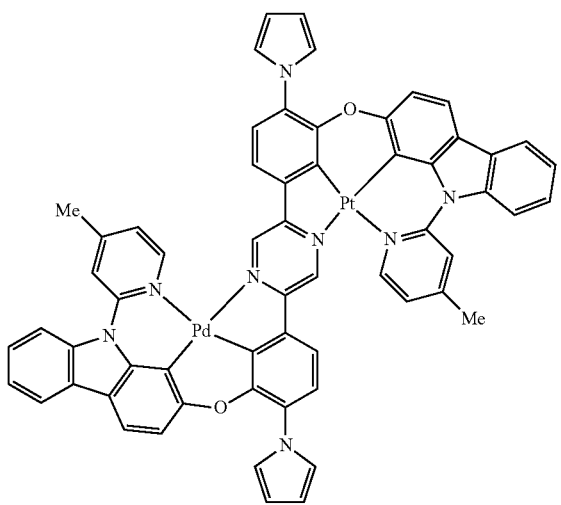

-continued
Compound PdPt288
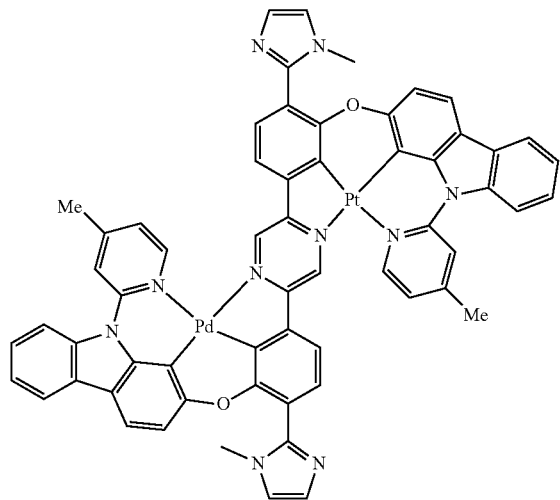
Compound PdPt289
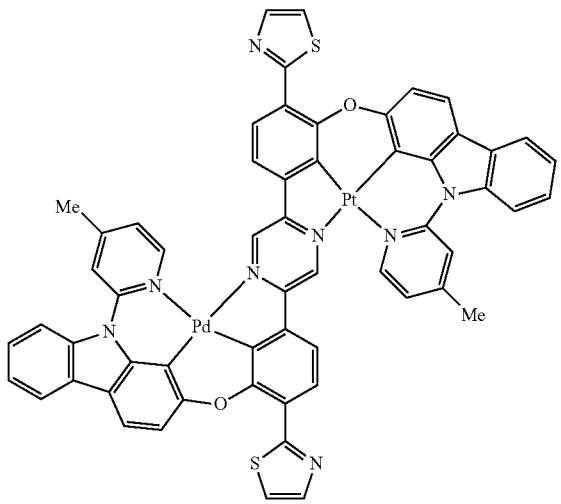
Compound PdPt290
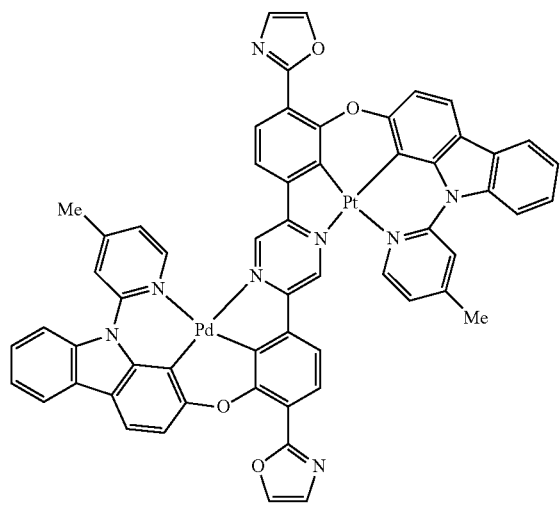
Compound PdPt291
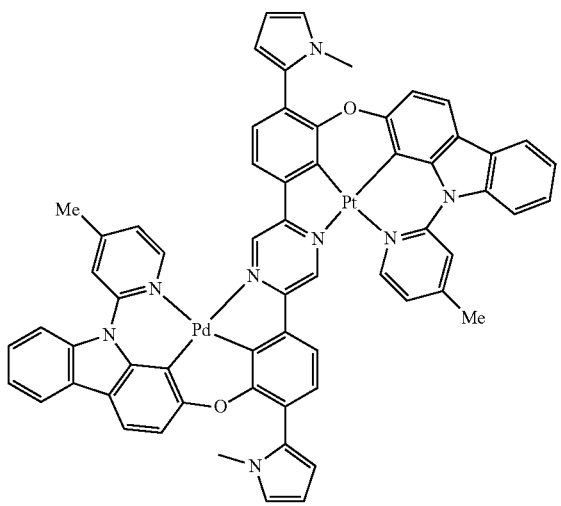
Compound PdPt292
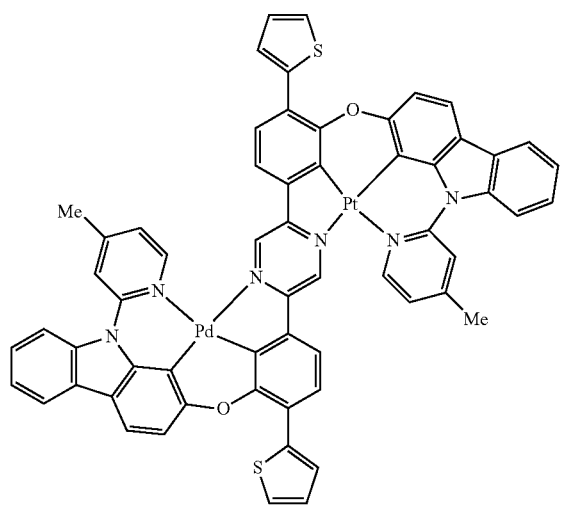
Compound PdPt293
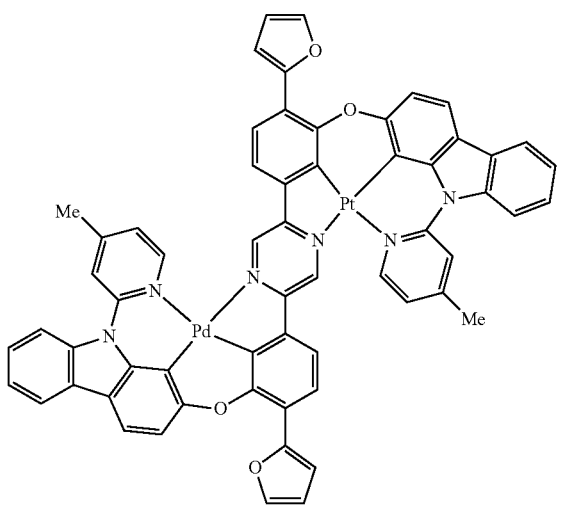

-continued
Compound PdPt294
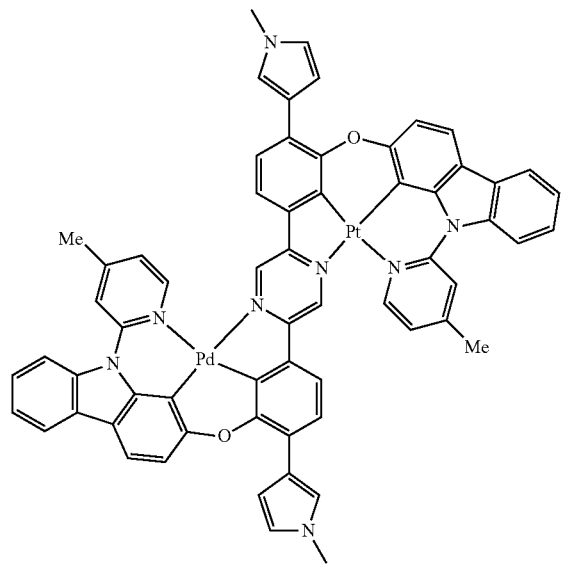
Compound PdPt295
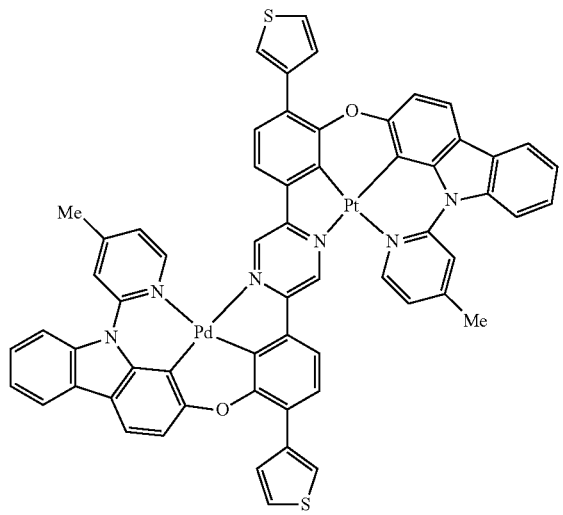
Compound PdPt296
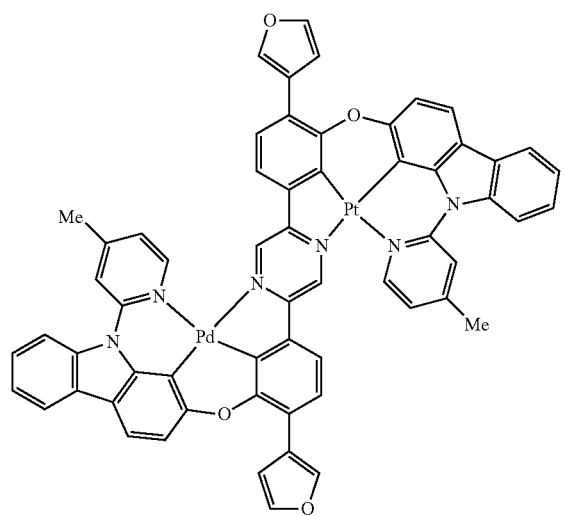
Compound PdPt297
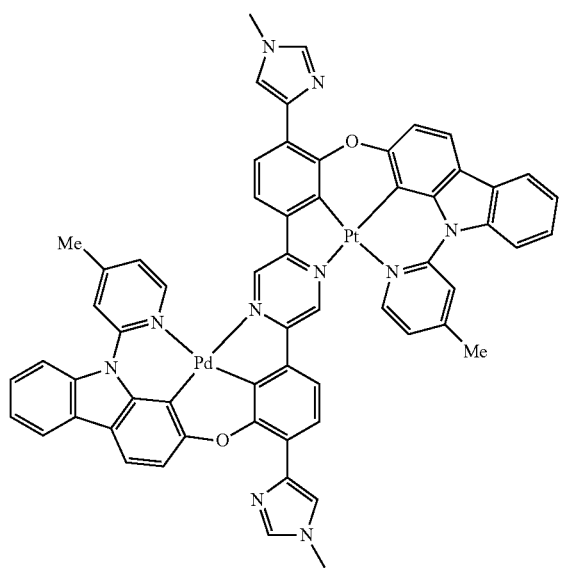

-continued
Compound PdPt298
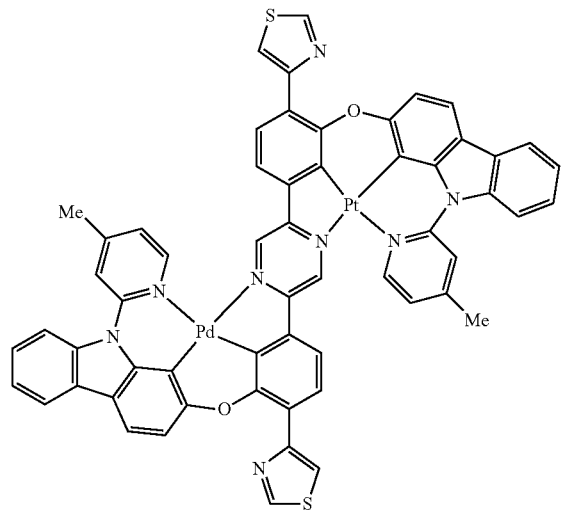
Compound PdPt299
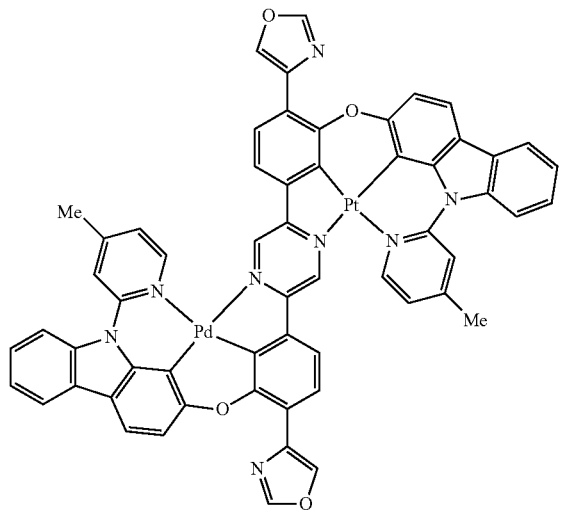
Compound PdPt300
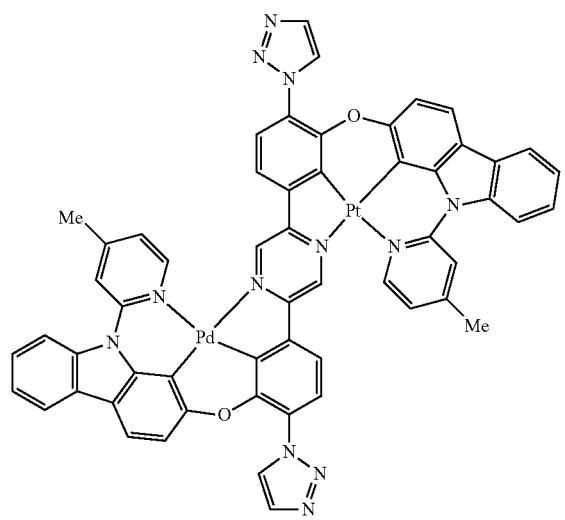
Compound PdPt301
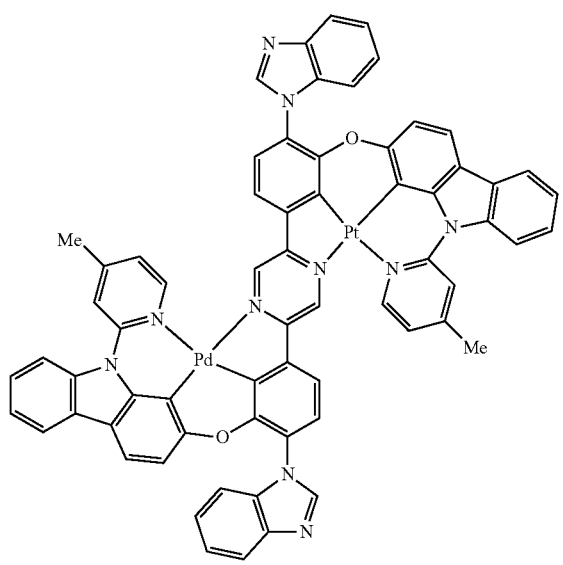

Compound PdPt302
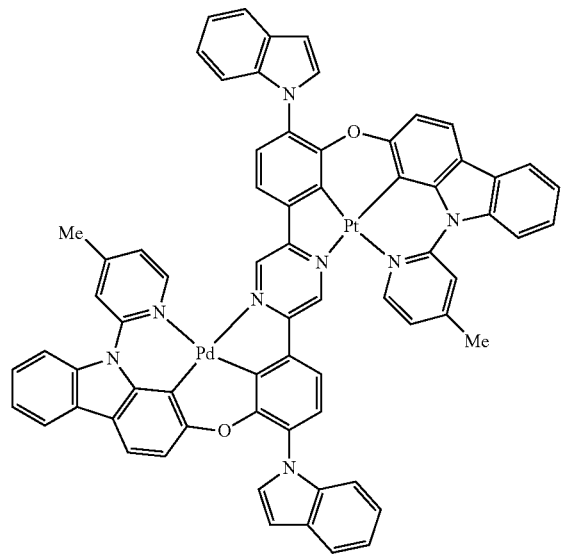
Compound PdPt303
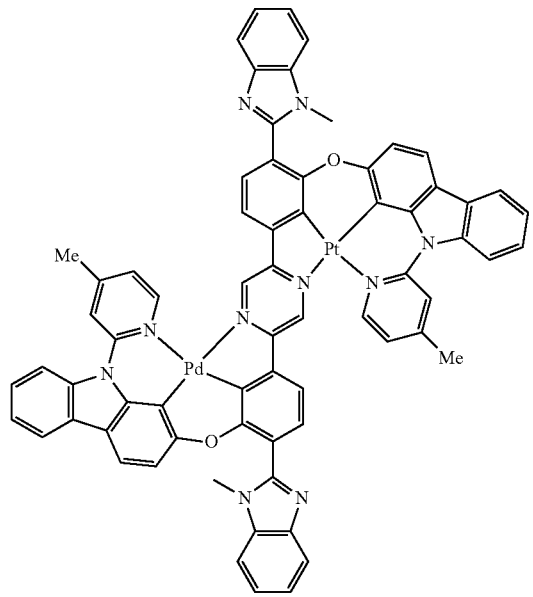
Compound PdPt304
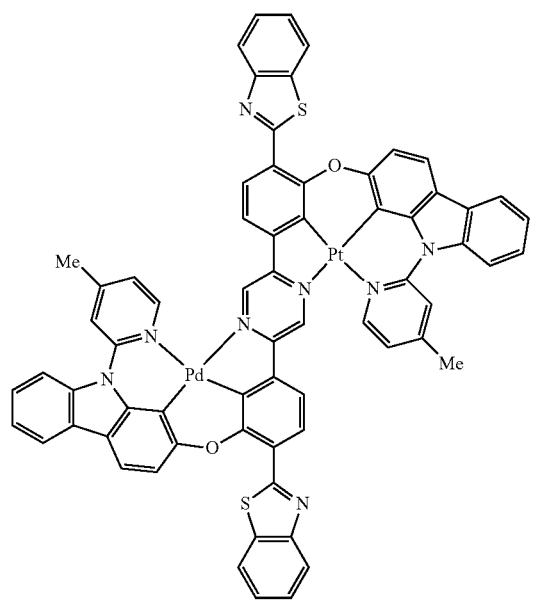
Compound PdPt305
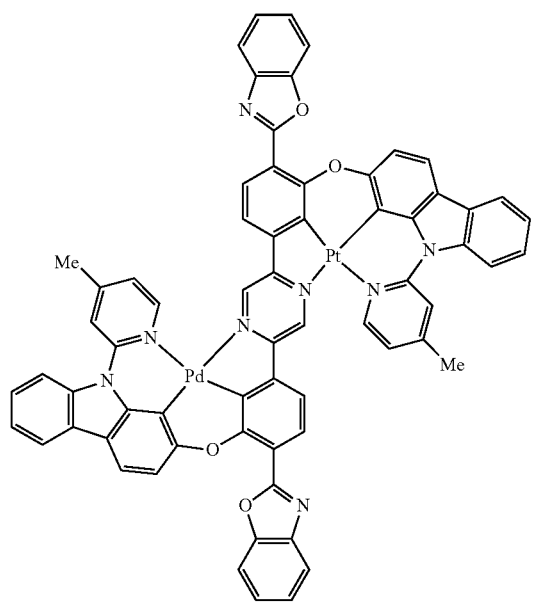

-continued
Compound PdPt306

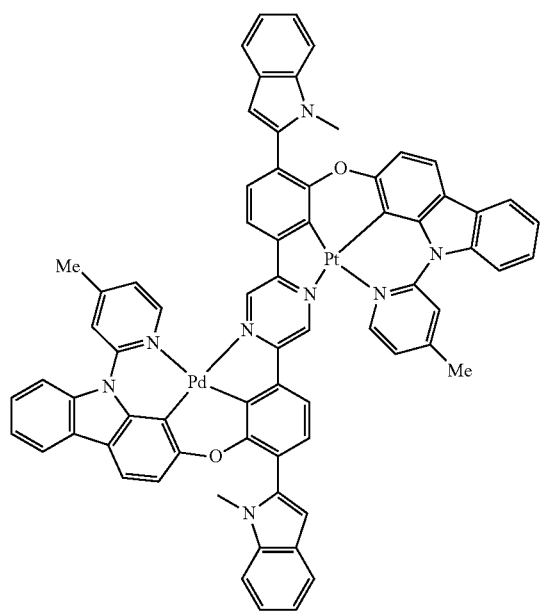

General Synthesis Route

The following embodiments of the present invention are used to provide a general skilled in the art with complete public content and descriptions of how to manufacture and evaluate compounds, compositions, products, devices and/or methods described herein. And the embodiment is intended only to be a demonstration of the disclosed content and does not intentionally limit the scope. Although efforts have been made to ensure the accuracy of values (e.g. quantities, temperatures, etc.), some errors and deviations should be taken into account. Unless otherwise stated, the number of shares is weight, the temperature is in ° C. or at ambient temperature, and the pressure is at or near atmospheric pressure.

Various methods for preparing the disclosed compounds described herein are described in an embodiment. These methods are provided to illustrate a plurality of preparation methods but this disclosure is not intended to be limited to any of the methods described herein. Accordingly, one or more of the disclosed compounds may be easily modified by the described method or prepared using different methods by the technical staff of the domain to which the content of the disclosure belongs. The following aspects are illustrative only instead of being intended to limit the scope of this disclosure. The temperature, catalyst, concentration, reactant composition, and other process conditions may be varied, and the technical staff in the field of the content of the disclosure can easily select suitable reactants and conditions for desired complexes.

$^1$H spectra were recorded by 400 MHz in $CDCl_3$ or DMSO-d6 solution on Varian Liquid State NMR instrument, and $^{13}$C NMR spectra were recorded at 100 MHz, and the chemical shifts were compared with the residual protiated solvents. If $CDCl_3$ is used as solvent, tetramethylsilane ($\delta$=0.00 ppm) is used as internal standard to record $^1$H NMR spectra; DMSO-d$_6$ ($\delta$=77.00 ppm) was used as the internal standard for recording $^{13}$C NMR spectra. If $H_2O$ ($\delta$=3.33 ppm) is used as solvent, the residual H_2O ($\delta$=3.33 ppm) is used as internal standard to record $^1$H NMR: DMSO-d$_6$ ($\delta$=39.52 ppm) was used as the internal standard for recording 13C NMR spectra. The following abbreviations (or combinations) are used to explain the multiplicity of $^1$H NMR; s=single, d=double, t=triple, q=quadruple, p=quintuple, m=multiple, br=width.

The generic synthesis route of the compounds disclosed in the present invention is as follows:

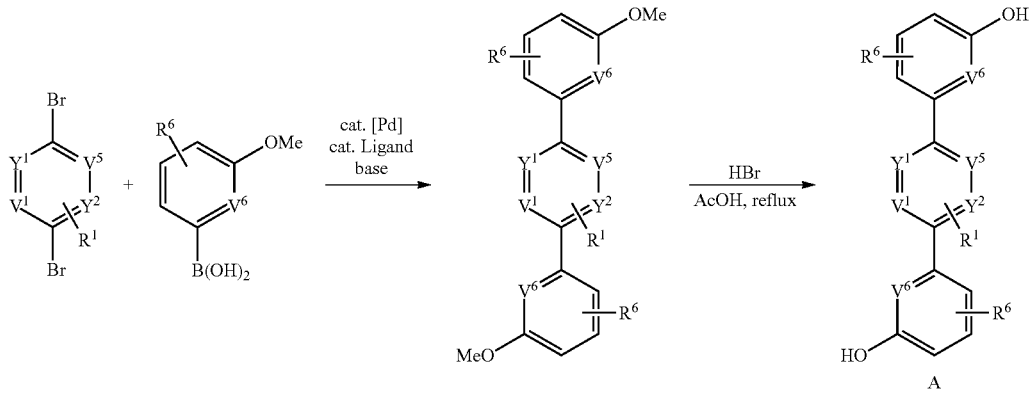

-continued
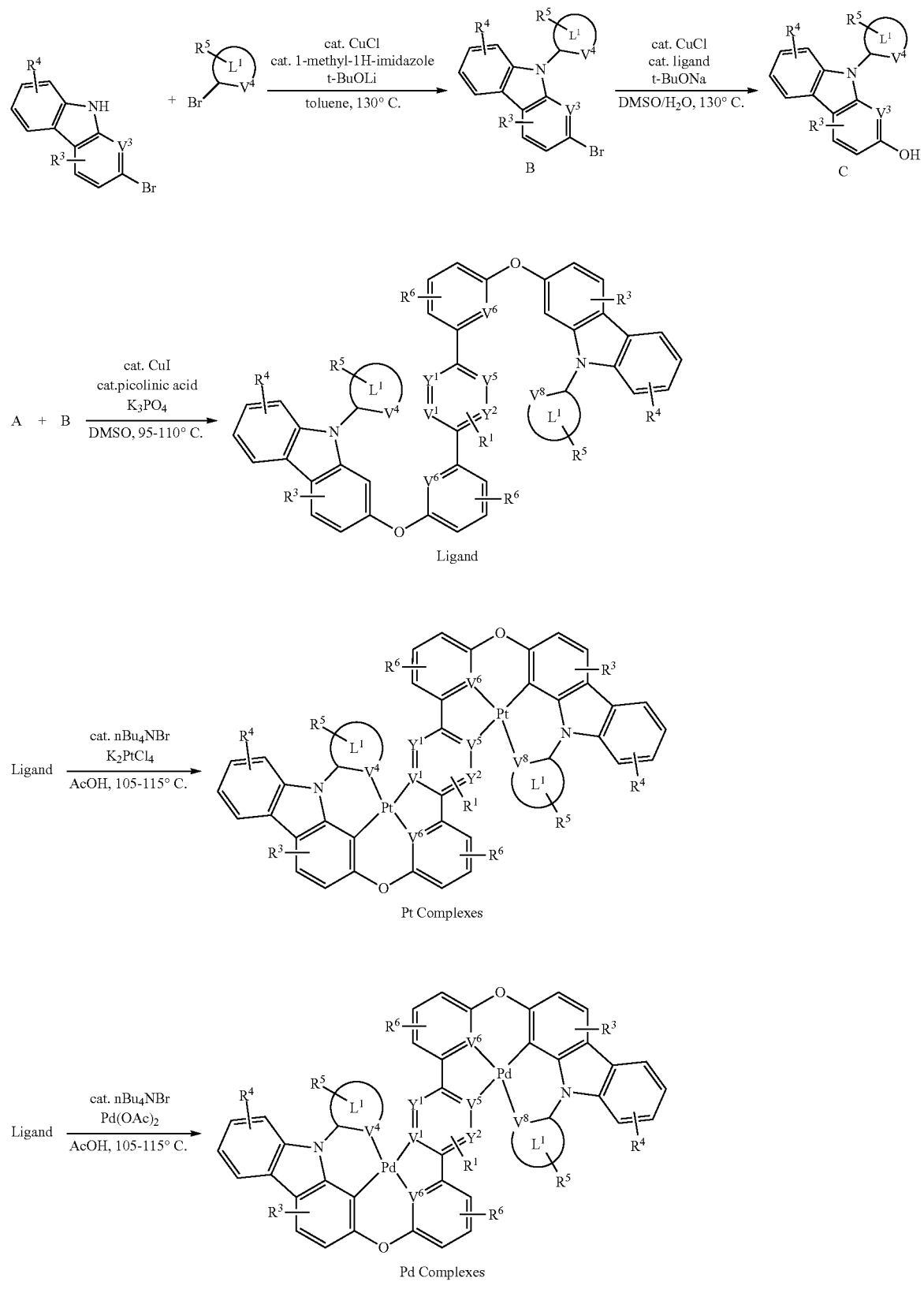

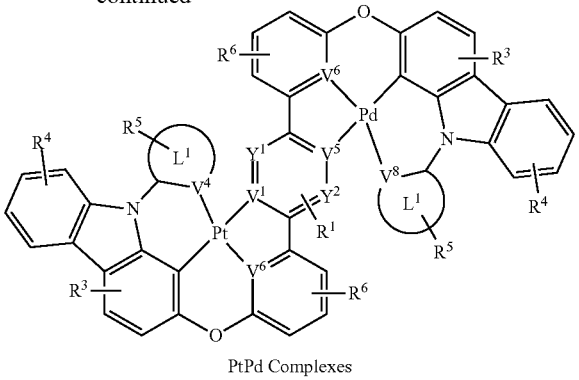

PtPd Complexes

Composite Examples

The complexes of the invention, Compound Pd7 and Compound Pt7, can be synthesized as follows:

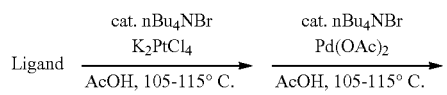

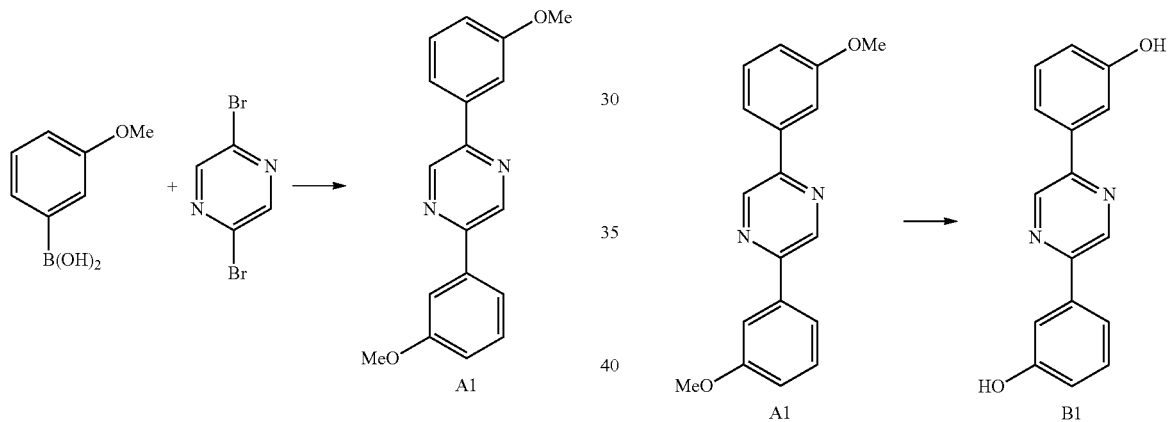

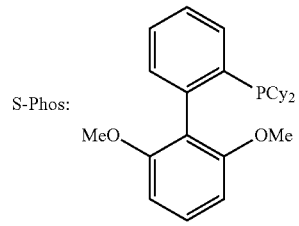

S-Phos:

2,5-dibromopyrazine (4.7562 g, 20.00 mmol, 1.00 equivalent), 3-methoxy phenylborate (9.3990 g, 60.00 mmol, 97%, 3.00 equivalent), palladium acetate (0.1363 g/m 0.60 mmo, 99%, 0.025 equivalent), ligand S-Phos (0.5027 g, 1.20 mmol, 98%, 0.06 equivalent)) and potassium phosphate (17.3278 g, 80.00 mmol, 4.00 equivalent) are added to the dry three-necked flask with magnetic rotor. The nitrogen is pumped and exchanged for three times and then 100 mL toluene is added under the protection of nitrogen. The nitrogen is bubbled for 15 minutes, then the reaction bottle is placed in 120° C. oil bath. After 12 hours of stirring, TLC thin-layer chromatography is used for monitoring reaction until completed. After cooling to room temperature, it is washed with 100 mL water. The aqueous phase is extracted by dichloromethane (40 mL×3). All organic phases are combined, and dried with anhydrous sodium sulfate. The crude product is recrystallized in dichloromethane to obtain A1. 3.5017 g light yellow solid is obtained, with 60% yield.

$^1$H NMR (500 MHz, DMSO-d$_6$): δ 3.87 (s, 6H), 7.10 (dd, J$_1$=7.8 Hz, J$_2$=2.3 Hz, 2H), 7.48 (t, J=7.8 Hz, 2H), 7.74 (t, J=2.0 Hz, 2H), 7.78 (d, J=7.5 Hz, 2H), 9.34 (s, 2H).

Under nitrogen protection, A1 (1.8991 g, 6.50 mmol), acetic acid (50 mL) and hydrobromic acid (50 mL, 48% aqueous solution) are added to the dry three-necked flask with magnetic rotor. Then the reaction bottle is placed in 120° C. oil bath. After stirring for 24 hours, the TLC thin-layer chromatography is used for monitoring reaction until completed. After cooling to room temperature, it is concentrated, and 50 mL ethyl acetate and 50 mL water are added, and pH is adjusted to 6 to 7 with sodium hydroxide solution. Then saturated sodium bicarbonate solution is added until there are no more bubbles. The organic phase is separated and the aqueous phase is extracted with ethyl acetate (30 mL). All organic phases are combined, saturated sodium bicarbonate solution is used for washing, and anhydrous sodium sulfate is used for drying. The crude product is separated and purified by rapid silica gel column chromatography (eluent: Petroleum ether/ethyl acetate=2/1). 1.7016 g light yellow solid is obtained, with 99% yield.

$^1$H NMR (500 MHz, DMSO-d$_6$): δ 6.95-6.89 (m, 2H), 7.36 (t, J=8.0 Hz, 2H), 7.65-7.58 (m, 4H), 9.23 (s, 2H), 9.71 (s, 2H).

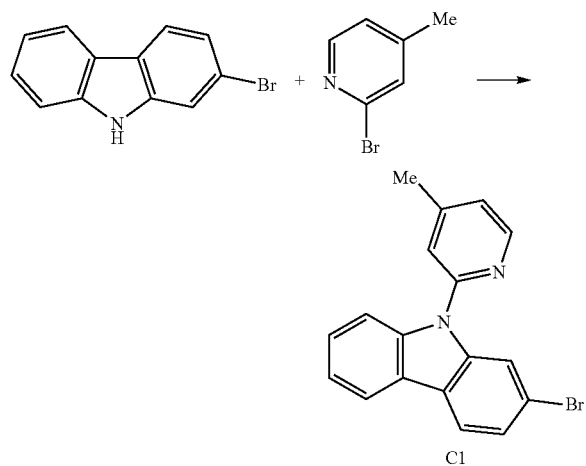

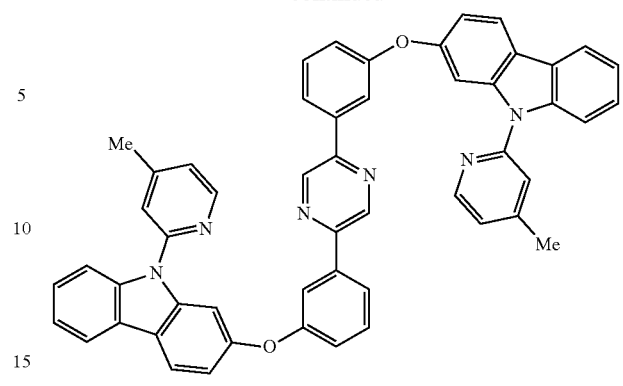

Ligand 2-bromocarbazole (3.7293 g, 15.00 mmol, 99%, 1.00 equivalent), cuprous chloride (0.0151 g, 0.15 mmol, 0.01 equivalent) and lithium tert-butanol (1.8190 g, 22.50 mmol. 1.50 equivalent) are added to the dry three-necked flask with magnetic rotor. The nitrogen is pumped and exchanged for three times, and then, 2-bromo-4-methylpyridine (2.53 mL, 22.5 mmol, 99%, 1.5 equivalent), 1-methyl imidazole (24.2 μL, 0.30 mmol, 0.02 equivalent) and toluene (56.6 mL) are added under nitrogen protection. The reaction bottle was then placed in an oil bath at 130° C. After 12 hours of stirring, the TLC thin-layer chromatography is used for monitoring reaction until completed. After cooling to room temperature, the diatomite is used for filtration, ethyl acetate is used for washing insoluble. The filtrate is washed by 50 mL water and dried by anhydrous sodium sulfate. The crude product is separated and purified by rapid silica gel column chromatography (eluent: Petroleum ether/dichloromethane=10/1~1/1). 4.6019 g white solid is obtained with 91% yield.

$^1$H NMR (500 MHz, CDCl$_6$): δ 2.47 (s, 3H), 7.13 (d, J=5.0 Hz, 1H), 7.29-7.32 (m, 1H), 7.39-7.46 (m, 3H), 7.72 (d, J=8.0 Hz, 1H), 7.93 (d, J=8.0 Hz, 1H), 7.97 (d, J=1.5 Hz, 1H), 8.06 (d, J=7.5 Hz, 1H), 8.56 (d, J=5.0 Hz, 1H).

B1 (0.5285 g, 2.00 mmol, 1.00 equivalent), C1 (1.6188 g, 4.80 mmol, 2.40 equivalent), iodide copper (0.0771 g, 0.40 mmol, 0.20 equivalent). 2-pyridinate (0.0995 g, 0.80 mmol, 0.40 equivalent) and potassium phosphate (1.6987 g, 8.00 mmol. 4.00 equivalent) are added to the dry three-necked flask with magnetic rotor. The nitrogen is pumped and exchanged three times, and then 6 mL dimethyl sulfoxide is added under nitrogen protection. Nitrogen is bubbled for 15 minutes, then the reaction bottle is placed in 105° C. oil bath. After stirring for 17 hours, the TLC thin-layer chromatography is used for monitoring reaction until completed. After cooling to room temperature, 50 mL dichloromethane is added, and it is washed by water (30 mL×3). The mixture of water phase and dichloromethane are used to extract (10 mL×2). All organic phases are combined and dried, filtered and concentrated with anhydrous sodium sulfate. The crude product is separated and purified by rapid silica gel column chromatography (eluent: petroleum ether/ethyl acetate=5/1~petroleum ether/ethyl acetate/dichloromethane=5/1/2). Ligand. 1.3185 g white solid is obtained with 85% yield.

$^1$H NMR (500 MHz, DMSO-d$_6$): δ 2.41 (s, 6H), 7.09 (dd, J$_1$=8.5 Hz, J$_2$=2.5 Hz, 2H), 7.19 (dd, J$_1$=7.8 Hz, J$_2$=2.3 Hz, 2H), 7.27 (d, J=5.5 Hz, 2H), 7.34 (t, J=7.5 Hz, 2H), 7.45 (t, J=7.8 Hz, 2H), 7.51 (d, J=2.0 Hz, 2H), 7.54 (t, J=8.0 Hz, 2H), 7.59 (s, 2H), 7.77 (d, J=8.5 Hz, 2H), 7.81 (t, J=1.8 Hz, 2H), 7.92 (d, J=8.0 Hz, 2H), 8.22 (d, J=7.5 Hz, 2H), 8.28 (d, J=8.5 Hz, 2H), 8.51 (d, J=5.0 Hz, 2H), 9.27 (s, 2H).

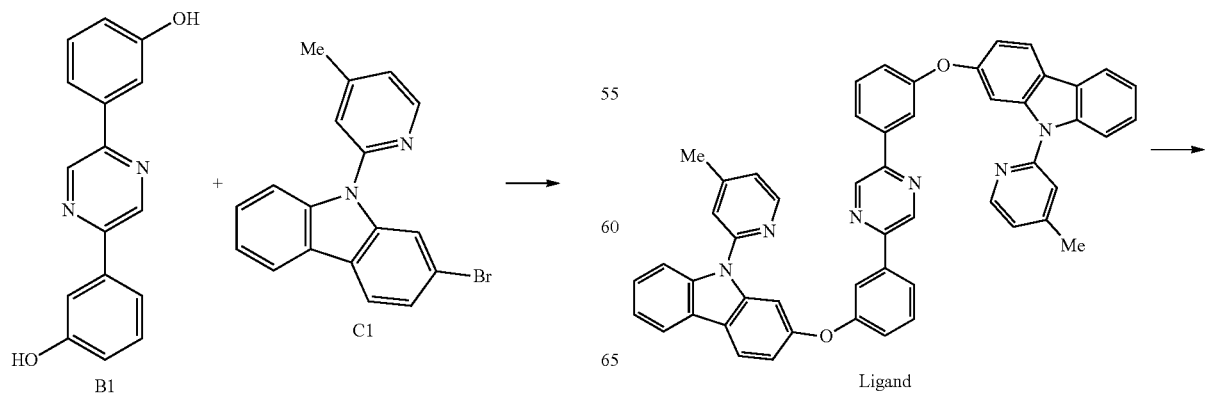

Ligand

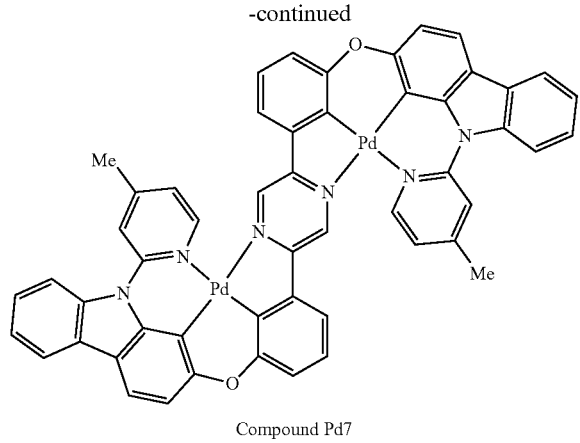

Compound Pd7 ligand (0.2003 g, 0.26 mmol, 1.00 equivalent), palladium acetate (0.1218 g, 0.54 mmol, 2.10 equivalent) and TBAb (0.0178 g, 0.052 mmol. 0.20 equivalent) are added to the dry three-necked flask with magnetic rotor in turn. The nitrogen is pumped and exchanged for three times and then 31 mL acetic acid is added under the protection of nitrogen. Nitrogen is bubbled for 30 minutes, stirring at room temperature for 15 hours, then the reaction bottle is placed in 110° C. oil bath. After stirring for 3 days, the TLC thin-layer chromatography is used for monitoring reaction until completed. The crude product is separated and purified by rapid silica gel column chromatography (eluent: Petroleum ether/ethyl acetate=2/1~1/2).dPdLA1m is obtained and 0.1647 g yellow solid is obtained, with 65% yield.

$^1$H NMR (400 MHz. DMSO-$d_6$): δ 2.25 (s, 6H), 7.26 (t, J=8.6 Hz, 4H), 7.36 (t, J=7.6 Hz, 4H), 7.41 (t, J=7.4 Hz, 2H), 7.53 (t, J=7.6 Hz, 2H), 7.86 (d, J=7.6 Hz, 2H), 7.98 (d, J=8.4 Hz, 2H), 8.03 (s, 2H), 8.12 (d, J=8.0 Hz, 2H), 8.18 (d, J=7.2 Hz, 2H), 9.02 (d, J=5.6 Hz, 2H), 9.46 (s, 2H).

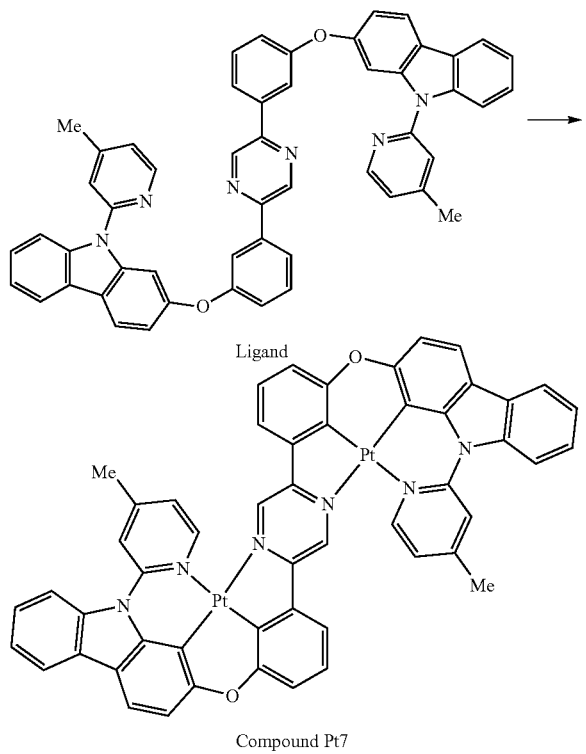

Compound Pt7 ligand (0.2005 g, 0.26 mmol, 1.00 equivalent), potassium chloroplatinate (0.2249 g, 0.54 mmol, 2.10 equivalent) and TBAb (0.0171 g, 0.052 mmol. 0.20 equivalent) are added to the dry three-necked flask with magnetic rotor in turn. The nitrogen is pumped and exchanged for three times and then 40 mL acetic acid is added under the protection of nitrogen. Nitrogen is bubbled for 30 minutes, stirring at room temperature for 18 hours, then the reaction bottle is placed in 110° C. oil bath. After stirring for 4 days, the TLC thin-layer chromatography is used for monitoring reaction until completed. The crude product is separated and purified by rapid silica gel column chromatography (eluent: Petroleum ether/ethyl acetate=2/1~1/2).dPtLA1m is obtained and 0.0286 g yellow solid is obtained, with 10% yield.

Device

The device provided by the invention comprises the polydentate binuclear ring to metal complex or its composition.

In some embodiments of the invention, the devices comprising the polydentate binuclear ring metal complexes or their compositions may be optical and electro-optic devices; optical absorption devices, such as solar and photosensitive devices; Organic light-emitting diode (OLEDs); An optical emission device or a device capable of being compatible with optical absorption and emission; And biomarkers.

Ordinary technicians in the art can understand that the above embodiments are specific embodiments for realizing the invention; in practical applications, various changes can be made to them in form and in detail, without deviating from the spirit and scope of the invention.

It is to be understood, however, that even though numerous characteristics and advantages of the present exemplary embodiments have been set forth in the foregoing description, together with details of the structures and functions of the embodiments, the disclosure is illustrative only, and changes may be made in detail, especially in matters of shape, size, and arrangement of parts within the principles of the invention to the full extent indicated by the broad general meaning of the terms where the appended claims are expressed.

What is claimed is:

1. A polydentate binuclear ring metal complex, wherein structure of the complex is as shown in Formula I:

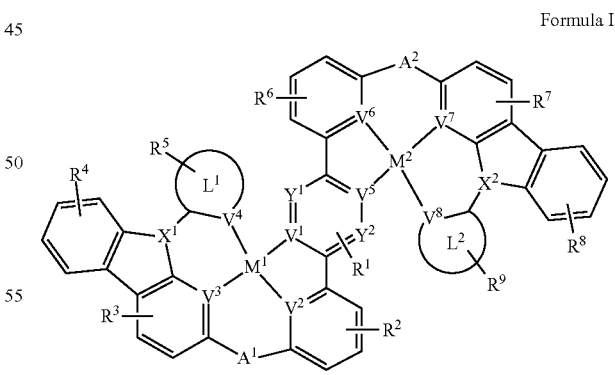

Formula I in which, $M^1$ and $M^2$ are palladium, respectively;
$L^1$ and $L^2$ are heterocyclic respectively;
$V^1$, $V^2$, $V^3$, $V^4$, $V^5$, $V^6$, $V^7$ and $V^8$ are coordinated with palladium; $V^1$, $V^4$, $V^5$, and $V^8$ are N, $V^2$, $V^3$, $V^6$, and $V^7$ are C;
$Y^1$ and $Y^2$ are CH respectively;
$A^1$ and $A^2$ is O respectively;
$X^1$ and $X^2$ are N respectively;

$R^1$, $R^2$, $R^3$, $R^4$, $R^6$, $R^7$, and $R^8$ are hydrogen, $R^5$ and $R^9$ are methyl.

2. The polydentate binuclear ring metal complex as described in claim 1 wherein the complex is electrically neutral.

3. A device comprising one or more of the polydentate binuclear ring metal complexes described in claim 1.

4. The device as described in claim 3, wherein the device is an optical and electro-optic device, an optical absorption device, an organic light-emitting diode device, an optical emission device, a device capable of compatible optical absorption and emission, or a biomarker device.

5. The device as described in claim 4, wherein the polydentate binuclear ring metal complex has 100% internal quantum efficiency in the device.

* * * * *